(12) United States Patent
Hilinski et al.

(10) Patent No.: US 11,834,482 B2
(45) Date of Patent: Dec. 5, 2023

(54) AGENTS MODULATING BETA-CATENIN FUNCTIONS AND METHODS THEREOF

(71) Applicant: FOG PHARMACEUTICALS, INC., Cambridge, MA (US)

(72) Inventors: Gerard Hilinski, Somerville, MA (US); So Youn Shim, Watertown, MA (US); Matthew Reiser Patton, Somerville, MA (US); John Hanney McGee, Somerville, MA (US); Paula Cristina Ortet, Malden, MA (US); Gregory L Verdine, Boston, MA (US)

(73) Assignee: FOG PHARMACEUTICALS, INC., Cambridge, MA (US)

( * ) Notice: Subject to any disclaimer, the term of this patent is extended or adjusted under 35 U.S.C. 154(b) by 175 days.

(21) Appl. No.: 17/518,247

(22) Filed: Nov. 3, 2021

(65) Prior Publication Data

US 2022/0213154 A1   Jul. 7, 2022

Related U.S. Application Data

(63) Continuation of application No. 16/645,407, filed as application No. PCT/US2018/050102 on Sep. 7, 2018, now Pat. No. 11,198,713.

(60) Provisional application No. 62/555,519, filed on Sep. 7, 2017.

(51) Int. Cl.
| | | |
|---|---|---|
| *A61K 38/03* | (2006.01) | |
| *C07K 4/00* | (2006.01) | |
| *C07K 14/47* | (2006.01) | |
| *C07K 7/08* | (2006.01) | |
| *A61K 38/00* | (2006.01) | |
| *C07K 16/28* | (2006.01) | |

(52) U.S. Cl.
CPC .......... *C07K 14/4703* (2013.01); *A61K 38/03* (2013.01); *C07K 4/00* (2013.01); *C07K 7/08* (2013.01); *A61K 38/00* (2013.01); *C07K 16/2818* (2013.01); *C07K 16/2827* (2013.01)

(58) Field of Classification Search
CPC ........ A61K 38/00; A61K 38/03; A61K 38/08; A61K 38/10; C07K 2/00; C07K 4/00; C07K 7/06
See application file for complete search history.

(56) References Cited

U.S. PATENT DOCUMENTS

| | | |
|---|---|---|
| 6,444,425 B1 | 9/2002 | Reed et al. |
| 7,192,713 B1 | 3/2007 | Verdine et al. |
| 7,723,469 B2 | 5/2010 | Walensky et al. |
| 7,786,072 B2 | 8/2010 | Verdine et al. |
| 8,198,405 B2 | 6/2012 | Walensky et al. |
| 8,324,428 B2 | 12/2012 | Verdine et al. |
| 8,592,377 B2 | 11/2013 | Verdine et al. |
| 8,796,418 B2 | 8/2014 | Walensky et al. |
| 8,815,932 B2 | 8/2014 | Schmalz et al. |
| 8,889,632 B2 | 11/2014 | Bernal et al. |
| 8,895,699 B2 | 11/2014 | Verdine et al. |
| 8,921,323 B2 | 12/2014 | Walensky et al. |
| 8,957,026 B2 | 2/2015 | Verdine et al. |
| 9,056,891 B2 | 6/2015 | Tarasova et al. |
| 9,074,009 B2 | 7/2015 | Bradner et al. |
| 9,079,970 B2 | 7/2015 | Walensky et al. |
| 9,163,330 B2 | 10/2015 | Verdine et al. |
| 9,273,099 B2 | 3/2016 | Walensky et al. |
| 9,290,545 B2 | 3/2016 | Walensky et al. |
| 9,296,805 B2 | 3/2016 | Walensky et al. |
| 9,303,024 B2 | 4/2016 | Walensky et al. |
| 9,458,189 B2 | 10/2016 | Verdine et al. |
| 9,464,115 B2 | 10/2016 | Walensky et al. |
| 9,487,562 B2 | 11/2016 | Moellering et al. |
| 9,505,801 B2 | 11/2016 | Verdine et al. |
| 9,505,816 B2 | 11/2016 | Walensky et al. |
| 9,527,896 B2 | 12/2016 | Bernal et al. |
| 9,556,227 B2 | 1/2017 | Verdine et al. |
| 9,617,309 B2 | 4/2017 | Verdine et al. |
| 9,695,224 B2 | 7/2017 | Walensky et al. |
| 9,822,165 B2 | 11/2017 | Walensky et al. |
| 9,926,306 B2 | 3/2018 | Walensky |
| 10,000,478 B2 | 6/2018 | Walensky et al. |
| 10,000,511 B2 | 6/2018 | Walensky et al. |
| 10,077,290 B2 | 9/2018 | Walensky et al. |
| 10,081,654 B2 | 9/2018 | Verdine et al. |
| 10,087,215 B2 | 10/2018 | Leshchiner et al. |
| 10,106,590 B2 | 10/2018 | Walensky et al. |

(Continued)

FOREIGN PATENT DOCUMENTS

| | | |
|---|---|---|
| CN | 1906209 A | 1/2007 |
| JP | H02-124887 A | 5/1990 |

(Continued)

OTHER PUBLICATIONS

U.S. Appl. No. 16/298,093, filed Mar. 11, 2019, Verdine et al.

(Continued)

*Primary Examiner* — Jeffrey E. Russel
(74) *Attorney, Agent, or Firm* — Choate, Hall & Stewart LLP; Brenda Herschbach Jarrell; Xiaodong Li

(57) ABSTRACT

Among other things, the present disclosure provides technologies for modulating functions of beta-catenin. In some embodiments, the present disclosure provides stapled peptides that interact with beta-catenin. In some embodiments, provided stapled peptides interact with beta-catenin at an Axin-binding site of beta-catenin. In some embodiments, the present disclosure provides compounds, compositions and methods for preventing and/or treating conditions, disorders and diseases that are associated with beta-catenin.

21 Claims, 6 Drawing Sheets

Specification includes a Sequence Listing.

(56) References Cited

U.S. PATENT DOCUMENTS

| | | | |
|---|---|---|---|
| 10,202,431 B2 | 2/2019 | Bernal et al. |
| 10,227,390 B2 | 3/2019 | Verdine et al. |
| 10,259,848 B2 | 4/2019 | Walensky et al. |
| 10,273,290 B2 | 4/2019 | Walensky et al. |
| 10,301,351 B2 | 5/2019 | Verdine et al. |
| 10,308,926 B2 | 6/2019 | Walensky et al. |
| 10,351,554 B2 | 7/2019 | Walensky et al. |
| 10,464,975 B2 | 11/2019 | Walensky et al. |
| 10,487,129 B2 | 11/2019 | Walensky et al. |
| 10,533,039 B2 | 1/2020 | Verdine et al. |
| 10,703,785 B2 | 7/2020 | Walensky et al. |
| 10,716,828 B2 | 7/2020 | Danial et al. |
| 10,822,374 B2 | 11/2020 | Walensky et al. |
| 10,844,053 B2 | 11/2020 | Walensky et al. |
| 11,046,739 B2 | 6/2021 | Walensky et al. |
| 11,198,713 B2 | 12/2021 | Hilinski et al. |
| 11,332,496 B2 | 5/2022 | Verdine et al. |
| 11,377,476 B2 | 7/2022 | Verdine et al. |
| 2005/0032800 A1 | 2/2005 | Bigot et al. |
| 2006/0008848 A1 | 1/2006 | Verdine et al. |
| 2006/0281671 A1 | 12/2006 | Peters et al. |
| 2008/0220441 A1 | 9/2008 | Birnbaum et al. |
| 2010/0029552 A1 | 2/2010 | Watt et al. |
| 2010/0152103 A1 | 6/2010 | Phadke et al. |
| 2010/0273704 A1 | 10/2010 | Korsmeyer et al. |
| 2011/0218155 A1 | 9/2011 | Walensky et al. |
| 2012/0172311 A1 | 7/2012 | Nash et al. |
| 2013/0035304 A1 | 2/2013 | Walensky et al. |
| 2014/0005118 A1 | 1/2014 | Verdine et al. |
| 2014/0256912 A1 | 9/2014 | Moellering et al. |
| 2015/0225471 A1 | 8/2015 | Liang et al. |
| 2015/0239937 A1 | 8/2015 | Verdine et al. |
| 2015/0284437 A1 | 10/2015 | Verdine et al. |
| 2016/0024153 A1 | 1/2016 | Verdine et al. |
| 2016/0115215 A1 | 4/2016 | Dimarchi et al. |
| 2016/0122405 A1 | 5/2016 | Palchaudhuri et al. |
| 2016/0152667 A1 | 6/2016 | Walensky et al. |
| 2016/0171150 A1 | 6/2016 | Walensky et al. |
| 2016/0215036 A1 | 7/2016 | Verdine et al. |
| 2016/0244494 A1 | 8/2016 | Verdine et al. |
| 2016/0257725 A1 | 9/2016 | Verdine et al. |
| 2017/0008930 A1 | 1/2017 | Walensky et al. |
| 2017/0240604 A1 | 8/2017 | Verdine et al. |
| 2018/0009847 A1 | 1/2018 | Verdine et al. |
| 2018/0057565 A1 | 3/2018 | Liang et al. |
| 2018/0100001 A1 | 4/2018 | Verdine et al. |
| 2018/0201658 A1 | 7/2018 | Rezaei-Araghi et al. |
| 2018/0265524 A1 | 9/2018 | Walensky et al. |
| 2019/0002506 A1 | 1/2019 | Walensky et al. |
| 2019/0002514 A1 | 1/2019 | Walensky et al. |
| 2019/0092822 A1 | 3/2019 | Walensky et al. |
| 2019/0202862 A1 | 7/2019 | Verdine et al. |
| 2020/0231638 A1 | 7/2020 | Walensky et al. |
| 2020/0239533 A1 | 7/2020 | Verdine et al. |
| 2020/0247858 A1 | 8/2020 | Hilinski et al. |
| 2021/0002336 A1 | 1/2021 | Walensky et al. |
| 2021/0032234 A1 | 2/2021 | Walensky et al. |
| 2021/0179665 A1 | 6/2021 | McGee et al. |
| 2022/0177522 A1 | 6/2022 | Verdine et al. |
| 2022/0306708 A1 | 9/2022 | Verdine et al. |
| 2022/0372075 A1 | 11/2022 | Verdine et al. |
| 2023/0046728 A1 | 2/2023 | Chandhoke et al. |

FOREIGN PATENT DOCUMENTS

| | | |
|---|---|---|
| JP | 2006-523213 A | 10/2006 |
| JP | 2008-501623 A | 1/2008 |
| JP | 2008-510692 A | 4/2008 |
| JP | 2008-524167 A | 7/2008 |
| JP | 2010-510236 A | 4/2010 |
| JP | 2010-522769 A | 7/2010 |
| JP | 2012-532929 A | 12/2012 |
| WO | WO-97/17092 A1 | 5/1997 |
| WO | WO-2001/29247 A1 | 4/2001 |
| WO | WO-03/053996 A2 | 7/2003 |
| WO | WO-2004/084809 A2 | 10/2004 |
| WO | WO-2004/093798 A2 | 11/2004 |
| WO | WO-2005/044839 A2 | 5/2005 |
| WO | WO-2006/018450 A2 | 2/2006 |
| WO | WO-2006/067091 A1 | 6/2006 |
| WO | WO-2008/061192 A2 | 5/2008 |
| WO | WO-2008/095063 A1 | 8/2008 |
| WO | WO-2008/121767 A2 | 10/2008 |
| WO | WO-2008/137633 A2 | 11/2008 |
| WO | WO-2009/020477 A1 | 2/2009 |
| WO | WO-2009/042237 A2 | 4/2009 |
| WO | WO-2009/046407 A2 | 4/2009 |
| WO | WO-2009/108261 A2 | 9/2009 |
| WO | WO-2010/011313 A2 | 1/2010 |
| WO | WO-2010/042225 A2 | 4/2010 |
| WO | WO-2010/068684 A2 | 6/2010 |
| WO | WO-2010/121288 A1 | 10/2010 |
| WO | WO-2010/132869 A2 | 11/2010 |
| WO | WO-2010/148335 A2 | 12/2010 |
| WO | WO-2011/003626 A1 | 1/2011 |
| WO | WO-2011/008260 A2 | 1/2011 |
| WO | WO-2011/094708 A2 | 8/2011 |
| WO | WO-2011/146974 A1 | 12/2011 |
| WO | WO-2012/006598 A2 | 1/2012 |
| WO | WO-2012/040459 A2 | 3/2012 |
| WO | WO-2012/065181 A2 | 5/2012 |
| WO | WO-2012/142604 A2 | 10/2012 |
| WO | WO-2012/174409 A1 | 12/2012 |
| WO | WO-2012/174423 A1 | 12/2012 |
| WO | WO-2013/055949 A2 | 4/2013 |
| WO | WO-2013/102211 A2 | 7/2013 |
| WO | WO-2013/142281 A1 | 9/2013 |
| WO | WO-2014/047673 A1 | 4/2014 |
| WO | WO-2014/052647 A2 | 4/2014 |
| WO | WO-2014/055564 A1 | 4/2014 |
| WO | WO-2014/110420 A1 | 7/2014 |
| WO | WO-2014/144148 A1 | 9/2014 |
| WO | WO-2014/144768 A2 | 9/2014 |
| WO | WO-2014/151369 A2 | 9/2014 |
| WO | WO-2014/159969 A1 | 10/2014 |
| WO | WO-2014/197821 A1 | 12/2014 |
| WO | WO-2014/201370 A1 | 12/2014 |
| WO | WO-2015/051030 A2 | 4/2015 |
| WO | WO-2015/179635 A2 | 11/2015 |
| WO | WO-2016/149613 A2 | 9/2016 |
| WO | WO-2017/004591 A2 | 1/2017 |
| WO | WO-2017/040323 A2 | 3/2017 |
| WO | WO-2017/040329 A2 | 3/2017 |
| WO | WO-2017/062518 A1 | 4/2017 |
| WO | WO-2017/147283 A1 | 8/2017 |
| WO | WO-2019/051327 A2 | 3/2019 |
| WO | WO-2020/041270 A1 | 2/2020 |
| WO | WO-2021/119537 A1 | 6/2021 |
| WO | WO-2021/188659 A1 | 9/2021 |
| WO | WO-2022/020651 A1 | 1/2022 |
| WO | WO-2022/020652 A2 | 1/2022 |
| WO | WO-2022/261257 A1 | 12/2022 |

OTHER PUBLICATIONS

U.S. Appl. No. 16/822,722, filed Mar. 18, 2020, Walensky et al.
U.S. Appl. No. 16/876,779, filed May 18, 2020, Walensky et al.
U.S. Appl. No. 16/950,540, filed Nov. 17, 2020, Verdine et al.
U.S. Appl. No. 17/064,225, filed Oct. 6, 2020, Walensky et al.
U.S. Appl. No. 17/091,541, filed Nov. 6, 2020, Walensky et al.
U.S. Appl. No. 17/349,335, filed Jun. 16, 2021, Walensky et al.
U.S. Appl. No. 17/353,206, filed Jun. 21, 2021, Walensky et al.
Aihara, K. et al., Synthesis of lactam-bridged cyclic peptides using sequential olefin metathesis and diimide reduction reactions, Tetrahedron, 71:4183-4191 (2015).
Anderson, A. The process of structure-based drug design, Chem. Biol., 10: p. 787-797 (2003).
Azzarito, V. et al., Inhibition of α-helix-mediated protein-protein interactions using designed molecules, Nature Chemistry, 5: 161-173 (2013).
Baek, S. et al., Structure of the stapled p53 peptide bound to Mdm2, J. Am. Chem. Soc., 134(1):103-6 (2012).

(56) References Cited

OTHER PUBLICATIONS

Becker et al., Three-dimensional structure of the Stat3beta homodimer bound to DNA, Nature, 394: 145-151 (1998).
Bernal, F. et al., Reactivation of the p53 tumor suppressor pathway by a stapled p53 peptide, J. Am. Chem. Soc., 129(9)2456-7 (2007).
CAS RN: 933687-66-2; STN entry date: Apr. 30, 2007; 3-(methylamino)-1-(2-propen-1-yl)-3-pyrrolidinecarboxylic acid.
CAS RN: 933687-70-8; STN entry date: Apr. 30, 2007; 3-(dimethylamino)-1-(2-propen-1-yl)-3-pyrrolidinecarboxylic acid.
Chatterjee, N. et al., A stapled POL k peptide targets REV1 to inhibit mutagenic translesion synthesis, Environ. Mol. Mutagen., 61(8):830-836 (2020).
Clevers, H. and Nusse, R., Wnt/β-Catenin Signaling and Disease, Cell, 149:1192-1205 (2012).
Diderich, P. et al., Phage Selection of Chemically Stabilized α-Helical Peptide Ligands, ACS Chem. Biol., 11: 1422-1427 (2016).
Dietrich, L. et al., Cell permeable Stapled Peptide Inhibitor of Wnt Signaling that Targets β-Catenin Protein-Protein Interactions, Cell Chem. Bio., 24:958-968 (2017).
Dinh, T.T.T. et al., Antimicrobial activity of doubly-stapled alanine/lysine-based peptides, Bioorganic & Medicinal Chemistry Letters, 25: 4016-4019 (2015).
Fujimoto, et al., Development of a series of cross-linking agents that effectively stabilize alphahelical structures in various short peptides, Chem. Eur. J., 14(3):857-863 (2008).
Fujimoto, K. et al., Development of a Series of Cross-Linking Agents that Effectively Stabilize α-Helical Structures in Various Short Peptides., Chem. Eur. J., 14: 857-863 (2008).
Genin, M.J. et al., An improved method of oxazolidinone hydrolysis in the asymmetric synthesis of α-alkylprolines, Tetrahedron Letters, 35(28): 4967-4968 (1994).
Ghalit, N. et al., Synthesis of Bicyclic Alkene-/Alkane-Bridged Nisin Mimics by Ring-Closing Metathesis and their Biochemical Evaluation as Lipid II Binders: toward the Design of Potential Novel Antibiotics, Chem Bio Chem., 8(13): 1540-1554 (2007).
Goudreau, N. et al., Potent inhibitors of the hepatitis C virus NS3 protease: design and synthesis of macrocyclic substrate-based beta-strand mimics, Journal of Organic Chemistry, 69(19): 6185-6201 (2004).
Graham, T. A. et al., Crystal Structure of a β-Catenin/Tcf Complex, Cell, 103:885-896 (2000).
Grossmann, T. N. et al., Inhibition of oncogenic Wnt signaling through direct targeting of β-catenin, PNAS, 109(44):17942-17947 (2012).
Hilinski, G.J et al., Stitched α-helical peptides via bis ring-closing metathesis, J. Am. Chem. Soc., 136(35):12314-22 (2014).
Holland-Nell et al., Maintaining Biological Activity by Using Triazoles as Disufide Bond Mimetics, Angew. Chem. Int. Ed., 50: 5204-5206 (2011).
International Search Report for PCT/US2018/050101, 5 pages (dated Jan. 28, 2019).
International Search Report for PCT/US2018/050102, 5 pages (dated Mar. 13, 2019).
International Search Report for PCT/US2018/050103, 5 pages (dated Mar. 15, 2019).
Isidro-Llobet et al., Amino Acid-Protecting Groups, Chem Rev. 109(6): 2455-2504 (2009).
Isidro-Llobet et al., Amino Acid-Protecting Groups, Chemical Reviews, 109(6): 2455-2504 (2009).
Kawamoto, S.A. et al., Analysis of the Interaction of BCL9 with β-Catenin and Development of Fluorescence Polarization and Surface Plasmon Resonance Binding Assays for this Interaction, Biochemistry, 48, 9534-9541 (2009).
Khalil, E.M. et al., An efficient and high yield method for the N-tert-butoxycarbonyl protection of sterically hindered amino acids. Tetrahedron Lett., 37(20):3441-44 (1996).
Kim, Y. and Verdine, G.L., Stereochemical effects of all-hydrocarbon tethers in i,i+4 stapled peptides, Bioorg. Med. Chem. Lett., 19(9):2533-6 (2009).
Kim, Y. et al., Introduction of all-hydrocarbon i,i+3 staples into alpha-helices via ring-closing olefin metathesis, Org Lett., 12(13):3046-9 (2010).
Kim, Y. et al., Synthesis of all-hydrocarbon stapled α-helical peptides by ring-closing olefin metathesis, Nat. Protoc., 6(6):761-71 (2011).
Kramps, T. et al., Wnt/Wingless Signaling Requires BCL9/Legless-Mediated Recruitment of Pygopus to the Nuclear β-Catenin-TCF Complex, Cell, 109:47-60 (2002).
Kutchukian, P.S. et al., An All-atom model for stabilization of alpha-helical structure in peptides by hydrocarbon staples, J. Am. Chem. Soc., 131(13):4622-7 (2009).
Liu, F. et al., Application of ring-closing metathesis to Grb2 SH3 domain-binding peptides, Biopolymers, 96(6): 780-788 (2011).
MacDonald, B. T. et al., Wnt/β-Catenin Signaling: Components, Mechanisms, and Diseases, Dev. Cell, 17(1):9-26 (2009).
Mazzier, D. et al., Enhancement of the helical content and stability induced in a linear oligopeptide by an i, i+4 intramolecularly double stapled, overlapping, bicyclic [31, 22, 5]-(E)ene motif, Pep. Sci., 102(1):115-123 (2014).
McGhee, J.H. et al., Exceptionally high-affinity Ras binders that remodel its effector domain, J. Biol. Chem., 293(9):3265-3280 (2018).
Menting et al., How insulin engages its primary binding site on the insulin receptor, Nature. 493(7431):241-5 (2013).
Mitra, S. et al., Stapled peptide inhibitors of RAB25 target context-specific phenotypes in cancer, Nat. Commun., 8(1):660 (2017).
Moellering, R.E. et al., Direct inhibition of the NOTCH transcription factor complex, Nature, 462(7270):182-8 (2009).
Mosimann, C. et al., β-Catenin hits chromatin: regulation of Wnt target gene activation, Nat. Rev. Mol. Cell Biol., 10(4):276-286 (2009).
Narhi, L.A. et al., Role of native disulfide bonds in the structure and activity of insulin-like growth factor 1: genetic models of protein-folding intermediates, Biochemistry, 32(19): 5214- 5221 (1993).
Oh et al., A convergent synthesis of new β-turn mimics by click chemistry, Chem. Commun., 3069-3071(2006).
Robinson, β-Hairpin Peptidomimetics: Design, Structures and Biological Activities, Acct. Chem. Res., 41(10): 1278-1288(2008).
Sampietro, J. et al., Crystal Structure of a β-Catenin/BCL9/Tcf4 Complex, Molecular Cell, 24: 293-300 (2006).
Schafmeister et al., An All-Hydrocarbon Cross-Linking System for Enhancing the Helicity and Metabolic Stability of Peptides, J. Am. Chem. Soc., 122: 5891-5892 (2000).
Shim, S.Y. et al., A new i, i + 3 peptide stapling system for α-helix stabilization, Chem. Biol. Drug. Des., 82(6):635-42 (2013).
Somu, R.V. et al., Synthesis of Pipecolic Acid-Based Spiro Bicyclic Lactam Scaffolds as β-Turn Mimics, J. Org. Chem., 70(15): 5954-5963 (2005).
Stafstrom, J.P. et al., Dormancy-associated gene expression in pea axillary buds, Planta, 205:547-552 (1998).
Stewart, M.L. et al., The MCL-1 BH3 Helix is an Exclusive MCL-1 inhibitor and Apoptosis Sensitizer, Nat Chem Biol., 6(8): 595-601 (2010).
Traboulsi, H. Macrocyclic cell penetrating peptides: a study of structure-penetration properties, Bioconjug Chem., 26(3): 405-411 (2015).
Vartak, A.P. et al., Allosteric Modulation of the Dopamine Receptor by Conformationally Constrained Type VI β-Turn Peptidomimetics of Pro-Leu-Gly-NH2, J. Med. Chem., 50(26):6725-6729 (2007).
Verdine, G. L. and Hilinski, G. J., Stapled peptides for intracellular drug targets, Meth. Enzymol., 503: 3-33 (2012).
Verdine, G.L. and Walensky, L.D., The challenge of drugging undruggable targets in cancer: lessons learned from targeting BCL-2 family members, Clin. Cancer Res., 13(24):7264-70 (2007).
Voronkov, A. and Krauss, S., Wnt/beta-Catenin Signaling and Small Molecule Inhibitors, Curr. Pharm. Des., 19:634-664 (2013).
Walensky, L.D. and Bird, G.H., Hydrocarbon-Stapled Peptides: Principles, Practice, and Progress, J. Med. Chem., 57: 6275?6288 (2014).
Walensky, L.D. et al., A stapled BID BH3 helix directly binds and activates BAX, Mol. Cell., 24(2):199-210 (2006).

(56) References Cited

OTHER PUBLICATIONS

Walensky, L.D. et al., Activation of apoptosis in vivo by a hydrocarbon-stapled BH3 helix, Science, 305(5689):1466-70 (2004).

Woon, E.C.Y et al., Linking of 2-oxoglutarate and substrate binding sites enables potent and highly selective inhibition of JmjC histone demethylases. Angew Chem Int Ed Engl. Feb. 13, 2012;51(7):1631-4. doi: 10.1002/anie.201107833. Epub Jan. 12, 2012.

Written Opinion for PCT/US2018/050101, 11 pages (dated Jan. 28, 2019).

Written Opinion for PCT/US2018/050102, 6 pages (dated Mar. 13, 2019).

Written Opinion for PCT/US2018/050103, 8 pages (dated Mar. 15, 2019).

Xing, Y. et al., Crystal structure of a β-catenin/Axin complex suggests a mechanism for the b-catenin destruction complex, Genes & Development, 17:2753-2764 (2003).

Zhao et al., A Cell-permeable Stat3 SH2 Domain Mimetic Inhibits Stat3; Activation and Induces Antitumor Cell Effects in Vitro, J. Biol. Chem., 285(46): 35855-35865 (2010).

Zou, J. et al., A Concise, metathesis based approach to construction of the lepadiformine/cylindricine tricyclic framework, Tetrahedron, 66(32): 5955-5961 (2010).

U.S. Appl. No. 17/751,451, filed May 23, 2022, Verdine et al.
U.S. Appl. No. 17/912,029, filed Sep. 15, 2022, Verdine et al.
U.S. Appl. No. 18/017,024, filed Jan. 19, 2023, White et al.
U.S. Appl. No. 18/017,033, filed Jan. 19, 2023, Jewett et al.
U.S. Appl. No. 18/345,550, filed Jun. 30, 2023, Verdine et al.

Bernal, F. et al., A Stapled p53 Helix Targets HDMX to Overcome Nutlin-3 Resistance and Reactivate the p53 Tumor Suppressor Pathway in Cancer, Blood, 112(11):2645 (2008).

Bernal, F. et al., A Stapled p53 Helix Overcomes HDMX-Mediated Suppression of p53, Cancer Cell, 18(5):411-422 (2010).

De Paola, I. et al., Cullin3-BTB interface: a novel target for stapled peptides, PLoS One, 10(4):e012114 (2015).

Misawa, T. et al., Structural development of stapled short helical peptides as vitamin D receptor (VDR)-coactivator interaction inhibitors, Bioorg. Med. Chem., 23(5):1055-1061 (2015).

Nevola, L. et al., Light-regulated stapled peptides to inhibit protein-protein interactions involved in clathrin-mediated endocytosis, Angew. Chem. Int. Ed. Engl., 52(30):7704-7708 (2013).

Phillips, C. et al., Design and structure of stapled peptides binding to estrogen receptors, J. Am. Chem. Soc., 133(25):9696-9699 (2011).

Spiegel, J. et al., Direct targeting of Rab-GTPase-effector interactions, Angew. Chem. Int. Ed. Engl., 53(9):2498-2503 (2014).

Takeda, K. et al., Targeted disruption of the BCL9/β-catenin complex inhibits oncogenic Wnt signaling, Sci. Transl. Med., 4(148):148ra117 (2012).

PANEL A

PANEL B

PANEL C

PANEL D

SEQUENCE LISTING

<160> NUMBER OF SEQ ID NOS: 351

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 1

Pro Gln Xaa Ile Leu Asp Xaa His Val Arg Arg Val Trp Arg
1               5                   10

<210> SEQ ID NO 2
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (22)..(22)
<223> OTHER INFORMATION: Norleucine
<220> FEATURE:
<221> NAME/KEY: MOD_RES
<222> LOCATION: (24)..(24)
<223> OTHER INFORMATION: 3-(2-naphthyl)-L-alanine
<220> FEATURE:
<221> NAME/KEY: MOD_RES
<222> LOCATION: (25)..(25)
<223> OTHER INFORMATION: Beta-alanine
<220> FEATURE:
<221> NAME/KEY: MOD_RES
<222> LOCATION: (26)..(26)
<223> OTHER INFORMATION: Beta-alanine
<220> FEATURE:
<221> NAME/KEY: MOD_RES
<222> LOCATION: (27)..(27)
<223> OTHER INFORMATION: Lys-5FAM

<400> SEQUENCE: 2

Leu Ser Gln Glu Gln Leu Glu His Arg Glu Arg Ser Leu Gln Thr Leu
1               5                   10                  15

Arg Asp Ile Gln Arg Leu Leu Ala Ala Ala Lys
            20                  25

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine
<220> FEATURE:
<221> NAME/KEY: MOD_RES
<222> LOCATION: (4)..(4)
<223> OTHER INFORMATION: A non-natural amino acid useful for stapling
<220> FEATURE:
<221> NAME/KEY: MOD_RES

```
<222> LOCATION: (8)..(8)
<223> OTHER INFORMATION: A non-natural amino acid useful for stapling

<400> SEQUENCE: 3

Ala Pro Gln Xaa Ile Leu Asp Xaa His Val Arg Arg Val Trp Arg
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ile Leu Asp Ala His Ile Gln Arg Val Trp
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (8)..(8)
<223> OTHER INFORMATION: A non-natural amino acid useful for stapling
<220> FEATURE:
<223> OTHER INFORMATION: See specification as filed for detailed
      description of substitutions and preferred embodiments

<400> SEQUENCE: 5

Xaa Ile Leu Asp Ala His Ile Xaa Arg Val Trp
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 6

Pro Ala Xaa Ile Leu Asp Ala His Val Xaa Arg Val Trp
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 7

Ala Xaa Ile Leu Asp Ala His Ile Xaa Arg Val Trp
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 8

Ala Xaa Ile Leu Asp Ala His Ile Xaa Arg Val Trp
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 9

Pro Gln Xaa Ile Leu Asp Ala His Val Xaa Arg Val Leu
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 10

Pro Ala Xaa Ile Leu Asp Ala His Val Xaa Arg Val Leu
1               5                   10
```

```
<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 11

Pro Ala Xaa Ile Leu Asp Ala His Val Xaa Arg Val Trp
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 12

Pro Ala Xaa Ile Leu Asp Ala His Val Xaa Arg Val Trp
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 13

Pro Ala Xaa Ile Leu Asp Ala His Val Xaa Arg Trp
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
```

```
<222> LOCATION: (10)..(10)
<223> OTHER INFORMATION: A non-natural amino acid useful for stapling

<400> SEQUENCE: 14

Pro Ala Xaa Ile Ala Asp Ala His Val Xaa Arg Val Trp
1               5                   10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 15

Pro Gln Xaa Ile Leu Asp Ala His Val Xaa Arg Val Leu
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 16

Pro Ala Xaa Ile Leu Asp Ala His Val Xaa Arg Val Trp
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Pro Ala Ser Ile Leu Asp Ala His Val Gln Arg Val Trp
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
```

```
<221> NAME/KEY: MOD_RES
<222> LOCATION: (10)..(10)
<223> OTHER INFORMATION: A non-natural amino acid useful for stapling

<400> SEQUENCE: 18

Pro Ala Xaa Ile Leu Asp Ala His Val Xaa Arg Val Trp
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: Norleucine

<400> SEQUENCE: 19

Pro Glu Ser Ile Leu Asp Glu His Val Gln Arg Val Leu Lys
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 20

Pro Ala Xaa Ile Leu Asp Ala His Val Xaa Arg Val Trp
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 21

Pro Ala Xaa Ile Leu Thr Ala His Ile Xaa Arg Val Trp
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 22

Ala Xaa Ile Leu Asp Ala His Ile Xaa Arg Val Trp
1               5                   10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 23

Ala Xaa Ile Leu Asp Ala His Ile Xaa Arg Val Trp
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 24

Ala Xaa Ile Leu Asp Ala His Ile Xaa Arg Val Trp
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 25

Ala Xaa Ile Leu Asp Ala His Ile Xaa Arg Val Trp
1               5                   10
```

```
<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 26

Ala Xaa Ile Leu Asp Ala His Ile Xaa Arg Val Trp
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-alanine
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 27

Ala Ala Xaa Ile Leu Asp Ala His Ile Xaa Arg Val Trp
1               5                   10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 28

Ala Xaa Ile Leu Asp Ala His Ile Xaa Arg Val Trp
1               5                   10

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 29

Ala Xaa Ile Leu Asp Ala His Ile Xaa Arg Val Trp
1               5                   10

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 30

Ala Xaa Ile Leu Asp Ala His Ile Xaa Arg Val Trp
1               5                   10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 31

Ala Xaa Ile Leu Asp Ala His Ile Xaa Arg Val Trp
1               5                   10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 32

Ala Xaa Ile Leu Asp Ala His Ile Xaa Arg Val Trp
1               5                   10
```

```
<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 33

Ala Xaa Ile Leu Asp Ala His Ile Xaa Arg Val Trp
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 34

Ala Xaa Ile Leu Asn Ala His Ile Xaa Arg Val Trp
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 35

Ala Xaa Ile Leu Thr Ala His Ile Xaa Arg Val Trp
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
```

```
<220> FEATURE:
<221> NAME/KEY: MOD_RES
<222> LOCATION: (8)..(8)
<223> OTHER INFORMATION: A non-natural amino acid useful for stapling

<400> SEQUENCE: 36

Xaa Ile Leu Asp Ala His Ile Xaa Arg Val Trp
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (8)..(8)
<223> OTHER INFORMATION: A non-natural amino acid useful for stapling

<400> SEQUENCE: 37

Xaa Ile Leu Asn Ala His Ile Xaa Arg Val Trp
1               5                   10

<210> SEQ ID NO 38
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (8)..(8)
<223> OTHER INFORMATION: A non-natural amino acid useful for stapling

<400> SEQUENCE: 38

Xaa Ile Leu Thr Ala His Ile Xaa Arg Val Trp
1               5                   10

<210> SEQ ID NO 39
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 39

Pro Ala Xaa Ile Leu Asp Ala His Val Xaa Arg Val Trp
1               5                   10

<210> SEQ ID NO 40
<211> LENGTH: 13
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 40

Pro Ala Xaa Ile Leu Asp Ala His Ile Xaa Arg Val Trp
1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Pentafluorophenylalanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Asymmetric dimethylarginine

<400> SEQUENCE: 41

Ala Xaa Ile Leu Phe Ala His Ile Xaa Arg Val Trp
1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Pentafluorophenylalanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 42

Ala Xaa Ile Leu Phe Ala His Ile Xaa Tyr Val Trp
1               5                   10

<210> SEQ ID NO 43
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Asymmetric dimethylarginine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Asymmetric dimethylarginine

<400> SEQUENCE: 43

Ala Xaa Ile Leu Arg Ala His Ile Xaa Arg Val Trp
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Symmetric dimethylarginine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Asymmetric dimethylarginine

<400> SEQUENCE: 44

Ala Xaa Ile Leu Arg Ala His Ile Xaa Arg Val Trp
1               5                   10

<210> SEQ ID NO 45
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Asymmetric dimethylarginine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
```

```
<223> OTHER INFORMATION: Symmetric dimethylarginine

<400> SEQUENCE: 45

Ala Xaa Ile Leu Arg Ala His Ile Xaa Arg Val Trp
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Pentafluorophenylalanine

<400> SEQUENCE: 46

Ala Xaa Ile Leu Asn Ala His Ile Xaa Phe Val Trp
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Pentafluorophenylalanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 47

Ala Xaa Ile Leu Phe Ala His Ile Xaa Ala Val Trp
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 48

Ala Xaa Ile Leu Tyr Ala His Ile Xaa Tyr Val Trp
```

```
<210> SEQ ID NO 49
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Asymmetric dimethylarginine

<400> SEQUENCE: 49

Ala Xaa Ile Leu Asn Ala His Ile Xaa Arg Val Trp
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Asymmetric dimethylarginine
<220> FEATURE:
<221> NAME/KEY: MOD_RES
<222> LOCATION: (9)..(9)
<223> OTHER INFORMATION: A non-natural amino acid useful for stapling

<400> SEQUENCE: 50

Ala Xaa Ile Leu Arg Ala His Ile Xaa Asn Val Trp
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Asymmetric dimethylarginine
<220> FEATURE:
<221> NAME/KEY: MOD_RES
<222> LOCATION: (9)..(9)
<223> OTHER INFORMATION: A non-natural amino acid useful for stapling

<400> SEQUENCE: 51

Ala Xaa Ile Leu Arg Ala His Ile Xaa Asn Val Trp
1               5                   10
```

```
<210> SEQ ID NO 52
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Symmetric dimethylarginine

<400> SEQUENCE: 52

Ala Xaa Ile Leu Asn Ala His Ile Xaa Arg Val Trp
1               5                   10

<210> SEQ ID NO 53
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Asymmetric dimethylarginine
<220> FEATURE:
<221> NAME/KEY: MOD_RES
<222> LOCATION: (9)..(9)
<223> OTHER INFORMATION: A non-natural amino acid useful for stapling

<400> SEQUENCE: 53

Ala Xaa Ile Leu Arg Ala His Ile Xaa Leu Val Trp
1               5                   10

<210> SEQ ID NO 54
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Symmetric dimethylarginine
<220> FEATURE:
<221> NAME/KEY: MOD_RES
<222> LOCATION: (9)..(9)
<223> OTHER INFORMATION: A non-natural amino acid useful for stapling

<400> SEQUENCE: 54

Ala Xaa Ile Leu Arg Ala His Ile Xaa Leu Val Trp
1               5                   10
```

```
<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Asymmetric dimethylarginine
<220> FEATURE:
<221> NAME/KEY: MOD_RES
<222> LOCATION: (9)..(9)
<223> OTHER INFORMATION: A non-natural amino acid useful for stapling

<400> SEQUENCE: 55

Ala Xaa Ile Leu Arg Ala His Ile Xaa Leu Val Trp
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 56

Ala Xaa Ile Leu Gln Ala His Ile Xaa Arg Val Trp
1               5                   10

<210> SEQ ID NO 57
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 57

Ala Xaa Ile Leu Asn Ala His Ile Xaa Tyr Val Trp
1               5                   10

<210> SEQ ID NO 58
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 58

Ala Xaa Ile Leu Tyr Ala His Ile Xaa Asn Val Trp
1               5                   10

<210> SEQ ID NO 59
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 59

Ala Xaa Ile Leu Tyr Ala His Ile Xaa Asn Val Trp
1               5                   10

<210> SEQ ID NO 60
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 60

Ala Xaa Ile Leu Asn Ala His Ile Xaa Tyr Val Trp
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Symmetric dimethylarginine
<220> FEATURE:
<221> NAME/KEY: MOD_RES
<222> LOCATION: (9)..(9)
<223> OTHER INFORMATION: A non-natural amino acid useful for stapling

<400> SEQUENCE: 61
```

```
Ala Xaa Ile Leu Arg Ala His Ile Xaa Ala Val Trp
1               5                   10
```

```
<210> SEQ ID NO 62
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 62

Ala Xaa Ile Leu Asp Ala His Ile Xaa Arg Val Trp
1               5                   10
```

```
<210> SEQ ID NO 63
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 63

Ala Xaa Ile Leu Asn Ala His Ile Xaa Arg Val Trp
1               5                   10
```

```
<210> SEQ ID NO 64
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-cyclopropylalanine

<400> SEQUENCE: 64

Ala Xaa Ile Leu Asn Ala His Ile Xaa Ala Val Trp
1               5                   10
```

```
<210> SEQ ID NO 65
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 65

Ala Xaa Ile Leu Asp Ala His Ile Xaa Gln Val Trp
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 66

Ala Xaa Ile Leu Asp Ala His Ile Xaa Gln Val Trp
1               5                   10

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 67

Ala Xaa Ile Leu Gln Ala His Ile Xaa Asn Val Trp
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 68
```

```
Ala Xaa Ile Leu Gln Ala His Ile Xaa Asn Val Trp
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 69

Ala Xaa Ile Leu Gln Ala His Ile Xaa Thr Val Trp
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 70

Ala Xaa Ile Leu Gln Ala His Ile Xaa Thr Val Trp
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 71

Ala Xaa Ile Leu Asp Ala His Ile Xaa Asn Val Trp
1               5                   10

<210> SEQ ID NO 72
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 72

Ala Xaa Ile Leu Asn Ala His Ile Xaa Leu Val Trp
1               5                   10

<210> SEQ ID NO 73
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 73

Ala Xaa Ile Leu Thr Ala His Ile Xaa Asn Val Trp
1               5                   10

<210> SEQ ID NO 74
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 74

Pro Ala Xaa Ile Leu Asp Ala His Val Xaa Arg Val Trp
1               5                   10

<210> SEQ ID NO 75
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 75

Pro Ala Xaa Ile Leu Asp Ala His Val Xaa Arg Val Trp
1               5                   10
```

```
<210> SEQ ID NO 76
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 76

Pro Ala Xaa Ile Leu Asp Ala His Val Xaa Arg Val Trp
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 77

Pro Ala Xaa Ile Leu Asp Ala His Val Xaa Arg Val Trp
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 78

Pro Ala Xaa Ile Leu Asp Ala His Val Xaa Arg Val Trp
1               5                   10

<210> SEQ ID NO 79
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
```

```
<221> NAME/KEY: MOD_RES
<222> LOCATION: (10)..(10)
<223> OTHER INFORMATION: A non-natural amino acid useful for stapling

<400> SEQUENCE: 79

Pro Ala Xaa Ile Leu Asp Ala His Val Xaa Arg Val Trp
1               5                   10

<210> SEQ ID NO 80
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 80

Pro Ala Xaa Ile Leu Asp Ala His Val Xaa Arg Val Trp
1               5                   10

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 81

Pro Ala Xaa Ile Ala Asp Ala His Val Xaa Arg Val Trp
1               5                   10

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 82

Ala Xaa Ile Leu Asp Ala His Ile Xaa Arg Val Trp
1               5                   10

<210> SEQ ID NO 83
<211> LENGTH: 12
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 83

Ala Xaa Ile Leu Asp Ala His Ile Xaa Arg Val Trp
1               5                   10

<210> SEQ ID NO 84
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 84

Ala Xaa Ile Leu Asp Ala His Ile Xaa Arg Val Trp
1               5                   10

<210> SEQ ID NO 85
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 4-fluorophenylalanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 85

Ala Xaa Ile Leu Phe Ala His Ile Xaa Tyr Val Trp
1               5                   10

<210> SEQ ID NO 86
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
```

<221> NAME/KEY: MOD_RES
<222> LOCATION: (9)..(9)
<223> OTHER INFORMATION: A non-natural amino acid useful for stapling

<400> SEQUENCE: 86

Ala Xaa Ile Leu Asp Ala His Ile Xaa Arg Val Trp
1               5                   10

<210> SEQ ID NO 87
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 4-fluorophenylalanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 87

Ala Xaa Ile Leu Phe Ala His Ile Xaa Arg Val Trp
1               5                   10

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 4-fluorophenylalanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 88

Ala Xaa Ile Leu Phe Ala His Ile Xaa Tyr Val Trp
1               5                   10

<210> SEQ ID NO 89
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 4-fluorophenylalanine
<220> FEATURE:
<221> NAME/KEY: MOD_RES

```
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-fluorophenylalanine

<400> SEQUENCE: 89

Ala Xaa Ile Leu Phe Ala His Ile Xaa Phe Val Trp
1               5                   10

<210> SEQ ID NO 90
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: O-methyl tyrosine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-fluorophenylalanine

<400> SEQUENCE: 90

Ala Xaa Ile Leu Tyr Ala His Ile Xaa Phe Val Trp
1               5                   10

<210> SEQ ID NO 91
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 91

Ala Xaa Ile Leu Phe Ala His Ile Xaa Arg Val Trp
1               5                   10

<210> SEQ ID NO 92
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
```

```
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-fluorophenylalanine

<400> SEQUENCE: 92

Ala Xaa Ile Leu Phe Ala His Ile Xaa Phe Val Trp
1               5                   10

<210> SEQ ID NO 93
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 3-(1-naphthyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 93

Ala Xaa Ile Leu Ala Ala His Ile Xaa Arg Val Trp
1               5                   10

<210> SEQ ID NO 94
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 3-(1-naphthyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 94

Ala Xaa Ile Leu Ala Ala His Ile Xaa Tyr Val Trp
1               5                   10

<210> SEQ ID NO 95
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 3-(1-naphthyl)-L-alanine
```

```
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-fluorophenylalanine

<400> SEQUENCE: 95

Ala Xaa Ile Leu Ala Ala His Ile Xaa Phe Val Trp
1               5                   10

<210> SEQ ID NO 96
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 96

Ala Xaa Ile Leu Val Ala His Ile Xaa Tyr Val Trp
1               5                   10

<210> SEQ ID NO 97
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-(1-naphthyl)-L-alanine

<400> SEQUENCE: 97

Ala Xaa Ile Leu Asp Ala His Ile Xaa Ala Val Trp
1               5                   10

<210> SEQ ID NO 98
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
```

```
<221> NAME/KEY: MOD_RES
<222> LOCATION: (10)..(10)
<223> OTHER INFORMATION: 3-(1-naphthyl)-L-alanine

<400> SEQUENCE: 98

Ala Xaa Ile Leu Asp Ala His Ile Xaa Ala Val Trp
1               5                   10

<210> SEQ ID NO 99
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-(1-naphthyl)-L-alanine

<400> SEQUENCE: 99

Ala Xaa Ile Leu Asp Ala His Ile Xaa Ala Val Trp
1               5                   10

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 100

Ala Xaa Ile Leu Asp Ala His Ile Xaa Val Val Trp
1               5                   10

<210> SEQ ID NO 101
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 4-fluorophenylalanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 101
```

Ala Xaa Ile Leu Phe Ala His Ile Xaa Val Val Trp
1               5                   10

<210> SEQ ID NO 102
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 102

Ala Xaa Ile Leu Asp Ala His Ile Xaa Phe Val Trp
1               5                   10

<210> SEQ ID NO 103
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: 3-cyclohexyl-L-alanine

<400> SEQUENCE: 103

Ala Xaa Ile Leu Asp Ala His Ile Xaa Arg Ala Trp
1               5                   10

<210> SEQ ID NO 104
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (8)..(8)
<223> OTHER INFORMATION: 3-cyclohexyl-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 104

Ala Xaa Ile Leu Asp Ala His Ala Xaa Arg Val Trp
1               5                   10

```
<210> SEQ ID NO 105
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 3-(2-naphthyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-fluorophenylalanine

<400> SEQUENCE: 105

Ala Xaa Ile Leu Ala Ala His Ile Xaa Phe Val Trp
1               5                   10

<210> SEQ ID NO 106
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: 3-cyclohexyl-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 106

Ala Xaa Ile Leu Ala Ala His Ile Xaa Arg Val Trp
1               5                   10

<210> SEQ ID NO 107
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 107

Ala Xaa Ala Leu Asp Ala His Ile Xaa Arg Val Trp
1               5                   10

<210> SEQ ID NO 108
```

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 108

Ala Xaa Ile Ala Asp Ala His Ile Xaa Arg Val Trp
1               5                   10

<210> SEQ ID NO 109
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 109

Ala Xaa Ile Leu Ala Ala His Ile Xaa Arg Val Trp
1               5                   10

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 110

Ala Xaa Ile Leu Asp Ala Ala Ile Xaa Arg Val Trp
1               5                   10

<210> SEQ ID NO 111
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
```

```
<223> OTHER INFORMATION: A non-natural amino acid useful for stapling

<400> SEQUENCE: 111

Ala Xaa Ile Leu Asp Ala His Ala Xaa Arg Val Trp
1               5                   10

<210> SEQ ID NO 112
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 112

Ala Xaa Ile Leu Asp Ala His Ala Xaa Arg Val Trp
1               5                   10

<210> SEQ ID NO 113
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 113

Ala Xaa Ile Leu Asp Ala His Ala Xaa Arg Val Trp
1               5                   10

<210> SEQ ID NO 114
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 114

Ala Xaa Ile Leu Asp Ala His Ala Xaa Arg Val Trp
1               5                   10

<210> SEQ ID NO 115
<211> LENGTH: 12
<212> TYPE: PRT
<213> ORGANISM: Artificial Sequence
<220> FEATURE:
```

-continued

```
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 115

Ala Xaa Ile Leu Asp Ala His Ala Xaa Arg Val Trp
1               5                   10

<210> SEQ ID NO 116
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 116

Ala Xaa Ile Leu Asp Ala His Ile Xaa Ala Val Trp
1               5                   10

<210> SEQ ID NO 117
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 117

Ala Xaa Ile Leu Asp Ala His Ile Xaa Arg Ala Trp
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 118
```

Ala Xaa Ile Leu Asp Ala His Ile Xaa Arg Val Ala
1               5                   10

<210> SEQ ID NO 119
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 119

Ala Xaa Ile Leu Asp Ala His Ile Xaa Arg Val Trp
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 120

Ala Xaa Ile Leu Asp Ala His Ile Xaa Arg Val Trp
1               5                   10

<210> SEQ ID NO 121
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 121

Ala Xaa Ile Leu Asp Ala His Ile Xaa Arg Val Trp
1               5                   10

<210> SEQ ID NO 122
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES

```
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 122

Ala Xaa Ile Leu Asp Ala His Ile Xaa Arg Val Trp
1               5                   10

<210> SEQ ID NO 123
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 123

Ala Xaa Ile Leu Asp Ala His Ile Xaa Arg Val Trp
1               5                   10

<210> SEQ ID NO 124
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 124

Ala Xaa Ile Leu Asp Ala His Ile Xaa Arg Val Trp
1               5                   10

<210> SEQ ID NO 125
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 125

Ala Xaa Ile Leu Asp Ala His Ile Xaa Arg Val Trp
1               5                   10
```

```
<210> SEQ ID NO 126
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 126

Ala Xaa Ile Leu Asp Ala His Ile Xaa Arg Val Trp
1               5                   10

<210> SEQ ID NO 127
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 127

Ala Xaa Ile Leu Asp Ala His Ile Xaa Arg Val Trp
1               5                   10

<210> SEQ ID NO 128
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 128

Ala Xaa Ile Leu Asp Ala His Ile Xaa Arg Val Trp
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
```

```
<222> LOCATION: (9)..(9)
<223> OTHER INFORMATION: A non-natural amino acid useful for stapling

<400> SEQUENCE: 129

Ala Xaa Ile Leu Asp Ala His Ile Xaa Arg Val Trp
1               5                   10

<210> SEQ ID NO 130
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 130

Ala Xaa Ile Leu Asp Ala His Ile Xaa Arg Val Trp
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 131

Ala Xaa Ile Leu Asp Ala His Ile Xaa Arg Val Trp
1               5                   10

<210> SEQ ID NO 132
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 132

Ala Xaa Ile Leu Asp Ala His Ile Xaa Arg Val Trp
1               5                   10

<210> SEQ ID NO 133
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 133

Ala Xaa Ile Leu Asp Ala His Ile Xaa Arg Val Trp
1               5                   10

<210> SEQ ID NO 134
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 134

Ala Xaa Ile Leu Asp Ala His Ile Xaa Arg Val Trp
1               5                   10

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 135

Ala Xaa Ile Leu Asp Ala His Ile Xaa Arg Val Trp
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 136
```

```
Ala Xaa Ile Leu Asp Ala His Ile Xaa Arg Val Trp
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 137

Ala Xaa Ile Leu Asp Ala His Ile Xaa Arg Val Trp
1               5                   10

<210> SEQ ID NO 138
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 138

Ala Xaa Ile Leu Asp Ala His Ile Xaa Arg Val Trp
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 139

Ala Xaa Ile Leu Asp Ala His Ile Xaa Arg Val Trp
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 140

Ala Xaa Ile Leu Asp Ala His Ile Xaa Arg Val Trp
1               5                   10

<210> SEQ ID NO 141
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 141

Ala Xaa Ile Leu Asp Ala His Ile Xaa Arg Val Trp
1               5                   10

<210> SEQ ID NO 142
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 142

Ala Xaa Ile Leu Asp Ala His Ile Xaa Arg Val Trp
1               5                   10

<210> SEQ ID NO 143
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: Beta-2-thienylalanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 143
```

```
Ala Xaa Ile Leu Asp Ala Ala Ile Xaa Arg Val Trp
1               5                   10
```

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(3-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 144

```
Ala Xaa Ile Leu Asp Ala Ala Ile Xaa Arg Val Trp
1               5                   10
```

<210> SEQ ID NO 145
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(4-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 145

```
Ala Xaa Ile Leu Asp Ala Ala Ile Xaa Arg Val Trp
1               5                   10
```

<210> SEQ ID NO 146
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 146

Ala Xaa Ile Leu Asp Ala Ala Ile Xaa Arg Val Trp
1               5                   10

<210> SEQ ID NO 147
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 147

Ala Xaa Ile Leu Asp Ala Ala Ile Xaa Arg Val Trp
1               5                   10

<210> SEQ ID NO 148
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 148

Ala Xaa Ile Leu Asp Ala Ala Ile Xaa Arg Val Trp
1               5                   10

<210> SEQ ID NO 149
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 149

Ala Xaa Ile Leu Asp Ala Phe Ile Xaa Arg Val Trp
1               5                   10

<210> SEQ ID NO 150

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 2-furyl-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 150

Ala Xaa Ile Leu Asp Ala Ala Ile Xaa Arg Val Trp
1               5                   10

<210> SEQ ID NO 151
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 151

Ala Xaa Ile Leu Asp Ala His Ile Xaa Ser Val Trp
1               5                   10

<210> SEQ ID NO 152
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 152

Ala Xaa Ile Leu Asp Ala Ala Ile Xaa Ala Val Trp
1               5                   10

<210> SEQ ID NO 153
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
    peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 153

Ala Xaa Ile Leu Asp Ala Ala Ile Xaa Ala Val Trp
1               5                   10

<210> SEQ ID NO 154
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 154

Ala Xaa Ile Leu Asp Ala Ala Ile Xaa Phe Val Trp
1               5                   10

<210> SEQ ID NO 155
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 155

Ala Xaa Ile Leu Asp Ala Ala Ile Xaa Phe Val Trp
1               5                   10

<210> SEQ ID NO 156
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 156

Ala Xaa Ile Leu Asp Ala Ala Ile Xaa Ile Val Trp
1               5                   10

<210> SEQ ID NO 157
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 157

Ala Xaa Ile Leu Asp Ala Ala Ile Xaa Ile Val Trp
1               5                   10

<210> SEQ ID NO 158
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 158

Ala Xaa Ile Leu Asp Ala Ala Ile Xaa Leu Val Trp
1               5                   10

<210> SEQ ID NO 159
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 159

Ala Xaa Ile Leu Asp Ala Ala Ile Xaa Leu Val Trp
1               5                   10

<210> SEQ ID NO 160
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 160

Ala Xaa Ile Leu Asp Ala Ala Ile Xaa Asn Val Trp
1               5                   10

<210> SEQ ID NO 161
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 161

Ala Xaa Ile Leu Asp Ala Ala Ile Xaa Asn Val Trp
1               5                   10

<210> SEQ ID NO 162
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 162

Ala Xaa Ile Leu Asp Ala Ala Ile Xaa Gln Val Trp
1               5                   10

<210> SEQ ID NO 163
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 163

Ala Xaa Ile Leu Asp Ala Ala Ile Xaa Gln Val Trp
1               5                   10

<210> SEQ ID NO 164
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 164

Ala Xaa Ile Leu Asp Ala Ala Ile Xaa Ser Val Trp
1               5                   10

<210> SEQ ID NO 165
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

-continued

```
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 165

Ala Xaa Ile Leu Asp Ala Ala Ile Xaa Ser Val Trp
1               5                   10

<210> SEQ ID NO 166
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 166

Ala Xaa Ile Leu Asp Ala Ala Ile Xaa Thr Val Trp
1               5                   10

<210> SEQ ID NO 167
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 167

Ala Xaa Ile Leu Asp Ala Ala Ile Xaa Thr Val Trp
1               5                   10

<210> SEQ ID NO 168
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
```

```
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 168

Ala Xaa Ile Leu Asp Ala Ala Ile Xaa Val Val Trp
1               5                   10

<210> SEQ ID NO 169
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 169

Ala Xaa Ile Leu Asp Ala Ala Ile Xaa Val Val Trp
1               5                   10

<210> SEQ ID NO 170
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 170

Ala Xaa Ile Leu Asp Ala Ala Ile Xaa Trp Val Trp
1               5                   10

<210> SEQ ID NO 171
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
```

```
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 171

Ala Xaa Ile Leu Asp Ala Ala Ile Xaa Trp Val Trp
1               5                   10

<210> SEQ ID NO 172
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 172

Ala Xaa Ile Leu Asp Ala Ala Ile Xaa Tyr Val Trp
1               5                   10

<210> SEQ ID NO 173
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling

<400> SEQUENCE: 173

Ala Xaa Ile Leu Asp Ala Ala Ile Xaa Tyr Val Trp
1               5                   10

<210> SEQ ID NO 174
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
```

```
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-cyclobutylalanine

<400> SEQUENCE: 174

Ala Xaa Ile Leu Asp Ala Ala Ile Xaa Ala Val Trp
1               5                   10

<210> SEQ ID NO 175
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-cyclobutylalanine

<400> SEQUENCE: 175

Ala Xaa Ile Leu Asp Ala Ala Ile Xaa Ala Val Trp
1               5                   10

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-cyclohexyl-L-alanine

<400> SEQUENCE: 176

Ala Xaa Ile Leu Asp Ala Ala Ile Xaa Ala Val Trp
1               5                   10

<210> SEQ ID NO 177
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Norvaline

<400> SEQUENCE: 177

Ala Xaa Ile Leu Asp Ala Ala Ile Xaa Val Val Trp
1               5                   10

<210> SEQ ID NO 178
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Norvaline

<400> SEQUENCE: 178

Ala Xaa Ile Leu Asp Ala Ala Ile Xaa Val Val Trp
1               5                   10

<210> SEQ ID NO 179
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
```

```
<222> LOCATION: (10)..(10)
<223> OTHER INFORMATION: Tert-leucine

<400> SEQUENCE: 179

Ala Xaa Ile Leu Asp Ala Ala Ile Xaa Leu Val Trp
1               5                   10

<210> SEQ ID NO 180
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Tert-leucine

<400> SEQUENCE: 180

Ala Xaa Ile Leu Asp Ala Ala Ile Xaa Leu Val Trp
1               5                   10

<210> SEQ ID NO 181
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 2-furyl-L-alanine

<400> SEQUENCE: 181

Ala Xaa Ile Leu Asp Ala Ala Ile Xaa Ala Val Trp
1               5                   10

<210> SEQ ID NO 182
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
```

```
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 2-furyl-L-alanine

<400> SEQUENCE: 182

Ala Xaa Ile Leu Asp Ala Ala Ile Xaa Ala Val Trp
1               5                   10

<210> SEQ ID NO 183
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Aminoisobutyric acid

<400> SEQUENCE: 183

Ala Xaa Ile Leu Asp Ala Ala Ile Xaa Xaa Val Trp
1               5                   10

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Aminoisobutyric acid

<400> SEQUENCE: 184

Ala Xaa Ile Leu Asp Ala Ala Ile Xaa Xaa Val Trp
1               5                   10
```

```
<210> SEQ ID NO 185
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Beta-2-thienylalanine

<400> SEQUENCE: 185

Ala Xaa Ile Leu Asp Ala Ala Ile Xaa Ala Val Trp
1               5                   10

<210> SEQ ID NO 186
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Beta-2-thienylalanine

<400> SEQUENCE: 186

Ala Xaa Ile Leu Asp Ala Ala Ile Xaa Ala Val Trp
1               5                   10

<210> SEQ ID NO 187
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
```

```
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-(2-pyridyl)-L-alanine

<400> SEQUENCE: 187

Ala Xaa Ile Leu Asp Ala Ala Ile Xaa Ala Val Trp
1               5                   10

<210> SEQ ID NO 188
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-(3-pyridyl)-L-alanine

<400> SEQUENCE: 188

Ala Xaa Ile Leu Asp Ala Ala Ile Xaa Ala Val Trp
1               5                   10

<210> SEQ ID NO 189
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-(3-pyridyl)-L-alanine

<400> SEQUENCE: 189

Ala Xaa Ile Leu Asp Ala Ala Ile Xaa Ala Val Trp
1               5                   10

<210> SEQ ID NO 190
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-cyclopropylalanine

<400> SEQUENCE: 190

Ala Xaa Ile Leu Asp Ala Ala Ile Xaa Ala Val Trp
1               5                   10

<210> SEQ ID NO 191
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-cyclopropylalanine

<400> SEQUENCE: 191

Ala Xaa Ile Leu Asp Ala Ala Ile Xaa Ala Val Trp
1               5                   10

<210> SEQ ID NO 192
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: O-methyl tyrosine

<400> SEQUENCE: 192
```

-continued

```
Ala Xaa Ile Leu Asp Ala Ala Ile Xaa Tyr Val Trp
1               5                   10
```

<210> SEQ ID NO 193
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: O-methyl tyrosine

<400> SEQUENCE: 193

```
Ala Xaa Ile Leu Asp Ala Ala Ile Xaa Tyr Val Trp
1               5                   10
```

<210> SEQ ID NO 194
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-fluorophenylalanine

<400> SEQUENCE: 194

```
Ala Xaa Ile Leu Asp Ala Ala Ile Xaa Phe Val Trp
1               5                   10
```

<210> SEQ ID NO 195
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine

```
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-fluorophenylalanine

<400> SEQUENCE: 195

Ala Xaa Ile Leu Asp Ala Ala Ile Xaa Phe Val Trp
1               5                   10

<210> SEQ ID NO 196
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 3-(1-naphthyl)-L-alanine

<400> SEQUENCE: 196

Ala Xaa Ile Leu Asp Ala Ala Ile Xaa Ala Val Trp
1               5                   10

<210> SEQ ID NO 197
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-methyl-L-phenylalanine

<400> SEQUENCE: 197

Ala Xaa Ile Leu Asp Ala Ala Ile Xaa Phe Val Trp
1               5                   10

<210> SEQ ID NO 198
<211> LENGTH: 12
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: 3-(2-pyridyl)-L-alanine
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: 4-methyl-L-phenylalanine

<400> SEQUENCE: 198

Ala Xaa Ile Leu Asp Ala Ala Ile Xaa Phe Val Trp
1               5                   10

<210> SEQ ID NO 199
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 199

Ala Xaa Ile Leu Asp Ala His Ile Xaa Arg Val Trp
1               5                   10

<210> SEQ ID NO 200
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 200

Ala Xaa Ile Leu Asp Ala His Ile Xaa Arg Val Trp
1               5                   10

<210> SEQ ID NO 201
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 201

Ala Xaa Ile Leu Asp Ala His Ile Xaa Arg Val Trp
1               5                   10

<210> SEQ ID NO 202
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 202

Ala Xaa Ile Leu Asp Ala His Ile Xaa Arg Val Trp
1               5                   10

<210> SEQ ID NO 203
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 203

Ala Xaa Ile Leu Asp Ala His Ile Xaa Arg Val Trp
1               5                   10

<210> SEQ ID NO 204
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 204

Ala Xaa Ile Leu Asp Ala His Ile Xaa Arg Val Trp
1               5                   10
```

```
<210> SEQ ID NO 205
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 205

Ala Xaa Ile Leu Asp Ala His Ile Xaa Arg Val Trp
1               5                   10

<210> SEQ ID NO 206
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 206

Ala Xaa Ile Leu Asp Ala His Ile Xaa Arg Val Trp
1               5                   10

<210> SEQ ID NO 207
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 207

Ala Xaa Ile Leu Asp Ala His Ile Xaa Arg Val Trp
1               5                   10

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
```

<222> LOCATION: (9)..(9)
<223> OTHER INFORMATION: A non-natural amino acid useful for stapling

<400> SEQUENCE: 208

Ala Xaa Ile Leu Asp Ala His Ile Xaa Arg Val Trp
1               5                   10

<210> SEQ ID NO 209
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 209

Ala Xaa Ile Leu Asp Ala His Ile Xaa Arg Val Trp
1               5                   10

<210> SEQ ID NO 210
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 210

Ala Xaa Ile Leu Asp Ala His Ile Xaa Arg Val Trp
1               5                   10

<210> SEQ ID NO 211
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 211

Ala Xaa Ile Leu Asp Ala His Ile Xaa Arg Val Trp
1               5                   10

<210> SEQ ID NO 212
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 212

Ala Xaa Ile Leu Asp Ala His Ile Xaa Arg Val Trp
1               5                   10

<210> SEQ ID NO 213
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 213

Ala Xaa Ile Leu Asp Ala His Ile Xaa Arg Val Trp
1               5                   10

<210> SEQ ID NO 214
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 214

Ala Xaa Ile Leu Asp Ala His Ile Xaa Arg Val Trp
1               5                   10

<210> SEQ ID NO 215
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Aminoisobutyric acid
<220> FEATURE:
<221> NAME/KEY: MOD_RES
<222> LOCATION: (9)..(9)
<223> OTHER INFORMATION: Aminoisobutyric acid

<400> SEQUENCE: 215
```

```
Ala Xaa Ile Leu Asp Ala His Ile Xaa Arg Val Trp
1               5                   10
```

<210> SEQ ID NO 216
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: Methionine sulfone
<220> FEATURE:
<221> NAME/KEY: MOD_RES
<222> LOCATION: (9)..(9)
<223> OTHER INFORMATION: A non-natural amino acid useful for stapling

<400> SEQUENCE: 216

```
Ala Xaa Ile Leu Met Ala His Ile Xaa Arg Val Trp
1               5                   10
```

<210> SEQ ID NO 217
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (12)..(12)
<223> OTHER INFORMATION: D-tryptophan

<400> SEQUENCE: 217

```
Ala Xaa Ile Leu Asp Ala His Ile Xaa Arg Val Trp
1               5                   10
```

<210> SEQ ID NO 218
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (12)..(12)
<223> OTHER INFORMATION: Alpha-methyl-L-tryptophan

<400> SEQUENCE: 218

Ala Xaa Ile Leu Asp Ala His Ile Xaa Arg Val Trp
1               5                   10

<210> SEQ ID NO 219
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: Alpha-methyl-L-valine

<400> SEQUENCE: 219

Ala Xaa Ile Leu Asp Ala His Ile Xaa Arg Val Trp
1               5                   10

<210> SEQ ID NO 220
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: Alpha-methyl-L-leucine

<400> SEQUENCE: 220

Ala Xaa Ile Leu Asp Ala His Ile Xaa Arg Leu Trp
1               5                   10

<210> SEQ ID NO 221
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Homoarginine

<400> SEQUENCE: 221

Ala Xaa Ile Leu Asp Ala His Ile Xaa Arg Val Trp

```
1               5                   10

<210> SEQ ID NO 222
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 222

Ala Xaa Ile Leu Asp Ala His Ile Xaa Lys Val Trp
1               5                   10

<210> SEQ ID NO 223
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: N-epsilon-methyl-L-lysine

<400> SEQUENCE: 223

Ala Xaa Ile Leu Asp Ala His Ile Xaa Lys Val Trp
1               5                   10

<210> SEQ ID NO 224
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Asymmetric dimethylarginine

<400> SEQUENCE: 224

Ala Xaa Ile Leu Asp Ala His Ile Xaa Arg Val Trp
1               5                   10

<210> SEQ ID NO 225
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: Symmetric dimethylarginine

<400> SEQUENCE: 225

Ala Xaa Ile Leu Asp Ala His Ile Xaa Arg Val Trp
1               5                   10

<210> SEQ ID NO 226
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (4)..(4)
<223> OTHER INFORMATION: Alpha-methyl-L-leucine
<220> FEATURE:
<221> NAME/KEY: MOD_RES
<222> LOCATION: (9)..(9)
<223> OTHER INFORMATION: A non-natural amino acid useful for stapling

<400> SEQUENCE: 226

Ala Xaa Ile Leu Asp Ala His Ile Xaa Arg Val Trp
1               5                   10

<210> SEQ ID NO 227
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (6)..(6)
<223> OTHER INFORMATION: Aminoisobutyric acid
<220> FEATURE:
<221> NAME/KEY: MOD_RES
<222> LOCATION: (9)..(9)
<223> OTHER INFORMATION: A non-natural amino acid useful for stapling

<400> SEQUENCE: 227

Ala Xaa Ile Leu Asp Xaa His Ile Xaa Arg Val Trp
1               5                   10

<210> SEQ ID NO 228
<211> LENGTH: 14
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 228

Pro Gln Xaa Ile Leu Asp Xaa His Val Arg Arg Val Trp Arg
1               5                   10

<210> SEQ ID NO 229
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 229

Pro Gln Xaa Ile Leu Asp Xaa His Val Arg Arg Val Trp Arg
1               5                   10

<210> SEQ ID NO 230
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 230

Pro Gln Xaa Ile Leu Asp Xaa His Val Arg Arg Val Trp Arg
1               5                   10

<210> SEQ ID NO 231
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling
```

<400> SEQUENCE: 231

Pro Gln Xaa Ile Leu Asp Xaa His Val Arg Arg Val Trp Arg
1               5                   10

<210> SEQ ID NO 232
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 232

Pro Gln Xaa Ile Leu Asp Xaa His Val Arg Arg Val Trp Arg
1               5                   10

<210> SEQ ID NO 233
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 233

Pro Gln Xaa Ile Leu Asp Xaa His Val Arg Arg Val Trp Arg
1               5                   10

<210> SEQ ID NO 234
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 234

Pro Gln Xaa Ile Leu Asp Xaa His Val Arg Arg Val Trp Arg
1               5                   10

<210> SEQ ID NO 235
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 235

Pro Gln Xaa Ile Leu Asp Xaa His Val Arg Arg Val Trp Arg
1               5                   10

<210> SEQ ID NO 236
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 236

Pro Gln Xaa Ile Leu Asp Xaa His Val Arg Arg Val Trp Arg
1               5                   10

<210> SEQ ID NO 237
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 237

Pro Gln Xaa Ile Leu Asp Xaa His Val Arg Arg Val Trp Arg
1               5                   10

<210> SEQ ID NO 238
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 238

Pro Gln Xaa Ile Leu Asp Xaa His Val Arg Arg Val Trp Arg
1               5                   10
```

```
<210> SEQ ID NO 239
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 239

Pro Gln Xaa Ile Leu Asp Xaa His Val Arg Arg Val Trp Arg
1               5                   10

<210> SEQ ID NO 240
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 240

Pro Gln Xaa Ile Leu Asp Xaa His Val Arg Arg Val Trp Arg
1               5                   10

<210> SEQ ID NO 241
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 241

Pro Gln Xaa Ile Leu Asp Xaa His Val Arg Arg Val Trp Arg
1               5                   10

<210> SEQ ID NO 242
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
```

```
<220> FEATURE:
<221> NAME/KEY: MOD_RES
<222> LOCATION: (7)..(7)
<223> OTHER INFORMATION: A non-natural amino acid useful for stapling

<400> SEQUENCE: 242

Pro Gln Xaa Ile Leu Asp Xaa His Val Arg Arg Val Trp Arg
1               5                   10

<210> SEQ ID NO 243
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 243

Pro Gln Xaa Ile Leu Asp Xaa His Val Arg Arg Val Trp Arg
1               5                   10

<210> SEQ ID NO 244
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 244

Pro Gln Xaa Ile Leu Asp Xaa His Val Arg Arg Val Trp Arg
1               5                   10

<210> SEQ ID NO 245
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 245

Pro Gln Xaa Ile Leu Asp Xaa His Val Arg Arg Val Trp Arg
1               5                   10

<210> SEQ ID NO 246
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 246

Pro Gln Xaa Ile Leu Asp Xaa His Val Arg Arg Val Trp Arg
1               5                   10

<210> SEQ ID NO 247
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 247

Pro Gln Xaa Ile Leu Asp Xaa His Val Arg Arg Val Trp Arg
1               5                   10

<210> SEQ ID NO 248
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 248

Pro Gln Xaa Ile Leu Asp Xaa His Val Arg Arg Val Trp Arg
1               5                   10

<210> SEQ ID NO 249
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling
```

<400> SEQUENCE: 249

Pro Gln Xaa Ile Leu Asp Xaa His Val Arg Arg Val Trp Arg
1               5                   10

<210> SEQ ID NO 250
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 250

Pro Gln Xaa Ile Leu Asp Xaa His Val Arg Arg Val Trp Arg
1               5                   10

<210> SEQ ID NO 251
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 251

Pro Gln Xaa Ile Leu Asp Xaa His Val Arg Arg Val Trp Arg
1               5                   10

<210> SEQ ID NO 252
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 252

Pro Gln Xaa Ile Leu Asp Xaa His Val Arg Arg Val Trp Arg
1               5                   10

<210> SEQ ID NO 253
<211> LENGTH: 14
<212> TYPE: PRT
<213> ORGANISM: Artificial Sequence
<220> FEATURE:
<223> OTHER INFORMATION: Description of Artificial Sequence: Synthetic

```
                    peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 253

Pro Gln Xaa Ile Leu Asp Xaa His Val Arg Arg Val Trp Arg
1               5                   10

<210> SEQ ID NO 254
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 254

Pro Gln Xaa Ile Leu Asp Xaa His Val Arg Arg Val Trp Arg
1               5                   10

<210> SEQ ID NO 255
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 255

Pro Gln Xaa Ile Leu Asp Xaa His Val Arg Arg Val Trp Arg
1               5                   10

<210> SEQ ID NO 256
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 256

Pro Gln Xaa Ile Leu Asp Xaa His Val Arg Arg Val Trp Arg
```

```
1               5                   10
```

<210> SEQ ID NO 257
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 257

```
Pro Gln Xaa Ile Leu Asp Xaa His Val Arg Arg Val Trp Arg
1               5                   10
```

<210> SEQ ID NO 258
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 258

```
Pro Gln Xaa Ile Leu Asp Xaa His Val Arg Arg Val Trp Arg
1               5                   10
```

<210> SEQ ID NO 259
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 259

```
Pro Gln Xaa Ile Leu Asp Xaa His Val Arg Arg Val Trp Arg
1               5                   10
```

<210> SEQ ID NO 260
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)

<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 260

Pro Gln Xaa Ile Leu Asp Xaa His Val Arg Arg Val Trp Arg
1               5                   10

<210> SEQ ID NO 261
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 261

Pro Gln Xaa Ile Leu Asp Xaa His Val Arg Arg Val Trp Arg
1               5                   10

<210> SEQ ID NO 262
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 262

Pro Gln Xaa Ile Leu Asp Xaa His Val Arg Arg Val Trp Arg
1               5                   10

<210> SEQ ID NO 263
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 263

Pro Gln Xaa Ile Leu Asp Xaa His Val Arg Arg Val Trp Arg
1               5                   10

<210> SEQ ID NO 264

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 264

Pro Gln Xaa Ile Leu Asp Xaa His Val Arg Arg Val Trp Arg
1               5                   10

<210> SEQ ID NO 265
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 265

Pro Gln Xaa Ile Leu Asp Xaa His Val Arg Arg Val Trp Arg
1               5                   10

<210> SEQ ID NO 266
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 266

Pro Gln Xaa Ile Leu Asp Xaa His Val Arg Arg Val Trp Arg
1               5                   10

<210> SEQ ID NO 267
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
```

```
<223> OTHER INFORMATION: A non-natural amino acid useful for stapling

<400> SEQUENCE: 267

Pro Gln Xaa Ile Leu Asp Xaa His Val Arg Arg Val Trp Arg
1               5                   10

<210> SEQ ID NO 268
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 268

Pro Gln Xaa Ile Leu Asp Xaa His Val Arg Arg Val Trp Arg
1               5                   10

<210> SEQ ID NO 269
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 269

Pro Gln Xaa Ile Leu Asp Xaa His Val Arg Arg Val Trp Arg
1               5                   10

<210> SEQ ID NO 270
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 270

Pro Gln Xaa Ile Leu Asp Xaa His Val Arg Arg Val Trp Arg
1               5                   10

<210> SEQ ID NO 271
<211> LENGTH: 14
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 271

Pro Gln Xaa Ile Leu Asp Xaa His Val Arg Arg Val Trp Arg
1               5                   10

<210> SEQ ID NO 272
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 272

Pro Gln Xaa Ile Leu Asp Xaa His Val Arg Arg Val Trp Arg
1               5                   10

<210> SEQ ID NO 273
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 273

Pro Gln Xaa Ile Leu Asp Xaa His Val Arg Arg Val Trp Arg
1               5                   10

<210> SEQ ID NO 274
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 274
```

```
Pro Gln Xaa Ile Leu Asp Xaa His Val Arg Arg Val Trp Arg
1               5                   10

<210> SEQ ID NO 275
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 275

Pro Gln Xaa Ile Leu Asp Xaa His Val Arg Arg Val Trp Arg
1               5                   10

<210> SEQ ID NO 276
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 276

Pro Gln Xaa Ile Leu Asp Xaa His Val Arg Arg Val Trp Arg
1               5                   10

<210> SEQ ID NO 277
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 277

Pro Gln Xaa Ile Leu Asp Xaa His Val Arg Arg Val Trp Arg
1               5                   10

<210> SEQ ID NO 278
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (6)..(6)
<223> OTHER INFORMATION: A non-natural amino acid useful for stapling
<220> FEATURE:
<221> NAME/KEY: MOD_RES
<222> LOCATION: (10)..(10)
<223> OTHER INFORMATION: A non-natural amino acid useful for stapling

<400> SEQUENCE: 278

Arg Arg Trp Pro Arg Xaa Ile Leu Asp Xaa His Val Arg Arg Val Trp
1               5                   10                  15

Arg

<210> SEQ ID NO 279
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (24)..(24)
<223> OTHER INFORMATION: 2-naphthylalanine
<220> FEATURE:
<221> NAME/KEY: MOD_RES
<222> LOCATION: (25)..(25)
<223> OTHER INFORMATION: Beta-alanine
<220> FEATURE:
<221> NAME/KEY: MOD_RES
<222> LOCATION: (26)..(26)
<223> OTHER INFORMATION: Beta-alanine
<220> FEATURE:
<221> NAME/KEY: MOD_RES
<222> LOCATION: (27)..(27)
<223> OTHER INFORMATION: Lys-FAM

<400> SEQUENCE: 279

Leu Ser Gln Glu Gln Leu Glu His Arg Glu Arg Ser Leu Gln Thr Leu
1               5                   10                  15

Arg Asp Ile Gln Arg Met Leu Ala Ala Ala Lys
            20                  25

<210> SEQ ID NO 280
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling

<400> SEQUENCE: 280

Ala Xaa Ile Leu Asp Ala His Ile Xaa Arg Val Trp
1               5                   10

<210> SEQ ID NO 281
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 281

His Arg Glu Arg Ser Leu Gln Thr Leu Arg Xaa Ile Gln Arg Xaa Leu
1               5                   10                  15

Phe

<210> SEQ ID NO 282
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 282

His Arg Glu Arg Ser Leu Gln Thr Leu Arg Xaa Ile Gln Arg Xaa Leu
1               5                   10                  15

Phe

<210> SEQ ID NO 283
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 283

His Arg Glu Arg Ser Leu Gln Thr Leu Arg Xaa Ile Gln Arg Xaa Leu
1               5                   10                  15

Phe

<210> SEQ ID NO 284
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

```
<400> SEQUENCE: 284

His Arg Glu Arg Ser Leu Gln Thr Leu Arg Xaa Ile Gln Arg Xaa Leu
1               5                   10                  15

Phe

<210> SEQ ID NO 285
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: A non-natural amino acid useful for stapling
<220> FEATURE:
<221> NAME/KEY: MOD_RES
<222> LOCATION: (8)..(8)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: Norleucine

<400> SEQUENCE: 285

His Arg Glu Xaa Ser Leu Gln Xaa Leu Arg Asp Ile Gln Arg Leu Leu
1               5                   10                  15

Phe

<210> SEQ ID NO 286
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: A non-natural amino acid useful for stapling
<220> FEATURE:
<221> NAME/KEY: MOD_RES
<222> LOCATION: (8)..(8)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: Norleucine

<400> SEQUENCE: 286

His Arg Glu Xaa Ser Leu Gln Xaa Leu Arg Asp Ile Gln Arg Leu Leu
1               5                   10                  15

Phe

<210> SEQ ID NO 287
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: A non-natural amino acid useful for stapling
<220> FEATURE:
<221> NAME/KEY: MOD_RES
<222> LOCATION: (8)..(8)
<223> OTHER INFORMATION: A non-natural amino acid useful for stapling
```

```
<220> FEATURE:
<221> NAME/KEY: MOD_RES
<222> LOCATION: (15)..(15)
<223> OTHER INFORMATION: Norleucine

<400> SEQUENCE: 287

His Arg Glu Xaa Ser Leu Gln Xaa Leu Arg Asp Ile Gln Arg Leu Leu
1               5                   10                  15

Phe

<210> SEQ ID NO 288
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: A non-natural amino acid useful for stapling
<220> FEATURE:
<221> NAME/KEY: MOD_RES
<222> LOCATION: (8)..(8)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: Norleucine

<400> SEQUENCE: 288

His Arg Glu Xaa Ser Leu Gln Xaa Leu Arg Asp Ile Gln Arg Leu Leu
1               5                   10                  15

Phe

<210> SEQ ID NO 289
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: A non-natural amino acid useful for stapling

<400> SEQUENCE: 289

Xaa His Arg Glu Xaa Ser Leu Gln Xaa Leu Arg Asp Ile Gln Arg Xaa
1               5                   10                  15

Leu Phe

<210> SEQ ID NO 290
<211> LENGTH: 18
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: A non-natural amino acid useful for stapling

<400> SEQUENCE: 290

Xaa His Arg Glu Xaa Ser Leu Gln Xaa Leu Arg Asp Ile Gln Arg Xaa
1               5                   10                  15

Leu Phe

<210> SEQ ID NO 291
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: A non-natural amino acid useful for stapling

<400> SEQUENCE: 291

Xaa His Arg Glu Xaa Ser Leu Gln Xaa Leu Arg Asp Ile Gln Arg Xaa
1               5                   10                  15

Leu Phe

<210> SEQ ID NO 292
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
```

```
<222> LOCATION: (16)..(16)
<223> OTHER INFORMATION: A non-natural amino acid useful for stapling

<400> SEQUENCE: 292

Xaa His Arg Glu Xaa Ser Leu Gln Xaa Leu Arg Asp Ile Gln Arg Xaa
1               5                   10                  15

Leu Phe

<210> SEQ ID NO 293
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 293

Pro Gln Xaa Ile Leu Asp Xaa His Val Arg Arg Val Trp Arg
1               5                   10

<210> SEQ ID NO 294
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 294

Pro Gln Xaa Ile Leu Asp Xaa His Val Arg Arg Val Trp Arg
1               5                   10

<210> SEQ ID NO 295
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 295

Pro Gln Xaa Ile Leu Asp Xaa His Val Arg Arg Val Trp Arg
1               5                   10

<210> SEQ ID NO 296
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 296

Pro Gln Xaa Ile Leu Asp Xaa His Val Arg Arg Val Trp Arg
1               5                   10

<210> SEQ ID NO 297
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 297

Pro Gln Xaa Ile Leu Asp Xaa His Val Arg Arg Val Trp Arg
1               5                   10

<210> SEQ ID NO 298
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 298

Pro Gln Xaa Ile Leu Asp Xaa His Val Arg Arg Val Trp Arg
1               5                   10

<210> SEQ ID NO 299
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling
```

<400> SEQUENCE: 299

Pro Gln Xaa Ile Leu Asp Xaa His Val Arg Arg Val Trp Arg
1               5                   10

<210> SEQ ID NO 300
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 300

Pro Gln Xaa Ile Leu Asp Xaa His Val Arg Arg Val Trp Arg
1               5                   10

<210> SEQ ID NO 301
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 301

Pro Gln Xaa Ile Leu Asp Xaa His Val Arg Arg Val Trp Arg
1               5                   10

<210> SEQ ID NO 302
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 302

Pro Gln Xaa Ile Leu Asp Xaa His Val Arg Arg Val Trp Arg
1               5                   10

<210> SEQ ID NO 303
<211> LENGTH: 14
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 303

Pro Gln Xaa Ile Leu Asp Xaa His Val Arg Arg Val Trp Arg
1               5                   10

<210> SEQ ID NO 304
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 304

Pro Gln Xaa Ile Leu Asp Xaa His Val Arg Arg Val Trp Arg
1               5                   10

<210> SEQ ID NO 305
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 305

Pro Gln Xaa Ile Leu Asp Xaa His Val Arg Arg Val Trp Arg
1               5                   10

<210> SEQ ID NO 306
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 306

Pro Gln Xaa Ile Leu Asp Xaa His Val Arg Arg Val Trp Arg
```

```
1               5                   10
```

<210> SEQ ID NO 307
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 307

```
Pro Gln Xaa Ile Leu Asp Xaa His Val Arg Arg Val Trp Arg
1               5                   10
```

<210> SEQ ID NO 308
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 308

```
Pro Gln Xaa Ile Leu Asp Xaa His Val Arg Arg Val Trp Arg
1               5                   10
```

<210> SEQ ID NO 309
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 309

```
Pro Gln Xaa Ile Leu Asp Xaa His Val Arg Arg Val Trp Arg
1               5                   10
```

<210> SEQ ID NO 310
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)

```
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 310

Pro Gln Xaa Ile Leu Asp Xaa His Val Arg Arg Val Trp Arg
1               5                   10

<210> SEQ ID NO 311
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 311

Pro Gln Xaa Ile Leu Asp Xaa His Val Arg Arg Val Trp Arg
1               5                   10

<210> SEQ ID NO 312
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 312

Pro Gln Xaa Ile Leu Asp Xaa His Val Arg Arg Val Trp Arg
1               5                   10

<210> SEQ ID NO 313
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 313

Pro Gln Xaa Ile Leu Asp Xaa His Val Arg Arg Val Trp Arg
1               5                   10

<210> SEQ ID NO 314
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 314

Pro Gln Xaa Ile Leu Asp Xaa His Val Arg Arg Val Trp Arg
1               5                   10

<210> SEQ ID NO 315
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 315

Pro Gln Xaa Ile Leu Asp Xaa His Val Arg Arg Val Trp Arg
1               5                   10

<210> SEQ ID NO 316
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 316

Pro Gln Xaa Ile Leu Asp Xaa His Val Arg Arg Val Trp Arg
1               5                   10

<210> SEQ ID NO 317
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
```

<223> OTHER INFORMATION: A non-natural amino acid useful for stapling

<400> SEQUENCE: 317

Pro Gln Xaa Ile Leu Asp Xaa His Val Arg Arg Val Trp Arg
1               5                   10

<210> SEQ ID NO 318
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: Norleucine

<400> SEQUENCE: 318

Xaa His Arg Glu Xaa Ser Leu Gln Xaa Leu Arg Asp Ile Gln Arg Leu
1               5                   10                  15

Leu Phe

<210> SEQ ID NO 319
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: Norleucine

<400> SEQUENCE: 319

Xaa His Arg Glu Xaa Ser Leu Gln Xaa Leu Arg Asp Ile Gln Arg Leu
1               5                   10                  15

Leu Phe

<210> SEQ ID NO 320
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

```
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: Norleucine

<400> SEQUENCE: 320

Xaa His Arg Glu Xaa Ser Leu Gln Xaa Leu Arg Asp Ile Gln Arg Leu
1               5                   10                  15

Leu Phe

<210> SEQ ID NO 321
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: Norleucine

<400> SEQUENCE: 321

Xaa His Arg Glu Xaa Ser Leu Gln Xaa Leu Arg Asp Ile Gln Arg Leu
1               5                   10                  15

Leu Phe

<210> SEQ ID NO 322
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
```

<223> OTHER INFORMATION: Norleucine

<400> SEQUENCE: 322

Xaa His Arg Glu Xaa Ser Leu Gln Xaa Leu Arg Asp Ile Gln Arg Leu
1               5                   10                  15

Leu Phe

<210> SEQ ID NO 323
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: Norleucine

<400> SEQUENCE: 323

Xaa His Arg Glu Xaa Ser Leu Gln Xaa Leu Arg Asp Ile Gln Arg Leu
1               5                   10                  15

Leu Phe

<210> SEQ ID NO 324
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: A non-natural amino acid useful for stapling
<220> FEATURE:
<221> NAME/KEY: MOD_RES
<222> LOCATION: (5)..(5)
<223> OTHER INFORMATION: A non-natural amino acid useful for stapling
<220> FEATURE:
<221> NAME/KEY: MOD_RES
<222> LOCATION: (9)..(9)
<223> OTHER INFORMATION: A non-natural amino acid useful for stapling
<220> FEATURE:
<221> NAME/KEY: MOD_RES
<222> LOCATION: (16)..(16)
<223> OTHER INFORMATION: Norleucine

<400> SEQUENCE: 324

Xaa His Arg Glu Xaa Ser Leu Gln Xaa Leu Arg Asp Ile Gln Arg Leu
1               5                   10                  15

Leu Phe

<210> SEQ ID NO 325
<211> LENGTH: 17
<212> TYPE: PRT
<213> ORGANISM: Artificial Sequence
<220> FEATURE:

```
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 325

His Arg Glu Arg Ser Leu Xaa Thr Leu Arg Xaa Ile Gln Arg Xaa Leu
1               5                   10                  15

Phe

<210> SEQ ID NO 326
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 326

His Arg Glu Arg Ser Leu Xaa Thr Leu Arg Xaa Ile Gln Arg Xaa Leu
1               5                   10                  15

Phe

<210> SEQ ID NO 327
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 327

His Arg Glu Arg Ser Leu Xaa Thr Leu Arg Xaa Ile Gln Arg Xaa Leu
1               5                   10                  15

Phe
```

-continued

```
<210> SEQ ID NO 328
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 328

His Arg Glu Arg Ser Leu Xaa Thr Leu Arg Xaa Ile Gln Arg Xaa Leu
1               5                   10                  15

Phe

<210> SEQ ID NO 329
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 329

His Arg Glu Arg Ser Leu Xaa Thr Leu Arg Xaa Ile Gln Arg Xaa Leu
1               5                   10                  15

Phe

<210> SEQ ID NO 330
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 330

His Arg Glu Arg Ser Leu Xaa Thr Leu Arg Xaa Ile Gln Arg Xaa Leu
```

-continued

```
1               5                   10                  15

Phe

<210> SEQ ID NO 331
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A non-natural amino acid useful for stapling
<220> FEATURE:
<221> NAME/KEY: MOD_RES
<222> LOCATION: (11)..(11)
<223> OTHER INFORMATION: A non-natural amino acid useful for stapling
<220> FEATURE:
<221> NAME/KEY: MOD_RES
<222> LOCATION: (15)..(15)
<223> OTHER INFORMATION: A non-natural amino acid useful for stapling

<400> SEQUENCE: 331

His Arg Glu Arg Ser Leu Xaa Thr Leu Arg Xaa Ile Gln Arg Xaa Leu
1               5                   10                  15

Phe

<210> SEQ ID NO 332
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 332

Pro Gln Xaa Ile Leu Asp Xaa His Val Arg Arg Val Trp Arg
1               5                   10

<210> SEQ ID NO 333
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 333

Pro Gln Xaa Ile Leu Asp Xaa His Val Arg Arg Val Trp Arg
1               5                   10

<210> SEQ ID NO 334
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 334

Pro Gln Xaa Ile Leu Asp Xaa His Val Arg Arg Val Trp Arg
1               5                   10

<210> SEQ ID NO 335
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 335

Pro Gln Xaa Ile Leu Asp Xaa His Val Arg Arg Val Trp Arg
1               5                   10

<210> SEQ ID NO 336
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 336

Pro Gln Xaa Ile Leu Asp Xaa His Val Arg Arg Val Trp Arg
1               5                   10

<210> SEQ ID NO 337
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling
```

```
<400> SEQUENCE: 337

Pro Gln Xaa Ile Leu Asp Xaa His Val Arg Arg Val Trp Arg
1               5                   10

<210> SEQ ID NO 338
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 338

Pro Gln Xaa Ile Leu Asp Xaa His Val Arg Arg Val Trp Arg
1               5                   10

<210> SEQ ID NO 339
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 339

Pro Gln Xaa Ile Leu Asp Xaa His Val Arg Arg Val Trp Arg
1               5                   10

<210> SEQ ID NO 340
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 340

Pro Gln Xaa Ile Leu Asp Xaa His Val Arg Arg Val Trp Arg
1               5                   10

<210> SEQ ID NO 341
<211> LENGTH: 14
<212> TYPE: PRT
<213> ORGANISM: Artificial Sequence
<220> FEATURE:
<223> OTHER INFORMATION: Description of Artificial Sequence: Synthetic
```

```
            peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 341

Pro Gln Xaa Ile Leu Asp Xaa His Val Arg Arg Val Trp Arg
1               5                   10

<210> SEQ ID NO 342
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 342

Pro Gln Xaa Ile Leu Asp Xaa His Val Arg Arg Val Trp Arg
1               5                   10

<210> SEQ ID NO 343
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 343

Pro Gln Xaa Ile Leu Asp Xaa His Val Arg Arg Val Trp Arg
1               5                   10

<210> SEQ ID NO 344
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 344

Pro Gln Xaa Ile Leu Asp Xaa His Val Arg Arg Val Trp Arg
```

```
1               5                   10
```

<210> SEQ ID NO 345
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 345

```
Pro Gln Xaa Ile Leu Asp Xaa His Val Arg Arg Val Trp Arg
1               5                   10
```

<210> SEQ ID NO 346
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 346

```
Pro Gln Xaa Ile Leu Asp Xaa His Val Arg Arg Val Trp Arg
1               5                   10
```

<210> SEQ ID NO 347
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 347

```
Pro Gln Xaa Ile Leu Asp Xaa His Val Arg Arg Val Trp Arg
1               5                   10
```

<210> SEQ ID NO 348
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)

```
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 348

Pro Gln Xaa Ile Leu Asp Xaa His Val Arg Arg Val Trp Arg
1               5                   10

<210> SEQ ID NO 349
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 349

Pro Gln Xaa Ile Leu Asp Xaa His Val Arg Arg Val Trp Arg
1               5                   10

<210> SEQ ID NO 350
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 350

Pro Gln Xaa Ile Leu Asp Xaa His Val Arg Arg Val Trp Arg
1               5                   10

<210> SEQ ID NO 351
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: A non-natural amino acid useful for stapling
<220> FEATURE:
<221> NAME/KEY: MOD_RES
<222> LOCATION: (7)..(7)
<223> OTHER INFORMATION: A non-natural amino acid useful for stapling

<400> SEQUENCE: 351

Pro Gln Xaa Ile Leu Asp Xaa His Val Arg Arg Val Trp Arg
1               5                   10
```

US 11,834,482 B2

AGENTS MODULATING BETA-CATENIN FUNCTIONS AND METHODS THEREOF

CROSS-REFERENCE TO RELATED APPLICATIONS

This application is a continuation of U.S. application Ser. No. 16/645,407, which is a National Stage Entry of International Application No. PCT/US18/50102, filed Sep. 7, 2018, which claims priority to U.S. Provisional Application No. 62/555,519, filed Sep. 7, 2017, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Mar. 9, 2022, is named 2012675-0275_SL.txt and is 170,398 bytes in size.

BACKGROUND

Beta-catenin is a multifunctional protein and is involved in many biological pathways and processes.

SUMMARY

Beta-catenin has many functions and regulates and coordinates many processes, e.g., gene transcription, cell-cell adhesion, embryogenesis, cell growth, regeneration, etc. Among other things, beta-catenin plays important roles in the Wnt/beta-catenin pathway. Many conditions, disorders, and diseases, including a number of cancers (e.g., hepatocellular carcinoma, colorectal carcinoma, lung cancer, malignant breast tumors, ovarian and endometrial cancer, etc.), various forms of heart diseases, etc., are associated with beta-catenin (e.g., its abnormal levels, activities, localization, etc.).

Among other things, the present disclosure provides technologies (e.g., compounds, compositions, methods, etc.) for modulating beta-catenin function. In some embodiments, such technologies are useful for, e.g., preventing or treating beta-catenin associated conditions, disorders, or diseases.

In some embodiments, the present disclosure encompasses the recognition that it can be beneficial to selectively or specifically modulate one or more certain functions of beta-catenin, for example, functions that involve an Axin binding site of beta-catenin. In some embodiments, such functions involve interactions of Axin with beta-catenin. In some embodiments, the present disclosure provides technologies for selectively or specifically modulating beta-catenin functions. In some embodiments, provided technologies selectively or specifically modulate beta-catenin functions involving one or more beta-catenin sites that interact with Axin. In some embodiments, provided technologies selectively or specifically modulate beta catenin functions that involve interactions between beta-catenin and Axin.

Among other things, the present disclosure provides agents, e.g., stapled peptides, that physically interact with beta-catenin. In some embodiments, provided agents binds to beta-catenin at a site that Axin binds to beta-catenin (e.g., at a site that overlaps with or is identical to that at which Axin binds; alternatively or additionally, in some embodiments at a site with sufficient proximity to such Axin binding site that the provided agent competes with Axin for binding to beta-catenin). In some embodiments, provided agents interacts with some or all amino acid residues of beta-catenin that interact with Axin when Axin binds to beta-catenin. In some embodiments, provided agents compete with Axin for binding to beta-catenin.

In some embodiments, provided agents are stapled peptides. In some embodiments, provided stapled peptides comprise a number of natural or non-natural amino acid residues (e.g., 7-50, 10-25, 10-20, 8, 9, 10, 11, 12, 13, 14, 15, 16, 17, 18, 19, 20, 21, 22, 23, 24, 25, 26, 27, 28, 29, 30, etc.), and one or more staples, each of which is independently a linker that can link one amino acid residue to another amino acid residue and, as is understood by those skilled in the art, is not part of the peptide backbone.

In some embodiments, the present disclosure provides the insights that structural elements of staples (e.g., chemistry [e.g., hydrocarbon, non-hydrocarbon (e.g., comprising one or more heteroatoms or heteroatom-containing moieties such as amino, carbamate, etc.)], stereochemistry [e.g., stereochemistry of backbone atoms that staples are connected to (e.g., if staples are connected to alpha-carbon atoms of amino acid residues, such carbon atoms being chiral (R/S) or achiral)], positioning (to what amino acid residues/backbone atoms staples are connected), sizes (length of staples), etc.), peptide sequences, lengths, and/or other modifications (e.g., incorporation of unnatural amino acids, labels, targeting moieties [carbohydrate, protein ligand, etc.], etc.) can significantly impact properties and/or activities, and can be employed to design stapled peptides having significantly improved properties and/or activities (e.g., increased solubility, increased cell permeability, increased stability, increased selectivity, lowered toxicity, increased activity, etc.).

Among other things, the present disclosure provides staples with various structural elements, and peptides that contain them. In some embodiments, a staple is a hydrocarbon staple. In some embodiments, a staple is a non-hydrocarbon staple in that it comprises one or more heteroatoms. In some embodiments, a staple comprises an amino moiety (e.g., —N(R')—, wherein R' is as described in the present disclosure). In some embodiments, a staple comprises a carbamate moiety (e.g., —N(R)—C(O)—O—, wherein R is as described in the present disclosure). In some embodiments, a staple is a Pro-staple in that an end of the staple is connected to a proline residue. In some embodiments, a staple is -$L^s$- as described in the present disclosure.

In some embodiments, provided stapled peptides comprising a staple comprising an amino moiety or a carbamate moiety have improved solubility compared to an appropriate reference peptide (e.g., in some embodiments, peptides which are otherwise identical but do not contain any staples or contain hydrocarbon staples instead of staples comprising an amino or carbamate moiety). In some embodiments, provided peptides comprising a staple comprising an amino moiety or a carbamate moiety have increased cell permeability compared to an appropriate reference peptide. In some embodiments, provided peptides comprising a staple comprising an amino moiety or a carbamate moiety have increased activities, e.g., increased inhibition of gene expression, cell growth, etc.

In some embodiments, a staple connects amino acid residue i and i+m (wherein each of i and m is independently as described in the present disclosure), and the connecting atoms at amino acid residue i ($C^i$) and at amino acid residue i+m ($C^{i+m}$) are independently chiral and achiral, and if chiral, are independently racemic, R or S. In some embodiments, both $C^i$ and $C^{i+m}$ are carbon atoms. In some embodiments, $C^i$ is achiral and $C^{i+m}$ chiral. In some embodiments, $C^i$ is a chiral and $C^{i+m}$ is R. In some embodiments, $C^i$ is a chiral and $C^{i+m}$ is S. In some embodiments, $C^i$ is chiral and $C^{i+m}$ achiral. In some embodiments, $C^i$ is R and $C^{i+m}$ achiral. In some embodiments, $C^i$ is S and $C^{i+m}$ achiral. In some embodiments, $C^i$ is R and $C^{i+m}$ is R. In some embodiments, $C^i$ is R and $C^{i+m}$ is S. In some embodiments, $C^i$ is S and $C^{i+m}$ is R. In some embodiments, $C^i$ is S and $C^{i+m}$ is S. In some embodiments, controlling chemistry and/or stereochemistry significantly improves yields and/or purity of prepared stapled peptides, and/or properties and activities of provided stapled peptides.

In some embodiments, the present disclosure provides a peptide comprising:

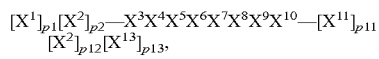

wherein:
each of p1, p2, p11, p12 and p13 is independently 0 or 1;
each of X, $X^1$, $X^2$, $X^3$, $X^4$, $X^5$, $X^6$, $X^7$, $X^8$, $X^9$, $X^{10}$, $X^{11}$, $X^{12}$, and $X^{13}$ is independently an amino acid residue;
at least two of X, $X^1$, $X^2$, $X^3$, $X^4$, $X^5$, $X^6$, $X^7$, $X^8$, $X^9$, $X^{10}$, $X^{11}$, $X^{12}$, and $X^{13}$ comprise side chains that are optionally linked together to form a staple.

In some embodiments, p1 is 0. In some embodiments, p1 is 1. In some embodiments, p2 is 0. In some embodiments, p2 is 1.

In some embodiments, p11 is 0. In some embodiments, p11 is 1. In some embodiments, p12 is 0. In some embodiments, p12 is 1. In some embodiments, p13 is 0. In some embodiments, p13 is 1.

In some embodiments, the present disclosure provides a peptide comprising a staple $L^s$, wherein $L^s$ is an optionally substituted, bivalent $C_{1-50}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each R' is independently —R, —C(O)R, —CO$_2$R, or —SO$_2$R;
each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, the present disclosure provides a peptide having the structure:

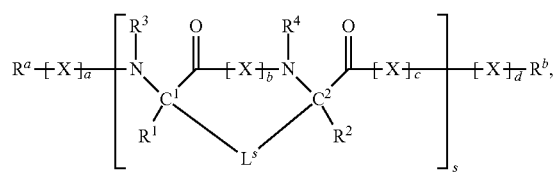

or a salt thereof, wherein
each of $R^a$, $R^1$, $R^2$, $R^3$, and $R^4$ is independently R';
$R^b$ is R', —OR' or —N(R')$_2$;
each of X is independently an amino acid residue;
each of a, b, c, s, and d is independently 1-20;
each of $C^1$ and $C^2$ is independently a carbon atom;
each $L^s$ is independently -$L^{s1}$-$L^{s2}$-$L^{s3}$-, wherein $L^{s1}$ is bonded to $C^1$ and $L^{s3}$ is bonded to $C^2$;
each of $L^{s1}$, $L^{s2}$, and $L^{s3}$ is independently L;
each L is independently a covalent bond, or an optionally substituted, bivalent $C_1$-$C_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each R' is independently —R, —C(O)R, —CO$_2$R, or —SO$_2$R;
each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $R^a$ is R', wherein R' is as described in the present disclosure. In some embodiments, $R^a$ is —H. In some embodiments, $R^a$ is R—C(O)—.

In some embodiments, X is a residue of an amino acid of formula A-I. In some embodiments, X is a residue of an amino acid of formula A-II. In some embodiments, X is a residue of an amino acid of formula A-III.

In some embodiments, a is 1. In some embodiments, a is 2. In some embodiments, a is 3. In some embodiments, a is 4. In some embodiments, a is 5. In some embodiments, a is 6. In some embodiments, a is 7. In some embodiments, a is 8. In some embodiments, a is 9. In some embodiments, a is 10. In some embodiments, a is 11. In some embodiments, a is 12. In some embodiments, a is 13. In some embodiments, a is 14. In some embodiments, a is 15. In some embodiments, a is 16. In some embodiments, a is 17. In some embodiments, a is 18. In some embodiments, a is 19. In some embodiments, a is 20.

In some embodiments, $R^1$ is R' as described in the present disclosure. In some embodiments, $R^1$ is R as described in the present disclosure. In some embodiments, $R^1$ is —H. In some embodiments, $R^1$ is not H. In some embodiments, $R^1$ and R' of a —N(R')— or —N(R')—C(O)O— moiety of $L^s$ or $L^{s1}$ are R and are taken together with their intervening atoms to form an optionally substituted ring as described in the present disclosure.

In some embodiments, $R^2$ is R' as described in the present disclosure. In some embodiments, $R^2$ is R as described in the present disclosure. In some embodiments, $R^2$ is —H. In some embodiments, $R^2$ is not H. In some embodiments, $R^1$ and R' of a —N(R')— or —N(R')—C(O)O— moiety of $L^s$ or $L_{s3}$ are R and are taken together with their intervening atoms to form an optionally substituted ring as described in the present disclosure.

In some embodiments, $R^3$ is R' as described in the present disclosure. In some embodiments, $R^3$ is R as described in the present disclosure. In some embodiments, $R^3$ is —H. In some embodiments, $R^3$ is not H.

In some embodiments, $R^4$ is R' as described in the present disclosure. In some embodiments, $R^4$ is R as described in the present disclosure. In some embodiments, $R^4$ is —H. In some embodiments, $R^4$ is not H.

In some embodiments, $C^1$ is achiral. In some embodiments, $C^1$ is chiral. In some embodiments, $C^1$ is R. In some embodiments, $C^1$ is S.

In some embodiments, $C^2$ is achiral. In some embodiments, $C^2$ is chiral. In some embodiments, $C^2$ is R. In some embodiments, $C^2$ is S.

In some embodiments, b is 2-11. In some embodiments, b is 2. In some embodiments, b is 3. In some embodiments, b is 4. In some embodiments, b is 5. In some embodiments, b is 6. In some embodiments, b is 7. In some embodiments, b is 8. In some embodiments, b is 9. In some embodiments, b is 10. In some embodiments, b is 11.

In some embodiments, c is 1. In some embodiments, c is 2. In some embodiments, c is 3. In some embodiments, c is 4. In some embodiments, c is 5. In some embodiments, c is 6. In some embodiments, c is 7. In some embodiments, c is 8. In some embodiments, c is 9. In some embodiments, c is 10. In some embodiments, c is 11. In some embodiments, c is 12. In some embodiments, c is 13. In some embodiments, c is 14. In some embodiments, c is 15. In some embodiments, c is 16. In some embodiments, c is 17. In some embodiments, c is 18. In some embodiments, c is 19. In some embodiments, c is 20.

In some embodiments, s is 1-5. In some embodiments, s is 1. In some embodiments, s is 2. In some embodiments, s is 3. In some embodiments, s is 4. In some embodiments, s is 5.

In some embodiments, d is 1. In some embodiments, d is 2. In some embodiments, d is 3. In some embodiments, d is 4. In some embodiments, d is 5. In some embodiments, d is 6. In some embodiments, d is 7. In some embodiments, d is 8. In some embodiments, d is 9. In some embodiments, d is 10. In some embodiments, d is 11. In some embodiments, d is 12. In some embodiments, d is 13. In some embodiments, d is 14. In some embodiments, d is 15. In some embodiments, d is 16. In some embodiments, d is 17. In some embodiments, d is 18. In some embodiments, d is 19. In some embodiments, d is 20.

In some embodiments, $R^b$ is R' as described in the present disclosure. In some embodiments, $R^b$ is R as described in the present disclosure. In some embodiments, $R^b$ is —H. In some embodiments, $R^b$ is —OR' wherein R' is as described in the present disclosure. In some embodiments, $R^b$ is —OH. In some embodiments, $R^b$ is —N(R')$_2$, wherein each R' is independently as described in the present disclosure. In some embodiments, $R^b$ is —NH(R') wherein R' is independently as described in the present disclosure.

In some embodiments, the present disclosure provides a stapled peptide comprising a staple having the structure of $L^s$. In some embodiments, the present disclosure provides a stapled peptide comprising a staple having the structure of $L^s$, wherein:

$L^s$ is -$L^{s1}$-$L^{s2}$-$L^{s3}$-;

one end of $L^s$ is connected to an atom $A^{n1}$ of the peptide backbone, wherein $A^{n1}$ is bonded to $R^1$;

one end of $L^s$ is connected to an atom $A^{n2}$ of the peptide backbone, wherein $A^{n2}$ is bonded to $R^2$;

each of $R^1$ and $R^2$ is independently R';

there are m amino acid residues between the amino acid residue comprising $A^{n1}$ and the amino acid residue comprising $A^{n2}$, not including the amino acid residue comprising $A^{n1}$ and the amino acid residue comprising $A^{n2}$;

m is an integer of 1-12; and wherein each other variable is independently as described in the present disclosure.

In some embodiments, $A^{n1}$ is a carbon atom. In some embodiments, $R^1$ bonded to $A^{n1}$ and R' of a —N(R')— or —N(R')—C(O)O— moiety of $L^s$ are R and are taken together with their intervening atoms to form an optionally substituted ring as described in the present disclosure. In some embodiments, $A^{n1}$ is achiral. In some embodiments, $A^{n1}$ is chiral. In some embodiments, $A^{n1}$ is R. In some embodiments, $A^{n1}$ is S.

In some embodiments, $A^{n2}$ is a carbon atom. In some embodiments, $R^2$ bonded to $A^{n1}$ and R' of a —N(R')— or —N(R')—C(O)O— moiety of $L^s$ are R and are taken together with their intervening atoms to form an optionally substituted ring as described in the present disclosure. In some embodiments, $A^{n2}$ is achiral. In some embodiments, $A^{n2}$ is chiral. In some embodiments, $A^{n2}$ is R. In some embodiments, $A^{n2}$ is S.

In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12.

In some embodiments, provided agents, e.g., stapled peptides, are optionally conjugated with a second entity, e.g., a targeting moiety (e.g., a carbohydrate, a receptor ligand, etc.), a second peptide, etc. In some embodiments, provided peptides are conjugated to one or more ligands for targeted delivery to cells expressing receptors to which the ligands bind to. In some embodiments, provided agents are conjugated to one or more second entities that have an enzymatic activity, or ligands for proteins that have an enzymatic activity (e.g., E3 ubiquitin ligase).

In some embodiments, provided agents, e.g., stapled peptides, have lower toxicity compared to an appropriate reference peptide (e.g., a peptide having the same sequence but lacking a staple or having a staple that differs in one or more features (e.g., chemistry [e.g., presence or absence, and/or number and/or type of heteroatoms, degree of saturation, etc.], stereochemistry, length, etc.). Among other things, as demonstrated in the present disclosure, in some embodiments provided peptides have low cytotoxicity, and in particular low non-specific cytotoxicity, as compared to an appropriate reference peptide (e.g., in certain particular embodiments, an otherwise identical stapled peptide having a hydrocarbon staple).

In some embodiments, provided agents, e.g., stapled peptides, have unexpected selectivity and/or specificity for modulating beta-catenin functions and/or Wnt pathway compared to other one or more comparable reference agents.

In some embodiments, provided agents, e.g., stapled peptides, selectively interact with Axin-interacting sites of beta-catenin and modulate beta-catenin interactions with other entities (e.g., proteins, small molecules, etc.) at such Axin-interacting sites. As demonstrated in the present disclosure, in some embodiments, provided agents, e.g., stapled peptides, can selectively disrupt beta-catenin interactions at Axin sites without significantly impacting interactions at BCL9-interacting sites of beta-catenin. Technologies for assessing selectivity are widely known in the art and can be utilized in accordance with the present disclosure, e.g., certain fluorescence assays described in the present disclosure.

In some embodiments, the present disclosure provides pharmaceutical compositions comprising a provided agent, e.g., a stapled peptide, and a pharmaceutically acceptable carrier.

In some embodiments, the present disclosure provides technologies for modulating one or more beta-catenin functions. In some embodiments, the present disclosure provides agents, e.g., stapled peptides, and compositions thereof for modulating beta-catenin functions. In some embodiments, the present disclosure provides technologies for inhibiting aberrant beta-catenin activities. As appreciated by those skilled in the art, beta-catenin plays important roles in Wnt signaling pathways and other biological pathways. In some embodiments, the present disclosure provides technologies for modulating Wnt signaling pathway. In some embodiments, the present disclosure provides technologies for inhibiting aberrant Wnt signaling. In some embodiments, the present disclosure provides technologies for modulating expression of a nucleic acid sequence in a system, comprising contacting a system comprising beta-catenin a provided stapled peptide, wherein expression of the nucleic acid sequence is associated with beta-catenin. In some embodiments, the present disclosure provides technologies for modulating level of a product encoded by a nucleic acid sequence in a system, comprising contacting a system comprising beta-catenin a provided peptide, wherein level of a product encoded by a nucleic acid sequence is associated with beta-catenin.

In some embodiments, the present disclosure provides methods for preventing and/or treating a condition, disorder, or diseases associated with beta-catenin. In some embodiments, the present disclosure provides methods for preventing and/or treating a condition, disorder, or diseases associated with Wnt signaling. In some embodiments, provided methods comprise administering to a subject susceptible to or suffering from a condition, disorder or disease associated with beta-catenin and/or Wnt signaling. In some embodiments, a condition, disorder, or disease is cancer.

BRIEF DESCRIPTION OF THE DRAWING

FIG. 1 depicts exemplary beta-catenin binding data from a competition fluorescence polarization assay. Peptide solutions were prepared in buffer (50 mM Tris pH 8.0, 250 mM NaCl, 2% glycerol, 0.5 mM EDTA, 0.02% w/v sodium azide) using a 3-fold serial dilution from 5 µM. Probe solution (15 nM full-length ß-Catenin, 20 nM FITC labeled peptide (FITC-PEG1-PQ-S5-ILD-S5-HVRRVWR (SEQ ID NO: 1) (hydrocarbon staple formed by two S5 via olefin metathesis)) in buffer) was prepared and incubated for 5 minutes, then 40 µL per well plated in a black polystyrene 384-well plate (Corning). Equal volume of the titrated peptide was added to the plate and incubated protected from light for 15 minutes prior to read. Reads were performed on a Spectramax M5 (Molecular Devices) in duplicate.

FIG. 2 depicts exemplary data from TCF/LEF reporter assays. Y-axes illustrate luminescence, and X-axes illustrate concentrations of peptides. Inhibition of TCF/LEF Reporter Activity by FP0025c and FP0217c Isomer 2. TCF/LEF Luciferase reporter HEK293 cell lines (BPS Bioscience) were treated with dilution series of FP0025c and FP00217c Isomer 2 for 18 hours. 300 ng/mL of Wnt3a (Peprotech) was added to the cells for the final 6 hours of incubation. Luciferase activity was measured using Bright-Glo Luciferase Assay (Promega) according to manufacturer's protocol.

FIG. 3 illustrates modulation of gene expression by an exemplary stapled peptide. DLD-1 cells were treated with a dilution series of FP0217c isomer 2 for 18 hours. Total RNA was extracted using the RNeasy Plus kit (Qiagen) according to manufacturer's protocols, and reverse transcribed to cDNA using SuperScript Vilo IV master mix (ThermoFisher Scientific). Gene expression levels were determined by qPCR using Taqman probes (Applied Biosciences) and Taqman Advanced Fast Master Mix (Applied Biosciences) on a QuantStudio 3 (Applied Biosciences). Relative expression was quantified using delta Ct method. For each group, from left to right, Axin 2, LEF1, Cyclin D, LRP6 and c-myc.

FIG. 4 illustrates modulation of gene expression by an exemplary stapled peptide. HCT-116 cells were treated with a dilution series of FP0217c isomer 2 for 18 hours. Total RNA was extracted using the RNeasy Plus kit (Qiagen) according to manufacturer's protocols, and reverse transcribed to cDNA using SuperScript Vilo IV master mix (ThermoFisher Scientific). Gene expression levels were determined by qPCR using Taqman probes (Applied Biosciences) and Taqman Advanced Fast Master Mix (Applied Biosciences) on a QuantStudio 3 (Applied Biosciences). Relative expression was quantified using delta Ct method. For each group, from left to right, Axin 2, VEGF, Cyclin D, LRP6 and c-myc.

DETAILED DESCRIPTION OF CERTAIN EMBODIMENTS

1. Definitions

Figure 1:
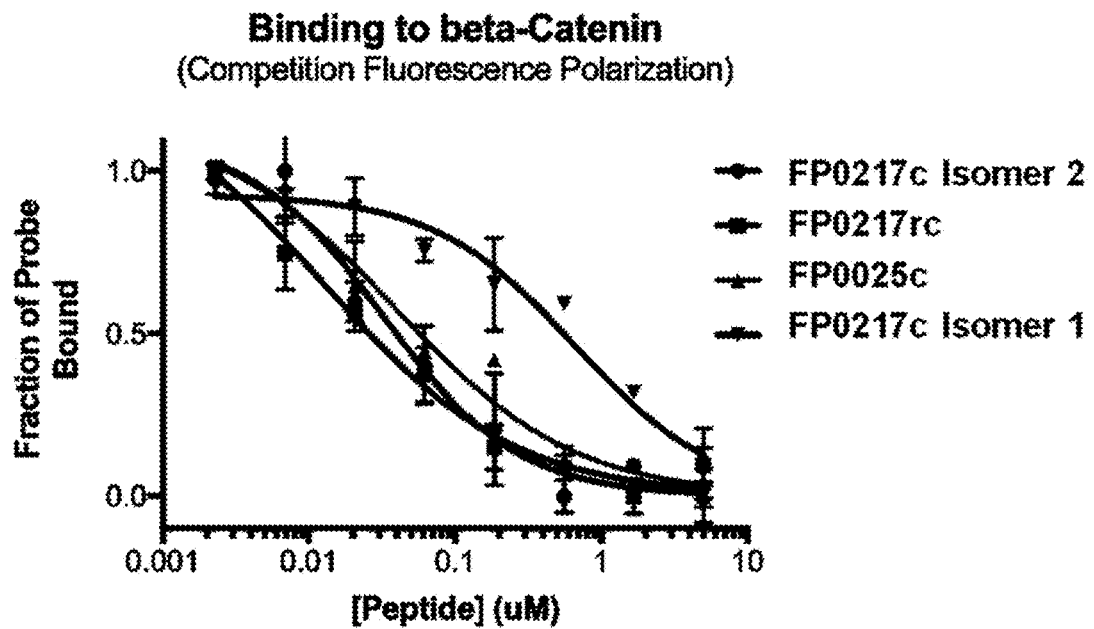
FIG. 1. Provided agents can bind to beta-catenin.

As used herein, the following definitions shall apply unless otherwise indicated. For purposes of this disclosure, the chemical elements are identified in accordance with the Periodic Table of the Elements, CAS version, Handbook of Chemistry and Physics, $75^{th}$ Ed. Additionally, general principles of organic chemistry are described in "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001.

Administration: As used herein, the term "administration" typically refers to the administration of a composition to a subject or system. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc), enteral, intra-arterial, intradermal, intragastric, intramedullary, intramuscular, intranasal, intraperitoneal, intrathecal, intravenous, intraventricular, within a specific organ (e. g., intrahepatic), mucosal, nasal, oral, rectal, subcutaneous, sublingual, topical, tracheal (e.g., by intratracheal instillation), vaginal, vitreal, etc. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Agent: In general, the term "agent", as used herein, may be used to refer to a compound or entity of any chemical class including, for example, a polypeptide, nucleic acid, saccharide, lipid, small molecule, metal, or combination or complex thereof. In appropriate circumstances, as will be clear from context to those skilled in the art, the term may be utilized to refer to an entity that is or comprises a cell or organism, or a fraction, extract, or component thereof. Alternatively or additionally, as context will make clear, the term may be used to refer to a natural product in that it is found in and/or is obtained from nature. In some instances, again as will be clear from context, the term may be used to refer to one or more entities that is man-made in that it is designed, engineered, and/or produced through action of the hand of man and/or is not found in nature. In some embodiments, an agent may be utilized in isolated or pure form; in some embodiments, an agent may be utilized in crude form. In some embodiments, potential agents may be provided as collections or libraries, for example that may be screened to identify or characterize active agents within them. In some cases, the term "agent" may refer to a compound or entity that is or comprises a polymer; in some cases, the term may refer to a compound or entity that comprises one or more polymeric moieties. In some embodiments, the term "agent" may refer to a compound or entity that is not a polymer and/or is substantially free of any polymer and/or of one or more particular polymeric moieties. In some embodiments, the term may refer to a compound or entity that lacks or is substantially free of any polymeric moiety. In some embodiments, an agent is a compound. In some embodiments, an agent is a stapled peptide.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation, or combinations thereof. Unless otherwise specified, aliphatic groups contain 1-100 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof.

Alkenyl: As used herein, the term "alkenyl" refers to an aliphatic group, as defined herein, having one or more double bonds.

Alkenylene: The term "alkenylene" refers to a bivalent alkenyl group.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkylene: The term "alkylene" refers to a bivalent alkyl group.

Amino acid: In its broadest sense, as used herein, refers to any compound and/or substance that can be incorporated into a polypeptide chain, e.g., through formation of one or more peptide bonds. In some embodiments, an amino acid comprising an amino group and an a carboxylic acid group. In some embodiments, an amino acid has the structure of NH($R^{a1}$)-$L^{a1}$-C($R^{a2}$)($R^{a3}$)-$L^{a2}$-COOH wherein each variable is independently as described in the present disclosure. In some embodiments, an amino acid has the general structure NH(R')—C(R')$_2$—COOH, wherein each R' is independently as described in the present disclosure. In some embodiments, an amino acid has the general structure $H_2N$—C(R')$_2$—COOH, wherein R' is as described in the present disclosure. In some embodiments, an amino acid has the general structure $H_2N$—C(H)(R')—COOH, wherein R' is as described in the present disclosure. In some embodiments, an amino acid is a naturally-occurring amino acid. In some embodiments, an amino acid is a non-natural amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, pegylation, glycosylation, phosphorylation, and/or substitution (e.g., of the amino group, the carboxylic acid group, one or more protons, one or more hydrogens, and/or the hydroxyl group) as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" may be used to refer to a free amino acid; in some embodiments it may be used to refer to an amino acid residue of a polypeptide.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Animal: As used herein refers to any member of the animal kingdom. In some embodiments, "animal" refers to humans, of either sex and at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically engineered animal, and/or a clone.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Aryl: The term "aryl" used alone or as part of a larger moiety as in "aralkyl," "aralkoxy," "aryloxyalkyl," etc. refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. In some embodiments, also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like, where a radical or point of attachment is on an aryl ring.

Associated with: Two events or entities are "associated" with one another, as that term is used herein, if the presence, level and/or form of one is correlated with that of the other. For example, a particular entity (e.g., nucleic acid (e.g., genomic DNA, transcripts, mRNA, etc.), polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population).

Carrier: as used herein, refers to a diluent, adjuvant, excipient, or vehicle with which a composition is administered. In some exemplary embodiments, carriers can include sterile liquids, such as, for example, water and oils, including oils of petroleum, animal, vegetable or synthetic origin, such as, for example, peanut oil, soybean oil, mineral oil, sesame oil and the like. In some embodiments, carriers are or include one or more solid components.

Comparable: As used herein, the term "comparable" refers to two or more agents, entities, situations, sets of conditions, etc., that may not be identical to one another but that are sufficiently similar to permit comparison there between so that one skilled in the art will appreciate that conclusions may reasonably be drawn based on differences or similarities observed. In some embodiments, comparable sets of conditions, circumstances, individuals, or populations are characterized by a plurality of substantially identical features and one or a small number of varied features. Those of ordinary skill in the art will understand, in context, what degree of identity is required in any given circumstance for two or more such agents, entities, situations, sets of conditions, etc. to be considered comparable. For example, those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied.

Composition: Those skilled in the art will appreciate that the term "composition" may be used to refer to a discrete physical entity that comprises one or more specified components. In general, unless otherwise specified, a composition may be of any form—e.g., gas, gel, liquid, solid, etc.

Comprising: A composition or method described herein as "comprising" one or more named elements or steps is open-ended, meaning that the named elements or steps are essential, but other elements or steps may be added within the scope of the composition or method. To avoid prolixity, it is also understood that any composition or method described as "comprising" (or which "comprises") one or more named elements or steps also describes the corresponding, more limited composition or method "consisting essentially of" (or which "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and closed-ended composition or method "consisting of" (or "consists of") the named elements or steps to the exclusion of any other unnamed element or step. In any composition or method disclosed herein, known or disclosed equivalents of any named essential element or step may be substituted for that element or step.

Cycloaliphatic: The term "cycloaliphatic," as used herein, refers to saturated or partially unsaturated aliphatic monocyclic, bicyclic, or polycyclic ring systems having, e.g., from 3 to 30, members, wherein the aliphatic ring system is optionally substituted. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The terms "cycloaliphatic" may also include aliphatic rings that are fused to one or more aromatic or nonaromatic rings, such as decahydronaphthyl or tetrahydronaphthyl, where a radical or point of attachment is on an aliphatic ring. In some embodiments, a carbocyclic group is bicyclic. In some embodiments, a carbocyclic group is tricyclic. In some embodiments, a carbocyclic group is polycyclic. In some embodiments, "cycloaliphatic" (or "carbocycle" or "cycloalkyl") refers to a monocyclic $C_3$-$C_6$ hydrocarbon, or a $C_8$-$C_{10}$ bicyclic hydrocarbon that is completely saturated or that contains one or more units of unsaturation, but which is not aromatic, or a $C_9$-$C_{16}$ tricyclic hydrocarbon that is completely saturated or that contains one or more units of unsaturation, but which is not aromatic.

Derivative: As used herein, the term "derivative" refers to a structural analogue of a reference substance. That is, a "derivative" is a substance that shows significant structural similarity with the reference substance, for example sharing a core or consensus structure, but also differs in certain discrete ways. In some embodiments, a derivative is a substance that can be generated from the reference substance by chemical manipulation. In some embodiments, a derivative is a substance that can be generated through performance of a synthetic process substantially similar to (e.g., sharing a plurality of steps with) one that generates the reference substance.

Dosage form or unit dosage form: Those skilled in the art will appreciate that the term "dosage form" may be used to refer to a physically discrete unit of an active agent (e.g., a therapeutic or diagnostic agent) for administration to a subject. Typically, each such unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen). Those of ordinary skill in the art appreciate that the total amount of a therapeutic composition or agent administered to a particular subject is determined by one or more attending physicians and may involve administration of multiple dosage forms.

Dosing regimen: Those skilled in the art will appreciate that the term "dosing regimen" may be used to refer to a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated in time from other doses. In some embodiments, individual doses are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second dose amount same as the first dose amount. In some embodiments, a dosing regimen is correlated with a desired or beneficial outcome when administered across a relevant population (i.e., is a therapeutic dosing regimen).

Halogen: The term "halogen" means F, Cl, Br, or I.

Heteroaliphatic: The term "heteroaliphatic" is given its ordinary meaning in the art and refers to aliphatic groups as described herein in which one or more carbon atoms are replaced with one or more heteroatoms (e.g., oxygen, nitrogen, sulfur, silicon, phosphorus, and the like).

Heteroalkyl: The term "heteroalkyl" is given its ordinary meaning in the art and refers to alkyl groups as described herein in which one or more carbon atoms is replaced with a heteroatom (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-," used alone or as part of a larger moiety, e.g., "heteroaralkyl," or "heteroaralkoxy," refer to monocyclic, bicyclic or polycyclic ring systems having, for example, a total of five to thirty, e.g., 5, 6, 9, 10, 14, etc., ring members, wherein at least one ring in the system is aromatic and at least one aromatic ring atom is a heteroatom. In some embodiments, a heteroatom is nitrogen, oxygen or sulfur. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where a radical or point of attachment is on a heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom" means an atom that is not carbon and is not hydrogen. In some embodiments, a heteroatom is oxygen, sulfur, nitrogen, phosphorus, boron or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or NR$^+$ (as in N-substituted pyrrolidinyl); etc.). In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur.

Heterocyclyl: As used herein, the terms "heterocycle," "heterocyclyl," "heterocyclic radical," and "heterocyclic ring" are used interchangeably and refer to a monocyclic, bicyclic or polycyclic ring moiety (e.g., 3-30 membered) that is saturated or partially unsaturated and has one or more heteroatom ring atoms. In some embodiments, a heteroatom is boron, nitrogen, oxygen, silicon, sulfur, or phosphorus. In some embodiments, a heteroatom is nitrogen, oxygen, silicon, sulfur, or phosphorus. In some embodiments, a heteroatom is nitrogen, oxygen, sulfur, or phosphorus. In some embodiments, a heteroatom is nitrogen, oxygen or sulfur. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where a radical or point of attachment is on a heteroaliphatic ring. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar (e.g., containing residues with related chemical properties at corresponding positions). For example, as is well known by those of ordinary skill in the art, certain amino acids are typically classified as similar to one another as "hydrophobic" or "hydrophilic" amino acids, and/or as having "polar" or "non-polar" side chains. Substitution of one amino acid for another of the same type may often be considered a "homologous" substitution. Typical amino acid categorizations are summarized below:

| | | | | | |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | nonpolar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

| Ambiguous Amino Acids | 3-Letter | 1-Letter |
|---|---|---|
| Asparagine or aspartic acid | Asx | B |
| Glutamine or glutamic acid | Glx | Z |
| Leucine or Isoleucine | Xle | J |
| Unspecified or unknown amino acid | Xaa | X |

As will be understood by those skilled in the art, a variety of algorithms are available that permit comparison of sequences in order to determine their degree of homology, including by permitting gaps of designated length in one sequence relative to another when considering which residues "correspond" to one another in different sequences. Calculation of the percent homology between two nucleic acid sequences, for example, can be performed by aligning the two sequences for optimal comparison purposes (e.g., gaps can be introduced in one or both of a first and a second nucleic acid sequences for optimal alignment and non-corresponding sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position; when a position in the first sequence is occupied by a similar nucleotide as the corresponding position in the second sequence, then the molecules are similar at that position. The percent homology between the two sequences is a function of the number of identical and similar positions shared by the sequences, taking into account the number of gaps, and the length of each gap, which needs to be introduced for optimal alignment of the two sequences. Representative algorithms and computer programs useful in determining the percent homology between two nucleotide sequences include, for example, the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent homology between two nucleotide sequences can, alternatively, be determined for example using the GAP program in the GCG software package using an NWSgapdna.CMP matrix.

"Improved," "increased" or "reduced": As used herein, these terms, or grammatically comparable comparative terms, indicate values that are relative to a comparable reference measurement. For example, in some embodiments, an assessed value achieved with an agent of interest may be "improved" relative to that obtained with a comparable reference agent. Alternatively or additionally, in some embodiments, an assessed value achieved in a subject or system of interest may be "improved" relative to that obtained in the same subject or system under different conditions (e.g., prior to or after an event such as administration of an agent of interest), or in a different, comparable subject (e.g., in a comparable subject or system that differs from the subject or system of interest in presence of one or more indicators of a particular disease, disorder or condition of interest, or in prior exposure to a condition or agent, etc). In some embodiments, comparative terms refer to statistically relevant differences (e.g., that are of a prevalence and/or magnitude sufficient to achieve statistical relevance). Those skilled in the art will be aware, or will readily be able to determine, in a given context, a degree and/or prevalence of difference that is required or sufficient to achieve such statistical significance.

Partially unsaturated: As used herein, the term "partially unsaturated" refers to a moiety that includes at least one double or triple bond. The term "partially unsaturated" is intended to encompass groups having multiple sites of unsaturation, but is not intended to include aryl or heteroaryl moieties.

Peptide: The term "peptide" as used herein refers to a polypeptide that is typically relatively short, for example having a length of less than about 100 amino acids, less than about 50 amino acids, less than about 40 amino acids less than about 30 amino acids, less than about 25 amino acids, less than about 20 amino acids, less than about 15 amino acids, or less than 10 amino acids.

Pharmaceutical composition: As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream, or foam; sublingually; ocularly; transdermally; or nasally, pulmonary, and to other mucosal surfaces.

Pharmaceutically acceptable: As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Pharmaceutically acceptable carrier: As used herein, the term "pharmaceutically acceptable carrier" means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

Pharmaceutically acceptable salt: The term "pharmaceutically acceptable salt", as used herein, refers to salts of such compounds that are appropriate for use in pharmaceutical contexts, i.e., salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known. For example, S. M. Berge, et al. describes pharmaceutically acceptable salts in detail in J. Pharmaceutical Sciences, 66: 1-19 (1977). In some embodiments, pharmaceutically acceptable salts include, but are not limited to, nontoxic acid addition salts, which are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other known methods such as ion exchange. In some embodiments, pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, pharmaceutically acceptable salts include, but are not limited to, nontoxic base addition salts, such as those formed by acidic groups of provided compounds (e.g., phosphate linkage groups of oligonucleotides, phosphorothioate linkage groups of oligonucleotides, etc.) with bases. Representative alkali or alkaline earth metal salts include salts of sodium, lithium, potassium, calcium, magnesium, and the like. In some embodiments, pharmaceutically acceptable salts are ammonium salts (e.g., —$N(R)_3^+$). In some embodiments, pharmaceutically acceptable salts are sodium salts. In some embodiments, pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

Polypeptide: As used herein refers to any polymeric chain of amino acids. In some embodiments, a polypeptide has an amino acid sequence that occurs in nature. In some embodiments, a polypeptide has an amino acid sequence that does not occur in nature. In some embodiments, a polypeptide has an amino acid sequence that is engineered in that it is designed and/or produced through action of the hand of man. In some embodiments, a polypeptide may comprise or consist of natural amino acids, non-natural amino acids, or both. In some embodiments, a polypeptide may comprise or consist of only natural amino acids or only non-natural amino acids. In some embodiments, a polypeptide may comprise D-amino acids, L-amino acids, or both. In some embodiments, a polypeptide may comprise only D-amino acids. In some embodiments, a polypeptide may comprise only L-amino acids. In some embodiments, a polypeptide may include one or more pendant groups or other modifications, e.g., modifying or attached to one or more amino acid side chains, at the polypeptide's N-terminus, at the polypeptide's C-terminus, or any combination thereof. In some embodiments, such pendant groups or modifications may be selected from the group consisting of acetylation, amidation, lipidation, methylation, pegylation, etc., including combinations thereof. In some embodiments, a polypeptide may be cyclic, and/or may comprise a cyclic portion. In some embodiments, a polypeptide is not cyclic and/or does not comprise any cyclic portion. In some embodiments, a polypeptide is linear. In some embodiments, a polypeptide may be or comprise a stapled polypeptide. In some embodiments, the term "polypeptide" may be appended to a name of a reference polypeptide, activity, or structure; in such instances it is used herein to refer to polypeptides that share the relevant activity or structure and thus can be considered to be members of the same class or family of polypeptides. For each such class, the present specification provides and/or those skilled in the art will be aware of exemplary polypeptides within the class whose amino acid sequences and/or functions are known; in some embodiments, such exemplary polypeptides are reference polypeptides for the polypeptide class or family. In some embodiments, a member of a polypeptide class or family shows significant sequence homology or identity with, shares a common sequence motif (e.g., a characteristic sequence element) with, and/or shares a common activity (in some embodiments at a comparable level or within a designated range) with a reference polypeptide of the class; in some embodiments with all polypeptides within the class). For example, in some embodiments, a member polypeptide shows an overall degree of sequence homology or identity with a reference polypeptide that is at least about 30-40%, and is often greater than about 50%, 60%, 70%, 80%, 90%, 91%, 92%, 93%, 94%, 95%, 96%, 97%, 98%, 99% or more and/or includes at least one region (e.g., a conserved region that may in some embodiments be or comprise a characteristic sequence element) that shows very high sequence identity, often greater than 90% or even 95%, 96%, 97%, 98%, or 99%. Such a conserved region usually encompasses at least 3-4 and often up to 20 or more amino acids; in some embodiments, a conserved region encompasses at least one stretch of at least 2, 3, 4, 5, 6, 7, 8, 9, 10, 11, 12, 13, 14, 15 or more contiguous amino acids. In some embodiments, a relevant polypeptide may comprise or consist of a fragment of a parent polypeptide. In some embodiments, a useful polypeptide as may comprise or consist of a plurality of fragments, each of which is found in the same parent polypeptide in a different spatial arrangement relative to one another than is found in the polypeptide of interest (e.g., fragments that are directly linked in the parent may be spatially separated in the polypeptide of interest or vice versa, and/or fragments may be present in a different order in the polypeptide of interest than in the parent), so that the polypeptide of interest is a derivative of its parent polypeptide.

Prevent or prevention: as used herein when used in connection with the occurrence of a disease, disorder, and/or condition, refers to reducing the risk of developing the disease, disorder and/or condition and/or to delaying onset of one or more characteristics or symptoms of the disease, disorder or condition. Prevention may be considered complete when onset of a disease, disorder or condition has been delayed for a predefined period of time.

Protecting Group: The phrase "protecting group," as used herein, refers to temporary substituents which protect a potentially reactive functional group from undesired chemical transformations. Examples of such protecting groups include esters of carboxylic acids, silyl ethers of alcohols, and acetals and ketals of aldehydes and ketones, respectively. A "Si protecting group" is a protecting group comprising a Si atom, such as Si-trialkyl (e.g., trimethylsilyl, tributylsilyl, t-butyldimethylsilyl), Si-triaryl, Si-alkyl-diphenyl (e.g., t-butyldiphenylsilyl), or Si-aryl-dialkyl (e.g., Si-phenyldialkyl). Generally, a Si protecting group is attached to an oxygen atom. The field of protecting group chemistry has been reviewed (Greene, T. W.; Wuts, P. G. M. Protective Groups in Organic Synthesis, 2nd ed.; Wiley: New York, 1991). Such protecting groups (and associated protected moieties) are described in detail below.

Protected hydroxyl groups are well known in the art and include those described in detail in Protecting Groups in Organic Synthesis, T. W. Greene and P. G. M. Wuts, $3^{rd}$ edition, John Wiley & Sons, 1999, the entirety of which is incorporated herein by reference. Examples of suitably protected hydroxyl groups further include, but are not limited to, esters, carbonates, sulfonates, allyl ethers, ethers, silyl ethers, alkyl ethers, arylalkyl ethers, and alkoxyalkyl ethers. Examples of suitable esters include formates, acetates, propionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl ethers include trimethylsilyl, triethylsilyl, t-butyldimethylsilyl, t-butyldiphenylsilyl, triisopropylsilyl ether, and other trialkylsilyl ethers. Examples of suitable alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of suitable arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Suitable mono-protected amines further include, but are not limited to, aralkylamines, carbamates, allyl amines, amides, and the like. Examples of suitable mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Suitable di-protected amines include amines that are substituted with two substituents independently selected from those described above as mono-protected amines, and further include cyclic imides, such as phthalimide, maleimide, succinimide, and the like. Suitable di-protected amines also include pyrroles and the like, 2,2,5,5-tetramethyl-[1,2,5] azadisilolidine and the like, and azide.

Protected aldehydes are well known in the art and include those described in detail in Greene (1999). Suitable protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Suitable protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional suitable protected carboxylic acids include oxazolines and ortho esters.

Protected thiols are well known in the art and include those described in detail in Greene (1999). Suitable protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Substitution: As described herein, compounds of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein. In some embodiments, example substituents are described below.

Suitable monovalent substituents are halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}Ph$, which may be substituted with $R^\circ$; $-(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)N(R^\circ)_2$; $-N(R^\circ)C(S)N(R^\circ)_2$; $-(CH_2)_{0-4}N(R^\circ)C(O)OR^\circ$; $-N(R^\circ)N(R^\circ)C(O)R^\circ$; $-N(R^\circ)N(R^\circ)C(O)N(R^\circ)_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSi(R^\circ)_3$; $-(CH_2)_{0-4}OC(O)R^\circ$; $-OC(O)(CH_2)_{0-4}SR^\circ$, $-SC(S)SR^\circ$; $-(CH_2)_{0-4}SC(O)R^\circ$; $-(CH_2)_{0-4}C(O)N(R^\circ)_2$; $-C(S)N(R^\circ)_2$; $-C(S)SR^\circ$; $-SC(S)SR^\circ$, $-(CH_2)_{0-4}OC(O)N(R^\circ)_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2N(R^\circ)_2$; $-(CH_2)_{0-4}S(O)R^\circ$; $-N(R^\circ)S(O)_2N(R^\circ)_2$; $-N(R^\circ)S(O)_2R^\circ$; $-N(OR^\circ)R^\circ$; $-C(NH)N(R^\circ)_2$; $-Si(R^\circ)_3$; $-OSi(R^\circ)_3$; $-P(R^\circ)_2$; $-P(OR^\circ)_2$; $-OP(R^\circ)_2$; $-OP(OR^\circ)_2$; $-N(R^\circ)P(R^\circ)_2$; $-B(R^\circ)_2$; $-OB(R^\circ)_2$; $-P(O)(R^\circ)_2$; $-OP(O)(R^\circ)_2$; $-N(R^\circ)P(O)(R^\circ)_2$; $-(C_{1-4}$ straight or branched alkylene)$O-N(R^\circ)_2$; or $-(C_{1-4}$ straight or branched alkylene)$C(O)O-N(R^\circ)_2$; wherein each $R^\circ$ may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, $-CH_2-(C_{6-14}$ aryl), $-O(CH_2)_{0-1}(C_{6-14}$ aryl), $-CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^\circ$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C_{1-4}$ straight or branched alkylene)$C(O)OR^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include $=O$ and $=S$.

Suitable divalent substituents are the following: $=O$, $=S$, $=NNR^*_2$, $=NNHC(O)R^*$, $=NNHC(O)OR^*$, $=NNHS(O)_2R^*$, $=NR^*$, $=NOR^*$, $-O(C(R^*_2))_{2-3}O-$, or $-S(C(R^*_2))_{2-3}S-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: $-O(CR^*_2)_{2-3}O-$, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of $R^*$ are halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, and sulfur.

In some embodiments, suitable substituents on a substitutable nitrogen are —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R† are independently halogen, —R•, -(haloR•), —OH, —OR•, —O(haloR•), —CN, —C(O)OH, —C(O)OR•, —NH$_2$, —NHR•, —NR•$_2$, or —NO$_2$, wherein each R• is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Subject: As used herein, the term "subject" or "test subject" refers to any organism to which a provided compound or composition is administered in accordance with the present disclosure e.g., for experimental, diagnostic, prophylactic, and/or therapeutic purposes. Typical subjects include animals (e.g., mammals such as mice, rats, rabbits, non-human primates, and humans; insects; worms; etc.) and plants. In some embodiments, a subject may be suffering from, and/or susceptible to a disease, disorder, and/or condition. In some embodiments, a subject is a human.

Susceptible to: An individual who is "susceptible to" a disease, disorder, and/or condition is one who has a higher risk of developing the disease, disorder, and/or condition than does a member of the general public. In some embodiments, an individual who is susceptible to a disease, disorder and/or condition may not have been diagnosed with the disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

Therapeutic agent: As used herein, the phrase "therapeutic agent" refers to an agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutic regimen: A "therapeutic regimen", as that term is used herein, refers to a dosing regimen whose administration across a relevant population may be correlated with a desired or beneficial therapeutic outcome.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unit dose: The expression "unit dose" as used herein refers to an amount administered as a single dose and/or in a physically discrete unit of a pharmaceutical composition. In many embodiments, a unit dose contains a predetermined quantity of an active agent. In some embodiments, a unit dose contains an entire single dose of the agent. In some embodiments, more than one unit dose is administered to achieve a total single dose. In some embodiments, administration of multiple unit doses is required, or expected to be required, in order to achieve an intended effect. A unit dose may be, for example, a volume of liquid (e.g., an acceptable carrier) containing a predetermined quantity of one or more therapeutic agents, a predetermined amount of one or more therapeutic agents in solid form, a sustained release formulation or drug delivery device containing a predetermined amount of one or more therapeutic agents, etc. It will be appreciated that a unit dose may be present in a formulation that includes any of a variety of components in addition to the therapeutic agent(s). For example, acceptable carriers (e.g., pharmaceutically acceptable carriers), diluents, stabilizers, buffers, preservatives, etc., may be included as described infra. It will be appreciated by those skilled in the art, in many embodiments, a total appropriate daily dosage of a particular therapeutic agent may comprise a portion, or a plurality, of unit doses, and may be decided, for example, by the attending physician within the scope of sound medical judgment. In some embodiments, the specific effective dose level for any particular subject or organism may depend upon a variety of factors including the disorder being treated and the severity of the disorder; activity of specific active compound employed; specific composition employed; age, body weight, general health, sex and diet of the subject; time of administration, and rate of excretion of the specific active compound employed; duration of the treatment; drugs and/ or additional therapies used in combination or coincidental with specific compound(s) employed, and like factors well known in the medical arts.

Unsaturated: The term "unsaturated" as used herein, means that a moiety has one or more units of unsaturation.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

Unless otherwise specified, salts, such as pharmaceutically acceptable acid or base addition salts, stereoisomeric forms, and tautomeric forms, of provided compound are included.

Unless otherwise clear from context, in the present disclosure, (i) the term "a" may be understood to mean "at least one"; (ii) the term "or" may be understood to mean "and/or"; (iii) the terms "comprising" and "including" may be understood to encompass itemized components or steps whether presented by themselves or together with one or more additional components or steps; and (iv) the terms "about" and "approximately" may be understood to permit standard variation as would be understood by those of ordinary skill in the art; and (v) where ranges are provided, endpoints are included.

2. Beta-Catenin

Beta-catenin is a protein that is important to many biological processes, e.g., the development of tissue in animals. As part of the Wingless and INT-1 (Wnt) signaling pathway, beta-catenin helps to regulate expression of genes, which among other things, are involved in cell differentiation, proliferation, and survival. Aberrant Wnt signaling and/or maintenance of beta-catenin levels underlies a number of human diseases including but not limited to cancer, diabetes, and obesity [Cell. 2012; 149(6): 1192-1205]. It is reported that when Wnt signaling is inactive, beta-catenin resides in a multicomponent destruction complex that includes the proteins Axin, adenomatous polypois coli (APC), casein kinase 1α (CK1α), and glycogen synthase kinase 3β (GSK3β). In the destruction complex, beta-catenin may be phosphorylated by CK1α and GSK3β. This consequently may tag beta-catenin for eventual ubiquitination and proteosomal degradation. It is also reported that when the Wnt signaling pathway is initiated at the cellular membrane by a ligand, a complex involving the proteins Frizzled and the low-density lipoprotein related receptor (LRP) is formed. This heterodimeric protein complex, reportedly, in turn recruits Axin to the membrane resulting in dissociation of the destruction complex and elevated levels of beta-catenin in the cytosol [Dev Cell. 2009; 18(1): 9-26].

It is reported that beta-catenin that has accumulated in the cytosol may subsequently translocate to the nucleus where it may influence the expression of genes through a transcription activation complex. In some reports, in this complex, beta-catenin associates with several proteins including different transcription factors, histone modifiers, and transcription co-activators including B-cell CLL/lymphoma 9 (BCL9) [Dev Cell. 2009; 18(1):9-26]. In some instances, BCL9 serves as a bridge between beta-catenin and another protein, pygopus; and studies have demonstrated that BCL9 mediated recruitment of pygopus is necessary for Wnt signaling [Nat Rev Mol Cell Biol. 2009; 10(4): 276-286., Cell. 2002; 109(1): 47-60].

In some embodiments, one strategy to address diseases related to Wnt signaling pathway is to affect the ability of β-catenin to interact with other components in the signaling pathway. Reported protein crystal structures reveal that β-catenin interacts with proteins such as Axin and BCL9 in the destruction complex and transcription complex, respectively. In some reported structures, Axin and BCL9 bind to β-catenin through interactions mediated by their α-helical Axin-CBD and HD2 domains, respectively. [Genes Dev. 2003; 17(22): 2753-2764, Mol Cell. 2006; 24(2): 293-300]. While some small molecules have been reported to modulate β-catenin protein-protein interactions [Curr Pharm Des. 2012; 19(40): 634-664], the present disclosure notes that it is generally challenging for small molecules to address interaction sites with extended surface areas as is the case between β-catenin and Axin or BCL9.

In some embodiments, one or more beta-catenin site interacting with Axin are those reported in, e.g., Xing et al., Genes & Development 2003, 17(22), 2753-2764. In some embodiments, interactions between beta-catenin and Axin comprise residues 469-481 of *Xenopus* Axin-CBD domain (which is highly homologous to human Axin) forming a continuous alpha helix that fits into a groove of beta-catenin formed by the armadillo repeats. It is reported that Axin-CBD specifically interacts with the third helices of beta-catenin armadillo repeats 3 and 4. As reported, the beta-catenin/Axin interface is rather hydrophobic. Reported interactions between beta-catenin and *Xenopus* Axin comprises hydrogen bonding (e.g. side chain of H476 in *Xenopus* Axin and H260 of beta-catenin), salt bridges (e.g. side chain or D474 in *Xenopus* Axin and K292 of beta-catenin), and/or hydrophobic interaction (e.g. I472, L473, V477, V480, M481 reside on helix surface complementary to a shallow beta-catenin groove; L473 in *Xenopus* Axin sits in a shallow hydrophobic pocket formed by F253, F293, and Y254 of beta-catenin; H476 and V477 of *Xenopus* Axin interact with T257 and I296 of beta-catenin respectively, P469 and M481 of *Xenopus* Axin interact with S250 and W338 of beta catenin, respectively). In some embodiments, residues 469-481 of *Xenopus* Axin are the human Axin residues corresponding to residues 469-481 in *Xenopus* Axin.

In some embodiments, one or more beta-catenin site interacting with BCL9 are those reported in, e.g., Sampietro et al., Molecular Cell, 24(2), 293-300, 2006; Kawamoto et al., Biochemistry 2009, 48, 9534-9541; etc. In some embodiments, interactions between beta-catenin and BCL9 comprise that residues 352-374 of human BCL9-HD2 form a continuous alpha helix that packs against a groove formed between helices 2 and 3 of armadillo repeat 1 of beta-catenin and forms a helix bundle with the three helices of the first armadillo repeat of beta-catenin. In some embodiments, interactions between beta-catenin and BCL9 comprises hydrogen bonding, salt bridge, (e.g., the N-terminal side of the BCL9 helix with conserved residues in beta-catenin that form an acidic knob (e.g., H358 and R359 of BCL9 forming hydrogen bond and salt bridge with D162 and D164 of beta-catenin, respectively; S362 of BCL9 potentially forming hydrogen bond with H358 of beta-catenin; etc.; see Sampietro 2006)), and/or hydrophobic interaction (e.g., the C-terminal side of BCL9 helix with a conserved beta-catenin surface, involving L366/L369/I373 in BCL9 and residues L156/L159/L178 of beta-catenin; M174 of beta-catenin protruding into hydrophobic interface; etc.; see Sampietro 2006)).

Among other things, the present disclosure provides stapled peptides that offer another therapeutic modality for targets such as β-catenin. In some embodiments, compared to small molecules, stapled peptides may better address the challenges of targeting protein-protein interactions. In some embodiments, stapled peptides present polypeptide side chain functional groups in a desired conformation for competing protein-protein interactions. Additionally or alternatively, stapled peptides in some embodiments may possess improved bioactivity, proteolytic stability, and cell permeability, than peptides without staples.

3. Peptide Agents

In some embodiments, provided agents are stapled peptides. In some embodiments, the present disclosure provides stapled peptides that interact with beta-catenin. In some embodiments, the present disclosure provides stapled peptides that interact with beta-catenin and compete with Axin for interaction with beta-catenin. In some embodiments, the present disclosure provides stapled peptides that physically interact with one or more beta-catenin amino acid residues that physically interact with Axin.

Among other things, provided stapled peptides can modulate one or more functions of beta-catenin, including those involved in Wnt/beta-catenin pathway. In some embodiments, provided stapled peptides are useful for treating various conditions, disorders, and/or diseases that are associated with beta-catenin. Exemplary structural elements of provided stapled peptides are described herein.

a. Amino Acid Sequence

In some embodiments, the present disclosure provides amino acid sequences for stapled peptides. In some embodiments, stapled peptides comprising provided amino acid sequences interact with beta-catenin, e.g., as determined by one or more methods as described in the present disclosure. In some embodiments, stapled peptides comprising provided amino acid sequences interact with beta-catenin at one or more beta-catenin sites that interact with Axin, e.g., as determined by one or more methods as described in the present disclosure.

As appreciated by those skilled in the art reading the present disclosure, various amino acid sequences, including those specifically exemplified in the present disclosure and appropriate variants thereof, can be incorporated into provided stapled peptides. In some embodiments, a provided amino acid sequence is derived from a human Axin sequence. In some embodiments, a provided amino acid sequence is derived from the beta-catenin binding region of Axin (see Xing, et al.). In some embodiments, a provided amino acid sequence is derived from Axin sequence that interacts with beta-catenin. In some embodiments, a provided amino acid sequence comprises a sequence of Axin or a variant thereof. In some embodiments, a provided amino acid sequence comprises a sequence of the beta-catenin binding region of Axin or a variant thereof. In some embodiments, a provided amino acid sequence comprises an Axin sequence that interacts with beta-catenin or a variant thereof. In some embodiments, a provided amino acid sequence comprises a set of Axin residues, or a homolog thereof. In some embodiments, the set of Axin residues are those that interact with beta-catenin. In some embodiments, the set of Axin residues comprises H476, D474, I472, L473, V477, V480, P469 and M481 of *Xenopus* Axin. In some embodiments, the set of Axin residues comprises or is L473, D474, and H476 of *Xenopus* Axin. In some embodiments, the set of Axin residues comprises H476 of *Xenopus* Axin. In some embodiments, the set of Axin residues comprises D474 of *Xenopus* Axin. In some embodiments, the set of Axin residues comprises I472 of *Xenopus* Axin. In some embodiments, the set of Axin residues comprises L473 of *Xenopus* Axin. In some embodiments, the set of Axin residues comprises V477 of *Xenopus* Axin. In some embodiments, the set of Axin residues comprises V480 of *Xenopus* Axin. In some embodiments, the set of Axin residues comprises P469 of *Xenopus* Axin. In some embodiments, the set of Axin residues comprises M481 of *Xenopus* Axin. In some embodiments, a homolog of a set of Axin residues is a set of Axin residues wherein one or more amino acid of the set are independently replaced with its or their homologs.

In some embodiments, a homolog of an amino acid is a naturally occurring or non-naturally occurring amino acid that has one or more similar properties to the amino acid, for example, that is typically classified as similar to one another as "hydrophobic", "hydrophilic", "basic", or "acidic" amino acids, and/or as having "polar", "non-polar", "hydrophobic", "hydrophilic", "basic", "acidic", and/or "similar size" side chains. For example, in some embodiments, depending on context, a homolog of leucine can be an optionally substituted (substituted or unsubstituted) amino acid selected from isoleucine, alanine, homoleucine, 3-cyclobutylalanine, alpha-neopentylglycine, 3-cyclopropylalanine, alpha-methylleucine, and 3-cyclohexylalanine; a homolog of isoleucine can be an optionally substituted amino acid selected from alanine, leucine, homoleucine, 3-cyclobutylalanine, alpha-neopentylglycine, 3-cyclopropylalanine, L-alloisoleucine, and alpha-methylleucine; a homolog of phenylalanine can be an optionally substituted amino acid residue selected from tryptophan, tyrosine, 3-(1-naphthylalanine), 3-(2-naphthylalanine), 2-chlorophenylalanine, 3-chlorophenylalanine, 4-chlorophenylalanine, 4-tert-butylphenylalanine, O-methyl tyrosine, homophenylalanine, 4-fluorophenylalanine, 4-methylphenylalanine, 4-bromophenylalanine, 4-phenyl-L-phenylalanine, 5-chlorotryptophan, 5-hydroxytryptophan, 4-trifluoromethylphenylalanine, 4-guanidino-L-phenylalanine, 2-quinoyl-L-alanine, 3-cyclobutylalanine, alpha-neopentylglycine, and L-2-aminoadipic acid; etc.

In some embodiments, a homolog of a hydrophobic amino acid is another hydrophobic amino acid. In some embodiments, a homolog of an amino acid comprising a hydrophobic side chain is another hydrophobic amino acid comprising a hydrophobic side chain.

In some embodiments, a homolog of a hydrophilic amino acid is another hydrophilic amino acid. In some embodiments, a homolog of an amino acid comprising a hydrophilic side chain is another hydrophilic amino acid comprising a hydrophilic side chain.

In some embodiments, a homolog of a basic amino acid is another basic amino acid. In some embodiments, a homolog of an amino acid comprising a basic side chain is another basic amino acid comprising a basic side chain.

In some embodiments, a homolog of an acidic amino acid is another acidic amino acid. In some embodiments, a homolog of an amino acid comprising an acidic side chain is another acidic amino acid comprising an acidic side chain.

In some embodiments, a homolog of an aromatic amino acid is another aromatic amino acid. In some embodiments, a homolog of an amino acid comprising an aromatic side chain is another aromatic amino acid comprising an aromatic side chain.

In some embodiments, a homolog of a polar amino acid is another polar amino acid. In some embodiments, a homolog of an amino acid comprising a polar side chain is another polar amino acid comprising a polar side chain.

In some embodiments, a homolog of a non-polar amino acid is another non-polar amino acid. In some embodiments, a homolog of an amino acid comprising a non-polar side chain is another non-polar amino acid comprising a non-polar side chain.

In some embodiments, a homolog of an amino acid is sterically similar to the amino acid. In some embodiments, a homolog of an amino acid comprises a side chain that has a similar size to the side chain of the amino acid.

In some embodiments, when an amino acid in a provided agent, e.g., a provided stapled peptide, is replaced with its homolog, one or more properties or activities of the provided agent is not significantly decreased. For example, in some embodiments, when an amino acid in a provided stapled peptide is replaced with its homolog, interaction of the stapled peptide with beta-catenin is not significantly decreased. In some embodiments, an interaction is not significantly decreased in that FP EC50 (e.g., as illustrated in Table 2 measured by competition fluorescence polarization assay described in the present disclosure (competition with FITC-StAx-33 from Grossmann et al. PNAS 109 17942-17947 (FITC-PEG1-PQ-S5-ILD-S5-HVRRVWR (SEQ ID NO: 1), hydrocarbon staple formed by two S5 via olefin metathesis) or FITC-bA-PQ-S5-ILD-S5-HVRRVWR (SEQ ID NO: 3) (hydrocarbon staple formed by two S5 via olefin metathesis)) after replacement of an amino acid with its homolog does not increase more than 2, 3, 4, 5, 6, 7, 8, 9, 10, 15, 20, 30, 40, 50, 60, 70, 80, 90, 100, 200, 300, 400, 500, 1000 fold. In some embodiments, an increase is no more than 10 fold. In some embodiments, an increase is no more than 20 fold. In some embodiments, an increase is no more than 30 fold. In some embodiments, an increase is no more than 40 fold. In some embodiments, an increase is no more than 50 fold. In some embodiments, an increase is no more than 60 fold. In some embodiments, an increase is no more than 70 fold. In some embodiments, an increase is no more than 80 fold. In some embodiments, an increase is no more than 90 fold. In some embodiments, an increase is no more than 100 fold. In some embodiments, an increase is no more than 200 fold. In some embodiments, an increase is no more than 500 fold. In some embodiments, as demonstrated in the present disclosure, replacement of an amino acid with a homolog improves one or more properties and/or activities of a provided stapled peptide. For example, in some embodiments, when an amino acid in a provided stapled peptide is replaced with its homolog, interaction of the stapled peptide with beta-catenin is enhanced. In some embodiments, an interaction is enhanced in that FP EC50 (e.g., as illustrated in Table 2 measured by competition fluorescence polarization assay described in the present disclosure (competition with FITC-StAx-33 from Grossmann et al. PNAS 109 17942-17947 (FITC-PEG1-PQ-S5-ILD-S5-HVRRVWR (SEQ ID NO: 1), hydrocarbon staple formed by two S5 via olefin metathesis) or FITC-bA-PQ-S5-ILD-S5-HVRRVWR (SEQ ID NO: 3) (hydrocarbon staple formed by two S5 via olefin metathesis)) after replacement of an amino acid with its homolog is decreased by at least 2, 3, 4, 5, 6, 7, 8, 9, 10, 15, 20, 30, 40, 50, 60, 70, 80, 90, 100, 200, 300, 400, 500, 1000 fold. In some embodiments, a decrease is at least 2 fold (no more 2 of the original value). In some embodiments, a decrease is at least 3 fold. In some embodiments, a decrease is at least 4 fold. In some embodiments, a decrease is at least 5 fold. In some embodiments, a decrease is at least 6 fold. In some embodiments, a decrease is at least 7 fold. In some embodiments, a decrease is at least 8 fold. In some embodiments, a decrease is at least 9 fold. In some embodiments, a decrease is at least 10 fold. In some embodiments, a decrease is at least 15 fold. In some embodiments, a decrease is at least 20 fold. In some embodiments, a decrease is at least 30 fold. In some embodiments, a decrease is at least 40 fold. In some embodiments, a decrease is at least 50 fold. In some embodiments, a decrease is at least 60 fold. In some embodiments, a decrease is at least 70 fold. In some embodiments, a decrease is at least 80 fold. In some embodiments, a decrease is at least 90 fold. In some embodiments, a decrease is at least 100 fold.

Homologs of amino acids, both naturally occurring and non-naturally occurring, may be utilized in amino acid sequences in accordance with the present disclosure, including those known in the art.

In some embodiments, a homolog of leucine is an optionally substituted amino acid selected from isoleucine, alanine, homoleucine, 3-cyclobutylalanine, alpha-neopentylglycine, and 3-cyclopropylalanine. In some embodiments, a homolog of leucine is isoleucine, alanine, homoleucine, 3-cyclobutylalanine, alpha-neopentylglycine, or 3-cyclopropylalanine. In some embodiments, a homolog of leucine is an optionally substituted amino acid selected from isoleucine, alpha-neopentylglycine, homoleucine, 3-cyclobutylalanine, 3-cyclopropylalanine. In some embodiments, a homolog of leucine is an amino acid selected from isoleucine, alpha-neopentylglycine, homoleucine, 3-cyclobutylalanine, 3-cyclopropylalanine. In some embodiments, a homolog of leucine is an optionally substituted amino acid selected from isoleucine, alpha-neopentylglycine, homoleucine, and 3-cyclobutylalanine. In some embodiments, a homolog of leucine is an amino acid selected from isoleucine, alpha-neopentylglycine, homoleucine, and 3-cyclobutylalanine. In some embodiments, a homolog of leucine is an optionally substituted amino acid selected from homoleucine and cyclobutylalanine. In some embodiments, a homolog of leucine is an amino acid selected from homoleucine and cyclobutylalanine.

In some embodiments, a homolog of isoleucine is an optionally substituted amino acid selected from leucine, homoleucine, 3-cyclobutylalanine, alpha-neopentylglycine, 3-cyclopropylalanine, and L-alloisoleucine. In some embodiments, a homolog of isoleucine is an amino acid selected from leucine, homoleucine, 3-cyclobutylalanine, alpha-neopentylglycine, 3-cyclopropylalanine, and L-alloisoleucine. In some embodiments, a homolog of isoleucine is an optionally substituted amino acid selected from leucine and cyclobutylalanine. In some embodiments, a homolog of isoleucine is an amino acid selected from leucine and cyclobutylalanine.

In some embodiments, a homolog of phenylalanine is selected from an optionally substituted amino acid selected from tryptophan, 3-(1-naphthylalanine), 3-(2-naphthylalanine), 2-chlorophenyalanine, 3-chlorophenylalanine, 4-chlorophenylalanine, 4-tert-butylphenylalanine, O-methyl tyrosine, and homophenylalanine. In some embodiments, a homolog of phenylalanine is selected from an amino acid selected from tryptophan, 3-(1-naphthylalanine), 3-(2-naphthylalanine), 2-chlorophenyalanine, 3-chlorophenylalanine, 4-chlorophenylalanine, 4-tert-butylphenylalanine, O-methyl tyrosine, and homophenylalanine. In some embodiments, a homolog of phenylalanine is an optionally substituted amino acid selected from 3-(1-naphthylalanine), 3-(2-naphthylalanine), 3-chlorophenylalanine, 4-chlorophenylalanine and O-methyl tyrosine. In some embodiments, a homolog of phenylalanine is an amino acid selected from 3-(1-naphthylalanine), 3-(2-naphthylalanine), 3-chlorophenylalanine, 4-chlorophenylalanine and O-methyl tyrosine.

In some embodiments, a provided amino acid sequence is or comprises an amino acid sequence or a variant of a peptide selected from Table 1. In some embodiments, a provided amino acid sequence is or comprises an amino acid sequence or a variant of an amino acid sequence described in Sampietro et al., Molecular Cell, 24(2), 293-300, 2006; or Kawamoto et al., Biochemistry 2009, 48, 9534-9541; or WO2017062518; which amino acid sequences are incorporated herein by reference. In some embodiments, a provided amino acid sequence preferably comprises a set of Axin residues, or a homolog thereof, as described in the present disclosure. In some embodiments, a provided amino acid sequence comprises one or more elements reported in the art as required for affinity binding to beta-catenin, e.g., those reported in Xing, et al.

In some embodiments, a provided amino acid sequence comprises a set of Axin residues, or a homolog thereof, as described in the present disclosure. In some embodiments, a homolog of a set of Axin residues is a set of Axin residues wherein one or more amino acid of the set are independently replaced with its or their homologs. In some embodiments, a provided amino acid sequence comprises H476, D474, I472, L473, V477, V480, P469 and M481 of *Xenopus* Axin, or one or more homologs thereof. In some embodiments, a provided amino acid sequence comprises L473, D474, and H476 of *Xenopus* Axin, or one or more homologs thereof. In some embodiments, a provided amino acid sequence comprises H476 of *Xenopus* Axin, or a homolog thereof. In some embodiments, a provided amino acid sequence comprises D474 of *Xenopus* Axin, or a homolog thereof. In some embodiments, a provided amino acid sequence comprises I472 of *Xenopus* Axin, or a homolog thereof. In some embodiments, a provided amino acid sequence comprises L473 of *Xenopus* Axin, or a homolog thereof. In some embodiments, a provided amino acid sequence comprises V477 of *Xenopus* Axin, or a homolog thereof. In some embodiments, a provided amino acid sequence comprises V480 of *Xenopus* Axin, or a homolog thereof. In some embodiments, a provided amino acid sequence comprises P469 of *Xenopus* Axin, or a homolog thereof. In some embodiments, a provided amino acid sequence comprises M481 of *Xenopus* Axin, or a homolog thereof.

In some embodiments, a provided amino acid sequence comprises H476, D474, I472, L473, V477, V480, P469 and M481 of *Xenopus* Axin. In some embodiments, a provided amino acid sequence comprises L473, D474, and H476 of *Xenopus* Axin. In some embodiments, a provided amino acid sequence comprises H476 of *Xenopus* Axin. In some embodiments, a provided amino acid sequence comprises D474 of *Xenopus* Axin. In some embodiments, a provided amino acid sequence comprises I472 of *Xenopus* Axin. In some embodiments, a provided amino acid sequence comprises L473 of *Xenopus* Axin. In some embodiments, a provided amino acid sequence comprises V477 of *Xenopus* Axin. In some embodiments, a provided amino acid sequence comprises V480 of *Xenopus* Axin. In some embodiments, a provided amino acid sequence comprises P469 of *Xenopus* Axin. In some embodiments, a provided amino acid sequence comprises M481 of *Xenopus* Axin.

In some embodiments, a provided amino acid sequence is one that, when incorporated into a stapled peptide, the stapled peptide interacts with beta-catenin. In some embodiments, a provided amino acid sequence is one that, when incorporated into a stapled peptide, the stapled peptide interacts with beta-catenin and competes with beta-catenin interaction with Axin. In some embodiments, a provided amino acid sequence is one that, when incorporated into a stapled peptide, the stapled peptide interacts with beta-catenin and competes with beta-catenin interaction with FITC-StAx-33 from Grossmann et al. PNAS 109 17942-17947, and/or FITC-bA-PQ-S5-ILD-S5-HVRRVWR (SEQ ID NO: 3) (hydrocarbon staple formed by two S5 via olefin metathesis). Various assays for assessing interactions with beta-catenin can be utilized in accordance with the present disclosure, including those described in the examples of the present disclosure.

In some embodiments, a provided amino acid sequence is homologous to a sequence of Axin. In some embodiments, a provided amino acid sequence is homologous to a sequence of the beta-catenin binding region of Axin. In some embodiments, a provided amino acid sequence is homologous to a sequence of Axin that interacts with beta-catenin. In some embodiments, a provided amino acid sequence is homologous to a sequence of an Axin helix that interacts with beta-catenin. In some embodiments, a provided amino acid sequence is homologous to a sequence of a peptide described in Table 1. In some embodiments, a provided amino acid sequence is homologous to a sequence of a peptide described in Xing et al.

In some embodiments, a provided amino acid sequence is homologous to a reference sequence in that the two sequences are at least 25%, 30/a, 35%, 40/a, 45%, 50%, 55%, 60%, 65%, 70%, 75%, 80%, 85%, 90%, 91%, 92%, 93%, 94%, 95%, 96%, 97%, 98%, or 99% identical. In some embodiments, a provided amino acid sequence is homologous to a reference sequence in that the two sequences are at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, or 99% similar (e.g., containing residues with related chemical properties at corresponding positions). In some embodiments, two residues are considered similar is both of them are hydrophobic, hydrophilic, polar, non-polar, acidic or basic. In some embodiments, two residues are considered similar in that one residue is a homolog of the other residue. In some embodiments, a percentage is at least 25%. In some embodiments, a percentage is at least 30%. In some embodiments, a percentage is at least 35%. In some embodiments, a percentage is at least 40%. In some embodiments, a percentage is at least 45%. In some embodiments, a percentage is at least 50%. In some embodiments, a percentage is at least 55%. In some embodiments, a percentage is at least 60%. In some embodiments, a percentage is at least 65%. In some embodiments, a percentage is at least 70%. In some embodiments, a percentage is at least 75%. In some embodiments, a percentage is at least 80%. In some embodiments, a percentage is at least 85%. In some embodiments, a percentage is at least 90%. In some embodiments, a percentage is at least 91%. In some embodiments, a percentage is at least 92%. In some embodiments, a percentage is at least 93%. In some embodiments, a percentage is at least 94%. In some embodiments, a percentage is at least 95%. In some embodiments, a percentage is at least 96%. In some embodiments, a percentage is at least 97%. In some embodiments, a percentage is at least 98%. In some embodiments, a percentage is at least 99%.

Provided amino acid sequences and stapled peptides can be various lengths, e.g., 2-100, 5-50, 5-40, 5-30, a range from and including 2, 3, 4, 5, 6, or 7 to and including 8, 9, 10, 11, 12, 13, 14, 15, 16, 17, 18, 19, 20, 21, 22, 23, 24 or 25, 5, 6, 7, 8, 9, 10, 11, 12, 13, 14, 15, 16, 17, 18, 19, 20, 21, 22, 23, 24, 25, 26, 27, 38, 29, or 30 amino acid residues.

In some embodiments, a length is at least 5 amino acid residues. In some embodiments, a length is at least 6 amino acid residues. In some embodiments, a length is at least 7 amino acid residues. In some embodiments, a length is at least 8 amino acid residues. In some embodiments, a length is at least 9 amino acid residues. In some embodiments, a length is at least 10 amino acid residues. In some embodiments, a length is at least 11 amino acid residues. In some embodiments, a length is at least 12 amino acid residues. In some embodiments, a length is at least 13 amino acid residues. In some embodiments, a length is at least 14 amino acid residues. In some embodiments, a length is at least 15 amino acid residues. In some embodiments, a length is at least 16 amino acid residues. In some embodiments, a length is at least 17 amino acid residues. In some embodiments, a length is at least 18 amino acid residues. In some embodiments, a length is at least 19 amino acid residues. In some embodiments, a length is at least 20 amino acid residues. In some embodiments, a length is at least 21 amino acid residues. In some embodiments, a length is at least 22 amino acid residues. In some embodiments, a length is at least 23 amino acid residues. In some embodiments, a length is at least 24 amino acid residues. In some embodiments, a length is at least 25 amino acid residues.

In some embodiments, a length is 5 amino acid residues. In some embodiments, a length is 6 amino acid residues. In some embodiments, a length is 7 amino acid residues. In some embodiments, a length is 8 amino acid residues. In some embodiments, a length is 9 amino acid residues. In some embodiments, a length is 10 amino acid residues. In some embodiments, a length is 11 amino acid residues. In some embodiments, a length is 12 amino acid residues. In some embodiments, a length is 13 amino acid residues. In some embodiments, a length is 14 amino acid residues. In some embodiments, a length is 15 amino acid residues. In some embodiments, a length is 16 amino acid residues. In some embodiments, a length is 17 amino acid residues. In some embodiments, a length is 18 amino acid residues. In some embodiments, a length is 19 amino acid residues. In some embodiments, a length is 20 amino acid residues. In some embodiments, a length is 21 amino acid residues. In some embodiments, a length is 22 amino acid residues. In some embodiments, a length is 23 amino acid residues. In some embodiments, a length is 24 amino acid residues. In some embodiments, a length is 25 amino acid residues.

In some embodiments, a length is no more than 17 amino acid residues. In some embodiments, a length is no more than 18 amino acid residues. In some embodiments, a length is no more than 19 amino acid residues. In some embodiments, a length is no more than 20 amino acid residues. In some embodiments, a length is no more than 21 amino acid residues. In some embodiments, a length is no more than 22 amino acid residues. In some embodiments, a length is no more than 23 amino acid residues. In some embodiments, a length is no more than 24 amino acid residues. In some embodiments, a length is no more than 25 amino acid residues. In some embodiments, a length is no more than 26 amino acid residues. In some embodiments, a length is no more than 27 amino acid residues. In some embodiments, a length is no more than 28 amino acid residues. In some embodiments, a length is no more than 29 amino acid residues. In some embodiments, a length is no more than 30 amino acid residues. In some embodiments, a length is no more than 35 amino acid residues. In some embodiments, a length is no more than 40 amino acid residues. In some embodiments, a length is no more than 50 amino acid residues.

Both naturally occurring and non-naturally occurring amino acids can be utilized in accordance with the present disclosure. In some embodiments, an amino acid is a compound comprising an amino group that can form an amide group with a carboxyl group and a carboxyl group.

In some embodiments, an amino acid is a compound having the structure of formula A-I:

$NH(R^{a1})$-$L^{a1}$-$(R^{a2})(R^{a3})$-$L^{a2}$-COOH,    A-I or a salt thereof, wherein:
  each of $R^{a1}$, $R^{a2}$, $R^{a3}$ is independently -$L^a$-R';
  each of $L^a$, $L^{a1}$ and $L^{a2}$ is independently L;
  each L is independently a covalent bond, or an optionally substituted, bivalent $C_1$-$C_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;
  each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
  each R' is independently —R, —C(O)R, —CO$_2$R, or —SO$_2$R;
  each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
  two R groups are optionally and independently taken together to form a covalent bond, or:
  two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or
  two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, $L^{a1}$ is a covalent bond. In some embodiments, a compound of formula A-1 is of the structure $NH(R^{a1})$—$C(R^{a2})(R^{a3})$-$L^{a2}$-COOH.

In some embodiments, $L^{a2}$ is a covalent bond. In some embodiments, a compound of formula A-1 is of the structure $NH(R^{a1})$—$C(R^{a2})(R^{a3})$-$L^{a2}$-COOH.

In some embodiments, $L^{a1}$ is a covalent bond and $L^{a2}$ is a covalent bond. In some embodiments, a compound of formula A-1 is of the structure $NH(R^{a1})$—$C(R^{a2})(R^{a3})$—COOH.

In some embodiments, $L^a$ is a covalent bond. In some embodiments, R' is R. In some embodiments, $R^{a1}$ is R, wherein R is as described in the present disclosure. In some embodiments, $R^{a2}$ is R, wherein R is as described in the present disclosure. In some embodiments, $R^3$ is R, wherein R is as described in the present disclosure. In some embodiments, each of $R^{a1}$, $R^{a2}$, and $R^{a3}$ is independently R, wherein R is as described in the present disclosure.

In some embodiments, $R^{a1}$ is hydrogen. In some embodiments, $R^{a2}$ is hydrogen. In some embodiments, $R^{a3}$ is hydrogen. In some embodiments, $R^{a1}$ is hydrogen, and at least one of $R^{a2}$ and $R^{a3}$ is hydrogen. In some embodiments, $R^{a1}$ is hydrogen, one of $R^{a2}$ and $R^{a3}$ is hydrogen, and the other is not hydrogen.

In some embodiments, $R^{a1}$ is -$L^a$-R, wherein R is as described in the present disclosure. In some embodiments, $R^{a2}$ is -$L^a$-R, wherein R is an optionally substituted group selected from $C_{3-30}$ cycloaliphatic, $C_{5-30}$ aryl, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon. In some embodiments, $R^{a2}$ is -$L^a$-R, wherein R is an optionally substituted group selected from $C_{6-30}$ aryl and 5-30 membered heteroaryl having 1-10 heteroatoms independently selected from oxygen, nitrogen, sulfur, phosphorus and silicon. In some embodiments, $R^{a2}$ is a side chain of an amino acid. In some embodiments, $R^{a2}$ is a side chain of a standard amino acid.

In some embodiments, $R^{a3}$ is -$L^a$-R, wherein R is as described in the present disclosure. In some embodiments, $R^{a3}$ is -$L^a$-R, wherein R is an optionally substituted group selected from $C_{3-30}$ cycloaliphatic, $C_{5-30}$ aryl, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon. In some embodiments, $R^{a3}$ is -$L^a$-R, wherein R is an optionally substituted group selected from $C_{6-30}$ aryl and 5-30 membered heteroaryl having 1-10 heteroatoms independently selected from oxygen, nitrogen, sulfur, phosphorus and silicon. In some embodiments, $R^{a3}$ is a side chain of an amino acid. In some embodiments, $R^{a3}$ is a side chain of a standard amino acid.

In some embodiments, in an amino acid, neither of $R^{a2}$ and $R^{a3}$ is hydrogen, e.g., as in certain amino acids exemplified in the present disclosure for stapling. In some embodiments, one or both of $R^{a2}$ and $R^{a3}$ comprise an olefin group. An amino acid residue comprising an amino group may form a staple with another amino acid residue comprising an olefin group through, e.g., olefin metathesis of the olefin groups. In some embodiments, one of $R^{a2}$ and $R^{a3}$ comprises an olefin group. In some embodiments, one of $R^{a2}$ and $R^{a3}$ comprises an olefin group, and the other is optionally substituted $C_{1-4}$ alkyl. In some embodiments, one of $R^{a2}$ and $R^{a3}$ comprises an olefin group, and the other is methyl. In some embodiments, both $R^{a2}$ and $R^{a3}$ comprise an olefin group. In some embodiments, an olefin group is a terminal olefin group. In some embodiments, an olefin group is a terminal olefin group as in an allyl group. In some embodiments, an olefin group is a terminal olefin group as in an allyloxycarbonyl group. In some embodiments, $R^{a2}$ is an alkenyl group comprising a terminal olefin. In some embodiments, $R^{a3}$ is an alkenyl group comprising a terminal olefin. In some embodiments, $R^{a2}$ is —$(CH_2)_{1-10}$—CH=$CH_2$. In some embodiments, $R^{a2}$ is —$CH_2$—CH=$CH_2$. In some embodiments, $R^{a2}$ is —$(CH_2)_2$—CH=$CH_2$. In some embodiments, $R^{a2}$ is —$(CH_2)_3$—CH=$CH_2$. In some embodiments, $R^{a2}$ is —$(CH_2)_4$—CH=$CH_2$. In some embodiments, $R^{a2}$ is —$(CH_2)_5$—CH=$CH_2$. In some embodiments, $R^{a2}$ is —$(CH_2)_6$—CH=$CH_2$. In some embodiments, $R^{a2}$ is —$(CH_2)_7$—CH=$CH_2$. In some embodiments, $R^{a2}$ is —$(CH_2)_8$—CH=$CH_2$. In some embodiments, $R^{a3}$ is —$(CH_2)_{1-10}$—CH=$CH_2$. In some embodiments, $R^{a3}$ is —$CH_2$—CH=$CH_2$. In some embodiments, $R^{a3}$ is —$(CH_2)_2$—CH=$CH_2$. In some embodiments, $R^{a3}$ is —$(CH_2)_3$—CH=$CH_2$. In some embodiments, $R^{a3}$ is —$(CH_2)_4$—CH=$CH_2$. In some embodiments, $R^{a3}$ is —$(CH_2)_5$—CH=$CH_2$. In some embodiments, $R^{a3}$ is —$(CH_2)_6$—CH=$CH_2$. In some embodiments, $R^{a3}$ is —$(CH_2)_7$—CH=$CH_2$. In some embodiments, $R^{a3}$ is —$(CH_2)_8$—CH=$CH_2$.

In some embodiments, $R^{a2}$ and $R^{a3}$ are the same. In some embodiments, $R^{a2}$ and $R^{a3}$ are different.

In some embodiments, $L^a$ is L, wherein L is as described in the present disclosure. In some embodiments, $L^{a1}$ is L, wherein L is as described in the present disclosure. In some embodiments, $L^{a2}$ is L, wherein L is as described in the present disclosure.

In some embodiments, L is a covalent bond, or an optionally substituted, bivalent $C_{1-20}$, e.g., $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, or $C_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, L is a covalent bond. In some embodiments, L is an optionally substituted, bivalent $C_1$-$C_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, L is an optionally substituted, bivalent $C_1$-$C_{15}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, L is an optionally substituted, bivalent $C_1$-$C_{10}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—.

In some embodiments, at least one methylene group is replaced. In some embodiments, L is an optionally substituted, bivalent $C_3$-$C_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, L is an optionally substituted, bivalent $C_3$-$C_{15}$ aliphatic group wherein one or more methylene units of the aliphatic group are optionally and independently replaced with —C(R')$_2$—, -Cy-, —O—, —S—, —S—S—, —N(R')—, —C(S)—, —C(NR')—, —C(O)N(R')—, —N(R')C(O)N(R')—, —N(R')C(O)O—, —S(O)—, —S(O)$_2$—, —S(O)$_2$N (R')—, —C(O)S—, or —C(O)O—. In some embodiments, L is an optionally substituted, bivalent $C_3$-$C_{10}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—.

In some embodiments, L is an optionally substituted $C_{1-20}$ aliphatic wherein at least one methylene unit is replaced with —N(R')—. In some embodiments, L is an optionally substituted $C_{2-20}$ aliphatic wherein at least one methylene unit is replaced with —N(R')—. In some embodiments, L is an optionally substituted $C_{3-20}$ aliphatic wherein at least one methylene unit is replaced with —N(R')—. In some embodiments, $L^a$ is L, wherein L is an optionally substituted $C_{3-10}$ aliphatic wherein at least one methylene unit is replaced with —N(R')—. In some embodiments, only one methylene unit is replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, —N(R')— is —N(O(CO)OR), wherein R is as described in the present disclosure. In some embodiments, —N(R')— is —NAlloc-. In some embodiments, L is optionally substituted $C_{1-6}$ alkylene. In some embodiments, L is —(CH$_2$)$_2$—. In some embodiments, L is —(CH$_2$)$_3$—. In some embodiments, L is —(CH$_2$)$_4$—. In some embodiments, L is —(CH$_2$)$_5$—. In some embodiments, L is —(CH$_2$)$_6$—.

In some embodiments, one of $R^{2a}$ and $R^{3a}$ is -L-R', wherein at least one methylene unit of L is replaced with —N(R')—, wherein each of the variables is independently as described in the present disclosure. In some embodiments, both the R' of —N(R')— and the other of $R^{2a}$ and $R^{3a}$ are R and are taken together with their intervening atoms to form an optionally substituted ring as described in the present disclosure. In some embodiments, a formed ring has no additional heteroatom ring atoms other than the nitrogen atom. In some embodiments, a formed ring is saturated.

In some embodiments, one of $R^{2a}$ and $R^{3a}$ is -L-R', wherein at least one methylene unit of L is replaced with —N(R')C(O)O—, wherein each of the variables is independently as described in the present disclosure. In some embodiments, both the R' of —N(R')C(O)O— and the other of $R^{2a}$ and $R^{3a}$ are R and are taken together with their intervening atoms to form an optionally substituted ring as described in the present disclosure. In some embodiments, a formed ring has no additional heteroatom ring atoms other than the nitrogen atom. In some embodiments, a formed ring is saturated.

In some embodiments, one of $R^{2a}$ and $R^{3a}$ is —CH$_2$N(Alloc)CH$_3$. In some embodiments, one of $R^{2a}$ and $R^{3a}$ is —(CH$_2$)$_2$N(Alloc)CH$_3$. In some embodiments, one of $R^{2a}$ and $R^{3a}$ is —(CH$_2$)$_3$N(Alloc)CH$_3$.

In some embodiments, two or more of $R^{a1}$, $R^{a2}$, and $R^{a3}$ are R and are taken together to form an optionally substituted ring as described in the present disclosure.

In some embodiments, $R^{a1}$ and one of $R^{a2}$ and $R^{a3}$ are R and are taken together to form an optionally substituted 3-6 membered ring having no additional ring heteroatom other than the nitrogen atom to which $R^{a1}$ is bonded to. In some embodiments, a formed ring is a 5-membered ring as in proline.

In some embodiments, $R^{a2}$ and $R^{a3}$ are R and are taken together to form an optionally substituted 3-6 membered ring as described in the present disclosure. In some embodiments, $R^{a2}$ and $R^{a3}$ are R and are taken together to form an optionally substituted 3-6 membered ring having one or more nitrogen ring atom. In some embodiments, $R^{a2}$ and $R^{a3}$ are R and are taken together to form an optionally substituted 3-6 membered ring having one and no more than one ring heteroatom which is a nitrogen atom. In some embodiments, a ring is a saturated ring. In some embodiments, the nitrogen atom is optionally substituted with an alloc group (—N(Alloc)-).

In some embodiments, each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon. In some embodiments, -Cy- is an optionally substituted ring as described in the present disclosure, for example, for R and $Cy^L$, but is bivalent.

In some embodiments, -Cy- is monocyclic. In some embodiments, -Cy- is bicyclic. In some embodiments, -Cy- is polycyclic. In some embodiments, -Cy- is saturated. In some embodiments, -Cy- is partially unsaturated. In some embodiments, -Cy- is aromatic. In some embodiments, -Cy- comprises a saturated cyclic moiety. In some embodiments, -Cy-comprises a partially unsaturated cyclic moiety. In some embodiments, -Cy- comprises an aromatic cyclic moiety. In some embodiments, -Cy- comprises a combination of a saturated, a partially unsaturated, and/or an aromatic cyclic moiety. In some embodiments, -Cy- is 3-membered. In some embodiments, -Cy- is 4-membered. In some embodiments, -Cy- is 5-membered. In some embodiments, -Cy- is 6-membered. In some embodiments, -Cy- is 7-membered. In some embodiments, -Cy- is 8-membered. In some embodiments, -Cy- is 9-membered. In some embodiments, -Cy- is 10-membered. In some embodiments, -Cy- is 11-membered. In some embodiments, -Cy- is 12-membered. In some embodiments, -Cy- is 13-membered. In some embodiments, -Cy- is 14-membered. In some embodiments, -Cy- is 15-membered. In some embodiments, -Cy- is 16-membered. In some embodiments, -Cy- is 17-membered. In some embodiments, -Cy- is 18-membered. In some embodiments, -Cy- is 19-membered. In some embodiments, -Cy- is 20-membered.

In some embodiments, -Cy- is an optionally substituted bivalent $C_{3-20}$ cycloaliphatic ring. In some embodiments, -Cy- is an optionally substituted bivalent, saturated $C_{3-20}$ cycloaliphatic ring. In some embodiments, -Cy- is an optionally substituted bivalent, partially unsaturated $C_{3-20}$ cycloaliphatic ring. In some embodiments, -Cy-H is optionally substituted cycloaliphatic as described in the present disclosure, for example, cycloaliphatic embodiments for R.

In some embodiments, -Cy- is an optionally substituted $C_{6-20}$ aryl ring. In some embodiments, -Cy- is optionally substituted phenylene. In some embodiments, -Cy- is optionally substituted 1,2-phenylene. In some embodiments, -Cy- is optionally substituted 1,3-phenylene. In some embodiments, -Cy- is optionally substituted 1,4-phenylene. In some embodiments, -Cy- is an optionally substituted bivalent naphthalene ring. In some embodiments, -Cy-H is optionally substituted aryl as described in the present disclosure, for example, aryl embodiments for R.

In some embodiments, -Cy- is an optionally substituted bivalent 5-20 membered heteroaryl ring having 1-10 heteroatoms independently selected from oxygen, nitrogen, sulfur and silicon. In some embodiments, -Cy- is an optionally substituted bivalent 5-20 membered heteroaryl ring having 1-10 heteroatoms independently selected from oxygen, nitrogen, and sulfur. In some embodiments, -Cy- is an optionally substituted bivalent 5-6 membered heteroaryl ring having 1-4 heteroatoms independently selected from oxygen, nitrogen, sulfur. In some embodiments, -Cy- is an optionally substituted bivalent 5-6 membered heteroaryl ring having 1-3 heteroatoms independently selected from oxygen, nitrogen, sulfur. In some embodiments, -Cy- is an optionally substituted bivalent 5-6 membered heteroaryl ring having 1-2 heteroatoms independently selected from oxygen, nitrogen, sulfur. In some embodiments, -Cy- is an optionally substituted bivalent 5-6 membered heteroaryl ring having one heteroatom independently selected from oxygen, nitrogen, sulfur. In some embodiments, -Cy-H is optionally substituted heteroaryl as described in the present disclosure, for example, heteroaryl embodiments for R.

In some embodiments, -Cy- is an optionally substituted bivalent 3-20 membered heterocyclyl ring having 1-10 heteroatoms independently selected from oxygen, nitrogen, sulfur, phosphorus and silicon. In some embodiments, -Cy- is an optionally substituted bivalent 3-20 membered heterocyclyl ring having 1-10 heteroatoms independently selected from oxygen, nitrogen, and sulfur. In some embodiments, -Cy- is an optionally substituted bivalent 3-6 membered heterocyclyl ring having 1-4 heteroatoms independently selected from oxygen, nitrogen, sulfur. In some embodiments, -Cy- is an optionally substituted bivalent 5-6 membered heterocyclyl ring having 1-4 heteroatoms independently selected from oxygen, nitrogen, sulfur. In some embodiments, -Cy- is an optionally substituted bivalent 5-6 membered heterocyclyl ring having 1-3 heteroatoms independently selected from oxygen, nitrogen, sulfur. In some embodiments, -Cy- is an optionally substituted bivalent 5-6 membered heterocyclyl ring having 1-2 heteroatoms independently selected from oxygen, nitrogen, sulfur. In some embodiments, -Cy- is an optionally substituted bivalent 5-6 membered heterocyclyl ring having one heteroatom independently selected from oxygen, nitrogen, sulfur. In some embodiments, -Cy- is an optionally substituted saturated bivalent heterocyclyl group. In some embodiments, -Cy- is an optionally substituted partially unsaturated bivalent heterocyclyl group. In some embodiments, -Cy-H is optionally substituted heterocyclyl as described in the present disclosure, for example, heterocyclyl embodiments for R.

In some embodiments, R' is —R, —C(O)R, —C(O)OR, or —S(O)$_2$R, wherein R is as described in the present disclosure. In some embodiments, R' is R, wherein R is as described in the present disclosure. In some embodiments, R' is —C(O)R, wherein R is as described in the present disclosure. In some embodiments, R' is —C(O)OR, wherein R is as described in the present disclosure. In some embodiments, R' is —S(O)$_2$R, wherein R is as described in the present disclosure. In some embodiments, R' is hydrogen. In some embodiments, R' is not hydrogen. In some embodiments, R' is R, wherein R is optionally substituted $C_{1-20}$ aliphatic as described in the present disclosure. In some embodiments, R' is R, wherein R is optionally substituted $C_{1-20}$ heteroaliphatic as described in the present disclosure. In some embodiments, R' is R, wherein R is optionally substituted $C_{6-20}$ aryl as described in the present disclosure. In some embodiments, R' is R, wherein R is optionally substituted $C_{6-20}$ arylaliphatic as described in the present disclosure. In some embodiments, R' is R, wherein R is optionally substituted $C_{6-20}$ arylheteroaliphatic as described in the present disclosure. In some embodiments, R' is R, wherein R is optionally substituted 5-20 membered heteroaryl as described in the present disclosure. In some embodiments, R' is R, wherein R is optionally substituted 3-20 membered heterocyclyl as described in the present disclosure. In some embodiments, two or more R' are R, and are optionally and independently taken together to form an optionally substituted ring as described in the present disclosure.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
  two R groups are optionally and independently taken together to form a covalent bond, or:
  two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or
  two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
  two R groups are optionally and independently taken together to form a covalent bond, or:
  two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon.
  two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon.

two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon.

In some embodiments, each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon.

In some embodiments, each R is independently —H, or an optionally substituted group selected from $C_{1-20}$ aliphatic, $C_{1-20}$ heteroaliphatic having 1-10 heteroatoms independently selected from oxygen, nitrogen, sulfur, phosphorus and silicon, $C_{6-20}$ aryl, $C_{6-20}$ arylaliphatic, $C_{6-20}$ arylheteroaliphatic having 1-10 heteroatoms independently selected from oxygen, nitrogen, sulfur, phosphorus and silicon, 5-20 membered heteroaryl having 1-10 heteroatoms independently selected from oxygen, nitrogen, sulfur, phosphorus and silicon, and 3-20 membered heterocyclyl having 1-10 heteroatoms independently selected from oxygen, nitrogen, sulfur, phosphorus and silicon.

In some embodiments, R is hydrogen. In some embodiments, R is not hydrogen. In some embodiments, R is an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, a 5-30 membered heteroaryl ring having 1-10 heteroatoms independently selected from oxygen, nitrogen, sulfur, phosphorus and silicon, and a 3-30 membered heterocyclic ring having 1-10 heteroatoms independently selected from oxygen, nitrogen, sulfur, phosphorus and silicon.

In some embodiments, R is hydrogen or an optionally substituted group selected from $C_{1-20}$ aliphatic, phenyl, a 3-7 membered saturated or partially unsaturated carbocyclic ring, an 8-10 membered bicyclic saturated, partially unsaturated or aryl ring, a 5-6 membered monocyclic heteroaryl ring having 1-4 heteroatoms independently selected from nitrogen, oxygen, and sulfur, a 4-7 membered saturated or partially unsaturated heterocyclic ring having 1-3 heteroatoms independently selected from nitrogen, oxygen, and sulfur, a 7-10 membered bicyclic saturated or partially unsaturated heterocyclic ring having 1-5 heteroatoms independently selected from nitrogen, oxygen, and sulfur, or an 8-10 membered bicyclic heteroaryl ring having 1-5 heteroatoms independently selected from nitrogen, oxygen, and sulfur.

In some embodiments, R is optionally substituted $C_{1-30}$ aliphatic. In some embodiments, R is optionally substituted $C_{1-20}$ aliphatic. In some embodiments, R is optionally substituted $C_{1-15}$ aliphatic. In some embodiments, R is optionally substituted $C_{1-10}$ aliphatic. In some embodiments, R is optionally substituted $C_{1-6}$ aliphatic. In some embodiments, R is optionally substituted $C_{1-6}$ alkyl. In some embodiments, R is optionally substituted hexyl, pentyl, butyl, propyl, ethyl or methyl. In some embodiments, R is optionally substituted hexyl. In some embodiments, R is optionally substituted pentyl. In some embodiments, R is optionally substituted butyl. In some embodiments, R is optionally substituted propyl. In some embodiments, R is optionally substituted ethyl. In some embodiments, R is optionally substituted methyl. In some embodiments, R is hexyl. In some embodiments, R is pentyl. In some embodiments, R is butyl. In some embodiments, R is propyl. In some embodiments, R is ethyl. In some embodiments, R is methyl. In some embodiments, R is isopropyl. In some embodiments, R is n-propyl. In some embodiments, R is tert-butyl. In some embodiments, R is sec-butyl. In some embodiments, R is n-butyl. In some embodiments, R is —$(CH_2)_2CN$.

In some embodiments, R is optionally substituted $C_{3-30}$ cycloaliphatic. In some embodiments, R is optionally substituted $C_{3-20}$ cycloaliphatic. In some embodiments, R is optionally substituted $C_{3-10}$ cycloaliphatic. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, R is an optionally substituted 3-30 membered saturated or partially unsaturated carbocyclic ring. In some embodiments, R is an optionally substituted 3-7 membered saturated or partially unsaturated carbocyclic ring. In some embodiments, R is an optionally substituted 3-membered saturated or partially unsaturated carbocyclic ring. In some embodiments, R is an optionally substituted 4-membered saturated or partially unsaturated carbocyclic ring. In some embodiments, R is an optionally substituted 5-membered saturated or partially unsaturated carbocyclic ring. In some embodiments, R is an optionally substituted 6-membered saturated or partially unsaturated carbocyclic ring. In some embodiments, R is an optionally substituted 7-membered saturated or partially unsaturated carbocyclic ring. In some embodiments, R is optionally substituted cycloheptyl. In some embodiments, R is cycloheptyl. In some embodiments, R is optionally substituted cyclohexyl. In some embodiments, R is cyclohexyl. In some embodiments, R is optionally substituted cyclopentyl. In some embodiments, R is cyclopentyl. In some embodiments, R is optionally substituted cyclobutyl. In some embodiments, R is cyclobutyl. In some embodiments, R is optionally substituted cyclopropyl. In some embodiments, R is cyclopropyl.

In some embodiments, when R is or comprises a ring structure, e.g., cycloaliphatic, cycloheteroaliphatic, aryl, heteroaryl, etc., the ring structure can be monocyclic, bicyclic or polycyclic. In some embodiments, R is or comprises a monocyclic structure. In some embodiments, R is or comprises a bicyclic structure. In some embodiments, R is or comprises a polycyclic structure.

In some embodiments, R is optionally substituted $C_{1-30}$ heteroaliphatic having 1-10 heteroatoms independently selected from oxygen, nitrogen, sulfur, phosphorus and silicon. In some embodiments, R is optionally substituted $C_{1-20}$ heteroaliphatic having 1-10 heteroatoms. In some embodiments, R is optionally substituted $C_{1-20}$ heteroaliphatic having 1-10 heteroatoms independently selected from oxygen, nitrogen, sulfur, phosphorus or silicon, optionally including one or more oxidized forms of nitrogen, sulfur, phosphorus or selenium. In some embodiments, R is optionally substituted $C_{1-30}$ heteroaliphatic comprising 1-10 groups independently selected from

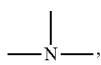

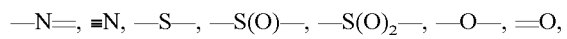

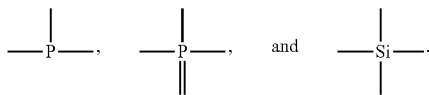

In some embodiments, R is optionally substituted $C_{6-30}$ aryl. In some embodiments, R is optionally substituted phenyl. In some embodiments, R is phenyl. In some embodiments, R is substituted phenyl.

In some embodiments, R is an optionally substituted 8-10 membered bicyclic saturated, partially unsaturated or aryl ring. In some embodiments, R is an optionally substituted 8-10 membered bicyclic saturated ring. In some embodiments, R is an optionally substituted 8-10 membered bicyclic partially unsaturated ring. In some embodiments, R is an optionally substituted 8-10 membered bicyclic aryl ring. In some embodiments, R is optionally substituted naphthyl.

In some embodiments, R is optionally substituted 5-30 membered heteroaryl ring having 1-10 heteroatoms independently selected from oxygen, nitrogen, sulfur, phosphorus and silicon. In some embodiments, R is optionally substituted 5-30 membered heteroaryl ring having 1-10 heteroatoms independently selected from oxygen, nitrogen, and sulfur. In some embodiments, R is optionally substituted 5-30 membered heteroaryl ring having 1-5 heteroatoms independently selected from oxygen, nitrogen, sulfur, phosphorus and silicon. In some embodiments, R is optionally substituted 5-30 membered heteroaryl ring having 1-5 heteroatoms independently selected from oxygen, nitrogen, and sulfur.

In some embodiments, R is an optionally substituted 5-6 membered monocyclic heteroaryl ring having 1-4 heteroatoms independently selected from nitrogen, oxygen, and sulfur. In some embodiments, R is a substituted 5-6 membered monocyclic heteroaryl ring having 1-4 heteroatoms independently selected from nitrogen, oxygen, and sulfur. In some embodiments, R is an unsubstituted 5-6 membered monocyclic heteroaryl ring having 1-4 heteroatoms independently selected from nitrogen, oxygen, and sulfur. In some embodiments, R is an optionally substituted 5-6 membered monocyclic heteroaryl ring having 1-3 heteroatoms independently selected from nitrogen, sulfur, and oxygen. In some embodiments, R is a substituted 5-6 membered monocyclic heteroaryl ring having 1-3 heteroatoms independently selected from nitrogen, oxygen, and sulfur. In some embodiments, R is an unsubstituted 5-6 membered monocyclic heteroaryl ring having 1-3 heteroatoms independently selected from nitrogen, sulfur, and oxygen.

In some embodiments, R is an optionally substituted 5-membered monocyclic heteroaryl ring having 1-4 heteroatoms independently selected from nitrogen, oxygen or sulfur. In some embodiments, R is an optionally substituted 6-membered monocyclic heteroaryl ring having 1-4 heteroatoms independently selected from nitrogen, oxygen, and sulfur.

In some embodiments, R is an optionally substituted 5-membered monocyclic heteroaryl ring having one heteroatom selected from nitrogen, oxygen, and sulfur. In some embodiments, R is selected from optionally substituted pyrrolyl, furanyl, or thienyl.

In some embodiments, R is an optionally substituted 5-membered heteroaryl ring having two heteroatoms independently selected from nitrogen, oxygen, and sulfur. In certain embodiments, R is an optionally substituted 5-membered heteroaryl ring having one nitrogen atom, and an additional heteroatom selected from sulfur or oxygen. Example R groups include but are not limited to optionally substituted pyrazolyl, imidazolyl, thiazolyl, isothiazolyl, oxazolyl or isoxazolyl.

In some embodiments, R is an optionally substituted 5-membered heteroaryl ring having three heteroatoms independently selected from nitrogen, oxygen, and sulfur. Example R groups include but are not limited to optionally substituted triazolyl, oxadiazolyl or thiadiazolyl.

In some embodiments, R is an optionally substituted 5-membered heteroaryl ring having four heteroatoms independently selected from nitrogen, oxygen, and sulfur. Example R groups include but are not limited to optionally substituted tetrazolyl, oxatriazolyl and thiatriazolyl.

In some embodiments, R is an optionally substituted 6-membered heteroaryl ring having 1-4 nitrogen atoms. In some embodiments, R is an optionally substituted 6-membered heteroaryl ring having 1-3 nitrogen atoms. In other embodiments, R is an optionally substituted 6-membered heteroaryl ring having 1-2 nitrogen atoms. In some embodiments, R is an optionally substituted 6-membered heteroaryl ring having four nitrogen atoms. In some embodiments, R is an optionally substituted 6-membered heteroaryl ring having three nitrogen atoms. In some embodiments, R is an optionally substituted 6-membered heteroaryl ring having two nitrogen atoms. In certain embodiments, R is an optionally substituted 6-membered heteroaryl ring having one nitrogen atom. Example R groups include but are not limited to optionally substituted pyridinyl, pyrimidinyl, pyrazinyl, pyridazinyl, triazinyl, or tetrazinyl.

In certain embodiments, R is an optionally substituted 8-10 membered bicyclic heteroaryl ring having 1-4 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having 1 heteroatom independently selected from nitrogen, oxygen, and sulfur. In some embodiments, R is an optionally substituted indolyl. In some embodiments, R is an optionally substituted azabicyclo[3.2.1]octanyl. In certain embodiments, R is an optionally substituted 5,6-fused heteroaryl ring having 2 heteroatoms independently selected from nitrogen, oxygen, and sulfur. In some embodiments, R is an optionally substituted azaindolyl. In some embodiments, R is an optionally substituted benzimidazolyl. In some embodiments, R is an optionally substituted benzothiazolyl. In some embodiments, R is an optionally substituted benzoxazolyl. In some embodiments, R is an optionally substituted indazolyl. In certain embodiments, R is an optionally substituted 5,6-fused heteroaryl ring having 3 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is an optionally substituted 5,6-fused heteroaryl ring having three heteroatoms independently selected from nitrogen, oxygen, and sulfur. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl orimidazo[5,1-b]thiazolyl.

In certain embodiments, R is an optionally substituted 6,6-fused heteroaryl ring having 1-4 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having 1 heteroatom independently selected from nitrogen, oxygen, and sulfur. In some embodiments, R is an optionally substituted quinolinyl. In some embodiments, R is an optionally substituted isoquinolinyl. In some embodiments, R is an optionally substituted 6,6-fused heteroaryl ring having 2 heteroatoms independently selected from nitrogen, oxygen, and sulfur. In some embodiments, R is optionally substituted quinazoline or a quinoxaline.

In some embodiments, R is 3-30 membered heterocyclic ring having 1-10 heteroatoms independently selected from oxygen, nitrogen, sulfur, phosphorus and silicon. In some embodiments, R is 3-30 membered heterocyclic ring having 1-10 heteroatoms independently selected from oxygen, nitrogen, and sulfur. In some embodiments, R is 3-30 membered heterocyclic ring having 1-5 heteroatoms independently selected from oxygen, nitrogen, sulfur, phosphorus and silicon. In some embodiments, R is 3-30 membered heterocyclic ring having 1-5 heteroatoms independently selected from oxygen, nitrogen, and sulfur.

In some embodiments, R is an optionally substituted 3-7 membered saturated or partially unsaturated heterocyclic ring having 1-3 heteroatoms independently selected from nitrogen, oxygen, and sulfur. In some embodiments, R is a substituted 3-7 membered saturated or partially unsaturated heterocyclic ring having 1-3 heteroatoms independently selected from nitrogen, oxygen, and sulfur. In some embodiments, R is an unsubstituted 3-7 membered saturated or partially unsaturated heterocyclic ring having 1-3 heteroatoms independently selected from nitrogen, oxygen, and sulfur. In certain embodiments, R is an optionally substituted 5-7 membered partially unsaturated monocyclic ring having 1-3 heteroatoms independently selected from nitrogen, oxygen, and sulfur. In certain embodiments, R is an optionally substituted 5-6 membered partially unsaturated monocyclic ring having 1-3 heteroatoms independently selected from nitrogen, oxygen, and sulfur. In certain embodiments, R is an optionally substituted 5-membered partially unsaturated monocyclic ring having 1-3 heteroatoms independently selected from nitrogen, oxygen, and sulfur. In certain embodiments, R is an optionally substituted 6-membered partially unsaturated monocyclic ring having 1-3 heteroatoms independently selected from nitrogen, oxygen, and sulfur. In certain embodiments, R is an optionally substituted 7-membered partially unsaturated monocyclic ring having 1-3 heteroatoms independently selected from nitrogen, oxygen, and sulfur. In some embodiments, R is optionally substituted 3-membered heterocyclic ring having one heteroatom selected from nitrogen, oxygen or sulfur. In some embodiments, R is optionally substituted 4-membered heterocyclic ring having 1-3 heteroatoms independently selected from nitrogen, oxygen, and sulfur. In some embodiments, R is optionally substituted 5-membered heterocyclic ring having 1-3 heteroatoms independently selected from nitrogen, oxygen, and sulfur. In some embodiments, R is optionally substituted 6-membered heterocyclic ring having 1-3 heteroatoms independently selected from nitrogen, oxygen, and sulfur. In some embodiments, R is optionally substituted 7-membered heterocyclic ring having 1-3 heteroatoms independently selected from nitrogen, oxygen, and sulfur.

In some embodiments, R is an optionally substituted 3-membered saturated or partially unsaturated heterocyclic ring having 1-2 heteroatoms independently selected from nitrogen, oxygen, and sulfur. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 7-membered saturated or partially unsaturated heterocyclic ring having 1-2 heteroatoms independently selected from nitrogen, oxygen, and sulfur.

In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms. In some embodiments, R is an optionally substituted 4-membered saturated or partially unsaturated heterocyclic ring having 1-2 heteroatoms independently selected from nitrogen, oxygen, and sulfur. In some embodiments, R is an optionally substituted 4-membered partially unsaturated heterocyclic ring having 2 heteroatoms independently selected from nitrogen, oxygen, and sulfur. In some embodiments, R is an optionally substituted 4-membered partially unsaturated heterocyclic ring having no more than 1 heteroatom. In some embodiments, R is an optionally substituted 4-membered partially unsaturated heterocyclic ring having no more than 1 heteroatom, wherein the heteroatom is nitrogen. In some embodiments, R is an optionally substituted 4-membered partially unsaturated heterocyclic ring having no more than 1 heteroatom, wherein the heteroatom is oxygen. In some embodiments, R is an optionally substituted 4-membered partially unsaturated heterocyclic ring having no more than 1 heteroatom, wherein the heteroatom is sulfur. In some embodiments, R is an optionally substituted 4-membered partially unsaturated heterocyclic ring having 2 oxygen atoms. In some embodiments, R is an optionally substituted 4-membered partially unsaturated heterocyclic ring having 2 nitrogen atoms.

In some embodiments, R is an optionally substituted 5-membered saturated or partially unsaturated heterocyclic ring having 1-2 heteroatoms independently selected from nitrogen, oxygen, and sulfur. In some embodiments, R is an optionally substituted 5-membered partially unsaturated heterocyclic ring having 2 heteroatoms independently selected from nitrogen, oxygen, and sulfur. In some embodiments, R is an optionally substituted 5-membered partially unsaturated heterocyclic ring having no more than 1 heteroatom. In some embodiments, R is an optionally substituted 5-membered partially unsaturated heterocyclic ring having no more than 1 heteroatom, wherein the heteroatom is nitrogen. In some embodiments, R is an optionally substituted 5-membered partially unsaturated heterocyclic ring having no more than 1 heteroatom, wherein the heteroatom is oxygen. In some embodiments, R is an optionally substituted 5-membered partially unsaturated heterocyclic ring having no more than 1 heteroatom, wherein the heteroatom is sulfur. In some embodiments, R is an optionally substituted 5-membered partially unsaturated heterocyclic ring having 2 oxygen atoms. In some embodiments, R is an optionally substituted 5-membered partially unsaturated heterocyclic ring having 2 nitrogen atoms.

In some embodiments, R is an optionally substituted 6-membered saturated or partially unsaturated heterocyclic ring having 1-2 heteroatoms independently selected from nitrogen, oxygen, and sulfur. In some embodiments, R is an optionally substituted 6-membered partially unsaturated heterocyclic ring having 2 heteroatoms independently selected from nitrogen, oxygen, and sulfur. In some embodiments, R is an optionally substituted 6-membered partially unsaturated heterocyclic ring having no more than 1 heteroatom. In some embodiments, R is an optionally substituted 6-membered partially unsaturated heterocyclic ring having no more than 1 heteroatom, wherein the heteroatom is nitrogen. In some embodiments, R is an optionally substituted 6-membered partially unsaturated heterocyclic ring having no more than 1 heteroatom, wherein the heteroatom is oxygen. In some embodiments, R is an optionally substituted 6-membered partially unsaturated heterocyclic ring having no more than 1 heteroatom, wherein the heteroatom is sulfur. In some embodiments, R is an optionally substituted 6-membered partially unsaturated heterocyclic ring having 2 oxygen atoms. In some embodiments, R is an optionally substituted 6-membered partially unsaturated heterocyclic ring having 2 nitrogen atoms.

In certain embodiments, R is a 3-7 membered saturated or partially unsaturated heterocyclic ring having 1-2 heteroatoms independently selected from nitrogen, oxygen, and sulfur. In certain embodiments, R is optionally substituted oxiranyl, oxetanyl, tetrahydrofuranyl, tetrahydropyranyl, oxepaneyl, aziridineyl, azetidineyl, pyrrolidinyl, piperidinyl, azepanyl, thiiranyl, thietanyl, tetrahydrothiophenyl, tetrahydrothiopyranyl, thiepanyl, dioxolanyl, oxathiolanyl, oxazolidinyl, imidazolidinyl, thiazolidinyl, dithiolanyl, dioxanyl, morpholinyl, oxathianyl, piperazinyl, thiomorpholinyl, dithianyl, dioxepanyl, oxazepanyl, oxathiepanyl, dithiepanyl, diazepanyl, dihydrofuranonyl, tetrahydropyranonyl, oxepanonyl, pyrolidinonyl, piperidinonyl, azepanonyl, dihydrothiophenonyl, tetrahydrothiopyranonyl, thiepanonyl, oxazolidinonyl, oxazinanonyl, oxazepanonyl, dioxolanonyl, dioxanonyl, dioxepanonyl, oxathiolinonyl, oxathianonyl, oxathiepanonyl, thiazolidinonyl, thiazinanonyl, thiazepanonyl, imidazolidinonyl, tetrahydropyrimidinonyl, diazepanonyl, imidazolidinedionyl, oxazolidinedionyl, thiazolidinedionyl, dioxolanedionyl, oxathiolanedionyl, piperazinedionyl, morpholinedionyl, thiomorpholinedionyl, tetrahydropyranyl, tetrahydrofuranyl, morpholinyl, thiomorpholinyl, piperidinyl, piperazinyl, pyrrolidinyl, tetrahydrothiophenyl, or tetrahydrothiopyranyl.

In certain embodiments, R is an optionally substituted 5-6 membered partially unsaturated monocyclic ring having 1-2 heteroatoms independently selected from nitrogen, oxygen, and sulfur. In certain embodiments, R is an optionally substituted tetrahydropyridinyl, dihydrothiazolyl, dihydrooxazolyl, or oxazolinyl group.

In some embodiments, R is an optionally substituted 7-10 membered bicyclic saturated or partially unsaturated heterocyclic ring having 1-5 heteroatoms independently selected from nitrogen, oxygen, and sulfur. In some embodiments, R is optionally substituted indolinyl. In some embodiments, R is optionally substituted isoindolinyl. In some embodiments, R is optionally substituted 1, 2, 3, 4-tetrahydroquinolinyl. In some embodiments, R is optionally substituted 1, 2, 3, 4-tetrahydroisoquinolinyl. In some embodiments, R is an optionally substituted azabicyclo[3.2.1]octanyl.

In some embodiments, R is an optionally substituted 8-10 membered bicyclic heteroaryl ring having 1-5 heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In some embodiments, R is an optionally substituted 5,6-fused heteroaryl ring having 1-4 heteroatoms independently selected from nitrogen, oxygen, and sulfur. In some embodiments, R is an optionally substituted 5,6-fused heteroaryl ring having 1-3 heteroatoms independently selected from nitrogen, oxygen, and sulfur. In some embodiments, R is an optionally substituted 5,6-fused heteroaryl ring having two heteroatoms independently selected from nitrogen, oxygen, and sulfur. In some embodiments, R is optionally substituted 1,4-dihydropyrrolo[3,2-b]pyrrolyl, 4H-furo[3,2-b]pyrrolyl, 4H-thieno[3,2-b]pyrrolyl, furo[3,2-b]furanyl, thieno[3,2-b]furanyl, thieno[3,2-b]thienyl, 1H-pyrrolo[1,2-a]imidazolyl, pyrrolo[2,1-b]oxazolyl or pyrrolo[2,1-b]thiazolyl. In some embodiments, R is an optionally substituted 5,6-fused heteroaryl ring having three heteroatoms independently selected from nitrogen, oxygen, and sulfur. In some embodiments, R is optionally substituted dihydropyrroloimidazolyl, 1H-furoimidazolyl, 1H-thienoimidazolyl, furooxazolyl, furoisoxazolyl, 4H-pyrrolooxazolyl, 4H-pyrroloisoxazolyl, thienooxazolyl, thienoisoxazolyl, 4H-pyrrolothiazolyl, furothiazolyl, thienothiazolyl, 1H-imidazoimidazolyl, imidazooxazolyl or imidazo[5,1-b]thiazolyl. In some embodiments, R is an optionally substituted 5,6-fused heteroaryl ring having four heteroatoms independently selected from nitrogen, oxygen, and sulfur. In some embodiments, R is an optionally substituted 5,6-fused heteroaryl ring having five heteroatoms independently selected from nitrogen, oxygen, and sulfur.

In some embodiments, R is an optionally substituted 5,6-fused heteroaryl ring having 1-5 heteroatoms independently selected from nitrogen, oxygen, and sulfur. In other embodiments, R is an optionally substituted 5,6-fused heteroaryl ring having 1-2 heteroatoms independently selected from nitrogen, oxygen, and sulfur. In certain embodiments, R is an optionally substituted 5,6-fused heteroaryl ring having one heteroatom independently selected from nitrogen, oxygen, and sulfur. In some embodiments, R is optionally substituted indolyl. In some embodiments, R is optionally substituted benzofuranyl. In some embodiments, R is optionally substituted benzo[b]thienyl. In certain embodiments, R is an optionally substituted 5,6-fused heteroaryl ring having two heteroatoms independently selected from nitrogen, oxygen, and sulfur. In some embodiments, R is optionally substituted azaindolyl. In some embodiments, R is optionally substituted benzimidazolyl. In some embodiments, R is optionally substituted benzothiazolyl. In some embodiments, R is optionally substituted benzoxazolyl. In some embodiments, R is an optionally substituted indazolyl. In certain embodiments, R is an optionally substituted 5,6-fused heteroaryl ring having three heteroatoms independently selected from nitrogen, oxygen, and sulfur. In some embodiments, R is optionally substituted oxazolopyridiyl, thiazolopyridinyl or imidazopyridinyl. In certain embodiments, R is an optionally substituted 5,6-fused heteroaryl ring having four heteroatoms independently selected from nitrogen, oxygen, and sulfur. In some embodiments, R is optionally substituted purinyl, oxazolopyrimidinyl, thiazolopyrimidinyl, oxazolopyrazinyl, thiazolopyrazinyl, imidazopyrazinyl, oxazolopyridazinyl, thiazolopyridazinyl or imidazopyridazinyl. In certain embodiments, R is an optionally substituted 5,6-fused heteroaryl ring having five heteroatoms independently selected from nitrogen, oxygen, and sulfur.

In certain embodiments, R is an optionally substituted 6,6-fused heteroaryl ring having 1-5 heteroatoms independently selected from nitrogen, oxygen, and sulfur. In some embodiments, R is an optionally substituted 6,6-fused heteroaryl ring having 1-2 heteroatoms independently selected from nitrogen, oxygen, and sulfur. In other embodiments, R is an optionally substituted 6,6-fused heteroaryl ring having one heteroatom selected from nitrogen, oxygen, and sulfur. In some embodiments, R is optionally substituted quinolinyl. In some embodiments, R is optionally substituted isoquinolinyl. In some embodiments, R is an optionally substituted 6,6-fused heteroaryl ring having two heteroatoms independently selected from nitrogen, oxygen, and sulfur. In some embodiments, R is optionally substituted quinazolinyl, phthalazinyl, quinoxalinyl or naphthyridinyl. In some embodiments, R is an optionally substituted 6,6-fused heteroaryl ring having three heteroatoms independently selected from nitrogen, oxygen, and sulfur. In some embodiments, R is optionally substituted pyridopyrimidinyl, pyridopyridazinyl, pyridopyrazinyl, or benzotriazinyl. In some embodiments, R is an optionally substituted 6,6-fused heteroaryl ring having four heteroatoms independently selected from nitrogen, oxygen, and sulfur. In some embodiments, R is optionally substituted pyridotriazinyl, pteridinyl, pyrazinopyrazinyl, pyrazinopyridazinyl, pyridazinopyridazinyl, pyrimidopyridazinyl or pyrimidopyrimidinyl. In some embodiments, R is an optionally substituted 6,6-fused heteroaryl ring having five heteroatoms independently selected from nitrogen, oxygen, and sulfur.

In some embodiments, R is optionally substituted $C_{6-30}$ arylaliphatic. In some embodiments, R is optionally substituted $C_{6-20}$ arylaliphatic. In some embodiments, R is optionally substituted $C_{6-10}$ arylaliphatic. In some embodiments, an aryl moiety of the arylaliphatic has 6, 10, or 14 aryl carbon atoms. In some embodiments, an aryl moiety of the arylaliphatic has 6 aryl carbon atoms. In some embodiments, an aryl moiety of the arylaliphatic has 10 aryl carbon atoms. In some embodiments, an aryl moiety of the arylaliphatic has 14 aryl carbon atoms. In some embodiments, an aryl moiety is optionally substituted phenyl.

In some embodiments, R is optionally substituted $C_{6-30}$ arylheteroaliphatic having 1-10 heteroatoms independently selected from oxygen, nitrogen, sulfur, phosphorus and silicon. In some embodiments, R is optionally substituted $C_{6-30}$ arylheteroaliphatic having 1-10 heteroatoms independently selected from oxygen, nitrogen, and sulfur. In some embodiments, R is optionally substituted $C_{6-20}$ arylheteroaliphatic having 1-10 heteroatoms independently selected from oxygen, nitrogen, sulfur, phosphorus and silicon. In some embodiments, R is optionally substituted $C_{6-20}$ arylheteroaliphatic having 1-10 heteroatoms independently selected from oxygen, nitrogen, and sulfur. In some embodiments, R is optionally substituted $C_{6-10}$ arylheteroaliphatic having 1-5 heteroatoms independently selected from oxygen, nitrogen, sulfur, phosphorus and silicon. In some embodiments, R is optionally substituted $C_{6-10}$ arylheteroaliphatic having 1-5 heteroatoms independently selected from oxygen, nitrogen, and sulfur.

In some embodiments, two R groups are optionally and independently taken together to form a covalent bond. In some embodiments, —C=O is formed. In some embodiments, —C=C— is formed. In some embodiments, —C≡C— is formed.

In some embodiments, two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-20 membered monocyclic, bicyclic or polycyclic ring having, in addition to the atom, 0-10 heteroatoms independently selected from oxygen, nitrogen, sulfur, phosphorus and silicon. In some embodiments, two or more R groups on the same atom are optionally and independently taken together with the atom to form an optionally substituted, 3-10 membered monocyclic, bicyclic or polycyclic ring having, in addition to the atom, 0-5 heteroatoms independently selected from oxygen, nitrogen, sulfur, phosphorus and silicon. In some embodiments, two or more R groups on the same atom are optionally and independently taken together with the atom to form an optionally substituted, 3-6 membered monocyclic, bicyclic or polycyclic ring having, in addition to the atom, 0-3 heteroatoms independently selected from oxygen, nitrogen, sulfur, phosphorus and silicon. In some embodiments, two or more R groups on the same atom are optionally and independently taken together with the atom to form an optionally substituted, 3-5 membered monocyclic, bicyclic or polycyclic ring having, in addition to the atom, 0-3 heteroatoms independently selected from oxygen, nitrogen, sulfur, phosphorus and silicon.

In some embodiments, two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-20 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-10 heteroatoms independently selected from oxygen, nitrogen, sulfur, phosphorus and silicon. In some embodiments, two or more R groups on two or more atoms are optionally and independently taken together with their intervening atoms to form an optionally substituted, 3-10 membered monocyclic, bicyclic or polycyclic ring having, in addition to the intervening atoms, 0-5 heteroatoms independently selected from oxygen, nitrogen, sulfur, phosphorus and silicon. In some embodiments, two or more R groups on two or more atoms are optionally and independently taken together with their intervening atoms to form an optionally substituted, 3-6 membered monocyclic, bicyclic or polycyclic ring having, in addition to the intervening atoms, 0-3 heteroatoms independently selected from oxygen, nitrogen, sulfur, phosphorus and silicon. In some embodiments, two or more R groups on two or more atoms are optionally and independently taken together with their intervening atoms to form an optionally substituted, 3-5 membered monocyclic, bicyclic or polycyclic ring having, in addition to the intervening atoms, 0-3 heteroatoms independently selected from oxygen, nitrogen, sulfur, phosphorus and silicon.

In some embodiments, heteroatoms in R groups, or in the structures formed by two or more R groups taken together, are selected from oxygen, nitrogen, and sulfur. In some embodiments, a formed ring is 3, 4, 5, 6, 7, 8, 9, 10, 11, 12, 13, 14, 15, 16, 17, 18, 19, or 20-membered. In some embodiments, a formed ring is saturated. In some embodiments, a formed ring is partially saturated. In some embodiments, a formed ring is aromatic. In some embodiments, a formed ring comprises a saturated, partially saturated, or aromatic ring moiety. In some embodiments, a formed ring comprises 5, 6, 7, 8, 9, 10, 11, 12, 13, 14, 15, 16, 17, 18, 19, or 20 aromatic ring atoms. In some embodiments, a formed contains no more than 5, 6, 7, 8, 9, 10, 11, 12, 13, 14, 15, 16, 17, 18, 19, or 20 aromatic ring atoms. In some embodiments, aromatic ring atoms are selected from carbon, nitrogen, oxygen and sulfur.

In some embodiments, a ring formed by two or more R groups (or two or more groups selected from R and variables that can be R) taken together is a $C_{3-30}$ cycloaliphatic, $C_{6-30}$ aryl, 5-30 membered heteroaryl having 1-10 heteroatoms independently selected from oxygen, nitrogen, sulfur, phosphorus and silicon, or 3-30 membered heterocyclyl having 1-10 heteroatoms independently selected from oxygen, nitrogen, sulfur, phosphorus and silicon, ring as described for R, but bivalent or multivalent.

In some embodiments, an amino acid of formula A-I is a compound having the structure of formula A-II:

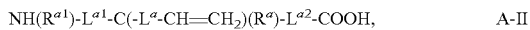

NH($R^{a1}$)-$L^{a1}$-C(-$L^a$-CH=CH$_2$)($R^a$)-$L^{a2}$-COOH,      A-II or a salt thereof, wherein each variable is independently as described in the present disclosure.

In some embodiments, an amino acid of formula A-I is a compound having the structure of formula A-III:

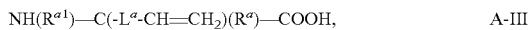

NH($R^{a1}$)—C(-$L^a$-CH=CH$_2$)($R^a$)—COOH,      A-III or a salt thereof, wherein each variable is independently as described in the present disclosure.

In some embodiments, $L^a$ comprises at least one —N(R')— wherein R' is independently as described in the present disclosure.

In some embodiments, an amino acid of formula A-I is a standard amino acid. In some embodiments, an amino acid of formula A-I is selected from Tables A-I, A-II, and A-III:

TABLE A-I
Exemplary amino acids (Fmoc-Protected).
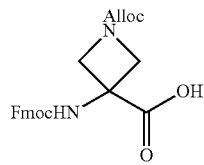
Monomer A (M$_A$)
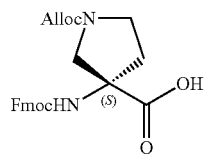
Monomer B (M$_B$)
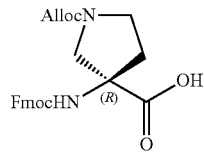
Monomer C (M$_C$)
TABLE A-II
Exemplary amino acids (Fmoc-Protected).
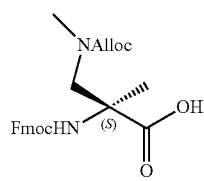
Monomer D (M$_D$)
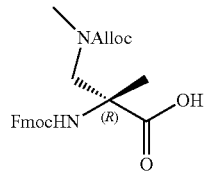
Monomer E (M$_E$)
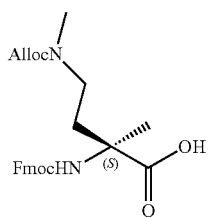
Monomer F (M$_F$)
TABLE A-II-continued
Exemplary amino acids (Fmoc-Protected).
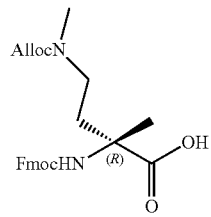
Monomer G (M$_G$)
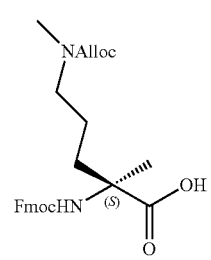
Monomer H (M$_H$)
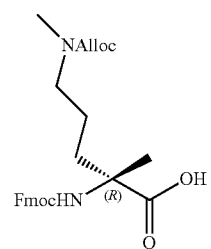
Monomer I (M$_I$)
TABLE A-III
Exemplary amino acids (Fmoc-Protected).
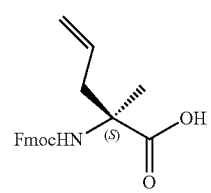
S$_3$
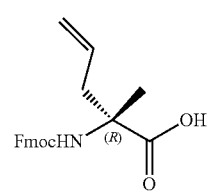
R$_3$ TABLE A-III-continued
Exemplary amino acids (Fmoc-Protected).
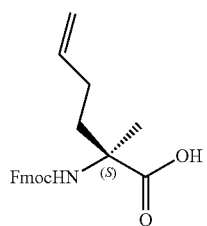
S₄
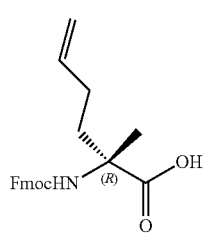
R₄
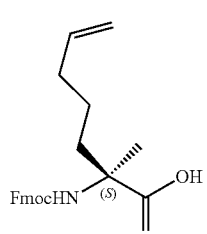
S₅
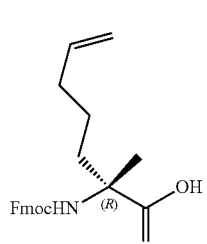
R₅
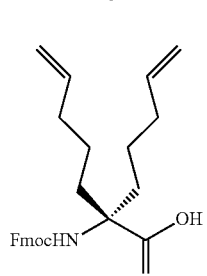
B₅
TABLE A-III-continued
Exemplary amino acids (Fmoc-Protected).
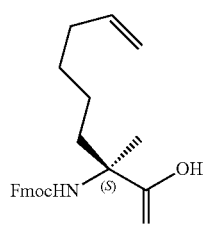
S₆
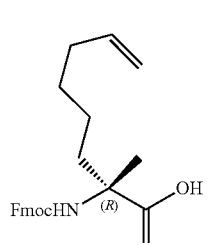
R₆
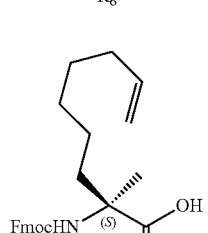
S₇
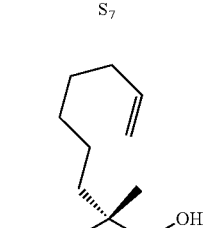
R₇
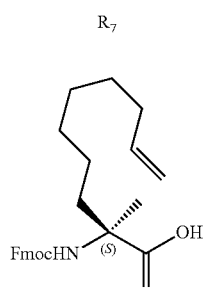
S₈

TABLE A-III-continued

Exemplary amino acids (Fmoc-Protected).

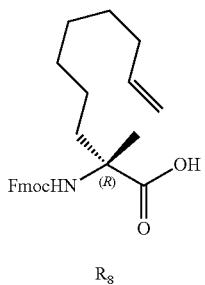

In some embodiments, an amino acid is an alpha-amino acid. In some embodiments, an amino acid is an L-amino acid. In some embodiments, an amino acid is a D-amino acid. In some embodiments, the alpha-carbon of an amino acid is achiral.

In some embodiments, an amino acid is a beta-amino acid. In some embodiments, an amino acid is beta-alanine.

In some embodiments, an amino acid is one whose residue is incorporated in a peptide in Table 1.

In some embodiments, a provided amino acid sequence contains two or more amino acid residues whose side chains are linked together to form one or more staples. In some embodiments, a provided amino acid sequence contains two or more amino acid residues, each of which independently has a side chain comprising an olefin. In some embodiments, a provided amino acid sequence contains two or more amino acid residues, each of which independently has a side chain comprising a terminal olefin. In some embodiments, a provided amino acid sequence contains two and no more than two amino acid residues, each of which independently has a side chain comprising an olefin. In some embodiments, a provided amino acid sequence contains two and no more than two amino acid residues, each of which independently has a side chain comprising a terminal olefin. In some embodiments, a provided amino acid sequence comprises at least one residue of an amino acid that comprises an olefin and a nitrogen atom other than the nitrogen atom of its amino group. In some embodiments, a provided amino acid sequence comprises at least one residue of an amino acid that comprises a terminal olefin and a nitrogen atom other than the nitrogen atom of its amino group. In some embodiments, a provided amino acid sequence comprises at least one residue of an amino acid that has a side chain than comprises a terminal olefin and a nitrogen atom. In some embodiments, a provided amino acid sequence comprises at least one residue of an amino acid of formula A-I, wherein $R^{a2}$ comprising an olefin and a —N(R')— moiety, wherein R' is as described in the present disclosure (including, in some embodiments, optionally taken together with $R^{a3}$ and their intervening atoms to form an optionally substituted ring as described in the present disclosure). In some embodiments, $R^{a2}$ comprising a terminal olefin and a —N(R')— moiety wherein R' is as described in the present disclosure. In some embodiments, a provided amino acid sequence comprises at least one residue of an amino acid selected from Table A-I. In some embodiments, a provided amino acid sequence comprises at least one residue of an amino acid selected from Table A-II. In some embodiments, a provided amino acid sequence comprises at least one residue of an amino acid selected from Table A-III. In some embodiments, two olefins from two side chains are linked together through olefin metathesis to form a staple. In some embodiments, a staple is preferably formed by side chains of amino acid residues that are not at the corresponding positions of the Axin residues that interact with beta-catenin. In some embodiments, a formed staple does not disrupt interaction between the peptide and beta-catenin.

In some embodiments, the present disclosure provides a peptide comprising:

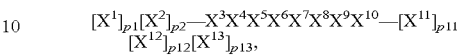

wherein:
each of p1, p2, p11, p12 and p13 is independently 0 or 1;
each of X, $X^1$, $X^2$, $X^3$, $X^4$, $X^5$, $X^6$, $X^7$, $X^8$, $X^9$, $X^{10}$, $X^{11}$, $X^{12}$, and $X^{13}$ is independently an amino acid residue;
at least two of X, $X^1$, $X^2$, $X^3$, $X^4$, $X^5$, $X^6$, $X^7$, $X^8$, $X^9$, $X^{10}$, $X^{11}$, $X^{12}$, and $X^{13}$ comprise side chains that are optionally linked together to form a staple.

In some embodiments, a provided peptide is a stapled peptide, and at least two of $X^1$ to $X^{13}$ comprise side chains that are linked together to form a staple. In some embodiments, a provided peptide is an unstapled peptide, wherein at least two of $X^1$ to $X^{13}$ comprise side chains that can be linked together to form a staple. In some embodiments, a stapled peptide, or an unstapled peptide once stapled, interact with beta-catenin at one or more beta-catenin sites that interact with Axin. In some embodiments, a stapled peptide, or an unstapled peptide once stapled, interact with beta-catenin and compete with beta-catenin interaction with Axin or an Axin peptide.

In some embodiments, each of $X^1$ to $X^{13}$ is independently an amino acid residue of an amino acid having the structure of formula A-I.

In some embodiments, $X_i$ and $X_{i+m}$, each independently comprises a side chain that comprises an olefin, and the two side chains can be linked together to form a staple, e.g., a staple as described in the present disclosure, through olefin metathesis of the two olefins. In some embodiments, both of the olefins are terminal olefins. In some embodiments, m is an integer of 3-12, and i is an integer of 1-18. In some embodiments, m is an integer of 3-8, and i is an integer of 1-13. In some embodiments, at least one of $X^i$ and $X^{i+m}$ comprises a side chain comprising an olefin and a nitrogen atom. In some embodiments, at least one of $X^i$ and $X^{i+m}$ comprises —C($R^{2a}$)($R^{3a}$) being —C(-$L^a$-R')($R^{3a}$), wherein at least one methylene unit of $L^a$ is replaced with —N(R')— and R' comprises an olefin. In some embodiments, at least one of $X^i$ and $X^{i+m}$ comprises —C($R^{2a}$)($R^{3a}$) being —C(-$L^a$-CH=$CH_2$)($R^{3a}$), wherein at least one methylene unit of $L^a$ is replaced with —N(R')—.

In some embodiments, i is 1, 2, 3, 4, 5, 6, 7, 8, 9, 10, 11, 12, 13, 14, 15, 16, or 17. In some embodiments, i is 1. In some embodiments, i is 2. In some embodiments, i is 3. In some embodiments, i is 4. In some embodiments, i is 5. In some embodiments, i is 6. In some embodiments, i is 7. In some embodiments, i is 8. In some embodiments, i is 9. In some embodiments, i is 10. In some embodiments, i is 11. In some embodiments, i is 12. In some embodiments, i is 13. In some embodiments, i is 14. In some embodiments, i is 15. In some embodiments, i is 16. In some embodiments, i is 17. In some embodiments, i is 18.

In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12.

In some embodiments, each of $X^i$ and $X^{i+m}$ is independently selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, $M_I$. In some embodiments, at least one of $X^i$ and $X^{i+m}$ is independently selected from $M_A$, $M_B$, $M_C$, $M_D$, $M_E$, $M_F$, $M_G$, $M_H$, $M_I$. In some embodiments, each of $X^i$ and $X^{i+m}$ is independently selected from $M_A$, $M_B$, $M_C$, $M_D$, $M_E$, $M_F$, $M_G$, $M_H$, $M_I$.

In some embodiments, $X^3$ is a residue of an amino acid selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, and $M_I$. In some embodiments, $X^3$ is a residue of an amino acid selected from $R_4$, $R_5$, $R_6$, $R_7$, $R_8$, $S_4$, $S_5$, $S_6$, $S_7$, and $S_8$. In some embodiments, wherein $X^3$ is an amino acid residue of $R_8$. In some embodiments, wherein $X^3$ is an amino acid residue of $M_G$. In some embodiments, wherein $X^3$ is an amino acid residue of $R_4$. In some embodiments, $X^{10}$ is a residue of an amino acid selected from $R_4$, $R_5$, $R_6$, $R_7$, $R_5$, $S_4$, $S_5$, $S_6$, $S_7$, $S_8$, $M_A$, $M_B$, $M_C$, $M_D$, $M_E$, $M_F$, $M_G$, $M_H$, and $M_I$. In some embodiments, $X^{10}$ is a residue of an amino acid selected from $M_A$, $M_B$, $M_C$, $M_D$, $M_E$, $M_F$, $M_G$, $M_H$, and $M_I$. In some embodiments, $X^{10}$ is a residue of R or a homolog thereof. In some embodiments, $X^{10}$ is a residue of R.

In some embodiments, $X^1$ is a residue of an amino acid selected from P, A, D, E, F, G, H, I, K, L, M, N, Q, R, S, T, V, W, Y, and α-methyl proline. In some embodiments, $X^1$ is a residue of an amino acid selected from P, A, D, E, F, G, H, I, K, L, M, N, Q, R, S, T, V, W, and Y. In some embodiments, $X^1$ is a residue of an amino acid selected from P, K, N, Q, R, Y, and α-methyl proline. In some embodiments, $X^1$ is a residue of an amino acid P. In some embodiments, $X^2$ is a residue of an amino acid selected from A, D, E, F, G, H, I, K, L, M, N, P, Q, R, S, T, V, W, and Y. In some embodiments, $X^2$ is a residue of an amino acid selected from A, D, E, K, N, Q, and R. In some embodiments, $X^2$ is a residue of A. In some embodiments, $X^4$ is a residue of an amino acid selected from I, F, H, L, V, homoleucine, tert-leucine, 3-cyclopropylalanine, 3-cyclobutylalanine, 3-cyclopentylalanine, 3-cyclohexylalanine, and alpha-neopentylglycine. In some embodiments, $X^4$ is a residue of an amino acid selected from I, F, H, L, and V. In some embodiments, $X^4$ is a residue of an amino acid selected from I, L, V, homoleucine, tert-leucine, 3-cyclopropylalanine, 3-cyclobutylalanine, 3-cyclopentylalanine, and alpha-neopentylglycine. In some embodiments, $X^4$ is a residue of I. In some embodiments, $X^5$ is a residue of an amino acid selected from L, F, H, I, V, alpha-methyl leucine, homoleucine, tert-leucine, 3-cyclopropylalanine, 3-cyclobutylalanine, 3-cyclopentylalanine, 3-cyclohexylalanine, and alpha-neopentylglycine. In some embodiments, $X^5$ is a residue of an amino acid selected from L, F, H, I, and V. In some embodiments, $X^5$ is a residue of an amino acid selected from L, I, V, alpha-methyl leucine, homoleucine, tert-leucine, 3-cyclopropylalanine, 3-cyclobutylalanine, 3-cyclopentylalanine, 3-cyclohexylalanine, and alpha-neopentylglycine. In some embodiments, $X^5$ is a residue of L. In some embodiments, $X^6$ is a residue of an amino acid selected from D, A, E, F, H, I, K, L, M, N, P, Q, R, S, T, V, W, Y, methionine sulfone, 2-aminoadipic acid, aspartic acid beta-methylester, aspartic acid beta-cyclohexylester, aspartic acid beta-benzylester, glutamic acid beta-methylester, glutamic acid beta-cyclohexylester, and glutamic acid beta-benzyl ester. In some embodiments, $X^6$ is a residue of an amino acid selected from D, A, E, F, H, I, K, L, M, N, P, Q, R, S, T, V, W, and Y. In some embodiments, $X^6$ is a residue of an amino acid selected from D, E, H, N, Q, S, T, Y, methionine sulfone, 2-aminoadipic acid, aspartic acid beta-methylester, aspartic acid beta-cyclohexylester, aspartic acid beta-benzylester, glutamic acid beta-methyl ester, glutamic acid beta-cyclohexylester, and glutamic acid beta-benzyl ester. In some embodiments, $X^6$ is a residue of an amino acid selected from D, N, and T. In some embodiments, $X^7$ is a residue of an amino acid selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, $M_I$, A, D, E, F, H, I, K, L, M, N, P, Q, R, S, T, V, W, Y and alpha-methyl alanine. In some embodiments, $X^7$ is a residue of an amino acid selected from A, D, E, F, H, I, K, L, M, N, P, Q, R, S, T, V, W, Y and alpha-methyl alanine. In some embodiments, $X^7$ is a residue of an amino acid selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, and $M_I$. In some embodiments, $X^7$ is a residue of an amino acid selected from A, D, E, F, H, I, K, L, M, N, P, Q, R, S, T, V, W, and Y. In some embodiments, $X^7$ is a residue of an amino acid selected from A, D, E, I, K, L, N, Q, R, S, T, V, W, Y and alpha-methyl alanine. In some embodiments, $X^7$ is a A or alpha-methyl alanine residue. In some embodiments, $X^8$ is a residue of an amino acid selected from H, F, I, L, N, Q, V, 1-methylhistidine, 3-methylhistidine, 3-(2-pyridyl)alanine, 3-(3-pyridyl)alanine, 3-(4-pyridyl)alanine, beta-2-furylalanine, beta-2-thienylalanine, 3-(2-tetrazolyl)alanine), and beta-4-thiazolylalanine. In some embodiments, $X^8$ is a residue of an amino acid selected from H, F, I, L, N, Q, and V. In some embodiments, $X^8$ is a residue of an amino acid selected from H, N, Q, 1-methylhistidine, 3-methylhistidine, 3-(2-pyridyl)alanine, 3-(3-pyridyl)alanine, 3-(4-pyridyl)alanine, beta-2-furylalanine, beta-2-thienylalanine, 3-(2-tetrazolyl)alanine), and beta-4-thiazolylalanine. In some embodiments, $X^8$ is a H residue. In some embodiments, $X^9$ is a residue of an amino acid selected from I, V, F, H, L, homoleucine, tert-leucine, 3-cyclopropylalanine, 3-cyclobutylalanine, 3-cyclopentylalanine, 3-cyclohexylalanine, and alpha-neopentylglycine. In some embodiments, $X^9$ is a residue of an amino acid selected from I, V, F, H, and L. In some embodiments, $X^9$ is a residue of an amino acid selected from I, V, L, homoleucine, tert-leucine, 3-cyclopropylalanine, 3-cyclobutylalanine, 3-cyclopentylalanine, 3-cyclohexylalanine, and alpha-neopentylglycine. In some embodiments, $X^9$ is a residue of an amino acid selected from I and V. In some embodiments, $X^{11}$ is a residue of an amino acid selected from R, A, D, E, F, H, I, K, L, M, N, P, Q, S, T, V, W, Y, 3-(1-naphthylalanine), 2-aminoadipic acid, asymmetric dimethylarginine, symmetric dimethylarginine, homoarginine, N-epsilon-methyllysine, N-epsilon-dimethyllysine, and N-epsilon-trimethyllysine. In some embodiments, $X^{11}$ is a residue of an amino acid selected from R, A, D, E, F, H, I, K, L, M, N, P, Q, S, T, V, W, and Y. In some embodiments, $X^{11}$ is a residue of an amino acid selected from R, A, E, F, K, Q, S, V, Y, 3-(1-naphthylalanine), 2-aminoadipic acid, asymmetric dimethylarginine, symmetric dimethylarginine, homoarginine, N-epsilon-methyllysine, N-epsilon-dimethyllysine, and N-epsilon-trimethyllysine. In some embodiments, $X^{11}$ is a residue of an amino acid selected from R, A, F, K, S, V, 3-(1-naphthylalanine), asymmetric dimethylarginine, symmetric dimethylarginine, homoarginine, and N-epsilon-methyllysine. In some embodiments, $X^{12}$ is a residue of an amino acid selected from V, F, H, I, L, alpha-methyl valine, alpha methyl leucine, homoleucine, tert-leucine, 3-cyclopropylalanine, 3-cyclobutylalanine, 3-cyclopentylalanine, 3-cyclohexylalanine, and alpha-neopentylglycine. In some embodiments, $X^{12}$ is a residue of an amino acid selected from V, F, H, I, and L. In some embodiments, $X^{12}$ is a residue of an amino acid selected from I, A, L, V, alpha-methylleucine, homoleucine, tert-leucine, 3-cyclopropylalanine, 3-cyclobutylalanine, 3-cyclopentylalanine, 3-cyclohexylalanine, alpha-neopentylglycine, O-propargylserine, L-octylglycine, and L-alloisoleucine. In some embodiments, $X^{12}$ is a residue of an amino acid selected from V, alpha-methyl valine, and alpha methyl leucine. In some embodiments, $X^{13}$ is a residue of an amino acid selected from W, A, D, E, F, H, I, K, L, M, N, P, Q, R, S, T, V, Y, d-tryptophan, alpha-methyl tryptophan, 3-(1-naphthylalanine), 3-(2-naphthylalanine), 4-chlorotryptophan, 5-chlorotryptophan, 6-chlorotryptophan, 7-chlorotryptophan, 4-bromotryptophan, 5-bromotryptophan, 6-bromotryptophan, 7-bromotryptophan, 4-fluorotryptophan, 5-fluorotryptophan, 6-fluorotryptophan, 7-fluorotryptophan, 1-methyltryptophan, 2-methyltryptophan, 4-methyltryptophan, 5-methyltryptophan, 6-methyltryptophan, 7-methyltryptophan, 2-hydroxytryptophan, 4-hydroxytryptophan, 5-hydroxytryptophan, 6-hydroxytryptophan, 7-hydroxytryptophan, 5-methoxytryptophan, 7-azatryptophan, 3-benzothienylalanine, and 4-phenyl-L-phenylalanine. In some embodiments, $X^{13}$ is a residue of an amino acid selected from W, A, D, E, F, H, I, K, L, M, N, P, Q, R, S, T, V, and Y. In some embodiments, $X^{13}$ is a residue of an amino acid selected from W, D, E, F, Y, d-tryptophan, alpha-methyl tryptophan, 3-(1-naphthylalanine), 3-(2-naphthylalanine), 5-chlorotryptophan, 6-chlorotryptophan, 7-chlorotryptophan, 5-bromotryptophan, 6-bromotryptophan, 7-bromotryptophan, 5-fluorotryptophan, 6-fluorotryptophan, 7-fluorotryptophan, 1-methyltryptophan, 2-methyltryptophan, 5-methyltryptophan, 6-methyltryptophan, 7-methyltryptophan, 2-hydroxytryptophan, 5-hydroxytryptophan, 6-hydroxytryptophan, 7-hydroxytryptophan, 5-methoxytryptophan, 7-azatryptophan, and 3-benzothienylalanine. In some embodiments, $X^{13}$ is a residue of an amino acid selected from W, D-tryptophan, and alpha-methyl tryptophan.

In some embodiments, a provided peptide comprises SILDAHIQRVW (SEQ ID NO: 4) or a homolog thereof, therein at least two amino acid residues of SILDAHIQRVW (SEQ ID NO: 4) or a homolog thereof is independently replaced with $X^i$ and $X^{i+m}$. In some embodiments, a provided peptide comprising $X^i$ILDAHI$X^{i+m}$RVW (SEQ ID NO: 5) or a homolog thereof. In some embodiments, the side chains of $X^i$ and $X^{i+m}$ are linked together through olefin metathesis to form a staple, e.g., one described in the present disclosure. In some embodiments, one or more, or more than half, or all of I, L, D, H, and V, corresponding to I472, L473, D474, H476, and V480 of *Xenopus* Axin are not replaced or replaced with a homolog that has similar properties (e.g., a basic residue with a basic homolog, an acid residue with an acidic homolog, a hydrophobic residue with a hydrophobic homolog, and/or an aromatic residue with an aromatic homolog). In some embodiments, one or more, or more than half, or all of I, L, D, and H, corresponding to I472, L473, D474, and H476 of *Xenopus* Axin are not replaced. In some embodiments, one of I, L, D, and H, corresponding to I472, L473, D474, and H476 of *Xenopus* Axin is not replaced. In some embodiments, two of I, L, D, and H, corresponding to I472, L473, D474, and H476 of *Xenopus* Axin are not replaced. In some embodiments, three of I, L, D, and H, corresponding to I472, L473, D474, and H476 of *Xenopus* Axin are not replaced. In some embodiments, four of I, L, D, and H, corresponding to I472, L473, D474, and H476 of *Xenopus* Axin are not replaced. In some embodiments, all replacement, if any, are each independently replaced with a homolog that has similar properties (e.g., a basic residue with a basic homolog, an acid residue with an acidic homolog, a hydrophobic residue with a hydrophobic homolog, and/or an aromatic residue with an aromatic homolog). In some embodiments, all replacement, if any, are each independently replaced with a homolog, wherein if a basic residue is replaced, it is replaced with a basic homolog; if an acid residue, with an acidic homolog; if a hydrophobic residue, with a hydrophobic homolog, and if an aromatic residue, with an aromatic homolog.

In some embodiments, a provide peptide has a sequence that is at least 50%, 60%, 70%, 80%, 90%, or 95% homologous to PAR$_8$ILDAHVM$_B$RVW (SEQ ID NO: 6). In some embodiments, a provide peptide has a sequence that is at least 50%, 60%, 70%, 80%, 90%, or 95% homologous to AR$_8$ILDAHIM$_B$RVW (SEQ ID NO: 7). In some embodiments, a provide peptide has a sequence that is at least 50%, 60%, 70%, 80%, 90%, or 95% homologous to AM$_G$ELDAHIM$_B$RVW (SEQ ID NO: 8). In some embodiments, the homology is at least 50%. In some embodiments, the homology is at least 60%. In some embodiments, the homology is at least 70%. In some embodiments, the homology is at least 80%. In some embodiments, the homology is at least 80%. In some embodiments, the homology is at least 95%.

Exemplary peptides are extensively described in the present disclosure, e.g., in the Tables, Examples, etc. In some cases, a "-" may be included in a compound (e.g., unstapled peptide, stapled peptide, etc.) ID number after "FP". Unless otherwise specified, a number with a "-" after "FP" and a number without a "-" after "FP" refer to the same compound. For example, unless otherwise specified, FP-0996 (with a "-" after "FP") and FP0996 (without a "-" after "FP") refer to the same compound (in this case, the same peptide). In some embodiments, a provided peptide is a peptide of Table 1. In some embodiments, a provided stapled peptide is a peptide of Table 1. In some embodiments, a provided peptide is a peptide that can undergo olefin metathesis to form a peptide of Table 1. In some embodiments, a provided stapled peptide is FP0217c. In some embodiments, a provided stapled peptide is FP0597c.

TABLE 1

Exemplary peptides.
Part A:

| ID* | SEQ ID NO: | Sequence |
|---|---|---|
| FP0001c | 9 | Ac-P-Q-Mc-I-L-D-A-H-V-S$_8$-R-V-L-NH2 |
| FP0003c | 10 | Ac-P-A-Mc-I-L-D-A-H-V-S$_8$-R-V-L-NH2 |
| FP0005c | 11 | Ac-P-A-Mc-I-L-D-A-H-V-S$_8$-R-V-W-NH2 |
| FP0006a | 12 | Ac-P-A-Mc-I-L-D-A-H-V-S$_8$-R-V-W-NH2 |
| FP0007c | 13 | Ac-P-A-Mc-I-L-D-A-H-V-S$_8$-R-W-NH2 |

TABLE 1-continued

Exemplary peptides.
Part A:

| ID* | SEQ ID NO: | Sequence |
|---|---|---|
| FP0009c | 14 | Ac-P-A-Mc-I-A-D-A-H-V-$S_8$-R-V-W-NH2 |
| FP0011c | 15 | Ac-P-Q-$R_8$-I-L-D-A-H-V-$M_B$-R-V-L-NH2 |
| FP0025c | 16 | Ac-P-A-$R_8$-I-L-D-A-H-V-$M_B$-R-V-W-NH2 |
| FP0098 | 17 | Ac-P-A-S-I-L-D-A-H-V-Q-R-V-W-NH2 |
| FP0099 | 18 | Ac-P-A-$M_C$-I-L-D-A-H-V-S8-R-V-W-NH2 |
| FP0110 | 19 | Ac-P-E-S-I-L-D-E-H-V-Q-R-V-nL-K-NH2 |
| FP0212s Isomer 2 | 20 | Ac-P-A-$R_5$-I-L-D-A-H-V-$S_8$-R-V-W-NH2 |
| FP0216c | 21 | Ac-P-A-$R_8$-I-L-T-A-H-I-$M_B$-R-V-W-NH2 |
| FP0217a | 22 | Ac-A-$R_8$-I-L-D-A-H-I-$M_B$-R-V-W-NH2 |
| FP0217c | 23 | Ac-A-$R_8$-I-L-D-A-H-I-$M_B$-R-V-W-NH2 |
| c14-FP0217a | 24 | Myr-A-$R_8$-I-L-D-A-H-I-$M_B$-R-V-W-NH2 |
| c14-FP0217c | 25 | Myr-A-$R_8$-I-L-D-A-H-I-$M_B$-R-V-W-NH2 |
| c16-FP0217a | 26 | Pal-A-$R_8$-I-L-D-A-H-I-$M_B$-R-V-W-NH2 |
| FP0217c_bAfree | 27 | bA-A-$R_8$-I-L-D-A-H-I-$M_B$-R-V-W-NH2 |
| FP0217c_btn | 28 | Btn-PEG3-A-$R_8$-I-L-D-A-H-I-$M_B$-R-V-W-NH2 |
| FP0217c_c18a | 29 | C18a-A-$R_8$-I-L-D-A-H-I-$M_B$-R-V-W-NH2 |
| FP0217rc | 30 | Ac-A-$R_8$-I-L-D-A-H-I-$M_B$-R-V-W-NH2 |
| FP0217s Isomer 1 | 31 | Ac-A-$R_8$-I-L-D-A-H-I-$S_5$-R-V-W-NH2 |
| FP0217s Isomer 2 | 32 | Ac-A-$R_8$-I-L-D-A-H-I-$S_5$-R-V-W-NH2 |
| FP0217u | 33 | Ac-A-$R_8$-I-L-D-A-H-I-$M_B$-R-V-W-NH2 |
| FP0218c | 34 | Ac-A-$R_8$-I-L-N-A-H-I-$M_B$-R-V-W-NH2 |
| FP0219c | 35 | Ac-A-$R_8$-I-L-T-A-H-I-$M_B$-R-V-W-NH2 |
| FP0220c | 36 | Ac-$R_8$-I-L-D-A-H-I-$M_B$-R-V-W-NH2 |
| FP0221c | 37 | Ac-$R_8$-I-L-N-A-H-I-$M_B$-R-V-W-NH2 |
| FP0222c | 38 | Ac-$R_8$-I-L-T-A-H-I-$M_B$-R-V-W-NH2 |
| FP0223a | 39 | Ac-P-A-$M_A$-I-L-D-A-H-V-$S_8$-R-V-W-NH2 |
| FP0224a | 40 | Ac-P-A-$R_8$-I-L-D-A-H-I-MA-R-V-W-NH2 |
| FP0243c | 41 | Ac-A-$M_A$-I-L-pff-A-H-I-S8-ADMA-V-W-NH2 |
| FP0244c | 42 | Ac-A-$M_A$-I-L-pff-A-H-I-S8-Y-V-W-NH2 |
| FP0247c | 43 | Ac-A-$M_A$-I-L-ADMA-A-H-I-$S_8$-ADMA-V-W-NH2 |
| FP0249c | 44 | Ac-A-$R_8$-I-L-SDMA-A-H-I-$M_A$-ADMA-V-W-NH2 |
| FP0250c | 45 | Ac-A-$M_A$-I-L-ADMA-A-H-I-$S_8$-SDMA-V-W-NH2 |
| FP0253c | 46 | Ac-A-$R_8$-I-L-N-A-H-I-$M_A$-pff-V-W-NH2 |
| FP0264c | 47 | Ac-A-$M_A$-I-L-pff-A-H-I-$S_8$-A-V-W-NH2 |
| FP0265c | 48 | Ac-A-$R_8$-I-L-Y-A-H-I-$M_A$-Y-V-W-NH2 |
| FP0268c | 49 | Ac-A-$M_A$-I-L-N-A-H-I-$S_8$-ADMA-V-W-NH2 |
| FP0269c | 50 | Ac-A-$R_8$-I-L-ADMA-A-H-I-$M_A$-N-V-W-NH2 |

TABLE 1-continued

Exemplary peptides.
Part A:

| ID* | SEQ ID NO: | Sequence |
|---|---|---|
| FP0270c | 51 | Ac-A-$M_A$-I-L-ADMA-A-H-I-$S_8$-N-V-W-NH2 |
| FP0271c | 52 | Ac-A-$M_A$-I-L-N-A-H-I-$S_8$-SDMA-V-W-NH2 |
| FP0272c | 53 | Ac-A-$R_8$-I-L-ADMA-A-H-I-$M_A$-L-V-W-NH2 |
| FP0273c | 54 | Ac-A-$M_A$-I-L-SDMA-A-H-I-$S_8$-L-V-W-NH2 |
| FP0274c | 55 | Ac-A-$M_A$-I-L-ADMA-A-H-I-$S_8$-L-V-W-NH2 |
| FP0278c | 56 | Ac-A-$M_A$-I-L-Q-A-H-I-$S_8$-R-V-W-NH2 |
| FP0279c | 57 | Ac-A-$R_8$-I-L-N-A-H-I-$M_A$-Y-V-W-NH2 |
| FP0280c | 58 | Ac-A-$M_A$-I-L-Y-A-H-I-$S_8$-N-V-W-NH2 |
| FP0281c | 59 | Ac-A-$R_8$-I-L-Y-A-H-I-$M_A$-N-V-W-NH2 |
| FP0282c | 60 | Ac-A-$M_A$-I-L-N-A-H-I-$S_8$-Y-V-W-NH2 |
| FP0284c | 61 | Ac-A-$M_A$-I-L-SDMA-A-H-I-$S_8$-A-V-W-NH2 |
| FP0285c | 62 | Ac-A-$M_A$-I-L-D-A-H-I-$S_8$-R-V-W-NH2 |
| FP0286c | 63 | Ac-A-$M_A$-I-L-N-A-H-I-$S_8$-R-V-W-NH2 |
| FP0290c | 64 | Ac-A-$M_A$-I-L-N-A-H-I-$S_8$-cpa-V-W-NH2 |
| FP0292c | 65 | Ac-A-$R_8$-I-L-D-A-H-I-$M_A$-Q-V-W-NH2 |
| FP0293c | 66 | Ac-A-$M_A$-I-L-D-A-H-I-$S_8$-Q-V-W-NH2 |
| FP0295c | 67 | Ac-A-$R_8$-I-L-Q-A-H-I-$M_A$-N-V-W-NH2 |
| FP0296c | 68 | Ac-A-$M_A$-I-L-Q-A-H-I-$S_8$-N-V-W-NH2 |
| FP0298c | 69 | Ac-A-$M_A$-I-L-Q-A-H-I-$S_8$-T-V-W-NH2 |
| FP0299c | 70 | Ac-A-$R_8$-I-L-Q-A-H-I-$M_A$-T-V-W-NH2 |
| FP0300c | 71 | Ac-A-$M_A$-I-L-D-A-H-I-$S_8$-N-V-W-NH2 |
| FP0302c | 72 | Ac-A-$M_A$-I-L-N-A-H-I-$S_8$-L-V-W-NH2 |
| FP0306c | 73 | Ac-A-$M_A$-I-L-T-A-H-I-$S_8$-N-V-W-NH2 |
| FP0317a | 74 | Dodec-P-A-$R_8$-I-L-D-A-H-V-$M_B$-R-V-W-NH2 |
| FP0318a | 75 | Dec-P-A-$R_8$-I-L-D-A-H-V-$M_B$-R-V-W-NH2 |
| FP0318c | 76 | Dec-P-A-$R_8$-I-L-D-A-H-V-$M_B$-R-V-W-NH2 |
| FP0321c | 77 | Bua-P-A-$R_8$-I-L-D-A-H-V-$M_B$-R-V-W-NH2 |
| FP0324c | 78 | Oct-P-A-$R_8$-I-L-D-A-H-V-$M_B$-R-V-W-1NH2 |
| FP0325a | 79 | Hex-P-A-$R_8$-I-L-D-A-H-V-$M_B$-R-V-W-NH2 |
| FP0325c | 80 | Hex-P-A-$R_8$-I-L-D-A-H-V-$M_B$-R-V-W-NH2 |
| FP0327c | 81 | Ac-P-A-$R_8$-I-A-D-A-H-V-$M_B$-R-V-W-NH2 |
| FP0327c | 81 | Ac-P-A-$R_8$-I-A-D-A-H-V-$M_B$-R-V-W-NH2 |
| FP0335a | 82 | Ac-A-$M_E$-I-L-D-A-H-I-$S_8$-R-V-W-NH2 |
| FP0335c Isomer 1 | 83 | Ac-A-$M_E$-I-L-D-A-H-I-$S_8$-R-V-W-NH2 |
| FP0335c Isomer 2 | 84 | Ac-A-$M_E$-I-L-D-A-H-I-$S_8$-R-V-W-NH2 |
| FP0336c | 85 | Ac-A-$M_E$-I-L-4FF-A-H-I-$S_8$-Y-V-W-NH2 |
| FP0338c | 86 | Ac-A-$R_8$-I-L-D-A-H-I-$M_D$-R-V-W-NH2 |

TABLE 1-continued

Exemplary peptides.
Part A:

| ID* | SEQ ID NO: | Sequence |
|---|---|---|
| FP0344c | 87 | Ac-A-$R_8$-I-L-4FF-A-H-I-$M_B$-R-V-W-NH2 |
| FP0345c | 88 | Ac-A-$M_A$-I-L-4FF-A-H-I-$S_8$-Y-V-W-NH2 |
| FP0346c | 89 | Ac-A-$R_8$-I-L-4FF-A-H-I-$M_A$-4FF-V-W-NH2 |
| FP0349c | 90 | Ac-A-$R_8$-I-L-MeY-A-H-I-$M_A$-4FF-V-W-NH2 |
| FP0350c | 91 | Ac-A-$R_8$-I-L-F-A-H-I-$M_B$-R-V-W-NH2 |
| FP0352c | 92 | Ac-A-$R_8$-I-L-F-A-H-I-$M_A$-4FF-V-W-NH2 |
| FP0353c | 93 | Ac-A-$R_8$-I-L-1NapA-A-H-I-$M_B$-R-V-W-NH2 |
| FP0354c | 94 | Ac-A-$M_A$-I-L-1NapA-A-H-I-$S_8$-Y-V-W-NH2 |
| FP0355c | 95 | Ac-A-$R_8$-I-L-1NapA-A-H-I-$M_A$-4FF-V-W-NH2 |
| FP0357c | 96 | Ac-A-$M_A$-I-L-V-A-H-I-$S_8$-Y-V-W-NH2 |
| FP0365c | 97 | Ac-A-$R_8$-I-L-D-A-H-I-$M_B$-1NapA-V-W-NH2 |
| FP0365c Isomer 1 | 98 | Ac-A-$R_8$-I-L-D-A-H-I-$M_B$-1NapA-V-W-NH2 |
| FP0365c Isomer 2 | 99 | Ac-A-$R_8$-I-L-D-A-H-I-$M_B$-1NapA-V-W-NH2 |
| FP0368c | 100 | Ac-A-$R_8$-I-L-D-A-H-I-$M_B$-V-V-W-NH2 |
| FP0369c | 101 | Ac-A-$M_A$-I-L-4FF-A-H-I-$S_8$-V-V-W-NH2 |
| FP0371c | 102 | Ac-A-$R_8$-I-L-D-A-H-I-$M_B$-F-V-W-NH2 |
| FP0380c | 103 | Ac-A-$R_8$-I-L-D-A-H-I-$M_B$-R-Cha-W-NH2 |
| FP0383c | 104 | Ac-A-$R_8$-I-L-D-A-H-Cha-$M_B$-R-V-W-NH2 |
| FP0391c | 105 | Ac-A-$R_8$-I-L-2NapA-A-H-I-$M_A$-4FF-V-W-NH2 |
| FP0395c | 106 | Ac-A-$R_8$-I-L-Cha-A-H-I-$M_B$-R-V-W-NH2 |
| FP0405c | 107 | Ac-A-$R_8$-A-L-D-A-H-I-$M_B$-R-V-W-NH2 |
| FP0406c | 108 | Ac-A-$R_8$-I-A-D-A-H-I-$M_B$-R-V-W-NH2 |
| FP0407c | 109 | Ac-A-$R_8$-I-L-A-A-H-I-$M_B$-R-V-W-NH2 |
| FP0408c | 110 | Ac-A-$R_8$-I-L-D-A-A-I-$M_B$-R-V-W-NH2 |
| FP0409a | 111 | Ac-A-$R_8$-I-L-D-A-H-A-$M_B$-R-V-W-NH2 |
| FP0409c | 112 | Ac-A-$R_8$-I-L-D-A-H-A-$M_B$-R-V-W-NH2 |
| FP0409c_free | 113 | A-$R_8$-I-L-D-A-H-A-$M_B$-R-V-W-NH2 |
| c16-FP0409a | 114 | Pal-A-$R_8$-I-L-D-A-H-A-$M_B$-R-V-W-NH2 |
| c16-FP0409c | 115 | Pal-A-$R_8$-I-L-D-A-H-A-$M_B$-R-V-W-NH2 |
| FP0410c | 116 | Ac-A-$R_8$-I-L-D-A-H-I-$M_B$-A-V-W-NH2 |
| FP0411c | 117 | Ac-A-$R_8$-I-L-D-A-H-I-$M_B$-R-A-W-NH2 |
| FP0412c | 118 | Ac-A-$R_8$-I-L-D-A-H-I-$M_B$-R-V-A-NH2 |
| FP0495a | 119 | Ac-A-$R_7$-I-L-D-A-H-I-$M_D$-R-V-W-NH2 |
| FP0495c | 120 | Ac-A-$R_7$-I-L-D-A-H-I-$M_D$-R-V-W-NH2 |
| FP0501c | 121 | Ac-A-$R_5$-I-L-D-A-H-I-$M_F$-R-V-W-NH2 |
| FP0502a | 122 | Ac-A-$R_6$-I-L-D-A-H-I-$M_F$-R-V-W-NH2 |
| FP0502c Isomer 1 | 123 | Ac-A-$R_6$-I-L-D-A-H-I-$M_F$-R-V-W-NH2 |

TABLE 1-continued

Exemplary peptides.
Part A:

| ID* | SEQ ID NO: | Sequence |
|---|---|---|
| FP0502c Isomer 2 | 124 | Ac-A-$R_6$-I-L-D-A-H-I-$M_F$-R-V-W-NH2 |
| FP0503a | 125 | Ac-A-$R_7$-I-L-D-A-H-I-$M_F$-R-V-W-NH2 |
| FP0503c | 126 | Ac-A-$R_7$-I-L-D-A-H-I-$M_F$-R-V-W-NH2 |
| FP0506a | 127 | Ac-A-$M_I$-I-L-D-A-H-I-$S_5$-R-V-W-NH2 |
| FP0506c Isomer 1 | 128 | Ac-A-$M_I$-I-L-D-A-H-I-$S_5$-R-V-W-NH2 |
| FP0506c Isomer 2 | 129 | Ac-A-$M_I$-I-L-D-A-H-I-$S_5$-R-V-W-NH2 |
| FP0507a | 130 | Ac-A-$M_I$-I-L-D-A-H-I-$S_6$-R-V-W-NH2 |
| FP0507c | 131 | Ac-A-$M_I$-I-L-D-A-H-I-$S_6$-R-V-W-NH2 |
| FP0509a | 132 | Ac-A-$R_4$-I-L-D-A-H-I-$M_H$-R-V-W-NH2 |
| FP0509c | 133 | Ac-A-$R_4$-I-L-D-A-H-I-$M_H$-R-V-W-NH2 |
| FP0510a | 134 | Ac-A-$R_5$-I-L-D-A-H-I-$M_H$-R-V-W-NH2 |
| FP0510c Isomer 1 | 135 | Ac-A-$R_5$-I-L-D-A-H-I-$M_H$-R-V-W-NH2 |
| FP0510c Isomer 2 | 136 | Ac-A-$R_5$-I-L-D-A-H-I-$M_H$-R-V-W-NH2 |
| FP0511a | 137 | Ac-A-$R_6$-I-L-D-A-H-I-$M_H$-R-V-W-NH2 |
| FP0511c Isomer 1 | 138 | Ac-A-$R_6$-I-L-D-A-H-I-$M_H$-R-V-W-NH2 |
| FP0511c Isomer 2 | 139 | Ac-A-$R_6$-I-L-D-A-H-I-$M_H$-R-V-W-NH2 |
| FP0516a Isomer 1 | 140 | Ac-A-$R_7$-I-L-D-A-H-I-$M_A$-R-V-W-NH2 |
| FP0516a Isomer 2 | 141 | Ac-A-$R_7$-I-L-D-A-H-I-$M_A$-R-V-W-NH2 |
| FP0516c | 142 | Ac-A-$R_7$-I-L-D-A-H-I-$M_A$-R-V-W-NH2 |
| FP0536c | 143 | Ac-A-$R_8$-I-L-D-A-thi-I-$M_B$-R-V-W-NH2 |
| FP0537c | 144 | Ac-A-$R_8$-I-L-D-A-3pyr-I-$M_B$-R-V-W-NH2 |
| FP0538c | 145 | Ac-A-$R_8$-I-L-D-A-4pyr-I-$M_B$-R-V-W-NH2 |
| FP0539c | 146 | Ac-A-$R_8$-I-L-D-A-2pyr-I-$M_B$-R-V-W-NH2 |
| FP0539c Isomer 1 | 147 | Ac-A-$R_8$-I-L-D-A-2pyr-I-$M_B$-R-V-W-NH2 |
| FP0539c Isomer 2 | 148 | Ac-A-$R_8$-I-L-D-A-2pyr-I-$M_B$-R-V-W-NH2 |
| FP0540c | 149 | Ac-A-$R_8$-I-L-D-A-F-I-$M_B$-R-V-W-NH2 |
| FP0541c | 150 | Ac-A-$R_8$-I-L-D-A-fur-I-$M_B$-R-V-W-NH2 |
| FP0542c | 151 | Ac-A-$R_8$-I-L-D-A-H-I-$M_B$-S-V-W-NH2 |
| FP0554c Isomer 1 | 152 | Ac-A-$R_8$-I-L-D-A-2pyr-I-$M_B$-A-V-W-NH2 |
| FP0554c Isomer 2 | 153 | Ac-A-$R_8$-I-L-D-A-2pyr-I-$M_B$-A-V-W-NH2 |
| FP0555c Isomer 1 | 154 | Ac-A-$R_8$-I-L-D-A-2pyr-I-$M_B$-F-V-W-NH2 |
| FP0555c Isomer 2 | 155 | Ac-A-$R_8$-I-L-D-A-2pyr-I-$M_B$-F-V-W-NH2 |
| FP0556c Isomer 1 | 156 | Ac-A-$R_8$-I-L-D-A-2pyr-I-$M_B$-I-V-W-NH2 |
| FP0556c Isomer 2 | 157 | Ac-A-$R_8$-I-L-D-A-2pyr-I-$M_B$-I-V-W-NH2 |
| FP0557c Isomer 1 | 158 | Ac-A-$R_8$-I-L-D-A-2pyr-I-$M_B$-L-V-W-NH2 |
| FP0557c Isomer 2 | 159 | Ac-A-$R_8$-I-L-D-A-2pyr-I-$M_B$-L-V-W-NH2 |
| FP0558c Isomer 1 | 160 | Ac-A-$R_8$-I-L-D-A-2pyr-I-$M_B$-N-V-W-NH2 |

TABLE 1-continued

Exemplary peptides.
Part A:

| ID* | SEQ ID NO: | Sequence |
|---|---|---|
| FP0558c Isomer 2 | 161 | Ac-A-$R_8$-I-L-D-A-2pyr-I-$M_B$-N-V-W-NH2 |
| FP0559c Isomer 1 | 162 | Ac-A-$R_8$-I-L-D-A-2pyr-I-$M_B$-Q-V-W-NH2 |
| FP0559c Isomer 2 | 163 | Ac-A-$R_8$-I-L-D-A-2pyr-I-$M_B$-Q-V-W-NH2 |
| FP0560c Isomer 1 | 164 | Ac-A-$R_8$-I-L-D-A-2pyr-I-$M_B$-S-V-W-NH2 |
| FP0560c Isomer 2 | 165 | Ac-A-$R_8$-I-L-D-A-2pyr-I-$M_B$-S-V-W-NH2 |
| FP0561c Isomer 1 | 166 | Ac-A-$R_8$-I-L-D-A-2pyr-I-$M_B$-T-V-W-NH2 |
| FP0561c Isomer 2 | 167 | Ac-A-$R_8$-I-L-D-A-2pyr-I-$M_B$-T-V-W-NH2 |
| FP0562c Isomer 1 | 168 | Ac-A-$R_8$-I-L-D-A-2pyr-I-$M_B$-V-V-W-NH2 |
| FP0562c Isomer 2 | 169 | Ac-A-$R_8$-I-L-D-A-2pyr-I-$M_B$-V-V-W-NH2 |
| FP0563c Isomer 1 | 170 | Ac-A-$R_8$-I-L-D-A-2pyr-I-$M_B$-W-V-W-NH2 |
| FP0563c Isomer 2 | 171 | Ac-A-$R_8$-I-L-D-A-2pyr-I-$M_B$-W-V-W-NH2 |
| FP0564c Isomer 1 | 172 | Ac-A-$R_8$-I-L-D-A-2pyr-I-$M_B$-Y-V-W-NH2 |
| FP0564c Isomer 2 | 173 | Ac-A-$R_8$-I-L-D-A-2pyr-I-$M_B$-Y-V-W-NH2 |
| FP0565c Isomer 1 | 174 | Ac-A-$R_8$-I-L-D-A-2pyr-I-$M_B$-Cba-V-W-NH2 |
| FP0565c Isomer 2 | 175 | Ac-A-$R_8$-I-L-D-A-2pyr-I-$M_B$-Cba-V-W-NH2 |
| FP0566c Isomer 1 | 176 | Ac-A-$R_8$-I-L-D-A-2pyr-I-$M_B$-Cha-V-W-NH2 |
| FP0567c Isomer 1 | 177 | Ac-A-$R_8$-I-L-D-A-2pyr-I-$M_B$-Nva-V-W-NH2 |
| FP0567c Isomer 2 | 178 | Ac-A-$R_8$-I-L-D-A-2pyr-I-$M_B$-Nva-V-W-NH2 |
| FP0568c Isomer 1 | 179 | Ac-A-$R_8$-I-L-D-A-2pyr-I-$M_B$-tLeu-V-W-NH2 |
| FP0568c Isomer 2 | 180 | Ac-A-$R_8$-I-L-D-A-2pyr-I-$M_B$-tLeu-V-W-NH2 |
| FP0569c Isomer 1 | 181 | Ac-A-$R_8$-I-L-D-A-2pyr-I-$M_B$-fur-V-W-NH2 |
| FP0569c Isomer 2 | 182 | Ac-A-$R_8$-I-L-D-A-2pyr-I-$M_B$-fur-V-W-NH2 |
| FP0570c Isomer 1 | 183 | Ac-A-$R_8$-I-L-D-A-2pyr-I-$M_B$-Aib-V-W-NH2 |
| FP0570c Isomer 2 | 184 | Ac-A-$R_8$-I-L-D-A-2pyr-I-$M_B$-Aib-V-W-NH2 |
| FP0571c Isomer 1 | 185 | Ac-A-$R_8$-I-L-D-A-2pyr-I-$M_B$-thi-V-W-NH2 |
| FP0571c Isomer 2 | 186 | Ac-A-$R_8$-I-L-D-A-2pyr-I-$M_B$-thi-V-W-NH2 |
| FP0572c Isomer 1 | 187 | Ac-A-$R_8$-I-L-D-A-2pyr-I-$M_B$-2pyr-V-W-NH2 |
| FP0573c Isomer 1 | 188 | Ac-A-$R_8$-I-L-D-A-2pyr-I-$M_B$-3pyr-V-W-NH2 |
| FP0573c Isomer 2 | 189 | Ac-A-$R_8$-I-L-D-A-2pyr-I-$M_B$-3pyr-V-W-NH2 |
| FP0574c Isomer 1 | 190 | Ac-A-$R_8$-I-L-D-A-2pyr-I-$M_B$-cpa-V-W-NH2 |
| FP0574c Isomer 2 | 191 | Ac-A-$R_8$-I-L-D-A-2pyr-I-$M_B$-cpa-V-W-NH2 |
| FP0575c Isomer 1 | 192 | Ac-A-$R_8$-I-L-D-A-2pyr-I-$M_B$-MeY-V-W-NH2 |
| FP0575c Isomer 2 | 193 | Ac-A-$R_8$-I-L-D-A-2pyr-I-$M_B$-MeY-V-W-NH2 |
| FP0576c Isomer 1 | 194 | Ac-A-$R_8$-I-L-D-A-2pyr-I-$M_B$-4FF-V-W-NH2 |
| FP0576c Isomer 2 | 195 | Ac-A-$R_8$-I-L-D-A-2pyr-I-$M_B$-4FF-V-W-NH2 |
| FP0577c Isomer 1 | 196 | Ac-A-$R_8$-I-L-D-A-2pyr-I-$M_B$-1NapA-V-W-NH2 |
| FP0578c Isomer 1 | 197 | Ac-A-$R_8$-I-L-D-A-2pyr-I-$M_B$-4MeF-V-W-NH2 |

TABLE 1-continued

Exemplary peptides.
Part A:

| ID* | SEQ ID NO: | Sequence |
|---|---|---|
| FP0578c Isomer 2 | 198 | Ac-A-$R_8$-I-L-D-A-2pyr-I-$M_B$-4MeF-V-W-NH2 |
| FP0587c | 199 | Ac-A-$M_I$-I-L-D-A-H-I-$M_F$-R-V-W-NH2 |
| FP0588c | 200 | Ac-A-$M_I$-I-L-D-A-H-I-$M_G$-R-V-W-NH2 |
| FP0594c | 201 | Ac-A-$M_G$-I-L-D-A-H-I-$M_F$-R-V-W-NH2 |
| FP0596c | 202 | Ac-A-$M_G$-I-L-D-A-H-I-$M_E$-R-V-W-NH2 |
| FP0597c | 203 | Ac-A-$M_G$-I-L-D-A-H-I-$M_B$-R-V-W-NH2 |
| FP0597c_c12 | 204 | Dodec-A-$M_G$-I-L-D-A-H-I-$M_B$-R-V-W-NH2 |
| FP0597c_c8 | 205 | Oct-A-$M_G$-I-L-D-A-H-I-$M_B$-R-V-W-NH2 |
| FP0598c | 206 | Ac-A-$M_G$-I-L-D-A-H-I-$M_C$-R-V-W-NH2 |
| FP0601c | 207 | Ac-A-$M_E$-I-L-D-A-H-I-$M_F$-R-V-W-NH2 |
| FP0604c | 208 | Ac-A-$M_E$-I-L-D-A-H-I-$M_B$-R-V-W-NH2 |
| FP0605c | 209 | Ac-A-$M_E$-I-L-D-A-H-I-$M_C$-R-V-W-NH2 |
| FP0611c | 210 | Ac-A-$M_A$-I-L-D-A-H-I-$M_F$-R-V-W-NH2 |
| FP0616c | 211 | Ac-A-$M_A$-I-L-D-A-H-I-$M_C$-R-V-W-NH2 |
| FP0617c | 212 | Ac-A-$M_A$-I-L-D-A-H-I-$M_B$-R-V-W-NH2 |
| FP0625c | 213 | Ac-A-$M_A$-I-L-D-A-H-I-$M_I$-R-V-W-NH2 |
| FP0626c | 214 | Ac-A-$M_F$-I-L-D-A-H-I-$M_B$-R-V-W-NH2 |
| FP0628_aib | 215 | Ac-A-Aib-I-L-D-A-H-I-Aib-R-V-W-NH2 |
| FP0629c | 216 | Ac-A-$R_8$-I-L-M2O-A-H-I-$M_B$-R-V-W-NH2 |
| FP0630c | 217 | Ac-A-$R_8$-I-L-D-A-H-I-$M_B$-R-V-dW-NH2 |
| FP0631c | 218 | Ac-A-$R_8$-I-L-D-A-H-I-$M_B$-R-V-aMeW-NH2 |
| FP0632c | 219 | Ac-A-$R_8$-I-L-D-A-H-I-$M_B$-R-aMeV-W-NH2 |
| FP0633c | 220 | Ac-A-$R_8$-I-L-D-A-H-I-$M_B$-R-aMeL-W-NH2 |
| FP0634c | 221 | Ac-A-$R_8$-I-L-D-A-H-I-$M_B$-hArg-V-W-NH2 |
| FP0635c | 222 | Ac-A-$R_8$-I-L-D-A-H-I-$M_B$-K-V-W-NH2 |
| FP0636c | 223 | Ac-A-$R_8$-I-L-D-A-H-I-$M_B$-1meK-V-W-NH2 |
| FP0639c | 224 | Ac-A-$R_8$-I-L-D-A-H-I-$M_B$-ADMA-V-W-NH2 |
| FP0640c | 225 | Ac-A-$R_8$-I-L-D-A-H-I-$M_B$-SDMA-V-W-NH2 |
| FP0644c | 226 | Ac-A-$R_8$-I-aMeL-D-A-H-I-$M_B$-R-V-W-NH2 |
| FP0645c | 227 | Ac-A-$R_8$-I-L-D-Aib-H-I-$M_B$-R-V-W-NH2 |
| FP0721a | 228 | Ac-P-Q-$M_A$-I-L-D-$R_4$-H-V-R-R-V-W-R-NH2 |
| FP0721c | 229 | Ac-P-Q-$M_A$-I-L-D-$R_4$-H-V-R-R-V-W-R-NH2 |
| FP0723a | 230 | Ac-P-Q-$M_A$-I-L-D-$R_5$-H-V-R-R-V-W-R-NH2 |
| FP0723c | 231 | Ac-P-Q-$M_A$-I-L-D-$R_5$-H-V-R-R-V-W-R-NH2 |
| FP0724c | 232 | Ac-P-Q-$M_A$-I-L-D-$S_5$-H-V-R-R-V-W-R-NH2 |
| FP0725a | 233 | Ac-P-Q-$M_A$-I-L-D-$R_6$-H-V-R-R-V-W-R-NH2 |
| FP0725c | 234 | Ac-P-Q-$M_A$-I-L-D-$R_6$-H-V-R-R-V-W-R-NH2 |

TABLE 1-continued

Exemplary peptides.
Part A:

| ID* | SEQ ID NO: | Sequence |
| --- | --- | --- |
| FP0727c | 235 | Ac-P-Q-$M_4$-I-L-D-$R_7$-H-V-R-R-V-W-R-NH2 |
| FP0728c | 236 | Ac-P-Q-$M_4$-I-L-D-$S_7$-H-V-R-R-V-W-R-NH2 |
| FP0731c | 237 | Ac-P-Q-$R_4$-I-L-D-$M_4$-H-V-R-R-V-W-R-NH2 |
| FP0733c | 238 | Ac-P-Q-$R_5$-I-L-D-$M_4$-H-V-R-R-V-W-R-NH2 |
| FP0734a | 239 | Ac-P-Q-$S_5$-I-L-D-$M_4$-H-V-R-R-V-W-R-NH2 |
| FP0734c | 240 | Ac-P-Q-$S_5$-I-L-D-$M_4$-H-V-R-R-V-W-R-NH2 |
| FP0735a | 241 | Ac-P-Q-$R_6$-I-L-D-$M_4$-H-V-R-R-V-W-R-NH2 |
| FP0735c | 242 | Ac-P-Q-$R_6$-I-L-D-$M_4$-H-V-R-R-V-W-R-NH2 |
| FP0736a | 243 | Ac-P-Q-$S_6$-I-L-D-$M_4$-H-V-R-R-V-W-R-NH2 |
| FP0736c | 244 | Ac-P-Q-$S_6$-I-L-D-$M_4$-H-V-R-R-V-W-R-NH2 |
| FP0738a | 245 | Ac-P-Q-$S_7$-I-L-D-$M_4$-H-V-R-R-V-W-R-NH2 |
| FP0738c | 246 | Ac-P-Q-$S_7$-I-L-D-$M_4$-H-V-R-R-V-W-R-NH2 |
| FP0743a | 247 | Ac-P-Q-$M_C$-I-L-D-$R_5$-H-V-R-R-V-W-R-NH2 |
| FP0743c | 248 | Ac-P-Q-$M_C$-I-L-D-$R_5$-H-V-R-R-V-W-R-NH2 |
| FP0745a | 249 | Ac-P-Q-$M_C$-I-L-D-$R_6$-H-V-R-R-V-W-R-NH2 |
| FP0745c | 250 | Ac-P-Q-$M_C$-I-L-D-$R_6$-H-V-R-R-V-W-R-NH2 |
| FP0751a | 251 | Ac-P-Q-$M_B$-I-L-D-$S_5$-H-V-R-R-V-W-R-NH2 |
| FP0751c | 252 | Ac-P-Q-$M_B$-I-L-D-$S_5$-H-V-R-R-V-W-R-NH2 |
| FP0752c | 253 | Ac-P-Q-$M_B$-I-L-D-$S_6$-H-V-R-R-V-W-R-NH2 |
| FP0753a | 254 | Ac-P-Q-$M_B$-I-L-D-$S_7$-H-V-R-R-V-W-R-NH2 |
| FP0758a | 255 | Ac-P-Q-$R_5$-I-L-D-$M_B$-H-V-R-R-V-W-R-NH2 |
| FP0758c | 256 | Ac-P-Q-$R_5$-I-L-D-$M_B$-H-V-R-R-V-W-R-NH2 |
| FP0761c | 257 | Ac-P-Q-$S_6$-I-L-D-$M_B$-H-V-R-R-V-W-R-NH2 |
| FP0763a | 258 | Ac-P-Q-$S_7$-I-L-D-$M_B$-H-V-R-R-V-W-R-NH2 |
| FP0763c | 259 | Ac-P-Q-$S_7$-I-L-D-$M_B$-H-V-R-R-V-W-R-NH2 |
| FP0765c | 260 | Ac-P-Q-$R_4$-I-L-D-$M_C$-H-V-R-R-V-W-R-NH2 |
| FP0766c | 261 | Ac-P-Q-$R_5$-I-L-D-$M_C$-H-V-R-R-V-W-R-NH2 |
| FP0767a | 262 | Ac-P-Q-$R_6$-I-L-D-$M_C$-H-V-R-R-V-W-R-NH2 |
| FP0767c | 263 | Ac-P-Q-$R_6$-I-L-D-$M_C$-H-V-R-R-V-W-R-NH2 |
| FP0768a | 264 | Ac-P-Q-$R_7$-I-L-D-$M_C$-H-V-R-R-V-W-R-NH2 |
| FP0768c | 265 | Ac-P-Q-$R_7$-I-L-D-$M_C$-H-V-R-R-V-W-R-NH2 |
| FP0776c | 266 | Ac-P-Q-$R_5$-I-L-D-$M_G$-H-V-R-R-V-W-R-NH2 |
| FP0776a | 267 | Ac-P-Q-$R_5$-I-L-D-$M_G$-H-V-R-R-V-W-R-NH2 |
| FP0777c | 268 | Ac-P-Q-$R_5$-I-L-D-$M_I$-H-V-R-R-V-W-R-NH2 |
| FP0777a | 269 | Ac-P-Q-$R_5$-I-L-D-$M_I$-H-V-R-R-V-W-R-NH2 |
| FP0778c | 270 | Ac-P-Q-$M_D$-I-L-D-$S_5$-H-V-R-R-V-W-R-NH2 |
| FP0779c | 271 | Ac-P-Q-$M_F$-I-L-D-$S_5$-H-V-R-R-V-W-R-NH2 |

TABLE 1-continued

Exemplary peptides.
Part A:

| ID* | SEQ ID NO: | Sequence |
|---|---|---|
| FP0780c | 272 | Ac-P-Q-$M_H$-I-L-D-$S_5$-H-V-R-R-V-W-R-NH2 |
| FP0782c | 273 | Ac-P-Q-$M_G$-I-L-D-$R_5$-H-V-R-R-V-W-R-NH2 |
| FP0783c | 274 | Ac-P-Q-$M_I$-I-L-D-$R_5$-H-V-R-R-V-W-R-NH2 |
| FP0783a | 275 | Ac-P-Q-$M_I$-I-L-D-$R_5$-H-V-R-R-V-W-R-NH2 |
| FP0787s | 276 | Ac-P-Q-$S_5$-I-L-D-$S_5$-H-V-R-R-V-W-R-NH2 |

*u: unstapled;
a, c and s: stapled, typically (i, i + 4) and (i, i + 7). Some stapled peptides may contain two or more staples. For c, comprising a carbamate staple which comprises —N(R')—C(O)—O—. For s, comprising a hydrocarbon staple which comprises neither —N(R')—C(O)—O— nor —N(R')—. For a, comprising an amino staple which comprises —N(R')— which is not part of —N(R')—C(O)—O— (can be formed by removal of $CO_2$ from —N(R')—C(O)—O—). As appreciated by those skilled in the art, a staple formed by two side chains each independently having the structure of —$L^a$—CH=$CH_2$ has the structure of —$L^a$—CH=CH—$L^a$—, wherein the two $L^a$ are the same or different. For amino linker, —N(R')—C(O)—O— in $L^a$ of the corresponding carbamate linker is replaced with —N(R')—;
r: olefin (—CH=CH—) in staple formed by metathesis reduced to —$CH_2$—$CH_2$— (e.g., in rc).

Non-natural amino acids (or protected form thereof) or modifications (or reagents for introducing the modifications) in Table 1 (unless otherwise noted, all amino acids, if applicable, are L-amino acids):

Myr=myristoyl
Pal=palmitoyl
Ac=acetyl
nL=norleucine
bA=beta-alanine
Btn=biotin
PEG3=CAS #557756-85-1
C18a=CAS #871-70-5
pff=pentafluorophenylalanine
ADMA=asymmetric dimethylarginine
SDMA=symmetric dimethylarginine
cpa=3-cyclopropylalanine
Dodec=dodecanoyl
Dec=decanoyl
Bua=butyryl
Oct=octyl
Hex=hexyl
4FF=4-fluorophenylalanine
MeY=O-methyl tyrosine
1NapA=3-(1-naphthyl)-L-alanine
2NapA=3-(2-naphthyl)-L-alanine
Cha=3-cyclohexyl-L-alanine
thi=beta-2-thienylalanine
2pyr=3-(2-pyridyl)-L-alanine
3pyr=3-(3-pyridyl)-L-alanine
4pyr=3-(4-pyridyl)-L-alanine
fur=2-furyl-L-alanine
cba=3-cyclobutylalanine
Nva=norvaline
tLeu=tert-leucine
4MeF=4-methyl-L-phenylalanine
Aib=aminoisobutyric acid
M2O=methionine sulfone
dW=D-tryptophan
aMeW=alpha-methyl-L-tryptophan
aMeV=alpha-methyl-L-valine
aMeL=alpha-methyl-L-leucine
hArg=homoarginine
1meK=N-epsilon-methyl-L-lysine
FITC=fluorescein isothiocyanate
NHBut=aminobutyric acid
NHHex=aminohexanoic acid
NHOct=aminooctanoic acid
AzWT=azetidine-2-carboxylic acid
Bip=4-phenyl-L-phenylalanine
5C1W=5-chloro-L-tryptophan
HOW=5-hydroxy-L-tryptophan
H2W=2,3-dihydro-L-tryptophan
F3MeF=4-trifluoromethyl-L-phenylalanine
4ClF=4-chloro-L-phenylalanine Btn-PEG3 =

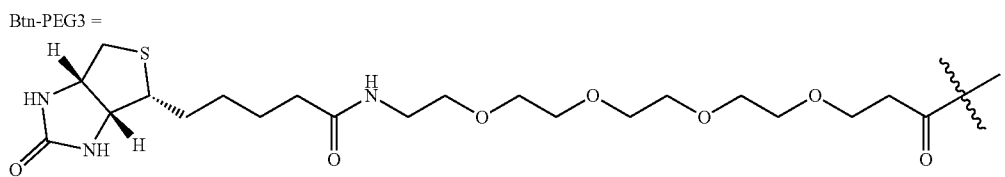

Biotin-PEG3

FITC-bA =
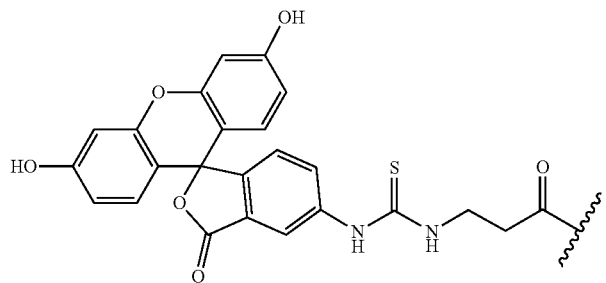
FITC-beta-alanine
PEG1 =
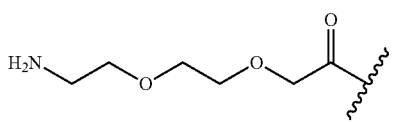
TABLE 1
Part B - Amino acid sequence the same as FP0217.
| Amino Acid 1 | Amino Acid 2 (i + 7) | ID | Carbamate Staple |
|---|---|---|---|
| Monomer A | $S_8$ | FP0512c | |
| Monomer A | $S_7$ | FP0513c | |
| Monomer A | $S_6$ | FP0514c | |
| $R_8$ | Monomer A | FP0515c | |

TABLE 1-continued
| | | Part B - Amino acid sequence the same as FP0217. | |
|---|---|---|---|
| $R_7$ | Monomer A | FP0516c | |
| $R_6$ | Monomer A | FP0517c | |
| Monomer E | $S_8$ | FP0335c | |
| Monomer E | $S_7$ | FP0492c | |
| Monomer E | $S_6$ | FP0491c | |
| Monomer E | $S_5$ | FP0490c | |
| $R_8$ | Monomer D | FP0338c | |
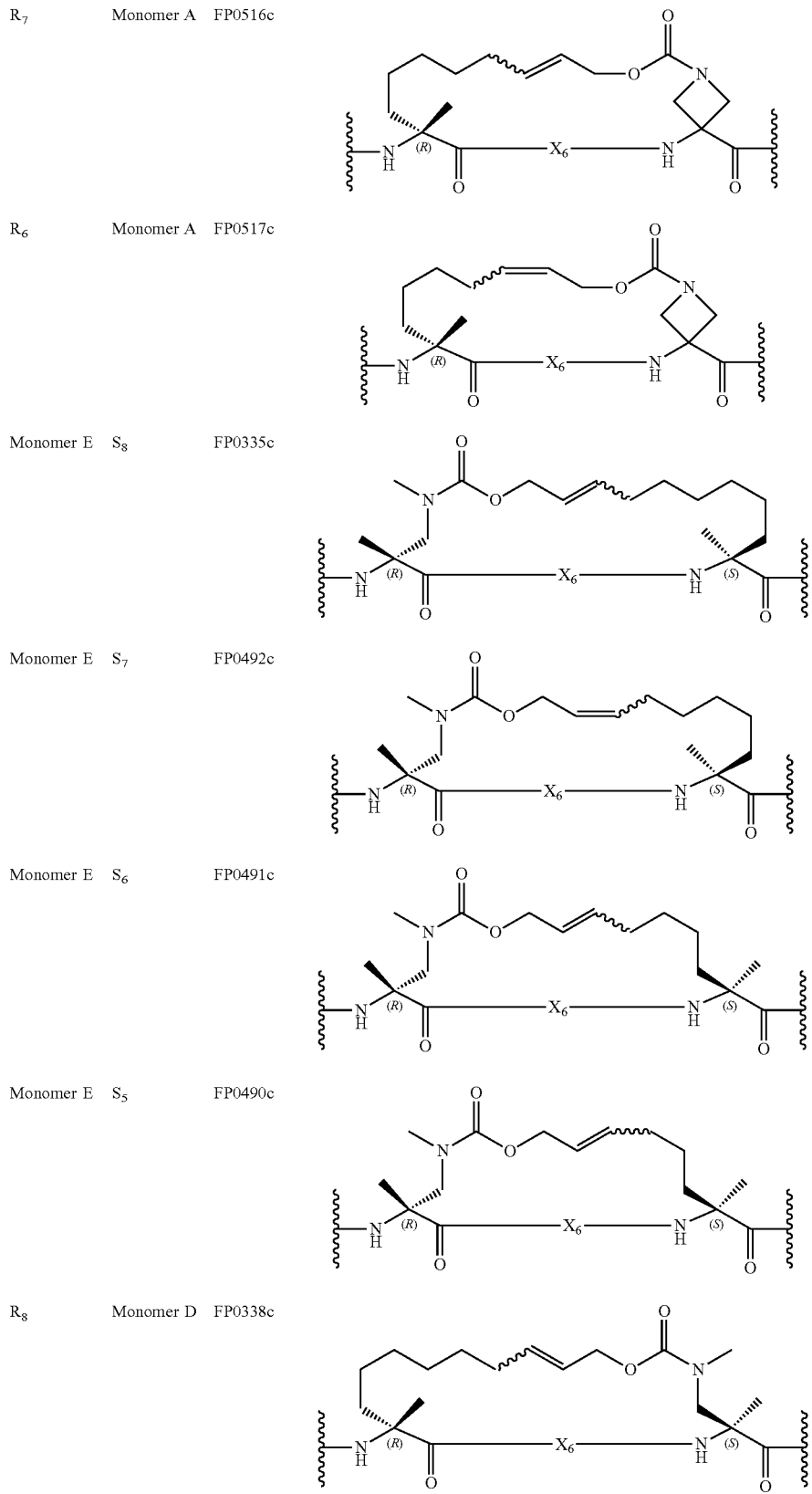

TABLE 1-continued
Part B - Amino acid sequence the same as FP0217.
| | | |
|---|---|---|
| R$_7$ | Monomer D | FP0495c |
| R$_6$ | Monomer D | FP0494c |
| R$_5$ | Monomer D | FP0493c |
| Monomer G | S$_7$ | FP0499c |
| Monomer G | S$_6$ | FP0498c |
| Monomer G | S$_5$ | FP0497c |
| Monomer G | S$_4$ | FP0496c |
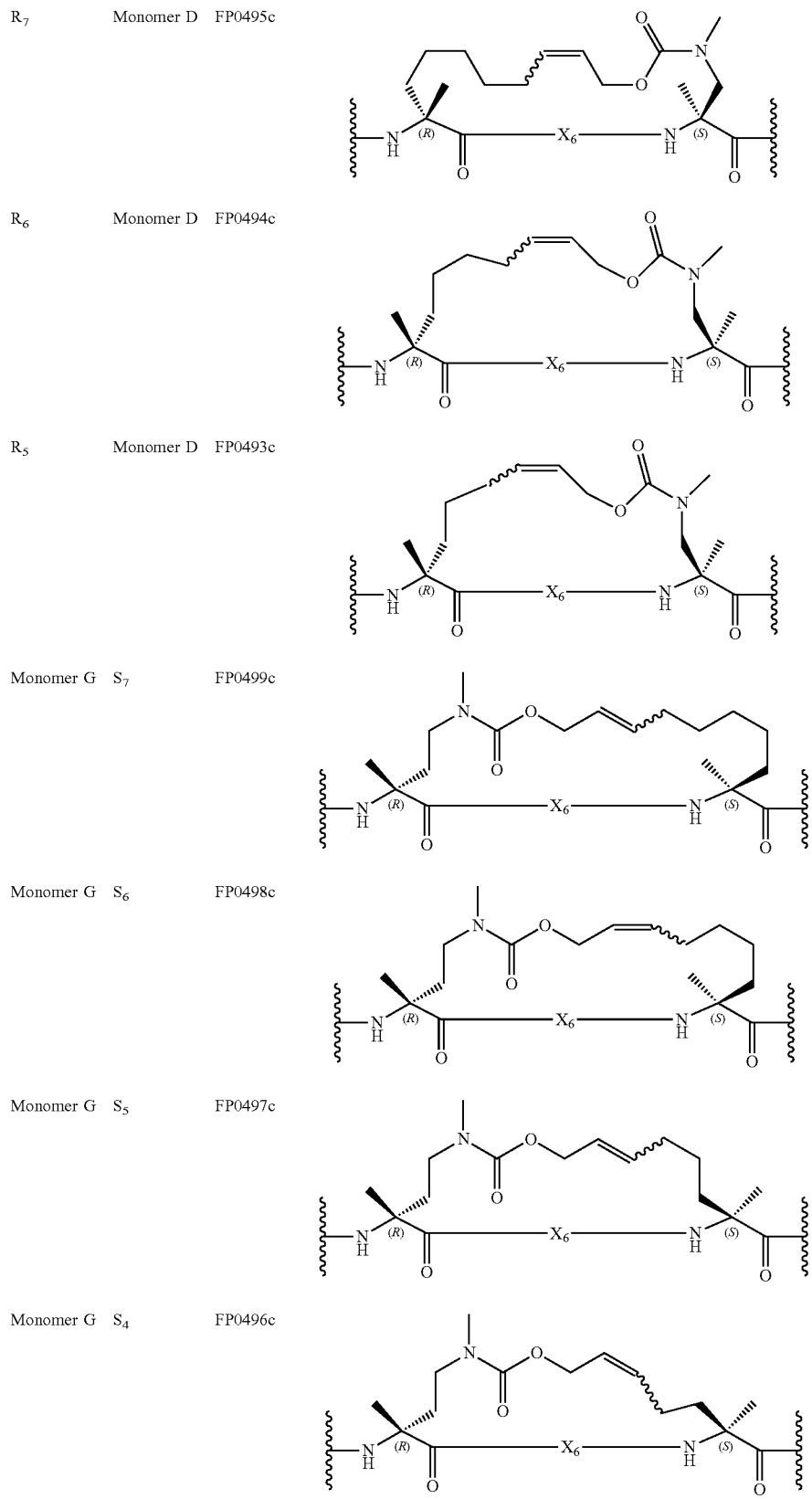

TABLE 1-continued
Part B - Amino acid sequence the same as FP0217.
| | | |
|---|---|---|
| R$_7$ | Monomer F | FP0503c |
| R$_6$ | Monomer F | FP0502c |
| R$_5$ | Monomer F | FP0501c |
| R$_5$ | Monomer F | FP0501c |
| R$_4$ | Monomer F | FP0500c |
| Monomer I | S$_6$ | FP0507c |
| Monomer I | S$_5$ | FP0506c |
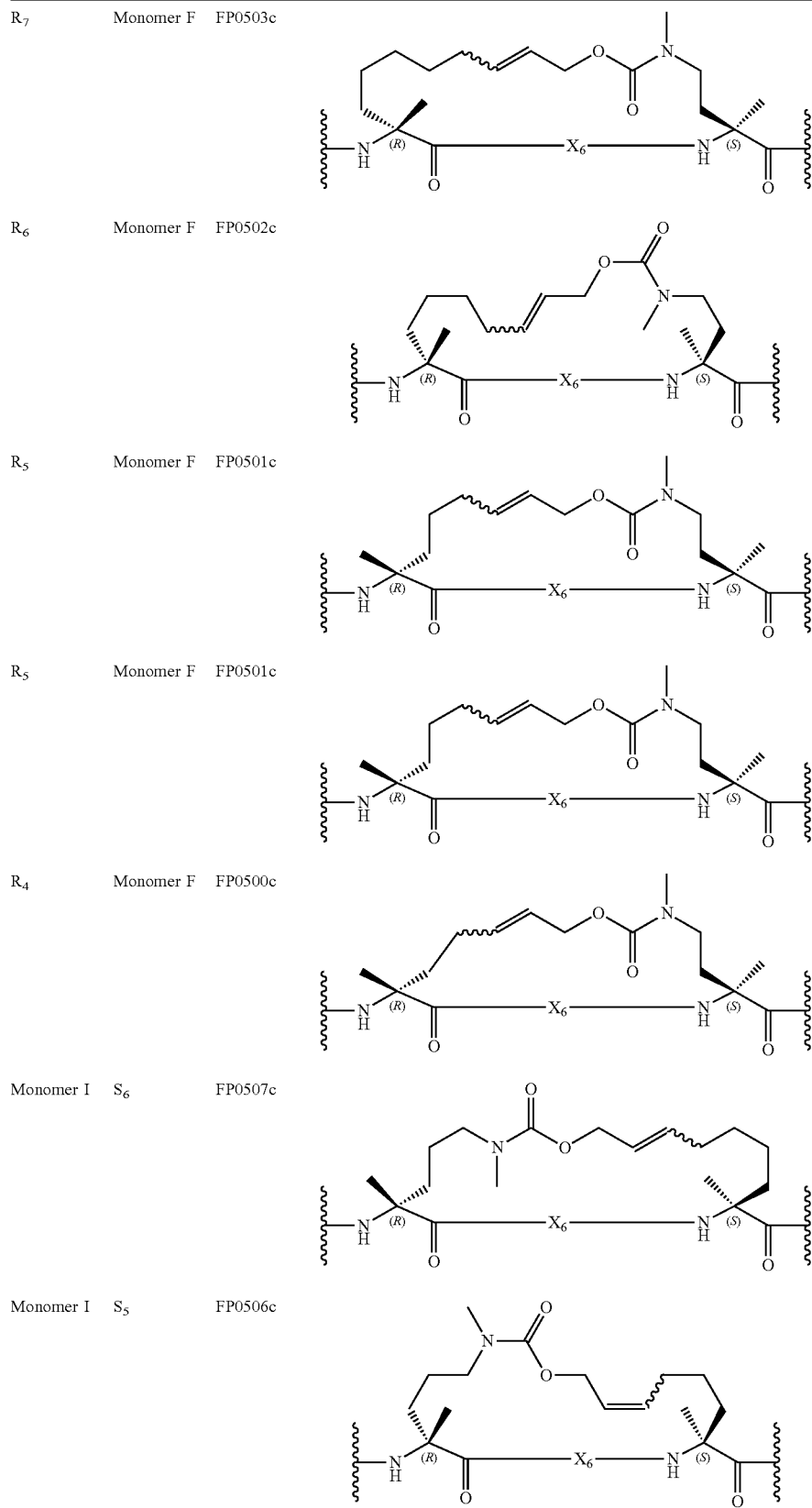

TABLE 1-continued
Part B - Amino acid sequence the same as FP0217.
| Monomer I | S₄ | FP0505c | 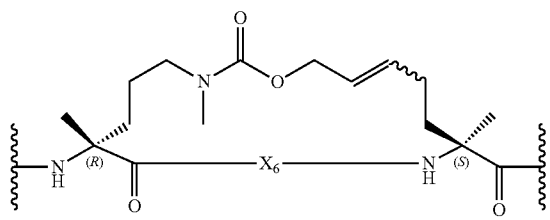 |
| Monomer I | S₃ | FP0504c | 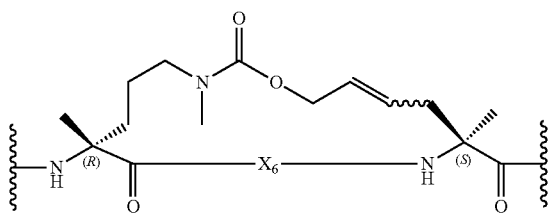 |
| Monomer C | S₈ | FP0486c | 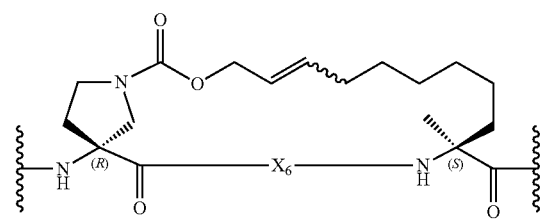 |
| Monomer C | S₇ | FP0485c | 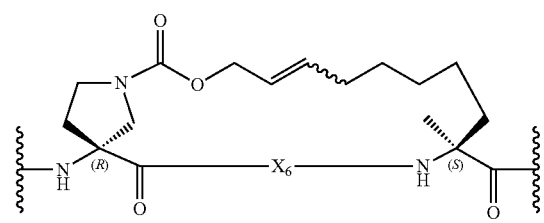 |
| Monomer C | S₆ | FP0484c | 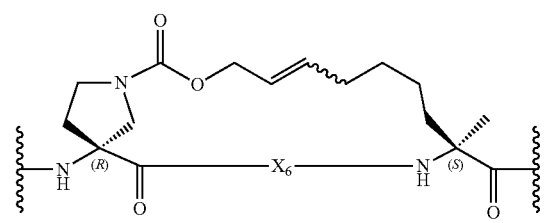 |
| Monomer C | S₅ | FP0483c | 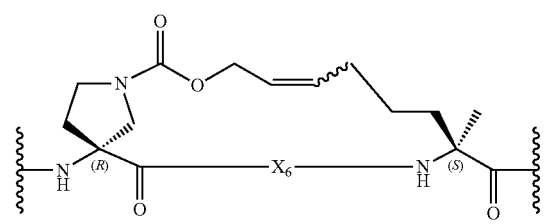 |
| R₈ | Monomer B | FP0217c | 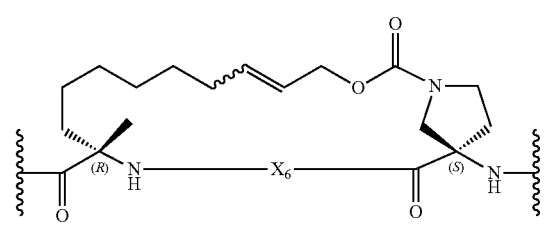 |

TABLE 1-continued
Part B - Amino acid sequence the same as FP0217.
| | | |
|---|---|---|
| $R_7$ | Monomer B | FP0489c |
| $R_6$ | Monomer B | FP0488c |
| $R_5$ | Monomer B | FP0487c |
| $R_3$ | Monomer H | FP0508c |
| $R_4$ | Monomer H | FP0509c |
| $R_5$ | Monomer H | FP0510c |
| $R_6$ | Monomer H | FP0511c |
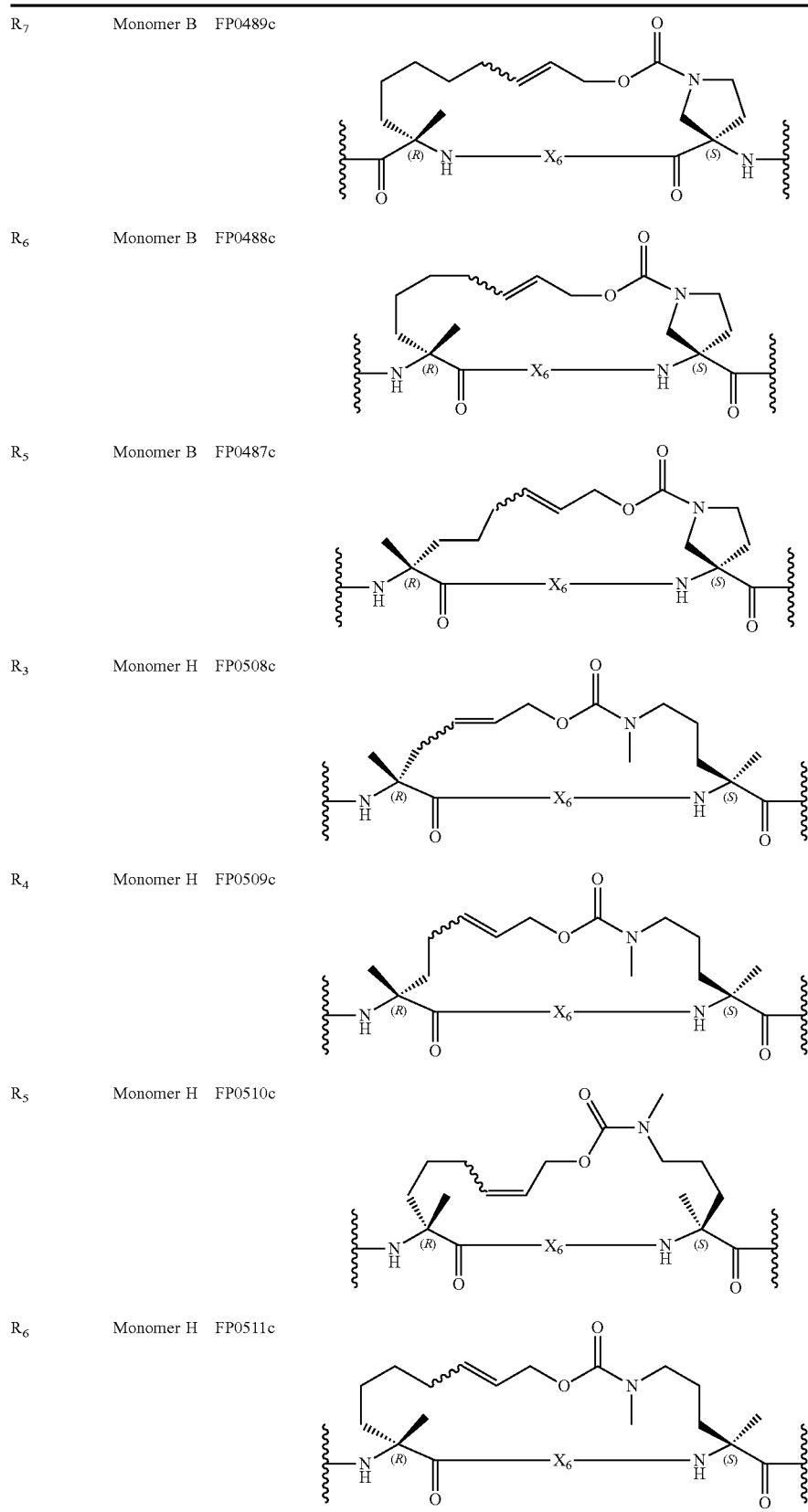

TABLE 1-continued
Part B - Amino acid sequence the same as FP0217.
| Monomer G | S₇ | FP0520c | 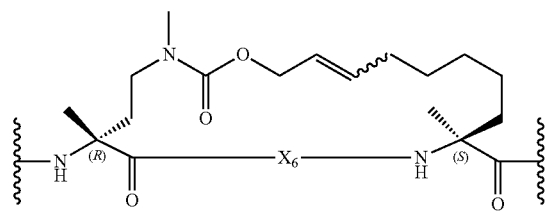 |
| R₇ | Monomer F | FP0521c | 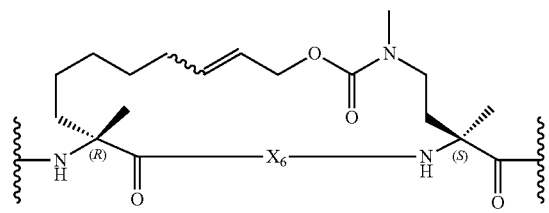 |
| Monomer I | S₆ | FP0522c | 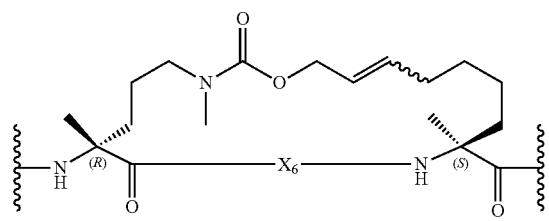 |
| R₆ | Monomer H | FP0523c | 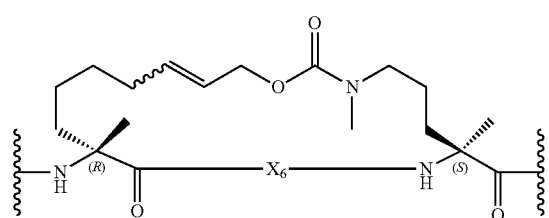 |
| Monomer A | Monomer B | FP0617c | 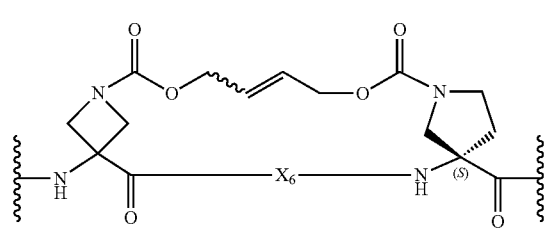 |
| Monomer A | Monomer C | FP0616c | 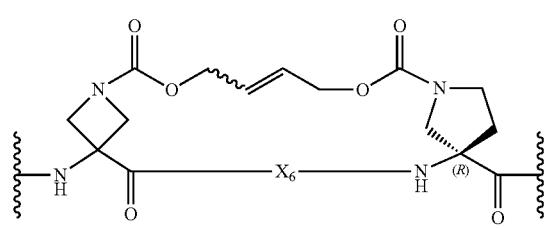 |
| Monomer A | Monomer A | FP0615c | 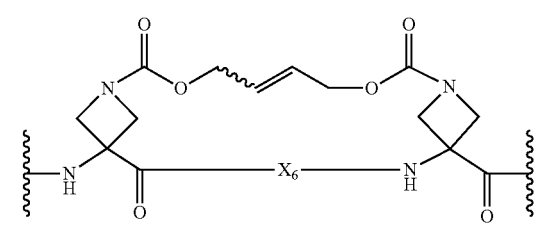 |

TABLE 1-continued
Part B - Amino acid sequence the same as FP0217.
| Monomer A | Monomer F | FP0611c | 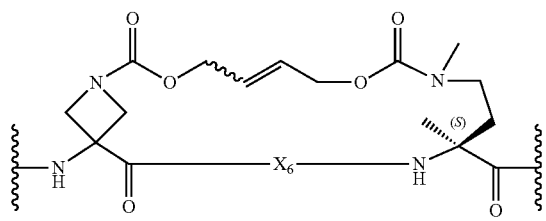 |
| Monomer A | Monomer E | FP0623c | 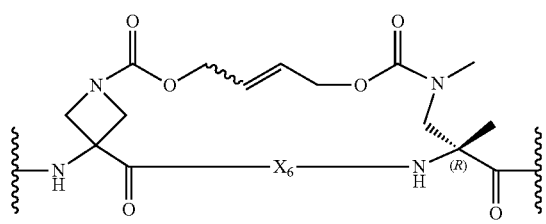 |
| Monomer A | Monomer G | FP0624c | 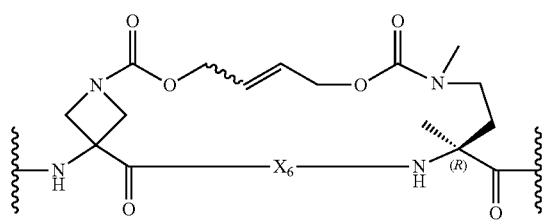 |
| Monomer A | Monomer I | FP0625c | 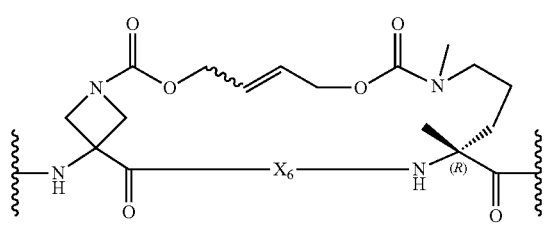 |
| Monomer I | Monomer A | FP0592c | 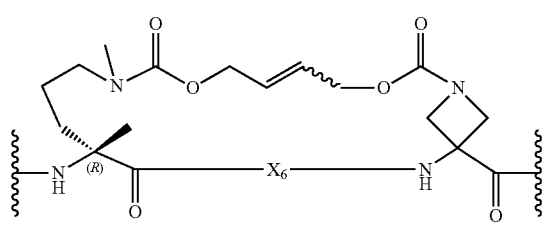 |
| Monomer G | Monomer A | FP0599c | 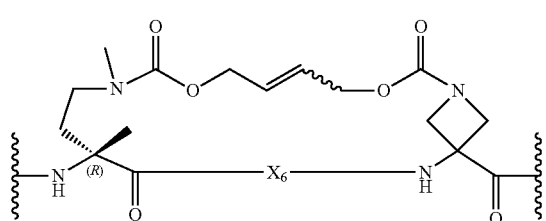 |
| Monomer E | Monomer A | FP0606c | 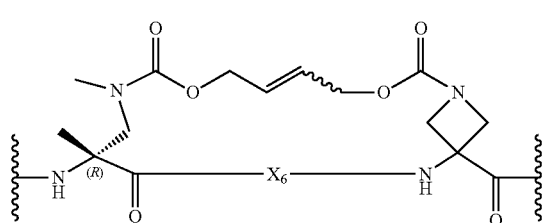 |

TABLE 1-continued
Part B - Amino acid sequence the same as FP0217.
| Monomer F | Monomer A | FP0627c | 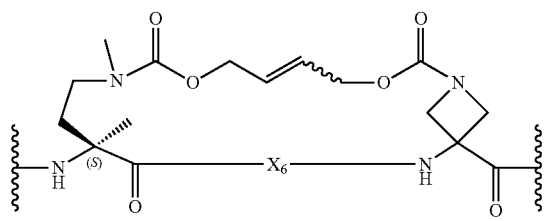 |
| Monomer C | Monomer A | FP0618c | 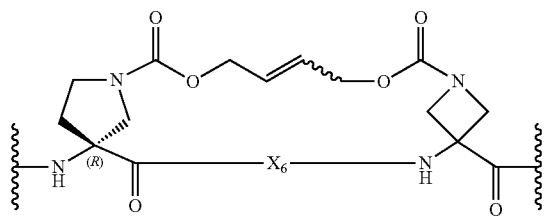 |
| Monomer B | Monomer A | FP0619c | 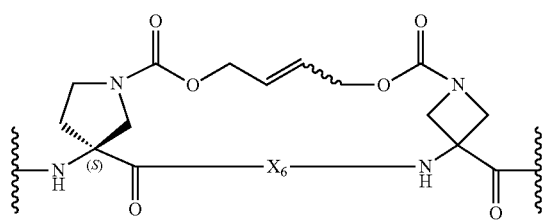 |
| Monomer B | Monomer B | FP0613c | 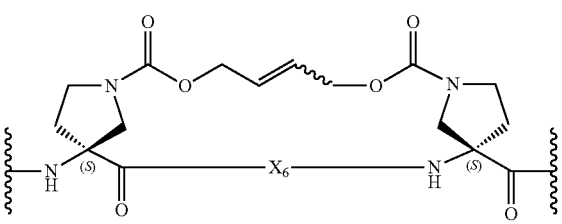 |
| Monomer B | Monomer F | FP0609c | 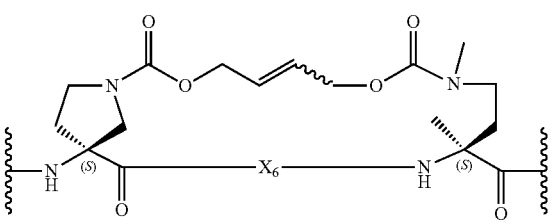 |
| Monomer C | Monomer F | FP0610c | 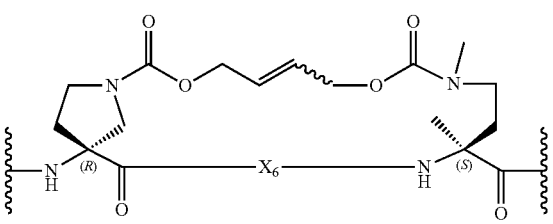 |
| Monomer C | Monomer C | FP0612c | 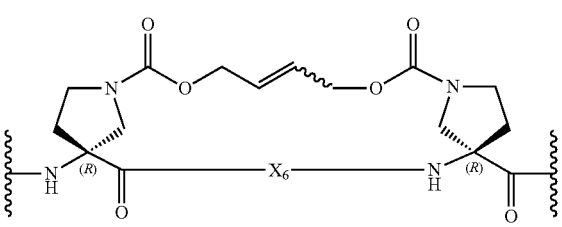 |

TABLE 1-continued
Part B - Amino acid sequence the same as FP0217.
| Monomer C | Monomer B | FP0614c | 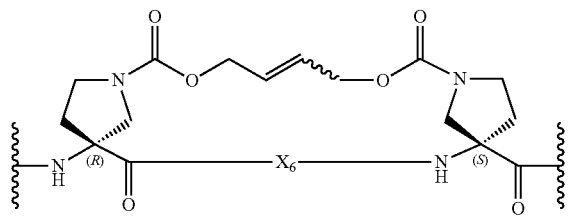 |
| Monomer C | Monomer E | FP0620c | 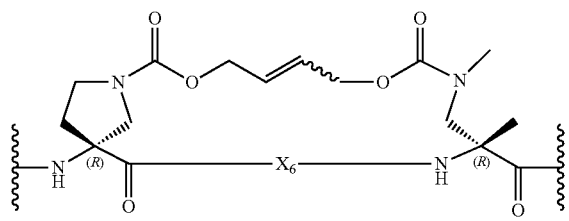 |
| Monomer C | Monomer G | FP0621c | 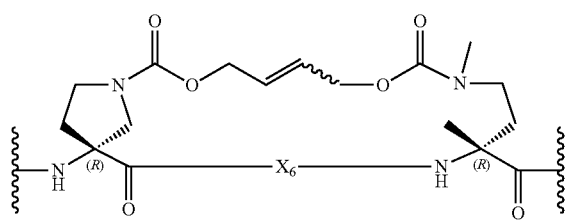 |
| Monomer C | Monomer I | FP0622c | 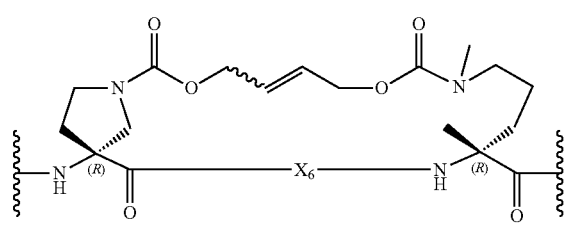 |
| Monomer I | Monomer F | FP0587c | 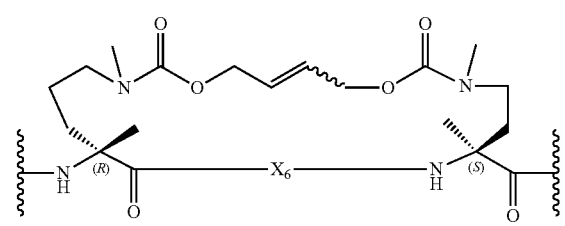 |
| Monomer I | Monomer G | FP0588c | 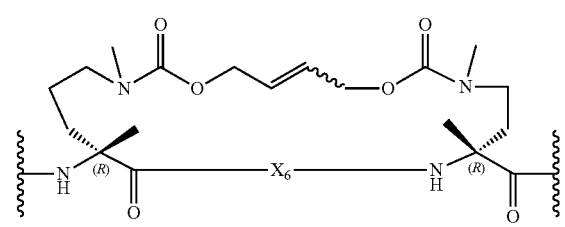 |
| Monomer I | Monomer E | FP0589c | 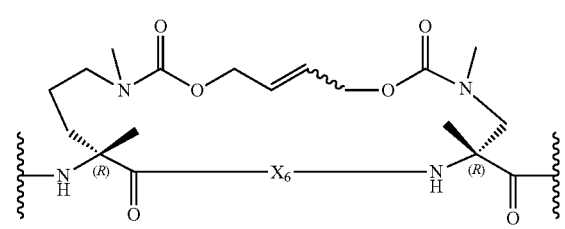 |

TABLE 1-continued
Part B - Amino acid sequence the same as FP0217.
| Monomer I | Monomer B | FP0590c | 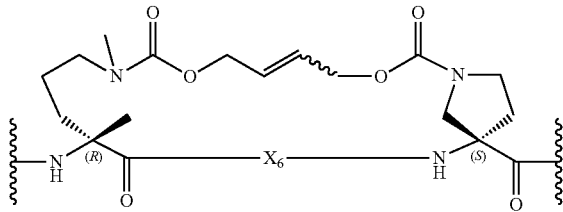 |
| Monomer I | Monomer C | FP0591c | 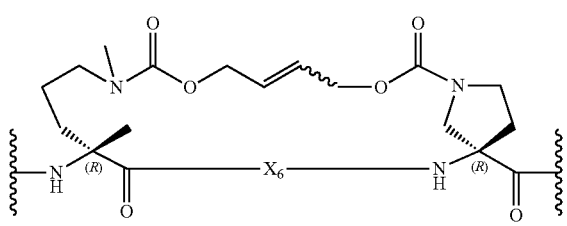 |
| Monomer I | Monomer I | FP0593c | 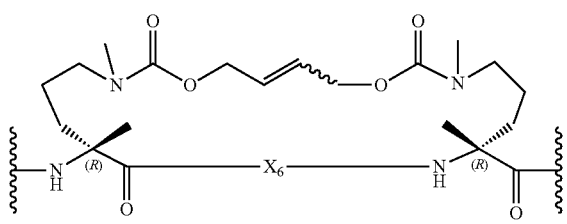 |
| Monomer G | Monomer F | FP0594c | 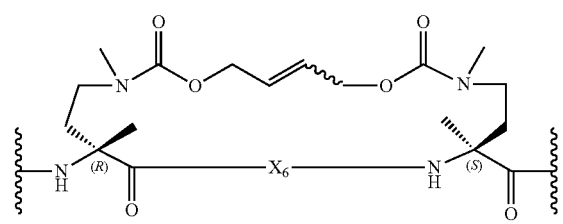 |
| Monomer G | Monomer G | FP0595c | 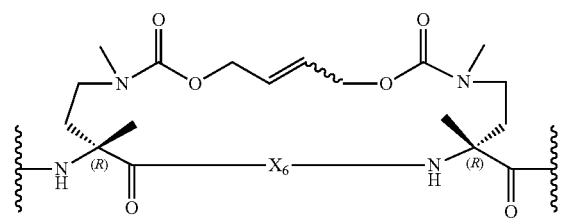 |
| Monomer G | Monomer E | FP0596c | 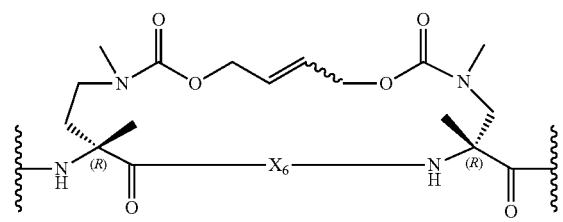 |
| Monomer G | Monomer B | FP0597c | 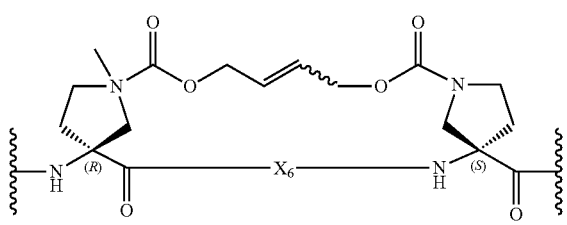 |

TABLE 1-continued
Part B - Amino acid sequence the same as FP0217.
| Monomer G | Monomer C | FP0598c | 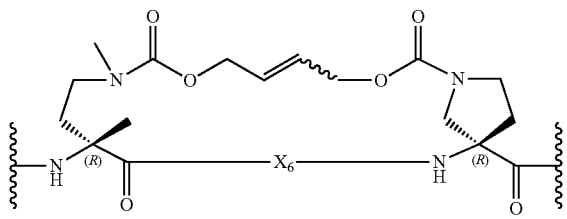 |
| Monomer G | Monomer I | FP0600c | 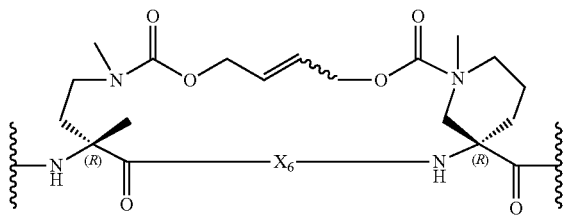 |
| Monomer E | Monomer F | FP0601c | 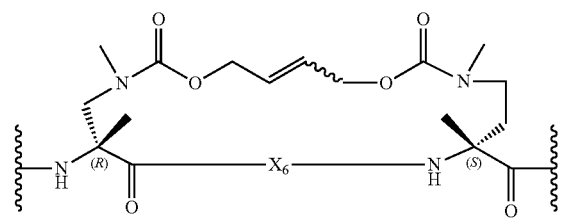 |
| Monomer E | Monomer G | FP0602c | 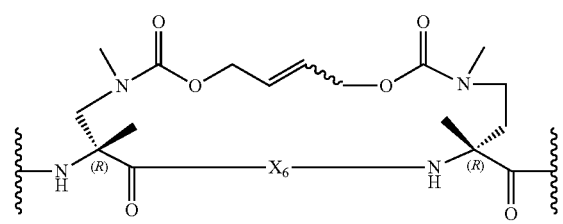 |
| Monomer E | Monomer E | FP0603c | 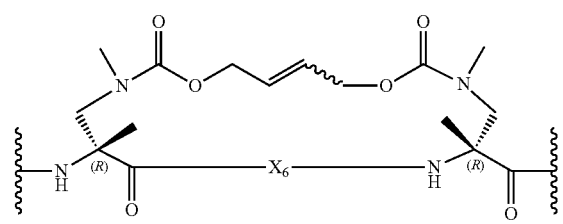 |
| Monomer E | Monomer B | FP0604c | 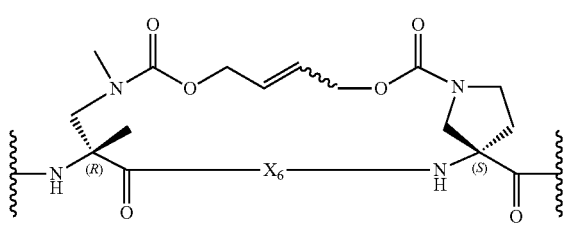 |
| Monomer E | Monomer C | FP0605c | 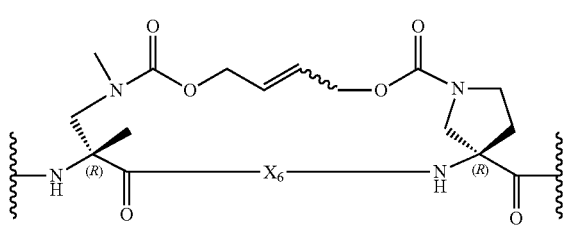 |

TABLE 1-continued
Part B - Amino acid sequence the same as FP0217.
| Monomer E | Monomer I | FP0607c | 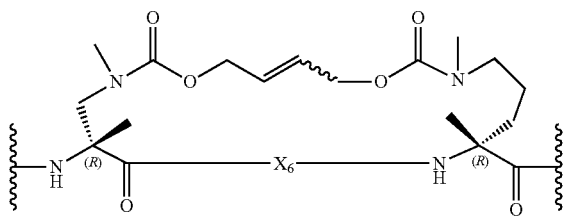 |
|---|---|---|---|
| Monomer F | Monomer F | FP0608c | 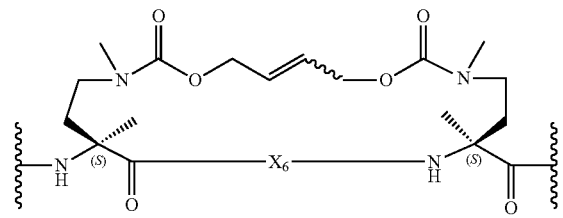 |
| Monomer F | Monomer B | FP0626c | 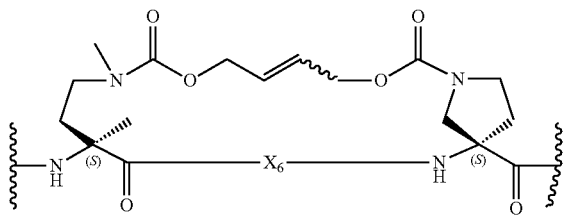 |
| Amino Acid 1 (i position) | Amino Acid 2 (i + 7 position) | ID (Carbamate) | ID | Amino Staple |
|---|---|---|---|---|
| $R_7$ | Monomer A | FP0516c | FP0516a | 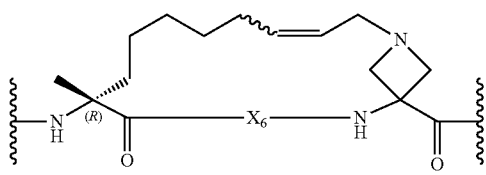 |
| Monomer E | $S_8$ | FP0335c | FP0335a | 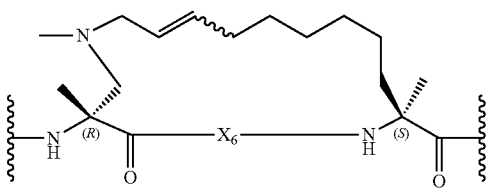 |
| $R_8$ | Monomer D | FP0338c | FP0338a | 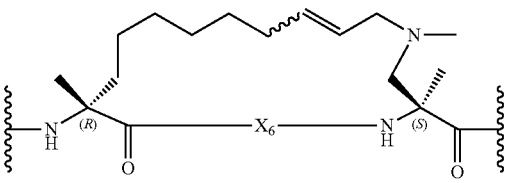 |
| $R_7$ | Monomer D | FP0495c | FP0495a | 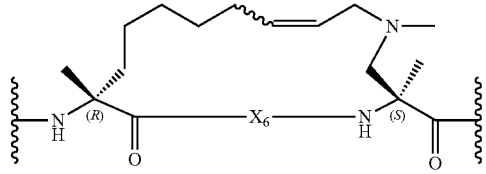 |

TABLE 1-continued
Part B - Amino acid sequence the same as FP0217.
| | | | |
|---|---|---|---|
| $R_7$ | Monomer F | FP0503c FP0503a | |
| $R_6$ | Monomer F | FP0502c FP0502a | |
| Monomer I | $S_6$ | FP0507c FP0507a | |
| Monomer I | $S_5$ | FP0506c FP0506a | |
| $R_8$ | Monomer B | FP0217c FP0217a | |
| $R_4$ | Monomer H | FP0509c FP0509a | |
| $R_5$ | Monomer H | FP0510c FP0510a | |
| $R_6$ | Monomer H | FP0511c FP0511a | |
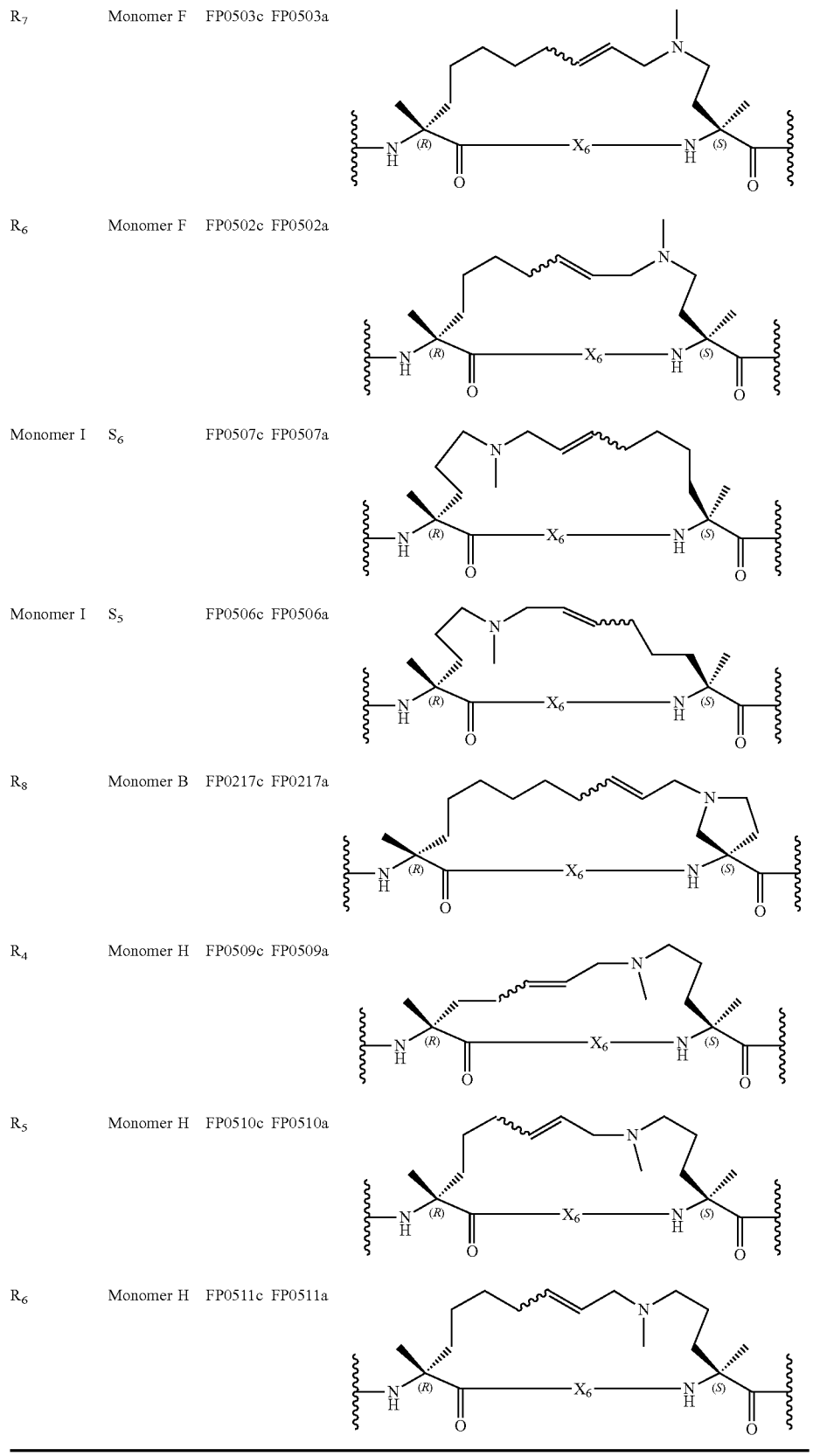

b. Staples

In some embodiments, a staple is a linker that can link one amino acid residue to another amino acid residue through bonding to peptide backbone atoms of the amino acid residues and, as is understood by those skilled in the art, is not through the peptide backbone between the linked amino acid residues. In some embodiments, a staple bonds to the peptide backbone by replacing one or more hydrogen and/or substituents (e.g., side chains, O, etc.) on peptide backbone atoms (e.g., C, N, etc.).

In some embodiments, a staple may contribute to one or more properties and/or activities of a stapled peptide, reportedly through stabilization of alpha-helix formed by a stapled peptide. Various types of staples have been reported and may be utilized in accordance with the present disclosure, for example, those described in U.S. Pat. No. 9,617,309, US 2015-0225471, US 2016-0024153, US 2016-0215036, US2016-0244494, WO2017/062518, Azzarito et al, Nature Chemistry 5: 161-173 (2013), etc., the staples of each of which are incorporated herein by reference.

In some embodiments, the present disclosure provides the insights that structural elements of staples (e.g., chemistry [e.g., hydrocarbon, non-hydrocarbon (e.g., comprising one or more heteroatoms or heteroatom-containing moieties such as amino, carbamate, etc.)], stereochemistry [e.g., stereochemistry of backbone atoms that staples are connected to (e.g., if staples are connected to alpha-carbon atoms of amino acid residues, such carbon atoms being chiral (R/S) or achiral)], positioning (to what amino acid residues/backbone atoms staples are connected), sizes (length of staples), etc.) can have significant impact on properties and/or activities, and can be employed to design and/or optimize stapled peptides having significantly improved properties and/or activities (e.g., increased solubility, increased cell permeability, increased stability, increased selectivity, lowered toxicity, increased activity, etc.).

In some embodiments, a provided staple is a hydrocarbon staple. In some embodiments, a hydrocarbon staple comprises no chain heteroatoms wherein a chain of a staple is the shortest covalent connection within the staple from one end of the staple to the other end of the staple.

In some embodiments, a provided staple is a non-hydrocarbon staple. In some embodiments, a non-hydrocarbon staple comprises one or more chain heteroatoms wherein a chain of a staple is the shortest covalent connection within the staple from one end of the staple to the other end of the staple. In some embodiments, a non-hydrocarbon staple is a carbamate staple in that it comprises a —N(R')—C(O)—O— moiety in its chain. In some embodiments, a non-hydrocarbon staple is an amino staple in that it comprises a —N(R')— moiety in its chain, wherein the —N(R')— moiety is not part of —N(R')—C(O)—O—. In some embodiments, a non-hydrocarbon staple is an amino staple in that it comprises a —N(R')— moiety in its chain, wherein the —N(R')-moiety is not bonded to a carbon atom that additionally forms a double bond with a heteroatom (e.g., —C(=O), —C(=S), —C(=N—R'), etc.).

In some embodiments, a provided stapled peptide comprises a staple which staple is $L^s$, wherein $L^s$ is -$L^{s1}$-$L^{s2}$-$L^{s3}$-, each of $L^{s1}$, $L^{s2}$, and $L^{s3}$ is independently L, wherein each L is independently as described in the present disclosure. In some embodiments, a provided staple is $L^s$.

In some embodiments, $L^{s1}$ comprises at least one —N(R')—, wherein R' is as described in the present disclosure. In some embodiments, the —N(R')— is bonded to two carbon atoms, wherein neither of the two carbon atoms forms a double bond with a heteroatom. In some embodiments, the —N(R')— is not bonded to —C(O)—. In some embodiments, the —N(R')— is not bonded to —C(S)—. In some embodiments, the —N(R')— is not bonded to —C(=NR')—. In some embodiments, $L^{s1}$ is -L'-N(R')—, wherein L' is optionally substituted bivalent $C_1$-$C_{19}$ aliphatic. In some embodiments, $L^{s1}$ is -L'-N(CH$_3$)—, wherein L' is optionally substituted bivalent $C_1$-$C_{19}$ aliphatic.

In some embodiments, R' is optionally substituted $C_{1-6}$ alkyl. In some embodiments, R' is $C_{1-6}$ alkyl. In some embodiments, R' is methyl. In some embodiments, the peptide backbone atom to which $L^{s1}$ is bonded is also bonded to $R^1$, and R' and $R^1$ are both R and are taken together with their intervene atoms to form an optionally substituted ring as described in the present disclosure. In some embodiments, a formed ring has no additional ring heteroatoms in addition to the nitrogen atom to which R' is bonded. In some embodiments, a formed ring is 3-membered. In some embodiments, a formed ring is 4-membered. In some embodiments, a formed ring is 5-membered. In some embodiments, a formed ring is 6-membered.

As defined herein, L' is optionally substituted bivalent $C_1$-$C_{19}$ aliphatic. In some embodiments, L' is optionally substituted bivalent $C_1$-$C_{15}$ aliphatic. In some embodiments, L' is optionally substituted bivalent $C_1$-$C_{10}$ aliphatic. In some embodiments, L' is optionally substituted bivalent $C_1$-$C_9$ aliphatic. In some embodiments, L' is optionally substituted bivalent $C_1$-$C_8$ aliphatic. In some embodiments, L' is optionally substituted bivalent $C_1$-$C_7$ aliphatic. In some embodiments, L' is optionally substituted bivalent $C_1$-$C_6$ aliphatic. In some embodiments, L' is optionally substituted bivalent $C_1$-$C_8$ aliphatic. In some embodiments, L' is optionally substituted bivalent $C_1$-$C_4$ aliphatic. In some embodiments, L' is optionally substituted alkylene. In some embodiments, L' is optionally substituted alkenylene. In some embodiments, L' is unsubstituted alkylene. In some embodiments, L' is —CH$_2$—. In some embodiments, L' is —(CH$_2$)$_2$—. In some embodiments, L' is —(CH$_2$)$_3$—. In some embodiments, L' is —(CH$_2$)$_4$—. In some embodiments, L' is —(CH$_2$)$_5$—. In some embodiments, L' is —(CH$_2$)$_6$—. In some embodiments, L' is —(CH$_2$)$_7$—. In some embodiments, L' is —(CH$_2$)$_8$—. In some embodiments, L' is bonded to a peptide backbone atom. In some embodiments, L' is optionally substituted alkenylene. In some embodiments, L' is unsubstituted alkenylene. In some embodiments, L' is —CH$_2$—CH=CH—CH$_2$—.

In some embodiments, $L^{s1}$ comprises at least one —N(R') C(O)—, wherein R' is as described in the present disclosure. In some embodiments, $L^{s1}$ is -L'-N(R')C(O)—, wherein each of L' and R' is independently as described in the present disclosure. In some embodiments, $L^{s1}$ is -L'-N(CH$_3$)C(O)—, wherein L' is independently as described in the present disclosure.

In some embodiments, $L^{s1}$ is a covalent bond.

In some embodiments, $L^{s1}$ is L', wherein L' is as described in the present disclosure.

In some embodiments, $L^{s3}$ is L, wherein L is as described in the present disclosure. In some embodiments, $L^{s2}$ is L', wherein L' is as described in the present disclosure. In some embodiments, $L^{s2}$ comprises —CH$_2$—CH=CH—CH$_2$—. In some embodiments, $L^{s2}$ is —CH$_2$—CH=CH—CH$_2$—. In some embodiments, $L^{s2}$ comprises —(CH$_2$)$_4$—. In some embodiments, $L^{s2}$ is —(CH$_2$)$_4$—.

In some embodiments, $L^{s3}$ comprises at least one —N(R')—, wherein R' is as described in the present disclosure. In some embodiments, the —N(R')— is bonded to two carbon atoms, wherein neither of the two carbon atoms forms a double bond with a heteroatom. In some embodiments, the —N(R')— is not bonded to —C(O)—. In some embodiments, the —N(R')— is not bonded to —C(S)—. In some embodiments, the —N(R')— is not bonded to —C(=NR')—. In some embodiments, $L^{s3}$ is -L'-N(R')—, wherein L' is optionally substituted bivalent $C_1$-$C_{19}$ aliphatic. In some embodiments, $L^{s3}$ is -L'-N($CH_3$)—, wherein L' is optionally substituted bivalent $C_1$-$C_{19}$ aliphatic.

In some embodiments, $L^{s3}$ comprises at least one —N(R')C(O)—, wherein R' is as described in the present disclosure. In some embodiments, $L^{s3}$ is -L'-N(R')C(O)—, wherein each of L' and R' is independently as described in the present disclosure. In some embodiments, $L^{s3}$ is -L'-N($CH_3$)C(O)—, wherein L' is independently as described in the present disclosure.

In some embodiments, $L^{s3}$ is L', wherein L' is as described in the present disclosure. In some embodiments, $L^{s3}$ is optionally substituted alkylene. In some embodiments, $L^{s3}$ is unsubstituted alkylene.

In some embodiments, $L^s$ comprises at least one —N(R')—, wherein R' is as described in the present disclosure. In some embodiments, the —N(R')— is bonded to two carbon atoms, wherein neither of the two carbon atoms forms a double bond with a heteroatom. In some embodiments, the —N(R')— is not bonded to —C(O)—. In some embodiments, the —N(R')— is not bonded to —C(S)—. In some embodiments, the —N(R')— is not bonded to —C(=NR')—. In some embodiments, $L^s$ comprises at least one —N(R')C(O)—, wherein R' is as described in the present disclosure.

In some embodiments, L comprises at least one —N(R')—, wherein R' is as described in the present disclosure. In some embodiments, the —N(R')— is bonded to two carbon atoms, wherein neither of the two carbon atoms forms a double bond with a heteroatom. In some embodiments, the —N(R')— is not bonded to —C(O)—. In some embodiments, the —N(R')— is not bonded to —C(S)—. In some embodiments, the —N(R')— is not bonded to —C(=NR')—. In some embodiments, L is -L'-N(R')—, wherein L' is optionally substituted bivalent $C_1$-$C_{19}$ aliphatic. In some embodiments, L is -L'-N($CH_3$)—, wherein L' is optionally substituted bivalent $C_1$-$C_{19}$ aliphatic.

In some embodiments, L comprises at least one —N(R')C(O)—, wherein R' is as described in the present disclosure. In some embodiments, L is -L'-N(R')C(O)—, wherein each of L' and R' is independently as described in the present disclosure. In some embodiments, L is -L'-N($CH_3$)C(O)—, wherein L' is independently as described in the present disclosure.

In some embodiments, L is L', wherein L' is as described in the present disclosure. In some embodiments, L is optionally substituted alkylene. In some embodiments, L is unsubstituted alkylene.

In some embodiments, L is optionally substituted bivalent $C_1$-$C_{15}$ aliphatic. In some embodiments, L is optionally substituted bivalent $C_1$-$C_{10}$ aliphatic. In some embodiments, L is optionally substituted bivalent $C_1$-$C_9$ aliphatic. In some embodiments, L is optionally substituted bivalent $C_1$-$C_8$ aliphatic. In some embodiments, L is optionally substituted bivalent $C_1$-$C_7$ aliphatic. In some embodiments, L is optionally substituted bivalent $C_1$-$C_6$ aliphatic. In some embodiments, L is optionally substituted bivalent $C_1$-$C_8$ aliphatic. In some embodiments, L is optionally substituted bivalent $C_1$-$C_4$ aliphatic. In some embodiments, L is optionally substituted alkylene. In some embodiments, L is optionally substituted alkenylene. In some embodiments, L is unsubstituted alkylene. In some embodiments, L is —$CH_2$—. In some embodiments, L is —$(CH_2)_2$—. In some embodiments, L is —$(CH_2)_3$—. In some embodiments, L is —$(CH_2)_4$—. In some embodiments, L is —$(CH_2)_5$—. In some embodiments, L is —$(CH_2)_6$—. In some embodiments, L is —$(CH_2)_7$—. In some embodiments, L is —$(CH_2)_8$—. In some embodiments, L is bonded to a peptide backbone atom. In some embodiments, L is optionally substituted alkenylene. In some embodiments, L is unsubstituted alkenylene. In some embodiments, L is —$CH_2$—CH=CH—$CH_2$—.

In some embodiments, one end of a staple is connected to an atom $A^{n1}$ of the peptide backbone, wherein $A^{n1}$ is optionally substituted with $R^1$ and is an atom of an amino acid residue at amino acid position $n^1$ of the peptide from the N-terminus, and the other end is connected to an atom $A^{n2}$ of the peptide backbone, wherein $A^{n2}$ is optionally substituted with $R^2$ (in some embodiments, $R^1$ and/or $R^2$ is R which can be hydrogen) and is an atom of an amino acid residue at amino acid position $n^2$ of the peptide from the N-terminus, wherein each of $n^1$ and $n^2$ is independently an integer, and $n^2=n^1+m$, wherein m is 3-12.

In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, a staple is referred to a (i, i+m) staple.

In some embodiments, $A^{n1}$ is a carbon atom. In some embodiments, $A^{n1}$ is achiral. In some embodiments, $A^{n1}$ is chiral. In some embodiments, $A^{n1}$ is R. In some embodiments, $A^{n1}$ is S.

In some embodiments, $A^{n2}$ is a carbon atom. In some embodiments, $A^{n2}$ is achiral. In some embodiments, $A^{n2}$ is chiral. In some embodiments, $A^{n2}$ is R. In some embodiments, $A^{n2}$ is S.

In some embodiments, $A^{n1}$ is achiral and $A^{n2}$ is achiral. In some embodiments, $A^{n1}$ is achiral and $A^{n2}$ is R. In some embodiments, $A^{n1}$ is achiral and $A^{n2}$ is S. In some embodiments, $A^{n1}$ is R and $A^{n2}$ is achiral. In some embodiments, $A^{n1}$ is R and $A^{n2}$ is R. In some embodiments, $A^{n1}$ is R and $A^{n2}$ is S. In some embodiments, $A^{n1}$ is S and $A^{n2}$ is achiral. In some embodiments, $A^{n1}$ is S and $A^{n2}$ is R. In some embodiments, $A^{n1}$ is S and $A^{n2}$ is S.

In some embodiments, provided stereochemistry at staple-backbone connection points and/or combinations thereof, optionally together with one or more structural elements of provided peptide, e.g., staple chemistry (hydrocarbon, non-hydrocarbon), staple length, etc. can provide various benefits, such as improved preparation yield, purity, and/or selectivity, improved properties (e.g., improved solubility, improved stability, lowered toxicity, improved selectivities, etc.), improved activities, etc. In some embodiments, provided stereochemistry and/or stereochemistry combinations are different from those typically used, e.g., those of U.S. Pat. No. 9,617,309, US 2015-0225471, US 2016-0024153, US 2016-0215036, US2016-0244494, WO2017/062518, and provided one or more of benefits described in the present disclosure.

In some embodiments, a staple can be of various lengths, in some embodiments, as represent by the number of chain atoms of a staple. In some embodiments, a chain of a staple is the shortest covalent connection in the staple from a first end (connection point with a peptide backbone) of a staple to a second end of the staple, wherein the first end and the second end are connected to two different peptide backbone atoms. In some embodiments, a staple comprises 5-30 chain atoms, e.g., 5, 6, 7, 8, 9, or 10 to 11, 12, 13, 14, 15, 16, 17, 18, 19, 20, 21, 22, 23, 24, or 25 chain atoms. In some embodiments, a staple comprises 5 chain atoms. In some embodiments, a staple comprises 6 chain atoms. In some embodiments, a staple comprises 7 chain atoms. In some embodiments, a staple comprises 8 chain atoms. In some embodiments, a staple comprises 9 chain atoms. In some embodiments, a staple comprises 10 chain atoms. In some embodiments, a staple comprises 11 chain atoms. In some embodiments, a staple comprises 12 chain atoms. In some embodiments, a staple comprises 13 chain atoms. In some embodiments, a staple comprises 14 chain atoms. In some embodiments, a staple comprises 15 chain atoms. In some embodiments, a staple comprises 16 chain atoms. In some embodiments, a staple comprises 17 chain atoms. In some embodiments, a staple comprises 18 chain atoms. In some embodiments, a staple comprises 19 chain atoms. In some embodiments, a staple comprises 20 chain atoms. In some embodiments, a staple has a length of 5 chain atoms. In some embodiments, a staple has a length of 6 chain atoms. In some embodiments, a staple has a length of 7 chain atoms. In some embodiments, a staple has a length of 8 chain atoms. In some embodiments, a staple has a length of 9 chain atoms. In some embodiments, a staple has a length of 10 chain atoms. In some embodiments, a staple has a length of 11 chain atoms. In some embodiments, a staple has a length of 12 chain atoms. In some embodiments, a staple has a length of 13 chain atoms. In some embodiments, a staple has a length of 14 chain atoms. In some embodiments, a staple has a length of 15 chain atoms. In some embodiments, a staple has a length of 16 chain atoms. In some embodiments, a staple has a length of 17 chain atoms. In some embodiments, a staple has a length of 18 chain atoms. In some embodiments, a staple has a length of 19 chain atoms. In some embodiments, a staple has a length of 20 chain atoms. In some embodiments, a staple has a length of 8-15 chain atoms. In some embodiments, a staple has 8-12 chain atoms. In some embodiments, a staple has 9-12 chain atoms. In some embodiments, a staple has 9-10 chain atoms. In some embodiments, a staple has 8-10 chain atoms. In some embodiments, length of a staple can be adjusted according to the distance of the amino acid residues it connects, for example, a longer staple may be needed for a (i, i+7) staple than a (i, i+4) staple. Staple lengths may be otherwise described. For example, in some embodiments, staple lengths may be described as the total number of chain atoms and non-chain ring atoms, where a non-chain ring atom is an atom of the staple which forms a ring with one or more chain atoms but is not a chain atom in that it is not within the shortest covalent connection from a first end of the staple to a second end of the staple. In some embodiments, staples formed using Monomer A (which comprises a azetidine moiety), Monomer B (which comprises a pyrrolidine moiety), and/or Monomer C (which comprises a pyrrolidine moiety) may comprise one or two non-chain ring atoms as illustrated in the exemplary stapled peptides.

In some embodiments, a staple has no heteroatoms in its chain. In some embodiments, a staple comprises at least one heteroatom in its chain. In some embodiments, a staple comprises at least one nitrogen atom in its chain.

In some embodiments, a staple is $L^s$, wherein $L^s$ is an optionally substituted, bivalent $C_{8-14}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, a staple is $L^s$, wherein LV is an optionally substituted, bivalent $C_{9-13}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, a staple is $L^s$, wherein $L^s$ is an optionally substituted, bivalent $C_{10-15}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, a staple is $L^s$, wherein $L^s$ is an optionally substituted, bivalent $C_{11-14}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—. In some embodiments, a staple is a (i, i+4) staple in that not including the two amino acid residues that are directly connected to the staple, there are three amino acid residues between the two amino acid residues that are directly connected to the staple. In some embodiments, a staple is a (i, i+7) staple in that not including the two amino acid residues that are directly connected to the staple, there are six amino acid residues between the two amino acid residues that are directly connected to the staple.

In some embodiments, for each of $L^s$, $L^{s1}$, $L^{s2}$, and $L^{s3}$, any replacement of methylene units, if any, is replaced with —N(R')— or —N(R')—C(O)—.

In some embodiments, an olefin in a staple is a Z-olefin. In some embodiments, an olefin in a staple in an E-olefin. In some embodiments, a provided composition comprises stapled peptides comprising a staple that contains a Z-olefin and stapled peptides comprising a staple that contains an E-olefin. In some embodiments, a provided composition comprises stapled peptides comprising a staple that contains a Z-olefin. In some embodiments, a provided composition comprises stapled peptides comprising a staple that contains an E-olefin. In some embodiments, otherwise identical stapled peptides that differ only in the E/Z configuration of staple olefin demonstrate different properties and/or activities as demonstrated herein. In some embodiments, stapled peptides with E-olefin in a staple may provide certain desirable properties and/or activities given the context. In some embodiments, stapled peptides with Z-olefin in a staple may provide certain desirable properties and/or activities given the context.

In some embodiments, two staples may be bonded to the same atom of the peptide backbone, forming a "stitch" structure.

In some embodiments, a staple is Pro-lock in that one end of the staple is bonded to the alpha-carbon of a proline residue.

In some embodiments, an exemplary staple is a staple as illustrated below in Tables S-1, S-2, S-3, and S-4 (with exemplary peptide backbone illustrated for clarity (can be applied to other peptide backbone), X being amino acid residues). In some embodiments, the olefin is Z. In some embodiments, the olefin is E. In some embodiments, an (i, i+4) staple is selected from Table S-1. In some embodiments, an (i, i+4) staple is selected from Table S-2. In some embodiments, an (i, i+7) staple is selected from Table S-3. In some embodiments, an (i, i+7) staple is selected from Table S-4.
TABLE S-1
Exemplary staples.
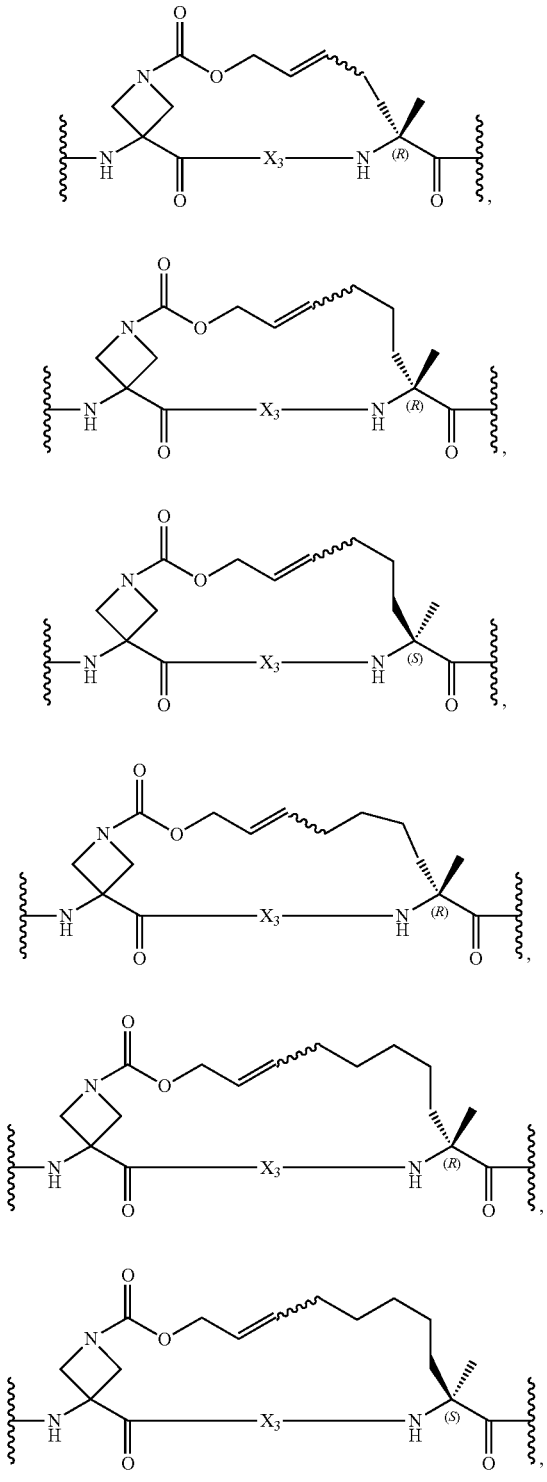
TABLE S-1-continued
Exemplary staples.
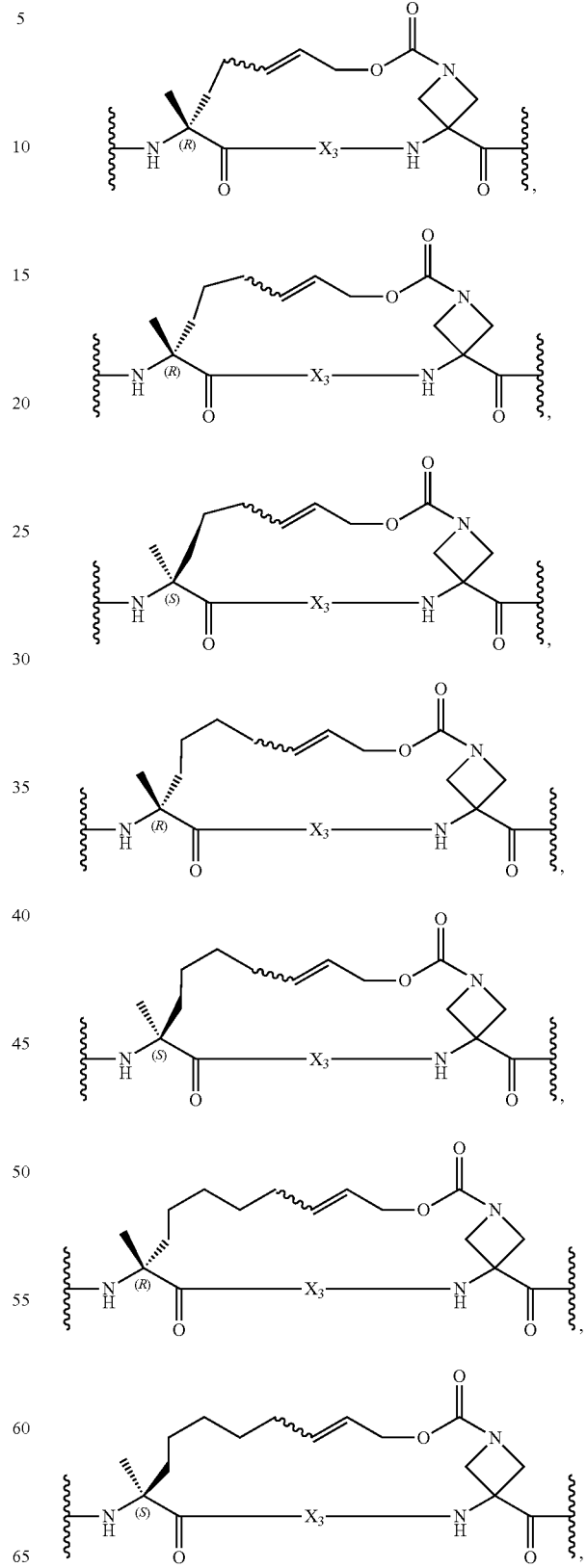

TABLE S-1-continued
Exemplary staples.
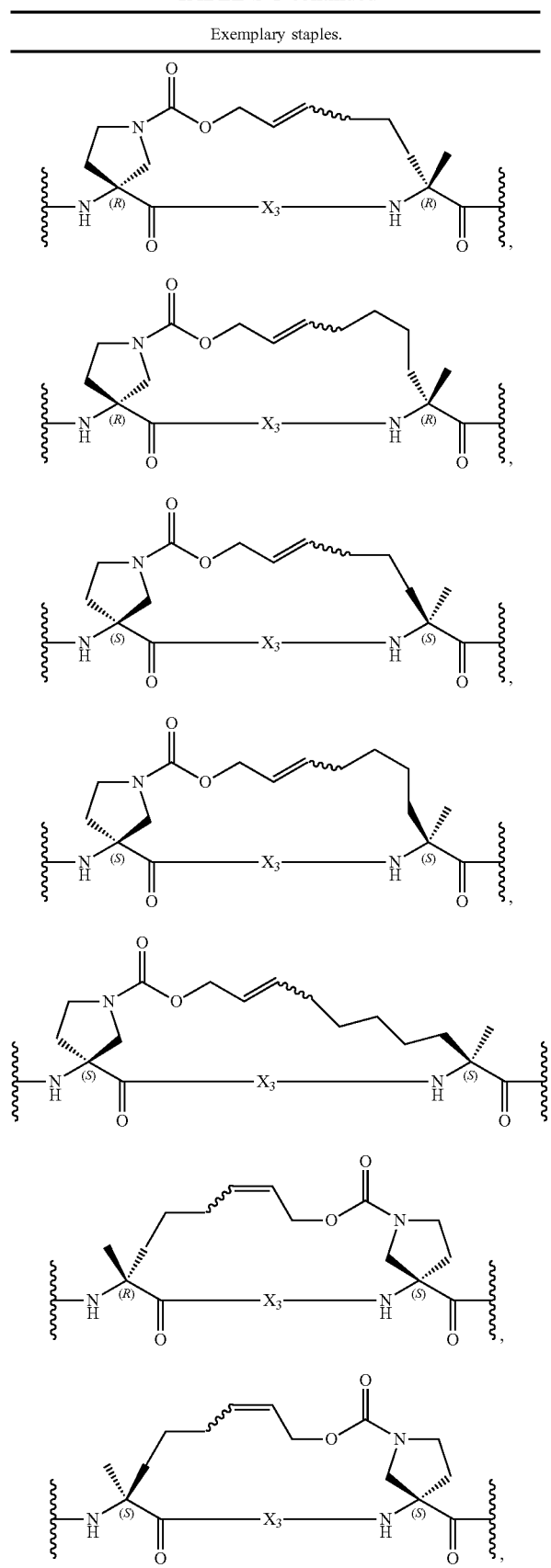
TABLE S-1-continued
Exemplary staples.
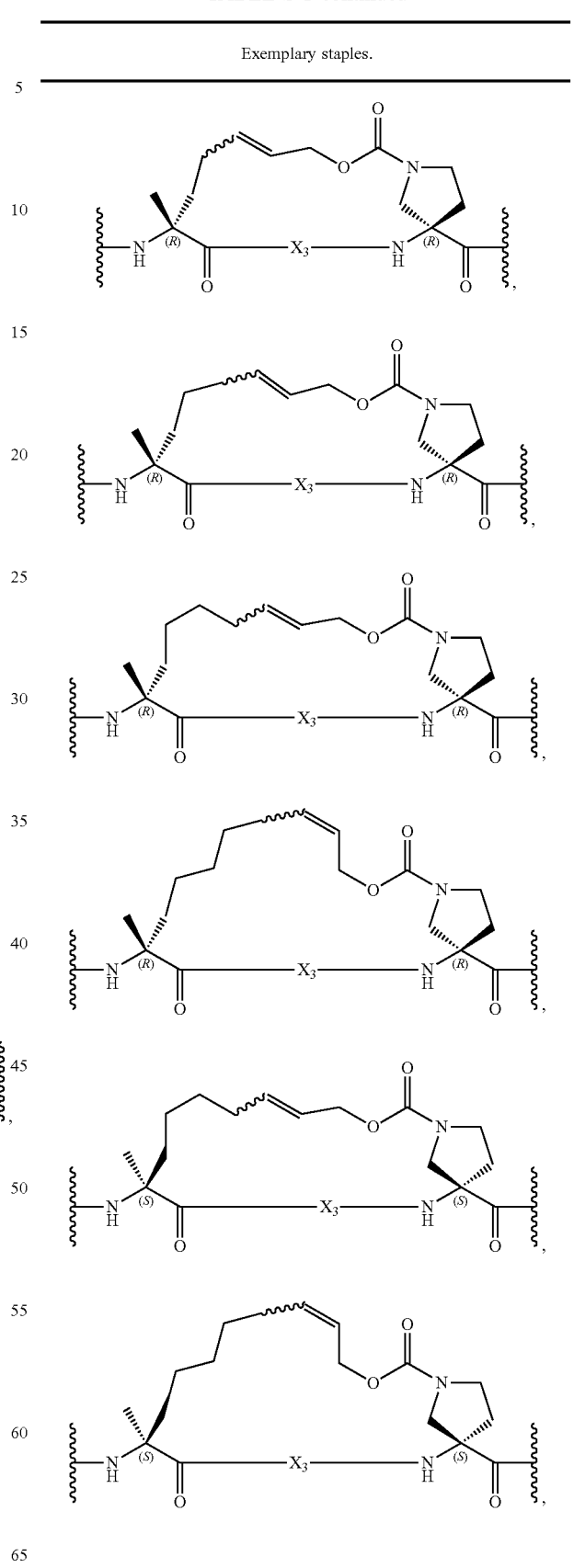

TABLE S-1-continued
Exemplary staples.
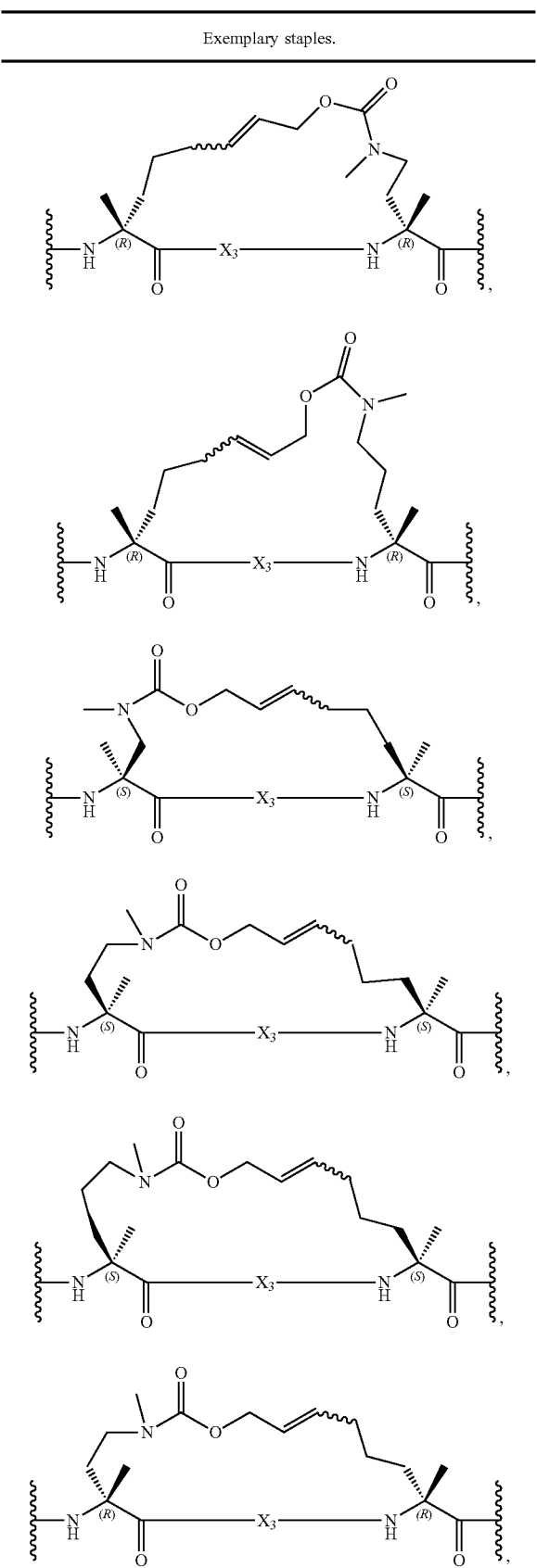
TABLE S-1-continued
Exemplary staples.
TABLE S-2
Exemplary staples.
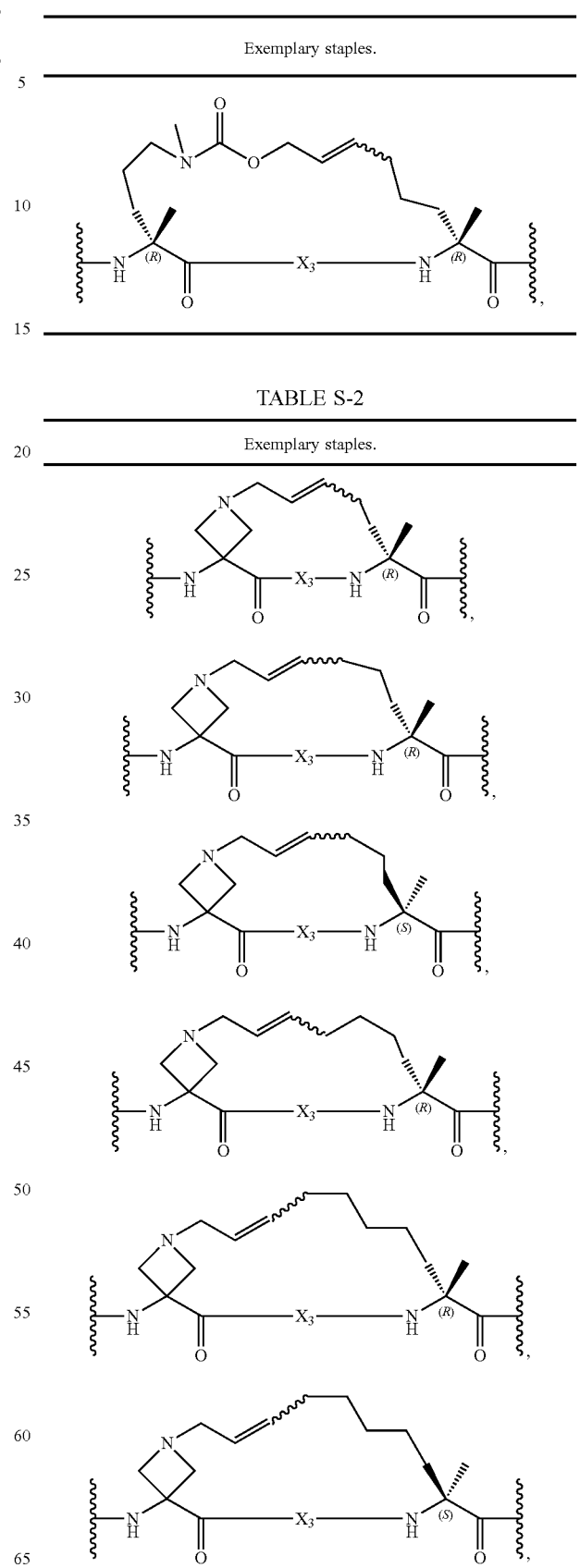

TABLE S-2-continued
Exemplary staples.
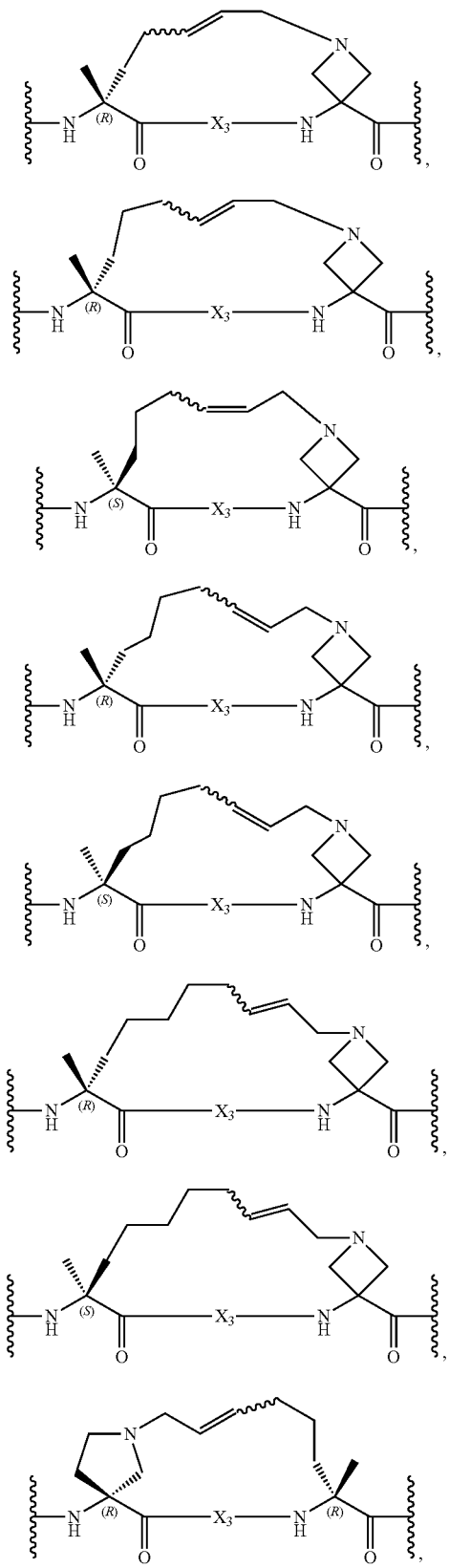
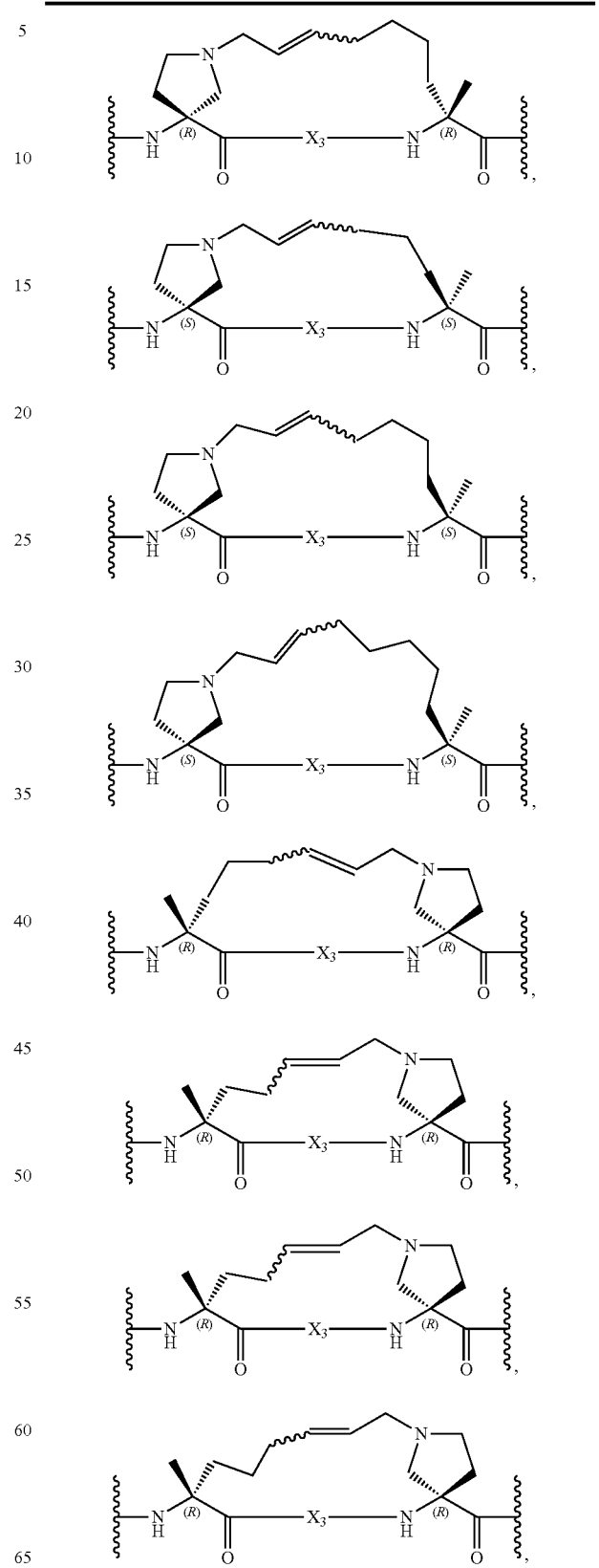

TABLE S-2-continued
Exemplary staples.
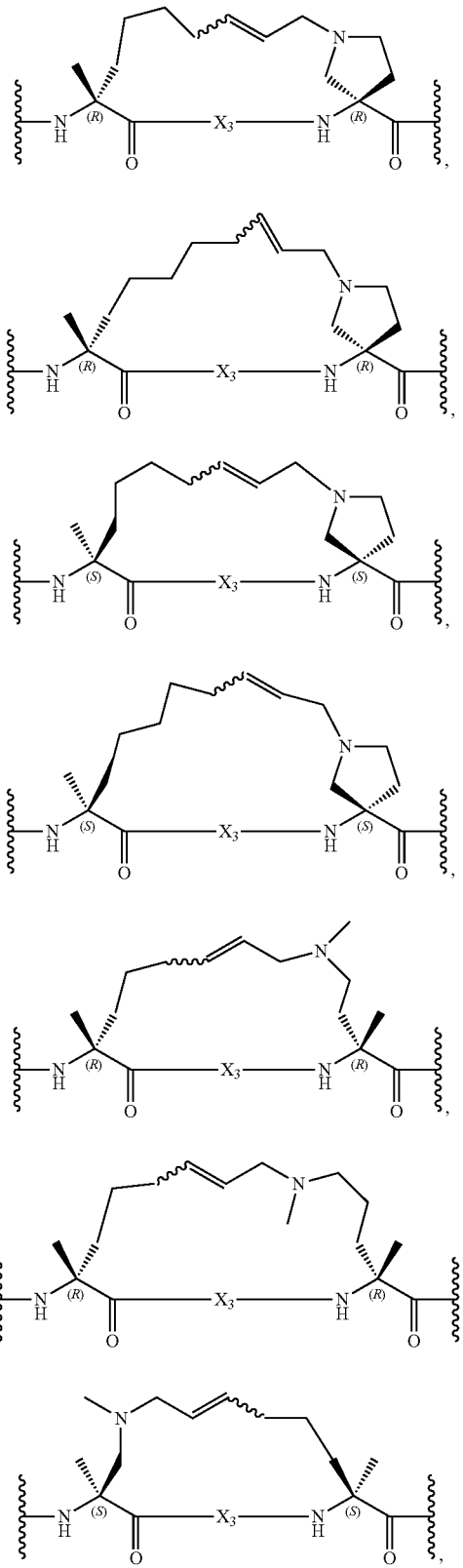
TABLE S-2-continued
Exemplary staples.
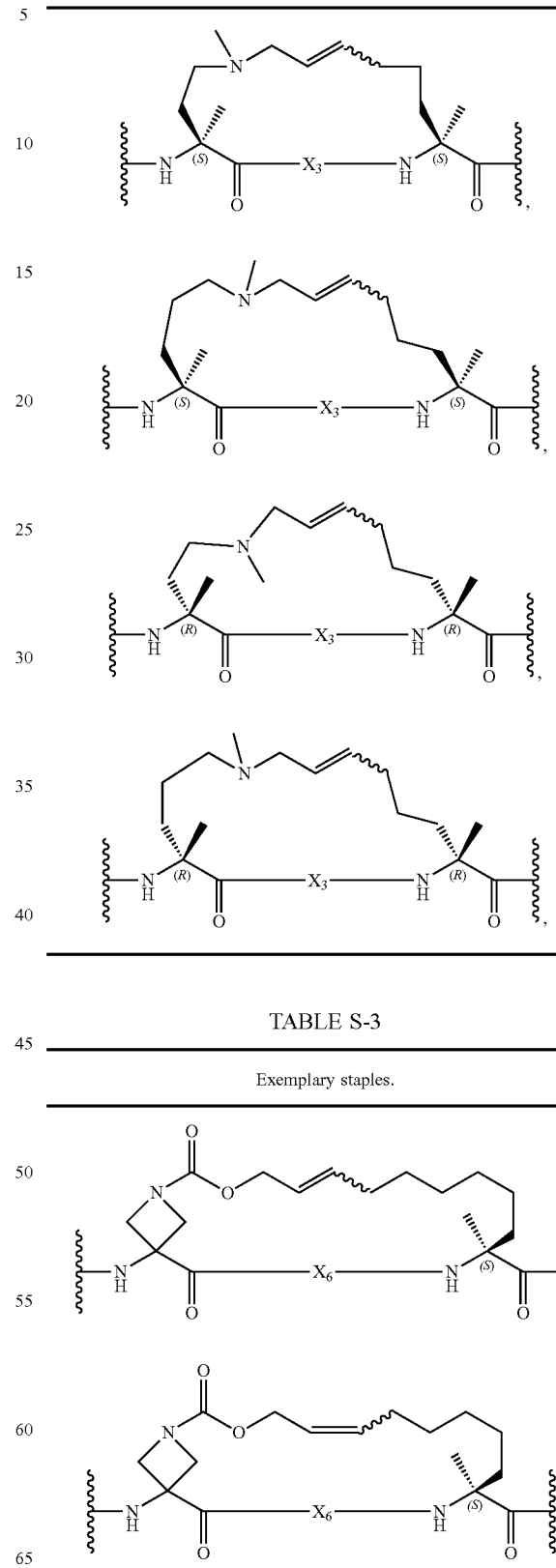
TABLE S-3
Exemplary staples.
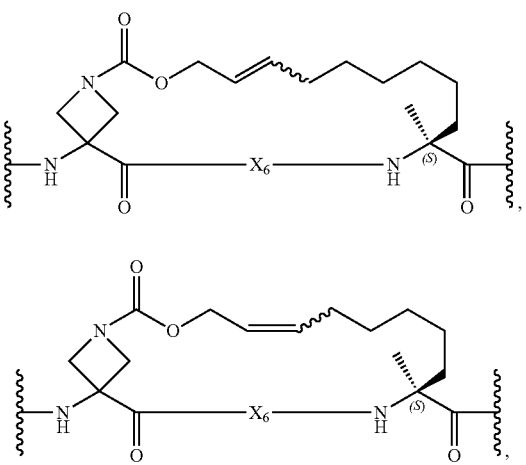

TABLE S-3-continued
Exemplary staples.
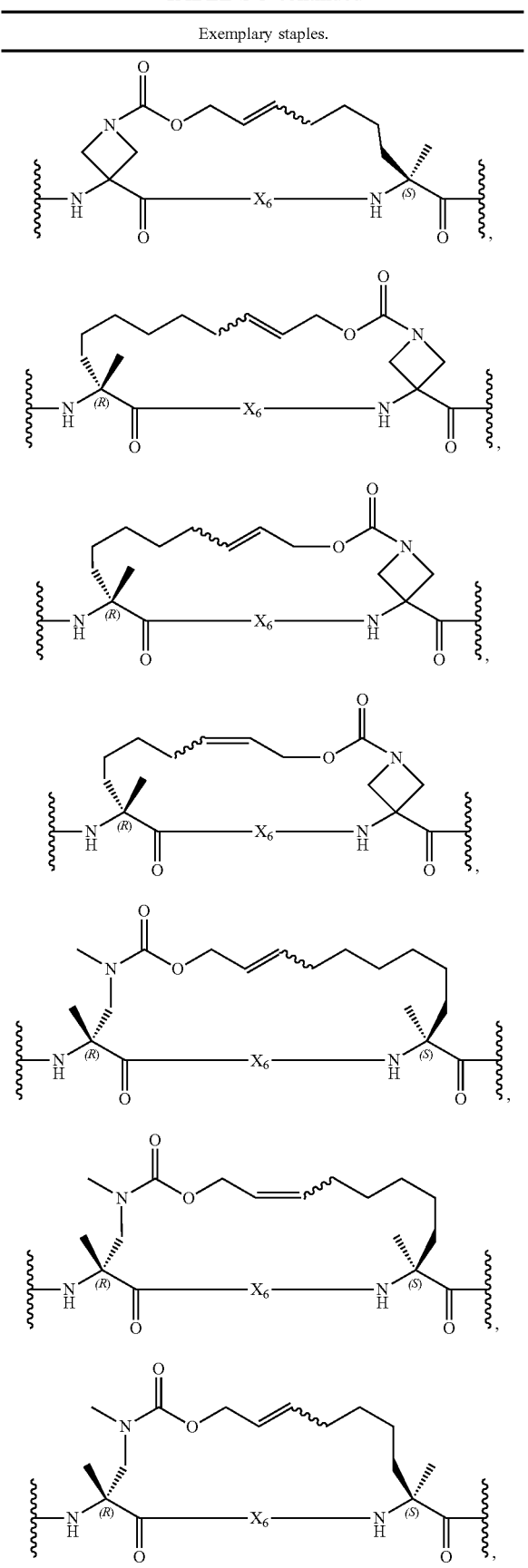
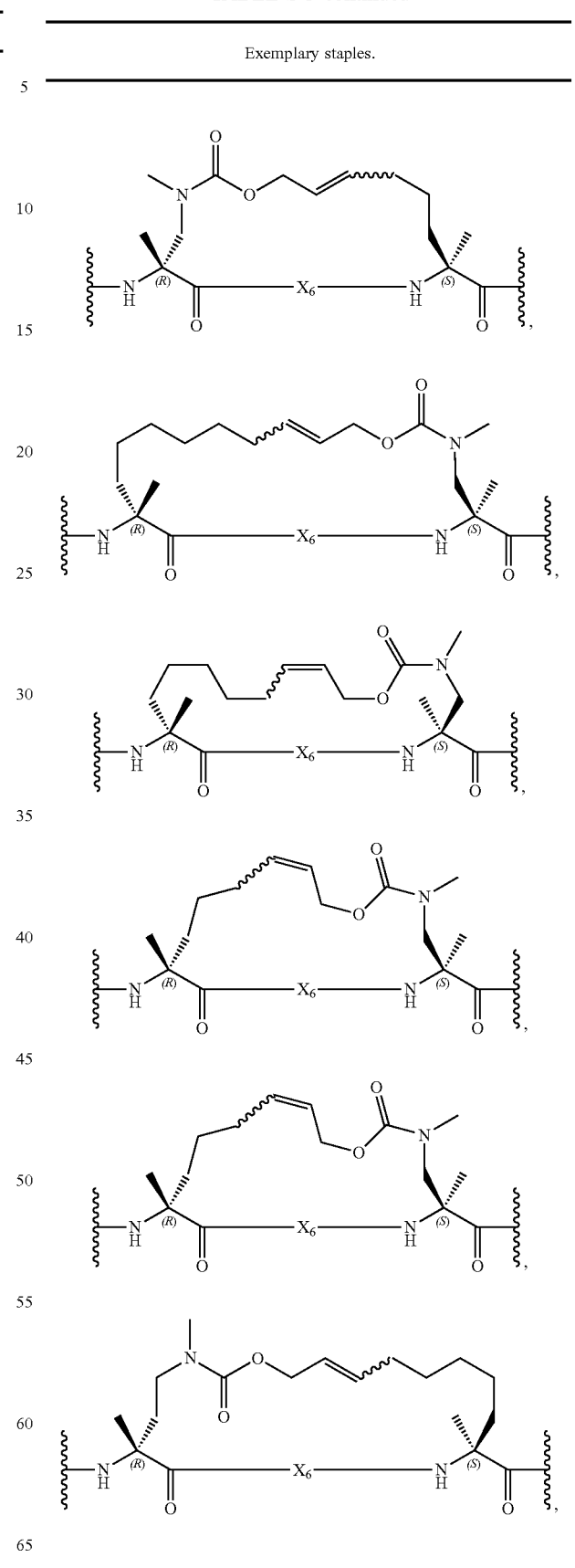

TABLE S-3-continued
Exemplary staples.
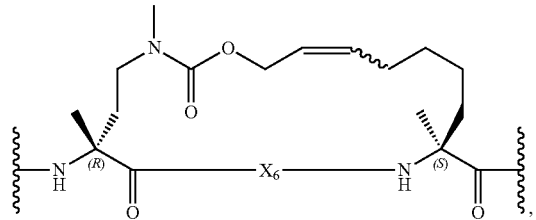
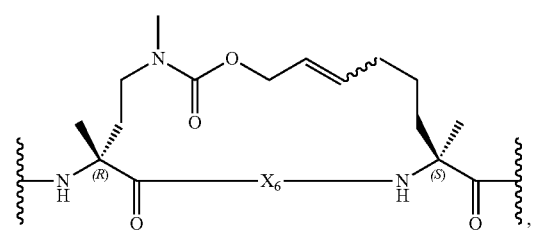
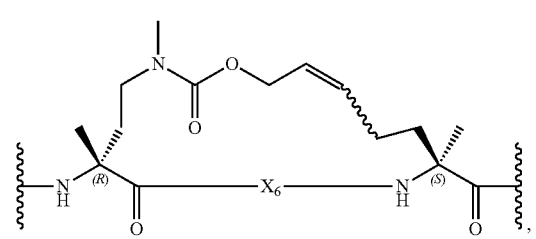
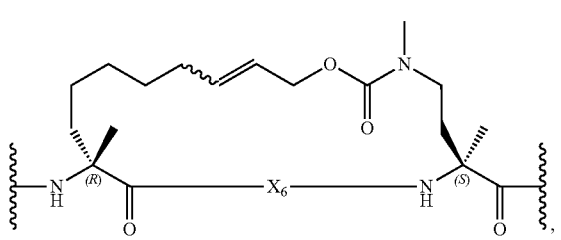
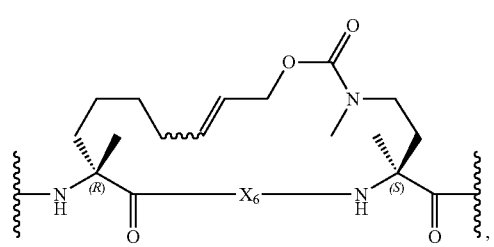
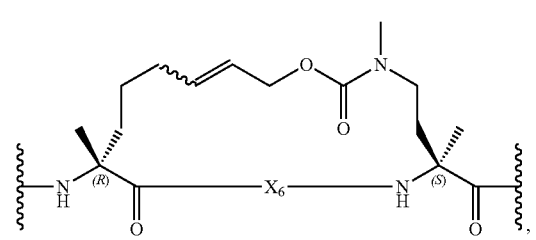
TABLE S-3-continued
Exemplary staples.
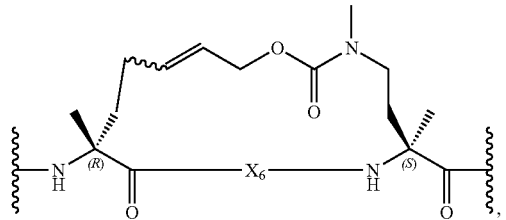
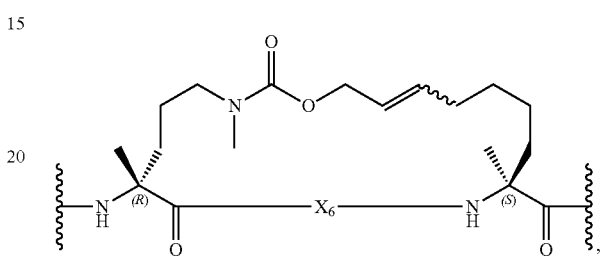
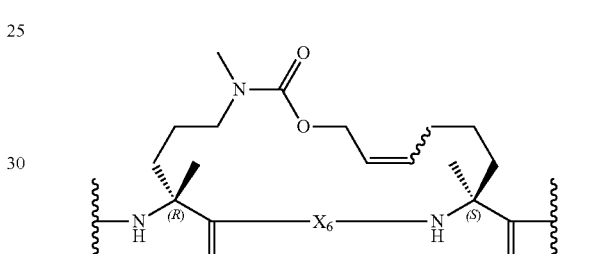
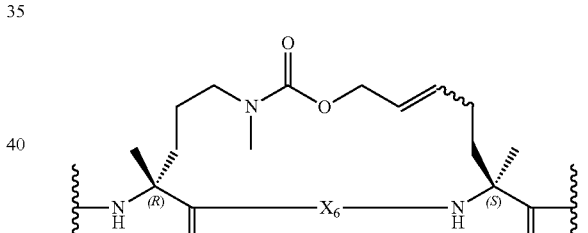
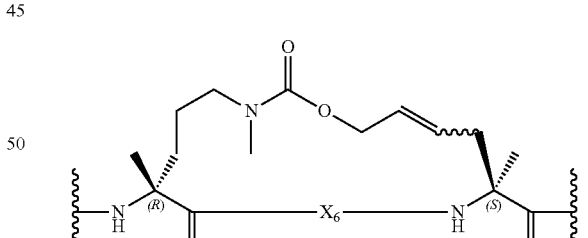
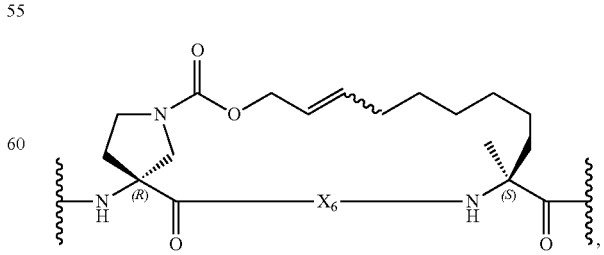

TABLE S-3-continued
Exemplary staples.
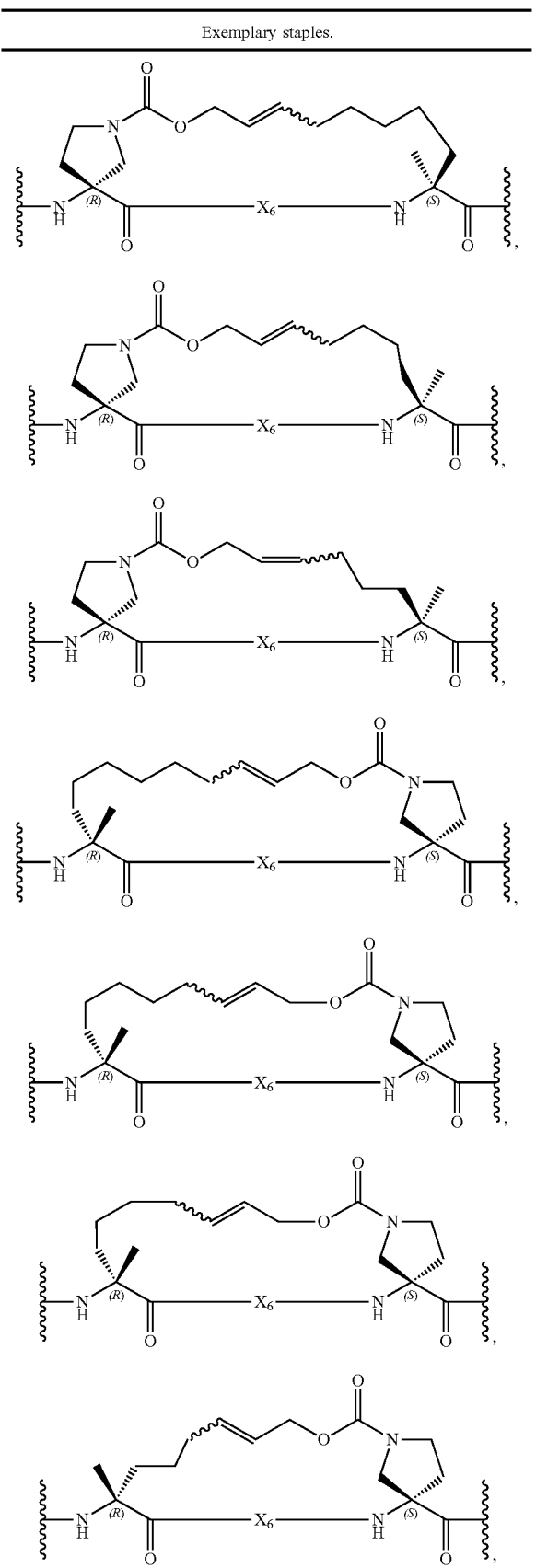
TABLE S-3-continued
Exemplary staples.
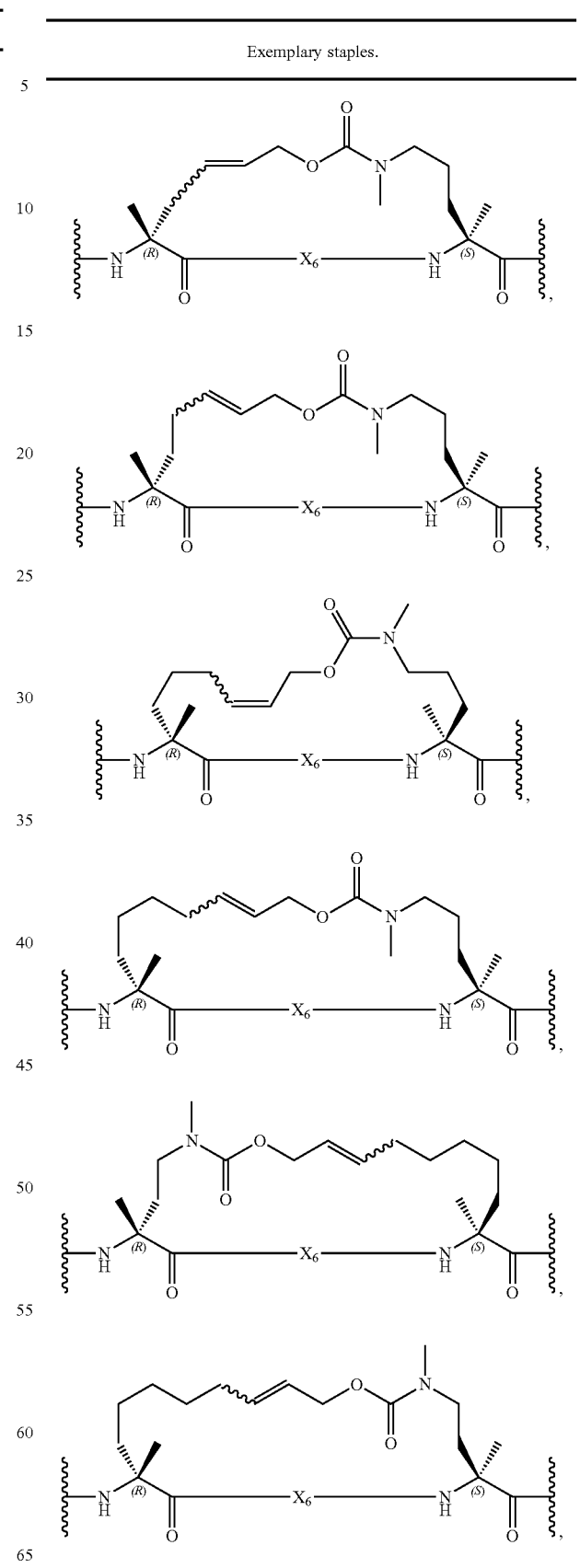

TABLE S-3-continued
Exemplary staples.
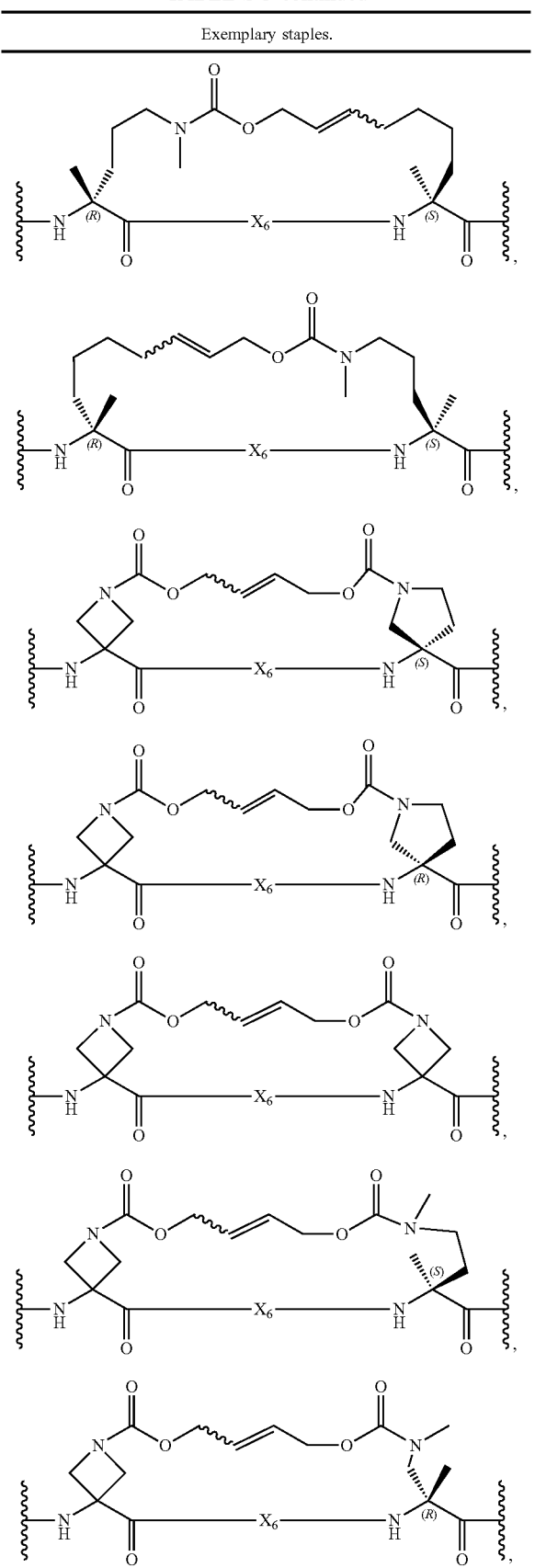
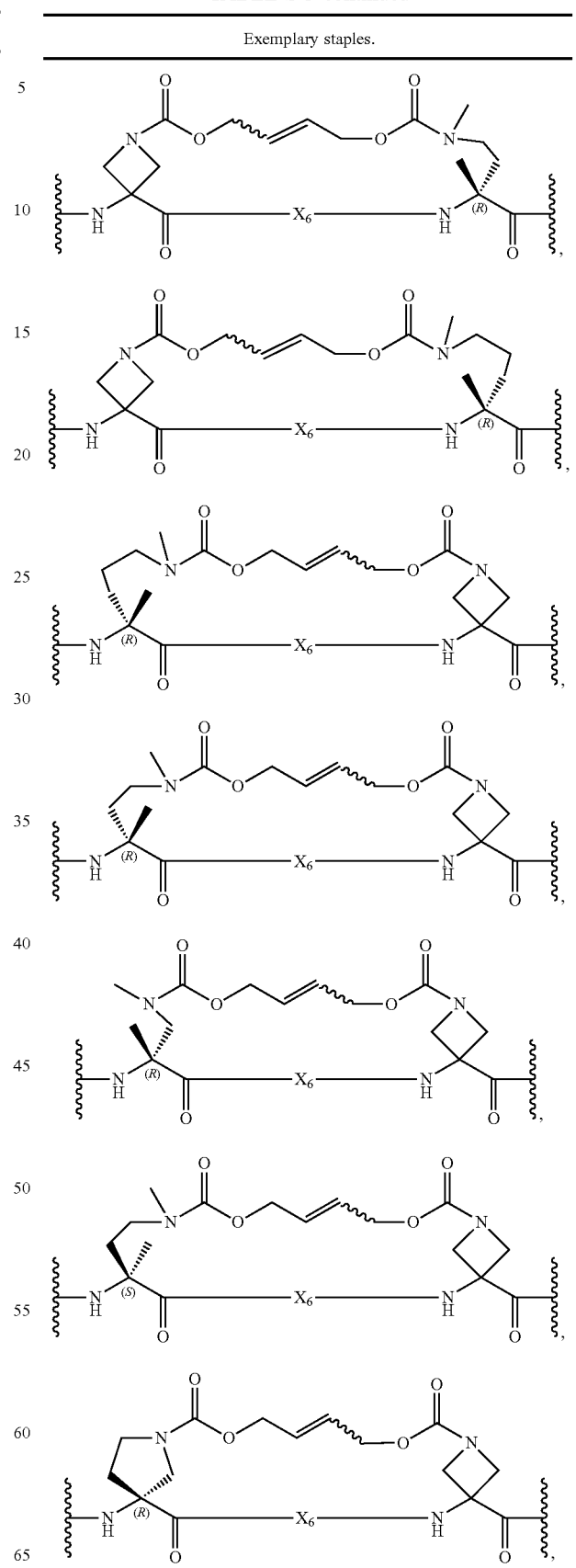

TABLE S-3-continued
Exemplary staples.
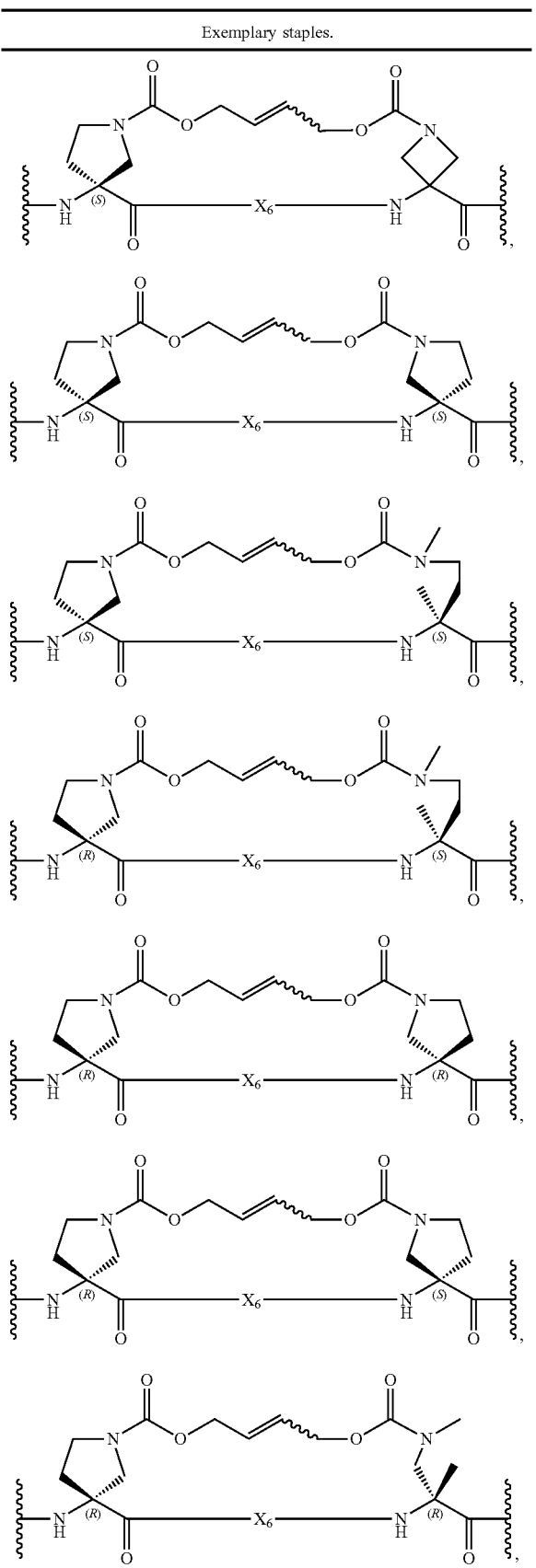
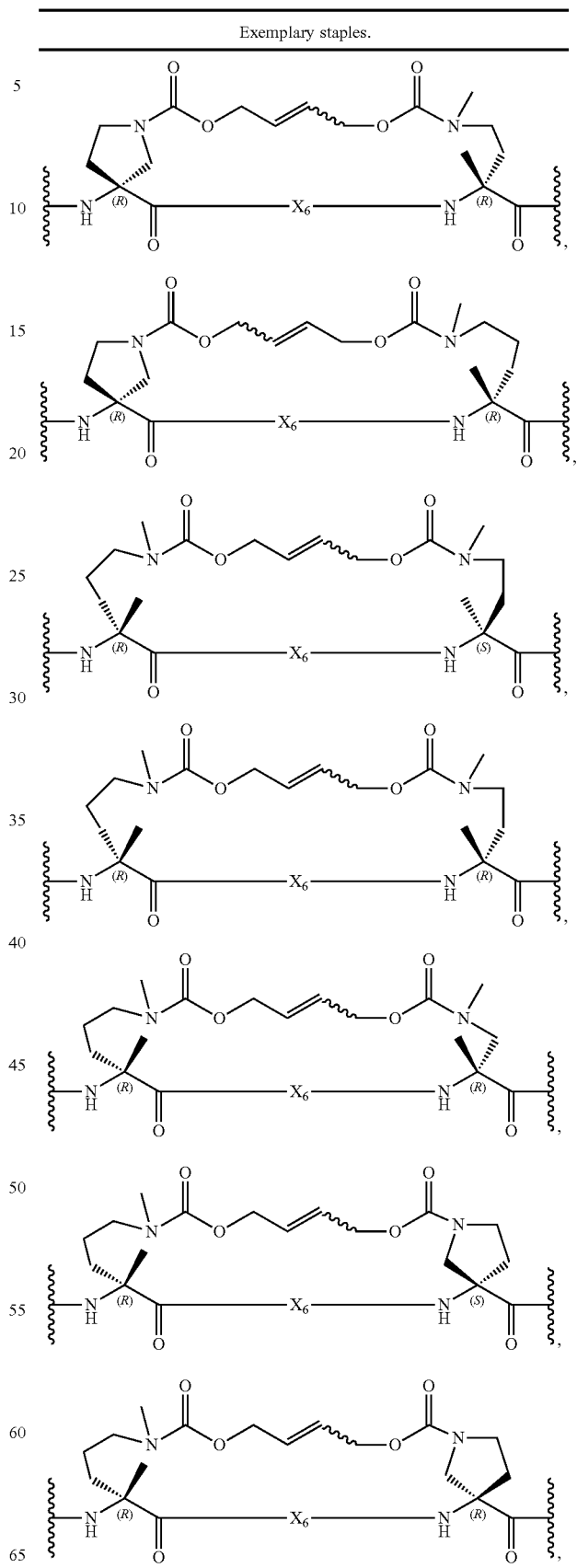

TABLE S-3-continued
Exemplary staples.
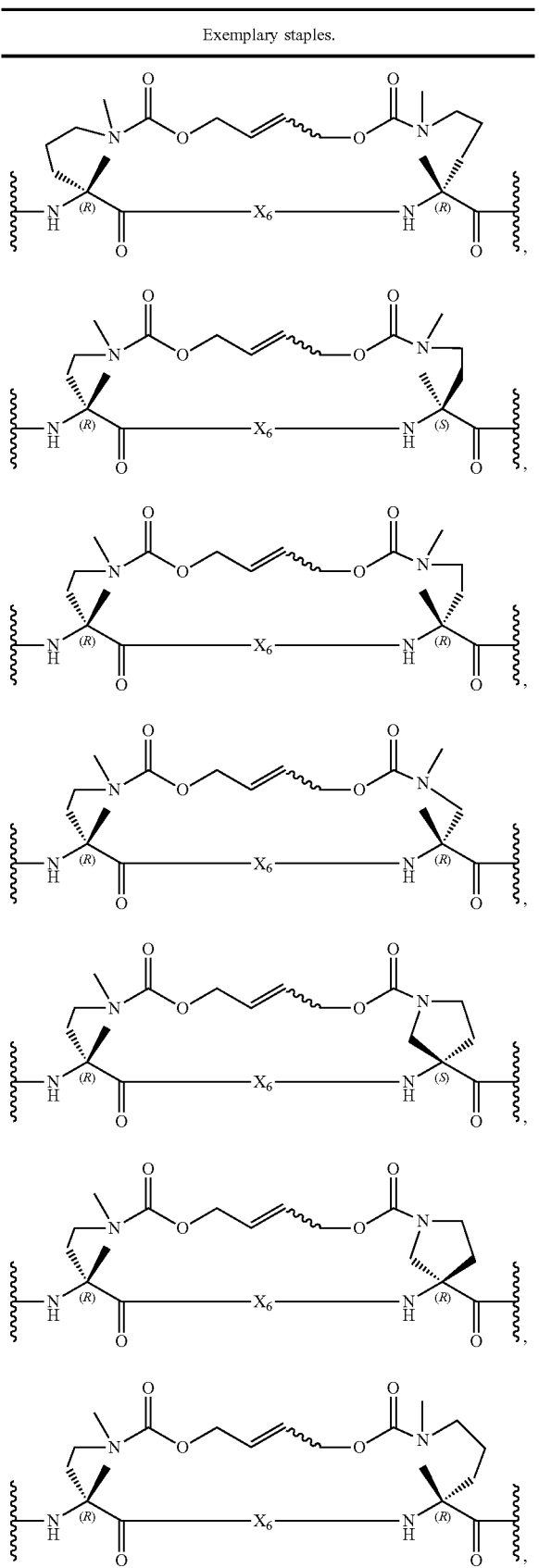
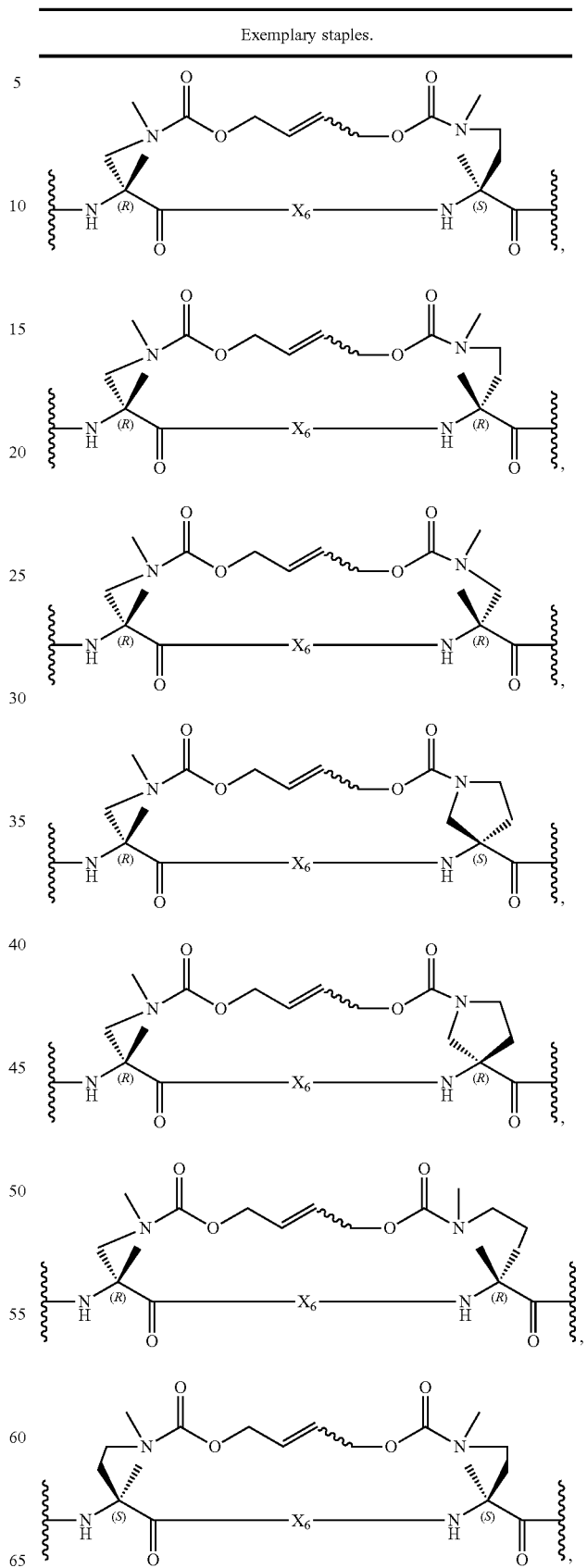

TABLE S-3-continued

Exemplary staples.

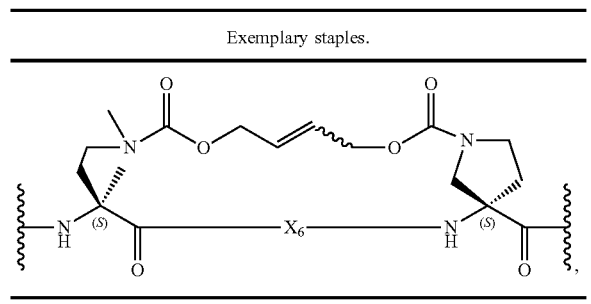

TABLE S-4

Exemplary staples.

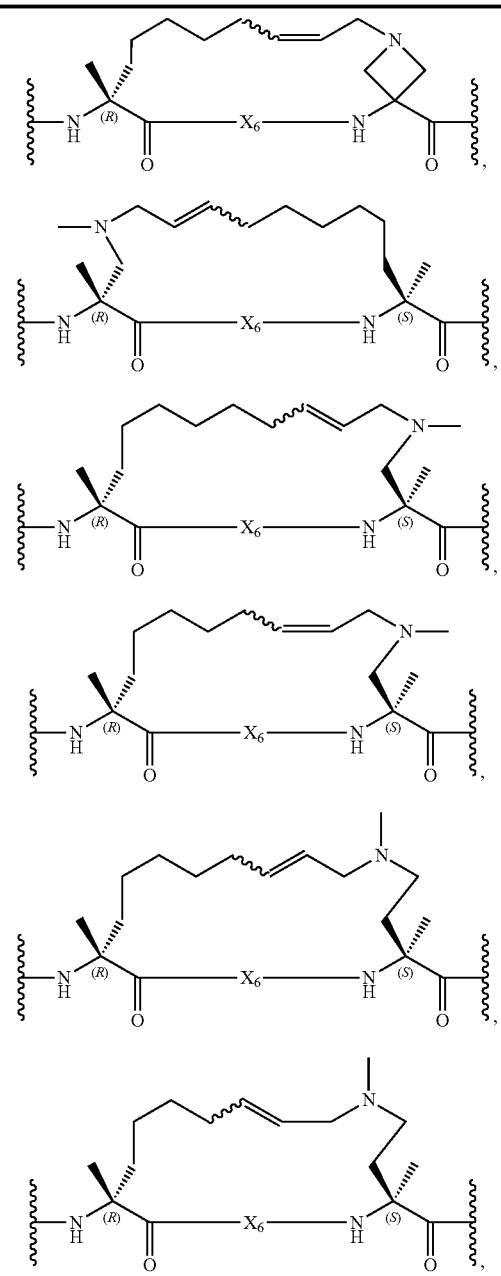

TABLE S-4-continued

Exemplary staples.

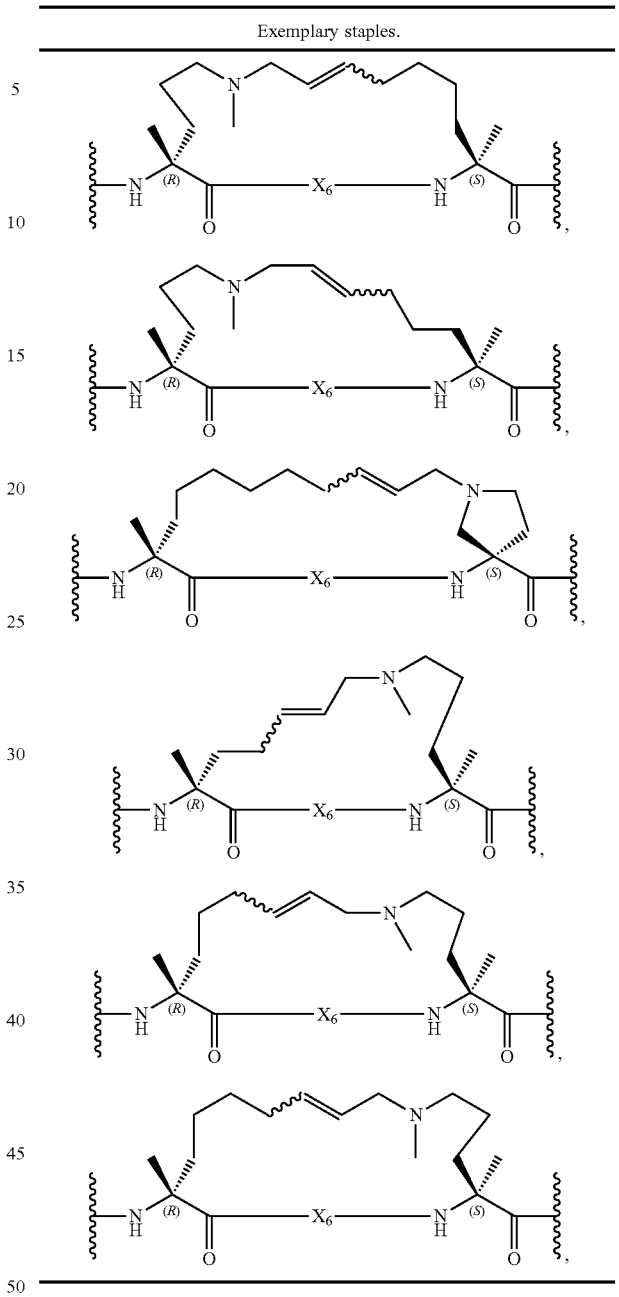

c. Modifications and Conjugations

In some embodiments, a provided peptide is optionally modified at its backbone, side chain, N-terminus and/or C-terminus, and is optionally conjugated to a second entity. Various modifications and/or conjugations are known in the art and can be utilized in accordance with the present disclosure.

In some embodiments, a provided peptide is capped. In some embodiments, a provided peptide is capped at the N-terminus. In some embodiments, a provided peptide is capped by an amidation reaction which convert the N-terminal —NH$_2$ into an amide. In some embodiments, the capping is acetylation.

In some embodiments, a modification and/or conjugation is to incorporate a targeting moiety, e.g., those can facilitate delivery to certain cells, organs, and/or organisms.

In some embodiments, a second entity is a ligand, e.g., a ligand for a protein receptor or an enzyme. In some embodiments, a ligand is a carbohydrate. In some embodiments, a modification is glycosylation. In some embodiments, a second entity for conjugation is a carbohydrate. In some embodiments, a carbohydrate is GalNac. In some embodiments, a second entity is a protein ligand.

In some embodiments, a provided peptide is conjugated to a lipid moiety, e.g., through coupling with a fatty acid with an N-terminus. In some embodiments, a lipid moiety is or comprises an optionally substituted $C_5$-$C_{100}$ aliphatic. In some embodiments, a lipid moiety is or comprises an unsubstituted $C_5$-$C_{100}$ aliphatic. In some embodiments, a lipid moiety is decanoyl, dodecanoyl, myristoyl, octyl, or palmitoyl.

In some embodiments, a provided peptide is conjugated to a degradation signal/entity. In some embodiments, a provided peptide is conjugated to a ligand for an E3 ubiquitin ligase.

In some embodiments, a provided peptide is conjugated to another peptide or protein. In some embodiments, a provided peptide is conjugated to another stapled peptide that interacts with beta-catenin at a different site than the provide peptide. In some embodiments, a provided peptide is conjugated to another stapled peptide that interacts with beta-catenin but does not compete with the provided peptide for beta-catenin binding.

In some embodiments, a provided stapled peptide comprises a helix in its 3-dimensional structure. In some embodiments, a provided stapled peptide can form an alpha-helix.

d. Properties and Activities

As demonstrated in the present disclosure, provided technologies can significantly improve properties and/or activities of stapled peptides.

In some embodiments, a provided peptide can form a helix structure.

In some embodiments, a provided peptide binds to beta-catenin. In some embodiments, a provided peptide has a Kd of no greater than 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, or 10 uM for beta-catenin. In some embodiments, a provided peptide has a Kd of no greater than 0.01 uM. In some embodiments, a provided peptide has a Kd of no greater than 0.05 uM. In some embodiments, a provided peptide has a Kd of no greater than 0.1 uM. In some embodiments, a provided peptide has a Kd of no greater than 0.2 uM. In some embodiments, a provided peptide has a Kd of no greater than 0.5 uM. In some embodiments, a provided peptide has a Kd of no greater than 1 uM. Various technologies can be utilized in accordance with the present disclosure to assess Kd, for example, fluorescence polarization, surface plasmon resonance, TR-FRET, etc.

In some embodiments, provided technologies provide improved stability. One challenge of using peptide as therapeutics is that peptides can be readily degraded when administered to a subject. Among other things, the present disclosure provides stapled peptides with greatly improved pharmacokinetics profiles. In some embodiments, provided stapled peptides have significantly improved half-life.

In some embodiments, provided technologies greatly improved solubility of stapled peptides. Among other things, the present disclosure recognize that a significant challenge of using stapled peptides is that stapled peptides, for example, those comprising hydrocarbon staples, may have low solubility in aqueous solutions, thereby complicating formulation and delivery. In some embodiments, the present disclosure provides stapled peptides with staples comprising —N(R')— and/or —N(R')—C(O)— moieties, which have improved solubility compared to stapled peptides that are otherwise identical but comprise hydrocarbon staples instead of staples comprising —N(R')— and/or —N(R')—C(O)— moieties. In some embodiments, provided stapled peptides comprising staples that comprise —N(R')— and/or —N(R')—C(O)— moieties have a solubility of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, or 250 uM in DPBS (per liter, 8 g sodium chloride, 0.2 g potassium phosphate, monobasic, 1.15 g sodium phosphate, dibasic, and 0.2 g potassium chloride). In some embodiments, the solubility is at least 1 uM in DPBS. In some embodiments, the solubility is at least 2 uM in DPBS. In some embodiments, the solubility is at least 3 uM in DPBS. In some embodiments, the solubility is at least 4 uM in DPBS. In some embodiments, the solubility is at least 5 uM in DPBS. In some embodiments, the solubility is at least 6 uM in DPBS. In some embodiments, the solubility is at least 7 uM in DPBS. In some embodiments, the solubility is at least 8 uM in DPBS. In some embodiments, the solubility is at least 9 uM in DPBS. In some embodiments, the solubility is at least 10 uM in DPBS. In some embodiments, the solubility is at least 20 uM in DPBS. In some embodiments, the solubility is at least 30 uM in DPBS. In some embodiments, the solubility is at least 40 uM in DPBS. In some embodiments, the solubility is at least 50 uM in DPBS. In some embodiments, the solubility is at least 60 uM in DPBS. In some embodiments, the solubility is at least 70 uM in DPBS. In some embodiments, the solubility is at least 80 uM in DPBS. In some embodiments, the solubility is at least 90 uM in DPBS. In some embodiments, the solubility is at least 100 uM in DPBS. In some embodiments, the solubility is at least 120 uM in DPBS. In some embodiments, the solubility is at least 150 uM in DPBS. In some embodiments, the solubility is at least 180 uM in DPBS. In some embodiments, the solubility is at least 200 uM in DPBS. In some embodiments, the solubility is at least 220 uM in DPBS. In some embodiments, the solubility is at least 250 uM in DPBS. In some embodiments, provided stapled peptides can achieve improved properties and/or activities using fewer acidic or basic amino acid residues, which, among other things, are often used to improve solubility (e.g., FP0597c v. StAx-35R, removal of the C-terminal R). Various methods can be utilized in accordance with the present disclosure to assess solubility, including those described in the examples.

Among other things, the present disclosure provides methods for improving solubility of stapled peptides. In some embodiments, the present disclosure encompasses the recognition and positioning of a staple can be utilized to modulate solubility. In some embodiments, the present disclosure provides methods for increasing or decreasing solubility of a stapled peptide by adjusting positioning of a staple. As demonstrate herein, structural similarly or otherwise identical stapled peptides can have greatly increased solubility (e.g., see FP0597c (98 uM) v. 7 FP0217c (7 uM)).

In some embodiments, provided stapled peptides with provided structural features, e.g., non-hydrocarbon staples (e.g., those comprising one or more staples that comprises one or more —N(R')—C(O)— or —N(R')—), staple positioning, connection stereochemistry, etc., provides improved properties and/or activities, e.g., increased cell permeability, increased cellular activities, etc., compared to an appropriate reference peptide which in some embodiments, is an unstapled peptide having the same sequence, or in some embodiments, is a stapled peptide that is otherwise identical but have a different type of staple, e.g., a hydrocarbon staple. For example, as reported in Grossmann et al. PNAS 109 17942-17947, a hydrocarbon-stapled peptide, StAx-33, (Ac-PEG1-PQS$_5$ILDS$_5$HVRRVWR (SEQ ID NO: 277)), was not cell-permeable and did not exhibit cell-based activity; to obtain a cell-permeable stapled peptide with cell-based activity, 3 amino acids were added to the N-terminus of the peptide and one other Q-+R mutation was made. However, these modifications can negatively impact other properties of the peptide. For example, the resulting peptide StAx-35R (Ac-PEG1-RRWPRS$_5$ILDS$_5$HVRRVWR (SEQ ID NO: 278)) had a reduced affinity compared to StAx-33. In some embodiments, provided stapled peptides can achieve improved properties and/or activities without using conjugation with other entries, e.g., PEG as in StAx-33 and StAx-35R (e.g., FP0597c v. StAx-35R). In some embodiments, provided stapled peptides can achieve improved properties and/or activities using a shorter amino acid sequence (e.g., FP0597c or FP0025c v. StAx-35R). In some embodiments, provided stapled peptides can achieve improved properties and/or activities using fewer acidic or basic amino acid residues, which, among other things, are often used to improve solubility (e.g., FP0597c or FP0025c v. StAx-35R). In a competition fluorescence polarization assay, FP0025c displaced a labeled probe from the axin site of beta-catenin with an EC$_{50}$<100 nM and showed better than 50% inhibition of signal at 10 µM in a beta-catenin luciferase reporter assay.

In some embodiments, provided stapled peptides provide selectivity in various aspects. In some embodiments, provided stapled peptides selectively interacts with beta-catenin sites that interact with Axin over those sites that interact with BCL9. In some embodiments, provided stapled peptides competes with FITC-PEG1-PQ-S5-ILD-S5-HVRRVWR (SEQ ID NO: 1), (with a hydrocarbon staple formed by two S5 via olefin metathesis) for interaction with beta-catenin, but not or to a significantly less extent with Ac-LSQEQLEHRERSLQTLRDIQRML-(2-Nal)-βA$_2$-K (FAM)-NH$_2$ (SEQ ID NO: 279). In some embodiments, provided stapled peptides competes with FITC-bA-PQ-S5-ILD-S5-HVRRVWR (SEQ ID NO: 3) (with a hydrocarbon staple formed by two S5 via olefin metathesis) for interaction with beta-catenin, but not or to a significantly less extent with Ac-LSQEQLEHRERSLQTLRDIQRML-(2-Nal)-βA$_2$-K(FAM)-NH$_2$ (SEQ ID NO: 279). In some embodiments, a reference stapled peptide that interacts with beta-catenin at sites that that interact with Axin is FITC-PEG1-PQ-S5-ILD-S5-HVRRVWR (SEQ ID NO: 1) (hydrocarbon staple formed by two S5 via olefin metathesis). In some embodiments, a reference stapled peptide that interacts with beta-catenin at sites that interact with Axin is FITC-bA-PQ-S5-ILD-S5-HVRRVWR (SEQ ID NO: 3) (hydrocarbon staple formed by two S5 via olefin metathesis). In some embodiments, a reference stapled peptide that interacts with beta-catenin at sites that interact with BCL9 is Ac-LSQEQLEHRERSLQTLRDIQRML-(2-Nal)-βA$_2$-K(FAM)-NH$_2$ (SEQ ID NO: 279). In some embodiments, a significantly less extent is EC50, e.g., as measured by competition assays described in the present disclosure, that is at least 2, 3, 4, 5, 6, 7, 8, 9, 10, 11, 12, 13, 14, 15, 20, 30, 40, 50, 100, 200, 300, 400, or 500 fold higher. In some embodiments, a fold is 5 fold. In some embodiments, a fold is 10 fold. In some embodiments, a fold is 20 fold. In some embodiments, a fold is 50 fold. In some embodiments, a fold is 100 fold. In some embodiments, a fold is 500 fold.

In some embodiments, provided stapled peptides provide more specific modulation of beta-catenin target gene expression compared to a reference Wnt pathway modulator (e.g., IWR-1, ICG-001, etc.). In some embodiments, provided stapled peptides decrease expression levels of one or more beta-catenin target genes in a type of cells that comprises aberrant Wnt/beta-catenin signaling pathway, while a reference Wnt pathway modulator does not do so or do so to a less extent. In some embodiments, provided stapled peptides do not decrease, or decrease to much less extent, expression levels of one or more beta-catenin target genes compared to a reference agent in a type of cells that comprises wild-type Wnt/beta-catenin signaling pathway.

In some embodiments, provided stapled peptides have low toxicity, e.g., non-specific toxicity, compared to an appropriate reference peptide. In some embodiments, a reference peptide is a stapled peptide that interacts with one or more beta-catenin sites that interact with Axin and comprises a hydrocarbon staple, e.g., WO2017062518. In some embodiments, a provided stapled peptide has less than 10%, 15%, 20%, 25%, 30%, 40%, 50% non-specific cytotoxicity at a concentration of no less than 1, 2, 3, 4, 5, 6, 7, 8, 9, or 10 uM as measured by a LDH release assay compared to an appreciate positive reference. In some embodiments, a provided stapled peptide comprises a staple comprising a —N(R')— or —N(R')—C(O)— moiety, and has lower non-specific cytotoxicity compared to a peptide comprising a hydrocarbon staple but is otherwise of the identical structure when assayed under a comparable condition.

In some embodiments, provided stapled peptides modulate one or more functions of beta-catenin. In some embodiments, provided stapled peptides modulate one or more functions of beta-catenin associated with Axin binding. In some embodiments, provided stapled peptides modulate one or more functions of beta-catenin associated with interactions at one or more sites that interact with Axin. In some embodiments, provided stapled peptides modulate beta-catenin target gene expression. In some embodiments, provided stapled peptides inhibit cancer cell growth. In some embodiments, provided stapled peptides provide increased activities compared to an appropriate reference agent. In some embodiments, a reference agent is a stapled peptide. In some embodiments, a reference agent is a stapled peptide that interacts with beta-catenin sites that interact with Axin.

4. Production of Stapled Peptides

Various technologies are known in the art can be utilized in accordance with the present disclosure to prepare provided stapled peptides, including those described in the methods. In many embodiments, peptides are prepared on solid phase on a synthesizer using, typically, Fmoc chemistry. In some embodiments, staples are formed by olefin metathesis. In some embodiments, a product double bond of metathesis is reduced/hydrogenated. In some embodiments, CO$_2$ are extruded from a carbamate moiety of a staple. In some embodiments, provided stapled peptides are further modified, and/or conjugated to other entities. Conditions and/or reagents of these reactions are widely know in the art and can be performed in accordance with the present disclosure to provide stapled peptides.

Properties and/or activities of provided stapled peptides can be readily assessed in accordance with the present disclosure, for example, through use of one or more methods described in the examples.

In some embodiments, the present disclosure encompasses the recognition that structural elements of staples, e.g., size, chemistry, stereochemistry, etc., can significantly impact yields and/or purity of stapling through olefin metathesis. As illustrated by exemplary data provided in the present disclosure, staples having certain structural elements, e.g., size, chemistry, stereochemistry, etc., and/or combination thereof, can facilitate production of provided stapled peptides including higher yields, purity, and selectivity, etc. In some embodiments, the present disclosure provides beneficial structural elements, e.g., size, chemistry, stereochemistry, etc., and/or combination thereof, for example, those exemplified in the examples.

In some embodiments, the present disclosure provides the recognition that catalysts other than Grubbs I may provide better results, e.g., yield, purity, selectivity, etc. for olefin metathesis. In some embodiments, the present disclosure demonstrates that Hoveyda-Grubbs II catalyst may provide better results, e.g., yield, purity, selectivity, etc. for olefin metathesis. In some embodiments, the present disclosure provides methods for preparing a provided stapled peptide, comprising providing a Hoveyda-Grubbs II in an olefin metathesis reaction.

In some embodiments, technologies for preparing and/or assessing provided stapled peptides include those described in U.S. Pat. No. 9,617,309, US 2015-0225471, US 2016-0024153, US 2016-0215036, US2016-0244494, WO2017/062518, etc.

In some embodiments, a provided agent, e.g, a provided peptide, has a purity of 60%-100%. In some embodiments, a provided agent has a purity of at least 60%, 65%, 70%, 75%, 80%, 85%, 90%, 91%, 92%, 93%, 94%, 95%, 96%, 97%, 98%, or 99%. In some embodiments, a purity is at least 60%. In some embodiments, a purity is at least 70%. In some embodiments, a purity is at least 80%. In some embodiments, a purity is at least 85%. In some embodiments, a purity is at least 90%. In some embodiments, a purity is at least 91%. In some embodiments, a purity is at least 92%. In some embodiments, a purity is at least 93%. In some embodiments, a purity is at least 94%. In some embodiments, a purity is at least 95%. In some embodiments, a purity is at least 96%. In some embodiments, a purity is at least 97%. In some embodiments, a purity is at least 98%. In some embodiments, a purity is at least 99%. In some embodiments, a purity is at least 99.5%.

In some embodiments, provided methods provide high yields. In some embodiments, a yield is 50%-100%. In some embodiments, a yield is at least 60%, 65%, 70%, 75%, 80%, 85%, 90%, 91%, 92%, 93%, 94%, 95%, 96%, 97%, 98% or 99%. In some embodiments, a yield is at least 60%. In some embodiments, a yield is at least 65%. In some embodiments, a yield is at least 70%. In some embodiments, a yield is at least 75%. In some embodiments, a yield is at least 80%. In some embodiments, a yield is at least 85%. In some embodiments, a yield is at least 90%. In some embodiments, a yield is at least 91%. In some embodiments, a yield is at least 92%. In some embodiments, a yield is at least 93%. In some embodiments, a yield is at least 94%. In some embodiments, a yield is at least 95%. In some embodiments, a yield is at least 96%. In some embodiments, a yield is at least 97%. In some embodiments, a yield is at least 98%. In some embodiments, a yield is at least 99%.

In some embodiments, a provided method delivers high E/Z selectivity for olefin. In some embodiments, provided selectivity favors the E isomer. In some embodiments, provided selectivity favors the Z isomer. In some embodiments, a E:Z ratio is at least 1:1, 1.5:1, 2:1, 3:1, 4:1, 5:1, 6:1, 7:1, 8:1, 9:1, 10:1, 20:1, 30:1, 40:1, 50:1, or 100:1. In some embodiments, a Z:E ratio is at least 1:1, 1.5:1, 2:1, 3:1, 4:1, 5:1, 6:1, 7:1, 8:1, 9:1, 10:1, 20:1, 30:1, 40:1, 50:1, 80:1, 90:1, 95:1, 99:1, or 100:1. In some embodiments, a ratio is at least 1:1. In some embodiments, a ratio is at least 1.5:1. In some embodiments, a ratio is at least 2:1. In some embodiments, a ratio is at least 3:1. In some embodiments, a ratio is at least 4:1. In some embodiments, a ratio is at least 5:1. In some embodiments, a ratio is at least 6:1. In some embodiments, a ratio is at least 7:1. In some embodiments, a ratio is at least 8:1. In some embodiments, a ratio is at least 9:1. In some embodiments, a ratio is at least 10:1. In some embodiments, a ratio is at least 20:1. In some embodiments, a ratio is at least 30:1. In some embodiments, a ratio is at least 40:1. In some embodiments, a ratio is at least 50:1. In some embodiments, a ratio is at least 80:1. In some embodiments, a ratio is at least 90:1. In some embodiments, a ratio is at least 95:1. In some embodiments, a ratio is at least 99:1. In some embodiments, a ratio is at least 100:1.

In some embodiments, a provide method comprises a period of time at a temperature higher than room temperature. In some embodiments, a temperature is about 25-200° C. In some embodiments, a temperature is about 25° C. In some embodiments, a temperature is about 30° C. In some embodiments, a temperature is about 35° C. In some embodiments, a temperature is about 40° C. In some embodiments, a temperature is about 45° C. In some embodiments, a temperature is about 50° C. In some embodiments, a temperature is about 55° C. In some embodiments, a temperature is about 60° C. In some embodiments, a temperature is about 65° C. In some embodiments, a temperature is about 70° C. In some embodiments, a temperature is about 75° C. In some embodiments, a temperature is about 80° C. In some embodiments, a temperature is about 85° C. In some embodiments, a temperature is about 90° C. In some embodiments, a temperature is about 95° C. In some embodiments, a temperature is about 100° C. In some embodiments, a temperature is about 150° C. In some embodiments, a temperature is higher than about 150° C.

5. Uses

Among other things, provided stapled peptides interacts with beta-catenin. In some embodiments, a condition, disorder, or disease is associated with one or more components involved in Wnt/beta-catenin signaling. In some embodiments, a condition, disorder, or disease is associated with one or more beta-catenin functions. In some embodiments, a condition disorder or disease is associated with interactions between beta-catenin and one or more beta-catenin sites that interact with one or more proteins in Wnt/beta-catenin signaling. In some embodiments, provided stapled peptides compete with and/or otherwise interfere with or reduce binding between beta-catenin and Axin. In some embodiments, a condition disorder or disease is associated with interactions between beta-catenin and one or more beta-catenin sites that interact with Axin. In some embodiments, a condition, disorder, or disease is associated with interactions with and one or more proteins that compete with Axin for interaction with beta-catenin. In some embodiments, a provided stapled peptide antagonizes beta-catenin interaction with another protein, such as TCF, whose one or more binding sites overlap with, or are in close proximity to, one or more beta-catenin sites that interact with Axin or a provided stapled peptide. In some embodiments, a condition, disorder, or disease is associated with interactions between beta-catenin and Axin. In some embodiments, provided stapled peptides interacts with beta-catenin at one or more beta-catenin sites that interacts with Axin. In some embodiments, provided stapled peptides inhibit one or more Axin activities. In some embodiments, provided stapled peptides inhibit one or more Wnt/beta-catenin pathway activities.

In some embodiments, provided stapled peptides is useful for preventing and/or treating one or more beta-catenin-associated conditions, disorders, and/or diseases. In some embodiments, the present disclosure provides a method for preventing or treating a beta-catenin-associated condition, disorder or disease, comprising administering to a subject susceptible to or suffering from provided stapled peptide or a pharmaceutical composition thereof.

In some embodiments, a condition, disorder, or disease is selected from cancer, cardiac disease, dilated cardiomyopathy, fetal alcohol syndrome, depression, and diabetes.

In some embodiments, a condition, disorder, or disease is a heart condition, disorder, or disease.

In some embodiments, a condition, disorder, or disease is cancer. In some embodiments a cancer is selected from: colon cancer, colorectal cancer, rectal cancer, prostate cancer familial adenomatous polyposis (FAP), Wilms Tumor, melanoma, hepatocellular carcinoma, ovarian cancer, endometrial cancer, medulloblastoma pilomatricomas, primary hetpatocellular carcinoma, ovarial carcinoma, breast cancer, lung cancer, glioblastoma, pliomatrixoma, medulloblastoma, thyroid tumors, ovarian neoplasms. In some embodiments, a cancer is colorectal cancer. In some embodiments, a cancer is hepatocellular cancer. In some embodiments, a cancer is prostate cancer. In some embodiments, a cancer is melanoma.

In some embodiments, a provided stapled peptide is administered in combination with an additional agent. In some embodiments, a provided stapled peptide is administered prior to, concurrently with, or subsequent to an additional agent. In some embodiments, a provided stapled peptide is administered at the same time as an additional agent. In some embodiments, an additional agent is a therapeutic agent. In some embodiments, an additional agent may optionally be formulated with a provided stapled peptide in the same pharmaceutical composition.

In some embodiments, an additional agent is a checkpoint inhibitor, an EGFR inhibitor, a VEGF inhibitor, a VEGFR inhibitor, a kinase inhibitor, or an anti-cancer drug.

In some embodiments, an additional agent is a checkpoint inhibitor. In some embodiments, an additional agent is an immune oncology agent. In some embodiments, an additional agent is an antibody against a checkpoint molecules. In some embodiments, an additional agent is an antibody of PD1, PDL-1, CTLA4, A2AR, B7-H3, B7-H4, BTLA, IDO, KIR, LAG3, TIM-s, C10orf54, etc. In some embodiments, an antibody is an anti-PD1 antibody. In some embodiments, an antibody is an anti-PD-L1 antibody. In some embodiments, an antibody is an anti-CTLA4.

In some embodiments, an additional agent is an EGFR inhibitor, e.g., erlotinib, gefitinib, lapatinib, panitumumab, vandetanib, cetuximab, etc.

In some embodiments, an additional agent is an VEGF and/or VEGFR inhibitor, e.g., pazopanib, bevacizumab, sorafenib, sunitinib, axitinib, ponatinib, regorafenib, vandetanib, cabozantinib, ramucirumab, lenvatinib, ziv-aflibercept, etc.

In some embodiments, an additional agent is a kinase inhibitor. In some embodiments, an additional therapeutic agent is a chemotherapeutic agent. In some embodiments, an additional therapeutic agent is an anti-cancer drug, e.g., cyclophosphamide, methotrexate, 5-fluorouracil (5-FU), doxorubicin, mustine, vincristine, procarbazine, prednisolone, dacarbazine, bleomycin, etoposide, cisplatin, epirubicin, capecitabine, folinic acid, actinomycin, all-trans retinoic acid, azacitidine, azathioprine, bortezomib, carboplatin, chlorambucil, cytarabine, daunorubicin, docetaxel, doxifluridine, fluorouracil, gemcitabine, hydroxyurea, idarubicin, imatinib, irinotecan, mechlorethamine, mercaptopurine, mitoxantrone, paclitaxel, pemetrexed, teniposide, tioguanine, topotecan, valrubicin, vinblastine, vindesine, vinorelbine, oxaliplatin, etc.

In some embodiments, an additional agent is a stapled peptide. In some embodiments, an additional agent is a stapled peptide that interacts with beta-catenin that does not compete with binding between beta-catenin and Axin. In some embodiments, an additional agent is a stapled peptide that interacts with beta-catenin at one or more sites that interacts with BCL9.

In some embodiments, a provided stapled peptide is administered in combination with an additional therapy. In some embodiments, an additional therapy is radiation therapy. In some embodiments, an additional therapy is surgery.

6. Example Embodiments

Among other things, the present disclosure provides the following Example Embodiments:

1. A peptide comprising:

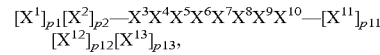
$$[X^1]_{p1}[X^2]_{p2}-X^3X^4X^5X^6X^7X^8X^9X^{10}-[X^{11}]_{p11}[X^{12}]_{p12}[X^{13}]_{p13},$$

wherein:
each of p1, p2, p11, p12 and p13 is independently 0 or 1;
each of X, $X^1$, $X^2$, $X^3$, $X^4$, $X^5$, $X^6$, $X^7$, $X^8$, $X^9$, $X^{10}$, $X^{11}$, $X^{12}$, and $X^{13}$ is independently an amino acid residue;
at least two of X, $X^1$, $X^2$, $X^3$, $X^4$, $X^5$, $X^6$, $X^7$, $X^8$, $X^9$, $X^{10}$, $X^{11}$, $X^{12}$, and $X^{13}$ comprise side chains that are optionally linked together to form a staple.

2. The peptide of embodiment 1, wherein at least two of $X^1$ to $X^3$ each independently comprise a side chain that comprise an olefin, wherein the two olefins can be connected together by olefin metathesis to form a staple.

3. The peptide of any one of the preceding embodiments, wherein side chains of the at least two of $X^1$ to $X^{11}$ are connected to form a staple.

4. The peptide of any one of the preceding embodiments, wherein each of $X^1$ to $X^{13}$ is independently a residue of an amino acid having the structure of formula A-I.

5. The peptide of any one of the preceding embodiments, wherein each of $X^1$ to $X^3$ is independently a residue of an amino acid having the structure of formula A-I and is an alpha amino acid.

6. The peptide of any one of the preceding embodiments, wherein each of p1, p2, p11, p12 and p13 is independently 0.

7. The peptide of any one of embodiments 1-5, wherein each of p1, p2, p11, p12 and p13 is independently 1.

8. The peptide of any one of embodiments 1-5, wherein each of p1 is 0.

9. The peptide of any one of the preceding embodiments, wherein $X^3$ is a residue of an amino acid selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, and $M_I$.

10. The peptide of any one of the preceding embodiments, wherein $X^3$ is a residue of an amino acid selected from $R_4$, $R_5$, $R_6$, $R_7$, $R_8$, $S_4$, $S_5$, $S_6$, $S_7$, and $S_8$.

11. The peptide of any one of the preceding embodiments, wherein $X^3$ is an amino acid residue of $R_8$.

12. The peptide of any one of embodiments 1-9, wherein $X^3$ is an amino acid residue of $M_G$.

13. The peptide of any one of embodiments 1-9, wherein $X^3$ is an amino acid residue of $R_4$.

14. The peptide of any one of the preceding embodiments, $X^{10}$ is a residue of an amino acid selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, and $M_I$.

15. The peptide of any one of the preceding embodiments, $X^{10}$ is a residue of an amino acid selected from $M_A$, $M_B$, $M_C$, $M_D$, $M_E$, $M_F$, $M_G$, $M_H$, and $M_I$.

16. The peptide of any one of embodiments 1-13, wherein $X^{10}$ is a residue of R or a homolog thereof.

17. The peptide of any one of embodiments 1-13, wherein $X^{10}$ is a residue of R.

18. The peptide of any one of the preceding embodiments, wherein the peptide comprises at least one residue of $R_4$, $R_5$, $R_6$, $R_7$, $R_8$, $S_4$, $S_5$, $S_6$, $S_7$, or $S_8$.

19. The peptide of any one of the preceding embodiments, wherein the peptide comprises at least one residue of $M_A$, $M_B$, $M_C$, $M_D$, $M_E$, $M_F$, $M_G$, $M_H$, or $M_I$.

20. The peptide of any one of the preceding embodiments, wherein a side chain of $X^3$ and a side chain of $X^{10}$ are taken together to form a staple.

21. The peptide of any one of the preceding embodiments, wherein $X^1$ is a residue of an amino acid selected from P, A, D, E, F, G, H, I, K, L, M, N, Q, R, S, T, V, W, Y, and α-methyl proline.

22. The peptide of any one of the preceding embodiments, wherein $X^1$ is a residue of an amino acid selected from P, A, D, E, F, G, H, I, K, L, M, N, Q, R, S, T, V, W, and Y.

23. The peptide of embodiment 21, wherein $X^1$ is a residue of an amino acid selected from P, K, N, Q, R, Y, and α-methyl proline.

24. The peptide of embodiment 21, wherein $X^1$ is a residue of an amino acid P.

25. The peptide of any one of the preceding embodiments, wherein $X^2$ is a residue of an amino acid selected from A, D, E, F, G, H, I, K, L, M, N, P, Q, R, S, T, V, W, and Y.

26. The peptide of embodiment 25, wherein $X^2$ is a residue of an amino acid selected from A, D, E, K, N, Q, and R.

27. The peptide of embodiment 25, wherein $X^2$ is a residue of A.

28. The peptide of any one of the preceding embodiments, wherein $X^4$ is a residue of an amino acid selected from I, F, H, L, V, homoleucine, tert-leucine, 3-cyclopropylalanine, 3-cyclobutylalanine, 3-cyclopentylalanine, 3-cyclohexylalanine, and alpha-neopentylglycine.

29. The peptide of any one of the preceding embodiments, wherein $X^4$ is a residue of an amino acid selected from I, F, H, L, and V.

30. The peptide of embodiment 28, wherein $X^4$ is a residue of an amino acid selected from I, L, V, homoleucine, tert-leucine, 3-cyclopropylalanine, 3-cyclobutylalanine, 3-cyclopentylalanine, and alpha-neopentylglycine.

31. The peptide of embodiment 28, wherein $X^4$ is a residue of I.

32. The peptide of any one of the preceding embodiments, wherein $X^5$ is a residue of an amino acid selected from L, F, H, I, V, alpha-methyl leucine, homoleucine, tert-leucine, 3-cyclopropylalanine, 3-cyclobutylalanine, 3-cyclopentylalanine, 3-cyclohexylalanine, and alpha-neopentylglycine.

33. The peptide of any one of the preceding embodiments, wherein $X^5$ is a residue of an amino acid selected from L, F, H, I, and V.

34. The peptide of embodiment 32, wherein $X^5$ is a residue of an amino acid selected from L, I, V, alpha-methyl leucine, homoleucine, tert-leucine, 3-cyclopropylalanine, 3-cyclobutylalanine, 3-cyclopentylalanine, 3-cyclohexylalanine, and alpha-neopentylglycine.

35. The peptide of embodiment 32, wherein $X^5$ is a residue of L.

36. The peptide of any one of the preceding embodiments, wherein $X^6$ is a residue of an amino acid selected from D, A, E, F, H, I, K, L, M, N, P, Q, R, S, T, V, W, Y, methionine sulfone, 2-aminoadipic acid, aspartic acid beta-methylester, aspartic acid beta-cyclohexylester, aspartic acid beta-benzylester, glutamic acid beta-methylester, glutamic acid beta-cyclohexylester, and glutamic acid beta-benzyl ester.

37. The peptide of any one of the preceding embodiments, wherein $X^6$ is a residue of an amino acid selected from D, A, E, F, H, I, K, L, M, N, P, Q, R, S, T, V, W, and Y.

38. The peptide of embodiment 36, wherein $X^6$ is a residue of an amino acid selected from D, E, H, N, Q, S, T, Y, methionine sulfone, 2-aminoadipic acid, aspartic acid beta-methylester, aspartic acid beta-cyclohexylester, aspartic acid beta-benzylester, glutamic acid beta-methylester, glutamic acid beta-cyclohexylester, and glutamic acid beta-benzyl ester.

39. The peptide of embodiment 36, wherein $X^6$ is a residue of an amino acid selected from D, N, and T.

40. The peptide of any one of the preceding embodiments, wherein $X^7$ is a residue of an amino acid selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, $M_I$, A, D, E, F, H, I, K, L, M, N, P, Q, R, S, T, V, W, Y and alpha-methyl alanine.

41. The peptide of any one of the preceding embodiments, wherein $X^7$ is a residue of an amino acid selected from A, D, E, F, H, I, K, L, M, N, P, Q, R, S, T, V, W, Y and alpha-methyl alanine.

42. The peptide of embodiment 40, wherein $X^7$ is a residue of an amino acid selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, and $M_I$.

43. The peptide of embodiment 40, wherein $X^7$ is a residue of an amino acid selected from A, D, E, F, H, I, K, L, M, N, P, Q, R, S, T, V, W, and Y.

44. The peptide of embodiment 40, wherein $X^7$ is a residue of an amino acid selected from A, D, E, I, K, L, N, Q, R, S, T, V, W, Y and alpha-methyl alanine.

45. The peptide of embodiment 40, wherein $X^7$ is a A or alpha-methyl alanine residue.

46. The peptide of any one of the preceding embodiments, wherein $X^8$ is a residue of an amino acid selected from H, F, I, L, N, Q, V, 1-methylhistidine, 3-methylhistidine, 3-(2-pyridyl)alanine, 3-(3-pyridyl)alanine, 3-(4-pyridyl)alanine, beta-2-furylalanine, beta-2-thienylalanine, 3-(2-tetrazolyl)alanine), and beta-4-thiazolylalanine.

47. The peptide of any one of the preceding embodiments, wherein $X^8$ is a residue of an amino acid selected from H, F, I, L, N, Q, and V.

48. The peptide of embodiment 46, wherein $X^8$ is a residue of an amino acid selected from H, N, Q, 1-methylhistidine, 3-methylhistidine, 3-(2-pyridyl)alanine, 3-(3-pyridyl)alanine, 3-(4-pyridyl)alanine, beta-2-furylalanine, beta-2-thienylalanine, 3-(2-tetrazolyl)alanine), and beta-4-thiazolylalanine.

49. The peptide of embodiment 46, wherein $X^8$ is a H residue.

50. The peptide of any one of the preceding embodiments, wherein $X^9$ is a residue of an amino acid selected from I, V, F, H, L, homoleucine, tert-leucine, 3-cyclopropylalanine, 3-cyclobutylalanine, 3-cyclopentylalanine, 3-cyclohexylalanine, and alpha-neopentylglycine.

51. The peptide of any one of the preceding embodiments, wherein $X^9$ is a residue of an amino acid selected from I, V, F, H, and L.

52. The peptide of embodiment 50, wherein $X^9$ is a residue of an amino acid selected from I, V, L, homoleucine, tert-leucine, 3-cyclopropylalanine, 3-cyclobutylalanine, 3-cyclopentylalanine, 3-cyclohexylalanine, and alpha-neopentylglycine.

53. The peptide of embodiment 50, wherein $X^9$ is a residue of an amino acid selected from I and V.

54. The peptide of any one of the preceding embodiments, wherein $X^{11}$ is a residue of an amino acid selected from R, A, D, E, F, H, I, K, L, M, N, P, Q, S, T, V, W, Y, 3-(1-naphthylalanine), 2-aminoadipic acid, asymmetric dimethylarginine, symmetric dimethylarginine, homoarginine, N-epsilon-methyllysine, N-epsilon-dimethyllysine, and N-epsilon-trimethyllysine.

55. The peptide of any one of the preceding embodiments, wherein $X^{11}$ is a residue of an amino acid selected from R, A, D, E, F, H, I, K, L, M, N, P, Q, S, T, V, W, and Y.

56. The peptide of embodiment 54, wherein $X^{11}$ is a residue of an amino acid selected from R, A, E, F, K, Q, S, V, Y, 3-(1-naphthylalanine), 2-aminoadipic acid, asymmetric dimethylarginine, symmetric dimethylarginine, homoarginine, N-epsilon-methyllysine, N-epsilon-dimethyllysine, and N-epsilon-trimethyllysine.

57. The peptide of embodiment 54, wherein $X^{11}$ is a residue of an amino acid selected from R, A, F, K, S, V, 3-(1-naphthylalanine), asymmetric dimethylarginine, symmetric dimethylarginine, homoarginine, and N-epsilon-methyllysine.

58. The peptide of any one of the preceding embodiments, wherein $X^{12}$ is a residue of an amino acid selected from V, F, H, I, L, alpha-methyl valine, alpha methyl leucine, homoleucine, tert-leucine, 3-cyclopropylalanine, 3-cyclobutylalanine, 3-cyclopentylalanine, 3-cyclohexylalanine, and alpha-neopentylglycine.

59. The peptide of any one of the preceding embodiments, wherein $X^{12}$ is a residue of an amino acid selected from V, F, H, I, and L.

60. The peptide of embodiment 58, wherein $X^{12}$ is a residue of an amino acid selected from I, A, L, V, alpha-methylleucine, homoleucine, tert-leucine, 3-cyclopropylalanine, 3-cyclobutylalanine, 3-cyclopentylalanine, 3-cyclohexylalanine, alpha-neopentylglycine, O-propargylserine, L-octylglycine, and L-alloisoleucine.

61. The peptide of embodiment 58, wherein $X^{12}$ is a residue of an amino acid selected from V, alpha-methyl valine, and alpha methyl leucine.

62. The peptide of any one of the preceding embodiments, wherein $X^{13}$ is a residue of an amino acid selected from W, A, D, E, F, H, I, K, L, M, N, P, Q, R, S, T, V, Y, d-tryptophan, alpha-methyl tryptophan, 3-(1-naphthylalanine), 3-(2-naphthylalanine), 4-chlorotryptophan, 5-chlorotryptophan, 6-chlorotryptophan, 7-chlorotryptophan, 4-bromotryptophan, 5-bromotryptophan, 6-bromotryptophan, 7-bromotryptophan, 4-fluorotryptophan, 5-fluorotryptophan, 6-fluorotryptophan, 7-fluorotryptophan, 1-methyltryptophan, 2-methyltryptophan, 4-methyltryptophan, 5-methyltryptophan, 6-methyltryptophan, 7-methyltryptophan, 2-hydroxytryptophan, 4-hydroxytryptophan, 5-hydroxytryptophan, 6-hydroxytryptophan, 7-hydroxytryptophan, 5-methoxytryptophan, 7-azatryptophan, 3-benzothienylalanine, and 4-phenyl-L-phenylalanine.

63. The peptide of any one of the preceding embodiments, wherein $X^{13}$ is a residue of an amino acid selected from W, A, D, E, F, H, I, K, L, M, N, P, Q, R, S, T, V, and Y.

64. The peptide of embodiment 62, wherein $X^{13}$ is a residue of an amino acid selected from W, D, E, F, Y, d-tryptophan, alpha-methyl tryptophan, 3-(1-naphthylalanine), 3-(2-naphthylalanine), 5-chlorotryptophan, 6-chlorotryptophan, 7-chlorotryptophan, 5-bromotryptophan, 6-bromotryptophan, 7-bromotryptophan, 5-fluorotryptophan, 6-fluorotryptophan, 7-fluorotryptophan, 1-methyltryptophan, 2-methyltryptophan, 5-methyltryptophan, 6-methyltryptophan, 7-methyltryptophan, 2-hydroxytryptophan, 5-hydroxytryptophan, 6-hydroxytryptophan, 7-hydroxytryptophan, 5-methoxytryptophan, 7-azatryptophan, and 3-benzothienylalanine.

65. The peptide of embodiment 62, wherein $X^{13}$ is a residue of an amino acid selected from W, D-tryptophan, and alpha-methyl tryptophan.

66. The peptide of any one of the preceding embodiments, wherein the peptide comprising a (i, i+4) staple wherein, not including the two amino acid residues that are directly connected to the staple, there are three amino acid residues between the two amino acid residues that are directly connected to the staple.

67. The peptide of any one of the preceding embodiments, wherein the peptide comprising a (i, i+7) staple wherein, not including the two amino acid residues that are directly connected to the staple, there are six amino acid residues between the two amino acid residues that are directly connected to the staple.

68. The peptide of any one of the preceding embodiments, wherein the staple is formed by olefin metathesis of two terminal olefins each of which is independently of a side chain of an amino acid residue.

69. The peptide of any one of the preceding embodiments, wherein the staple is formed by olefin metathesis of two terminal olefins each of which is independently of a side chain of a residue of an amino acid selected from $R_4$, $R_5$, $R_6$, $R_7$, $R_8$, $S_4$, $S_5$, $S_6$, $S_7$, $S_8$, $M_A$, $M_B$, $M_C$, $M_D$, $M_E$, $M_F$, $M_G$, $M_H$, and $M_I$.

70. The peptide of any one of the preceding embodiments, wherein the peptide comprises one and no more than one staple.

71. The peptide of any one of the preceding embodiments, wherein the peptide comprises two or more staples.

72. The peptide of embodiment 71, wherein at least two staples are bonded to the same peptide backbone atom.

73. The peptide of embodiment 71, wherein none of the staples are bonded to the same peptide backbone atom.

74. The peptide of any one of the preceding embodiments, wherein a staple is bonded to a peptide backbone atom of amino acid residue 1, 2, 3, 4, 5, 6, 7, 8, 9, 10, 11, 12, 13, 14, 15, 16, or 17.

75. The peptide of any one of the preceding embodiments, wherein a staple is $L^s$, wherein $L^s$ is an optionally substituted, bivalent $C_{1-50}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —CO$_2$R, or —SO$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

76. A peptide having the structure of:

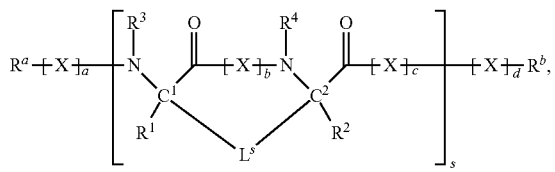

or a salt thereof, wherein
each of $R^a$, $R^1$, $R^2$, $R^3$, and $R^4$ is independently R';
$R^b$ is R', —OR' or —N(R')$_2$;
each of X is independently an amino acid residue;
each of a, b, c, s, and d is independently 1-20;
each of $C^1$ and $C^2$ is independently a carbon atom;
each $L^s$ is independently -$L^{s1}$-$L^{s2}$-$L^{s3}$-, wherein $L^{s1}$ is bonded to $C^1$ and $L^{s3}$ is bonded to $C^2$
each of $L^{s1}$, $L^{s2}$, and $L^{s3}$ is independently L;
each L is independently a covalent bond, or an optionally substituted, bivalent $C_1$-$C_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —CO$_2$R, or —SO$_2$R;

each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

77. The peptide of embodiment 76, wherein the sum of all a, b, c, and d is 5 to 70.

78. The peptide of embodiment 77, wherein the sum of all a, b, c, and d is 10 to 20.

79. The peptide of any one of embodiments 76-78, wherein a is 1-20.

80. The peptide of any one of embodiments 76-79, wherein b is 2-6.

81. The peptide of any one of embodiments 76-80, wherein c is 1-20.

82. The peptide of any one of embodiments 76-81, wherein d is 1-20.

83. The peptide of any one of embodiments 76-82, wherein the peptide is a peptide of any one of embodiments 1-74.

84. A stapled peptide comprising a staple having the structure of $L^s$, wherein:
$L^s$ is -$L^{s1}$-$L^{s2}$-$L^{s3}$-;
each of $L^{s1}$, $L^{s2}$, and $L^{s3}$ is independently L;
each L is independently a covalent bond, or an optionally substituted, bivalent $C_1$-$C_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;

each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;

each R' is independently —R, —C(O)R, —CO$_2$R, or —SO$_2$R;

each R is independently —H, or an optionally substituted group selected from C$_{1-30}$ aliphatic, C$_{1-30}$ heteroaliphatic having 1-10 heteroatoms independently selected from oxygen, nitrogen, sulfur, phosphorus and silicon, C$_{6-30}$ aryl, C$_{6-30}$ arylaliphatic, C$_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon.

85. The peptide of embodiment 84, wherein:
one end of L$^s$ is connected to an atom A$^{n1}$ of the peptide backbone, wherein A$^{n1}$ is bonded to R$^1$;
one end of L$^s$ is connected to an atom A$^{n2}$ of the peptide backbone, wherein A$^{n2}$ is bonded to R$^2$;
each of R$^1$ and R$^2$ is independently R';
there are m amino acid residues between the amino acid residue comprising A$^{n1}$ and the amino acid residue comprising A$^{n2}$, not including the amino acid residue comprising A$^{n1}$ and the amino acid residue comprising A$^{n2}$; and
m is an integer of 1-12.

86. The peptide of embodiment 85, wherein each of A$^{n1}$ and A$^{n2}$ is independently a carbon atom.

87. The peptide of embodiment 85, wherein each of A$^{n1}$ and A$^{n2}$ is independently an alpha carbon atom.

88. The peptide of any one of embodiments 85-87, wherein m is 1.

89. The peptide of any one of embodiments 85-87, wherein m is 2.

90. The peptide of any one of embodiments 85-87, wherein m is 3.

91. The peptide of any one of embodiments 85-87, wherein m is 4.

92. The peptide of any one of embodiments 85-87, wherein m is 5.

93. The peptide of any one of embodiments 85-87, wherein m is 6.

94. The peptide of any one of embodiments 85-87, wherein m is 7.

95. The peptide of any one of embodiments 76-94, wherein C$^1$ or A$^{n1}$ has an R configuration.

96. The peptide of any one of embodiments 76-94, wherein C$^1$ or A$^{n1}$ has an S configuration.

97. The peptide of any one of embodiments 76-94, wherein C$^1$ or A$^{n1}$ is achiral.

98. The peptide of any one of embodiments 76-97, wherein C$^2$ or A$^{n2}$ has an R configuration.

99. The peptide of any one of embodiments 76-97, wherein C$^2$ or A$^{n2}$ has an S configuration.

100. The peptide of any one of embodiments 76-97, wherein C$^2$ or A$^{n2}$ is achiral.

101. The peptide of any one of embodiments 76-97, wherein C$^2$ or A$^{n2}$ is achiral.

102. The peptide of any one of the preceding embodiments, wherein a staple is L$^s$, wherein L$^s$ is an optionally substituted, bivalent C$_{8-14}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—.

103. The peptide of any one of the preceding embodiments, wherein a staple is L$^s$, wherein L$^s$ is an optionally substituted, bivalent C$_{9-13}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—.

104. The peptide of any one of the preceding embodiments, wherein a staple is L$^s$, wherein L$^s$ is an optionally substituted, bivalent C$_{10-15}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—.

105. The peptide of any one of the preceding embodiments, wherein a staple is L$^s$, wherein L$^s$ is an optionally substituted, bivalent C$_{11-14}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—.

106. The peptide of any one of embodiments 102-105, wherein the staple is a (i, i+4) staple.

107. The peptide of any one of embodiments 102-105, wherein the staple is a (i, i+7) staple.

108. The peptide of any one of the preceding embodiments, wherein for each of L$^s$, L$^{s1}$, L$^{s2}$, and L$^{s3}$, any replacement of methylene units, if any, is replaced with —N(R')— or —N(R')—C(O)—.

109. The peptide of any one of the preceding embodiments, wherein a staple is a hydrocarbon staple.

110. The peptide of embodiment 109, wherein the hydrocarbon staple is L$^s$, wherein LV is C$_{5-20}$ bivalent aliphatic.

111. The peptide of any one of embodiments 1-108, wherein a staple comprises a —N(R')-moiety.

112. The peptide of any one of embodiments 1-108, wherein a staple comprises a —N(R')-moiety, wherein the —N(R')— moiety is not bonded to a carbon atom that also forms a double bond with a heteroatom.

113. The peptide of any one of embodiments 1-108, wherein a staple comprises a —N(R')-moiety, wherein the —N(R')— moiety is not bonded to —C(O)—.
114. The peptide of any one of embodiments 1-108, wherein a staple comprises a —N(R')—C(O)— moiety.
115. The peptide of any one of embodiments 75-108, wherein at least one methylene unit is replaced with —(NR')—.
116. The peptide of any one of embodiments 75-108, wherein at least one methylene unit is replaced with —(NR')—, wherein the —N(R')— moiety is not bonded to —C(O)—.
117. The peptide of any one of embodiments 75-108, wherein at least one methylene unit is replaced with —(NR')—C(O)—.
118. The peptide of any one of embodiments 111-117, wherein R' of the —N(R')— is R.
119. The peptide of any one of embodiments 111-117, wherein R' of the —N(R')— is optionally substituted $C_{1-6}$ alkyl.
120. The peptide of any one of embodiments 111-117, wherein R' of the —N(R')— is methyl.
121. The peptide of any one of embodiments 75-120, wherein $L^{s1}$ comprises at least one methylene units replaced with —N(R')—.
122. The peptide of any one of embodiments 75-120, wherein $L^{s1}$ comprises at least one methylene units replaced with —N(R')—, wherein none of the neighboring methylene unit is replaced with —C(O)—.
123. The peptide of any one of embodiments 75-120, wherein $L^{s1}$ comprises at least one —N(R')C(O)O—.
124. The peptide of any one of embodiments 75-120, wherein $L^{s1}$ is -L'-N(R')—.
125. The peptide of any one of embodiments 75-120, wherein $L^{s1}$ is -L'-N(R')C(O)O—.
126. The peptide of any one of embodiments 124-125, wherein L' is $C_{1-6}$ alkylene.
127. The peptide of any one of embodiments 124-126, wherein L' is bonded to a peptide backbone atom.
128. The peptide of any one of embodiments 75-120, wherein $L^{s1}$ is optionally substituted $C_{1-10}$ bivalent aliphatic.
129. The peptide of any one of embodiments 75-120, wherein $L^{s1}$ is optionally substituted $C_{1-10}$ bivalent alkylene.
130. The peptide of any one of embodiments 75-126, wherein $L^{s2}$ is optionally substituted bivalent $C_1$-$C_6$ aliphatic.
131. The peptide of any one of embodiments 75-126, wherein $L^{s2}$ is —CH$_2$—CH=CH—CH$_2$—.
132. The peptide of any one of embodiments 75-126, wherein $L^{s2}$ is -(E)-CH$_2$—CH=CH—CH$_2$—.
133. The peptide of any one of embodiments 75-126, wherein $L^{s2}$ is —(Z)—CH$_2$—CH=CH—CH$_2$—.
134. The peptide of any one of embodiments 75-126, wherein $L^{s2}$ is —(CH$_2$)$_4$—.
135. The peptide of any one of embodiments 75-134, wherein $L^{s3}$ comprises at least one methylene units replaced with —N(R')—.
136. The peptide of any one of embodiments 75-134, wherein $L^{s3}$ comprises at least one methylene units replaced with —N(R')—, wherein none of the neighboring methylene unit is replaced with —C(O)—.
137. The peptide of any one of embodiments 75-134, wherein $L^{s3}$ comprises at least one —N(R')C(O)O—.
138. The peptide of any one of embodiments 75-134, wherein $L^{s3}$, is -L'-N(R')—.
139. The peptide of any one of embodiments 75-134, wherein $L^{s3}$ is -L'-N(R')C(O)O—.
140. The peptide of any one of embodiments 138-139, wherein L' is $C_{1-6}$ alkylene.
141. The peptide of any one of embodiments 138-140, wherein L' is bonded to a peptide backbone atom.
142. The peptide of any one of embodiments 75-134, wherein $L^{s3}$ is optionally substituted $C_{1-10}$ bivalent aliphatic.
143. The peptide of any one of embodiments 75-134, wherein $L^3$ is optionally substituted $C_{1-10}$ bivalent alkylene.
144. The peptide of any one of embodiments 75-134, wherein $L^{s3}$ is optionally substituted $C_{1-10}$ bivalent alkylene.
145. The peptide of any one of embodiments 75-134, wherein $L^s$ is a staple of Table S-1.
146. The peptide of any one of embodiments 75-134, wherein $L^s$ is a staple of Table S-2.
147. The peptide of any one of embodiments 75-134, wherein $L^s$ is a staple of Table S-3.
148. The peptide of any one of embodiments 75-134, wherein $L^s$ is a staple of Table S-4.
149. The peptide of any one of the preceding embodiments, wherein a staple has 5-20 staple chain atoms, wherein the chain of the staple is the shortest covalent connection in the staple from a first end of a staple to a second end of the staple, wherein the first end and the second end connect to different peptide backbone atoms.
150. The peptide of embodiment 149, wherein a staple has 8 staple chain atoms.
151. The peptide of embodiment 149, wherein a staple has 9 staple chain atoms.
152. The peptide of embodiment 149, wherein a staple has 10 staple chain atoms.
153. The peptide of embodiment 149, wherein a staple has 11 staple chain atoms.
154. The peptide of embodiment 149, wherein a staple has 12 staple chain atoms.
155. The peptide of embodiment 149, wherein a staple has 13 staple chain atoms.
156. The peptide of embodiment 149, wherein a staple has 14 staple chain atoms.
157. The peptide of embodiment 149, wherein a staple has 15 staple chain atoms.
158. The peptide of embodiment 149, wherein a staple has 16 staple chain atoms.
159. The peptide of any one of embodiments 1-74, wherein the peptide is a peptide of any one of embodiments 75-158.
160. The peptide of any one of the preceding embodiments, wherein the peptide has a sequence that is at least 50%, 60%, 70%, 80%, 90%, or 95% homology with a peptide of Table 1.
161. The peptide of any one of the preceding embodiments, wherein the peptide is a peptide of Table 1.
162. The peptide of any one of the preceding embodiments, wherein the peptide can form a helix structure.
163. The peptide of any one of the preceding embodiments, wherein the peptide has a solubility of at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, or 250 uM in DPBS (per liter, 8 g sodium chloride, 0.2 g potassium phosphate, monobasic, 1.15 g sodium phosphate, dibasic, and 0.2 g potassium chloride).
164. The peptide of embodiment 163, wherein the solubility is at least 1 uM.
165. The peptide of embodiment 163, wherein the solubility is at least 5 uM.
166. The peptide of embodiment 163, wherein the solubility is at least 10 uM.
167. The peptide of embodiment 163, wherein the solubility is at least 50 uM.

168. The peptide of embodiment 163, wherein the solubility is at least 100 uM.
169. The peptide of embodiment 163, wherein the solubility is at least 200 uM.
170. The peptide of any one of the preceding embodiments, wherein the peptide binds to beta-catenin.
171. The peptide of any one of the preceding embodiments, wherein the peptide has a Kd of no greater than 1, 2, 3, 4, 5, or 10 uM for beta-catenin.
172. The peptide of any one of the preceding embodiments, wherein the peptide has a Kd of no greater than 1 uM for beta-catenin.
173. The peptide of any one of embodiments 171-172, wherein the Kd is measured by fluorescence polarization, surface plasmon resonance, or TR-FRET.
174. The peptide of any one of the preceding embodiments, wherein the peptide has less than 10%, 15%, 20%, 25%, 30%, 40%, 50% non-specific cytotoxicity at a concentration of no less than 1, 2, 3, 4, 5, 6, 7, 8, 9, or 10 uM as measured by a LDH release assay compared to an appreciate positive reference.
175. The peptide of any one of the preceding embodiments, wherein the peptide comprises a staple comprising a —N(R')— or —N(R')—C(O)— moiety, and has lower non-specific cytotoxicity compared to a peptide comprising a hydrocarbon staple but is otherwise of the identical structure when assayed under a comparable condition.
176. The peptide of any one of the preceding embodiments, wherein the peptide binds to beta-catenin selectively at sites that interact with Axin over sites that interacts with BCL9.
177. The peptide of any one of the preceding embodiments, wherein the peptide binds to beta-catenin selectively at sites that interact with Axin over sites that interacts with BCL9 as measured in an appropriate competition fluorescence polarization assay.
178. The peptide of any one of the preceding embodiments, wherein the peptide is conjugated with a second entity.
179. The peptide of embodiment 178, wherein the second entity is a label.
180. The peptide of embodiment 178, wherein the second entity a label selected from biotin and a fluorescence label.
181. The peptide of embodiment 178, wherein the second entity is a targeting moiety.
182. The peptide of embodiment 178 or 181, wherein the second entity is a carbohydrate moiety.
183. The peptide of embodiment 182, wherein the second entity is or comprises a GalNac moiety.
184. The peptide of embodiment 178, wherein the second entity is a lipid moiety.
185. The peptide of any one of the preceding embodiments, wherein each amino acid residue is independently a residue of an amino acid of formula A-I, A-II or A-III.
186. A pharmaceutical composition comprising a peptide of any one of the preceding embodiments and pharmaceutically acceptable carrier.
187. A method for modulating a function of beta-catenin, comprising contacting a system comprising beta-catenin with a peptide of any one of the preceding embodiments.
188. A method for modulating a function of Wnt signaling pathway, comprising contacting a system comprising the pathway with a peptide of any one of the preceding embodiments.
189. A method for modulating interaction of beta-catenin with Axin, comprising contacting a system comprising beta-catenin with a peptide of any one of the preceding embodiments.
190. A method for modulating expression of a nucleic acid sequence in a system, comprising contacting a system comprising beta-catenin a peptide of any one of the preceding embodiments; wherein expression of the nucleic acid sequence is associated with beta-catenin.
191. A method for modulating level of a product encoded by a nucleic acid sequence in a system, comprising contacting a system comprising beta-catenin a peptide of any one of the preceding embodiments; wherein level of a product encoded by a nucleic acid sequence is associated with beta-catenin.
192. The peptide of embodiment 191, wherein the product is a protein.
193. The peptide of embodiment 191, wherein the product is mRNA.
194. A method for preventing or treating a beta-catenin-associated condition, disorder, or disease, comprising administering to a subject susceptible thereto or suffering therefrom a peptide or a composition of any one of the preceding embodiments.
195. The method of embodiment 194, wherein the condition, disorder, or disease is cancer.
196. The method of embodiment 195, wherein the cancer is colorectal cancer.
197. The method of embodiment 195, wherein the cancer is hepatocellular cancer.
198. The method of embodiment 195, wherein the cancer is prostate cancer.
199. The method of embodiment 195, wherein the cancer is melanoma.
200. The method of any one of embodiments 194-199, wherein the peptide or composition is administered prior to, concurrently with, or subsequent to an additional agent.
201. The method of embodiment 200, wherein the additional agent is an anti-cancer drug.
202. The method of embodiment 200, wherein the additional agent is a chemotherapy agent.
203. The method of embodiment 200, wherein the additional agent is an immuno oncology drug.
204. The method of embodiment 200, wherein the additional agent is a checkpoint inhibitor.
205. The method of embodiment 200, wherein the additional agent is an anti-PD1 antibody, an anti-PD-L1 antibody, or an anti-CTLA4 antibody.
206. The method of embodiment 194, wherein the condition, disorder, or disease is a heart condition, disorder, or disease.

EXEMPLIFICATION

Non-limiting examples of provided technologies are described below. Those having ordinary skill in the art appreciates that various technologies can be utilized to prepare and access compounds, compositions and methods in accordance with the present disclosure.

Example 1. Exemplary Preparation of Provided Agents

Provided agents, e.g., stapled peptides, can be prepared using various technologies in accordance with the present disclosure, for example, methods as described herein. As appreciated by those skilled in the art, parameters of provided methods, e.g., steps, reagents, solvents, concentrations, temperatures, time, etc., may be optimized as desired.

In some embodiments, peptides can be prepared on a peptide synthesizer. For example, in some embodiments, provided peptides were typically synthesized on an Intavis Multipep RSi peptide synthesizer using Fmoc solid phase peptide chemistry on CEM ProTide Rink Amide resin (loading 0.55-0.8 mmol/g). In some embodiments, resin for synthesis is swelled in a suitable solvent, e.g., NMP, at a suitable temperature for a period of time (e.g., at 45 degrees for 20 minutes in a 5 mL or 2 mL plastic fritted reaction vessel). Amino acid residues are then added using peptide synthesis procedures (typically at 45 degrees; conditions can be adjusted as necessary). In some embodiments, provided stapled peptides, e.g., those described in Table 1, were prepared as described below.

Peptides were typically synthesized on an Intavis Multipep RSi peptide synthesizer using Fmoc solid phase peptide chemistry on CEM ProTide Rink Amide resin (loading 0.55-0.8 mmol/g). Resin for synthesis was swelled in NMP at 45 degrees for 20 minutes in a 5 mL or 2 mL plastic fritted reaction vessel. Amino acid residues were added using the following procedure (all steps at 45 degrees).

a) The Fmoc group was removed using one five-minute treatment and one ten-minute treatment with 20% Piperidine (v/v), 0.1 M HOBT in NMP.
b) The resin was washed eight times with NMP.
c) 5 equivalents of 0.5 M amino acid solution, 5 equivalents of 2 M DIC, and 5 equivalents of 0.5 M Oxyma were added to a preactivation vessel for one minute.
d) Reaction mixture was added to the reaction vessel and coupled for 30 minutes, vortexing intermittently.
e) Reaction vessel was washed once with NMP.
f) Steps c), d), and e) were repeated. In some embodiments, in the case of difficult positions, steps c), d), and e) were repeated twice.
g) Any unreacted amines were capped with 5% (v/v) acetic anhydride in NMP for two minutes.
h) The reaction vessels were washed, e.g., eight times with NMP.

Following the final residue, the Fmoc group was removed using the procedure from steps a) above and the peptides were typically capped (in some cases, were not capped so that the 5'-amino group can react with other entities as exemplified in the present disclosure), e.g., with 5% (v/v) acetic anhydride in NMP for 15 minutes at 45 degrees for Ac capping. The resin was washed 5 times with DCM.

Staples can be formed using various technologies in accordance with the present disclosure. In some embodiments, staples are formed by olefin metathesis. In some embodiments, two amino acid side chains each independently comprising an olefin (in some embodiments, terminal olefin) are reacted with each other under suitable olefin metathesis conditions so that olefin metathesis happens between the two side chains and a staple is formed. Many olefin metathesis conditions (e.g., catalyst, solvent, temperature, etc.) are known in the art and can be utilized in accordance with the present disclosure.

For example, in an exemplary procedure that was used to prepare provided staples, e.g., those in Table 1, resin with peptides, e.g., as prepared above, was swelled at 40 degrees in DCE for 20 minutes on the Intavis Multipep RSi. The peptides were treated with 30 mol % of a freshly prepared 5 mM solution of Bis(tricyclohexylphosphine)benzylidene ruthenium (IV) dichloride (Grubb's I) in DCE for one hour, with vortexing continuously. The treatment was repeated depending on e.g., conversion, purity, etc. The resin was then washed 5 times with DCM. The peptides were cleaved from the resin and de-protected using 95% trifluoroacetic acid, 2.5% triisopropylsilane, and 2.5% water for two and a half hours vortexing at room temperature. After TFA was evaporated under an inert atmosphere, e.g., nitrogen gas, the peptides were precipitated in a suitable solvent, e.g., tertbutyl methyl ether.

In some embodiments, Hoveyda-Grubbs catalyst may be used and may provide better yields, purity and/or selectivity.

Peptides can be further processed as desired. For example, in some embodiments, provided stapled peptides comprising an olefin in a staple can be subjected to a reduction (e.g., hydrogenation) condition, so that an olefin moiety in a staple is hydrogenated and converted into an alkane moiety. Described below is an exemplary procedure.

In an exemplary procedure for making FP0650rc, 100 umol FP0650c on peptide synthesis resin was swelled in N-methyl-2-pyrrolidone (NMP) in a Biotage Alstra microwave peptide synthesizer for 5 min at a temperature of, e.g., 50° C. The solvent was removed and 1.45 mL of 1.4 M piperidine (20 equivalents) in NMP was combined with 298 mg of 2,4,6-triisopropylbenzenesulfonyl hydrazide (20 equivalents) dissolved in 1.45 mL of NMP and subsequently added to the resin. The reaction was allowed to proceed at 50° C. for 2 hours and the resin was then washed 2× with NMP and 2× with 1,2-dichloroethane (DCE). If desired, the resin was then treated with freshly prepared reaction solution according to the above steps (in some cases, two or more additional times) until the reaction was complete (as monitored by LC/MS after analytical cleavage of a few beads of resin). After the reaction was complete, FP0650rc was cleaved from the resin and purified.

In some embodiments, provided stapled peptides comprises one or more amino staples which comprises an amino moiety (e.g., —N(R')—, wherein R' is as described in the present disclosure, and the —N(R')— is not bonded to —C(O)— groups). In some embodiments, a staple comprising an amino moiety is prepared from extraction of $CO_2$ from an appropriate staple comprising a corresponding carbamate moiety (e.g., converting —N(R')—C(O)—O— to —N(R')—). An exemplary procedure for preparing peptides comprising an amino staple (e.g., those in Table 1) through, e.g., $CO_2$ extrusion, is described below.

Stapled peptides comprising carbamate staples were treated with 80 mol % of freshly prepared 10 mM solution of tetrakis(triphenylphosphine) palladium (0) in DCM for 90 minutes, vortexing continuously. The resin was washed 5 times in DCM and further modifications and/or cleavage and purification were performed using standard procedures.

As described in the present disclosure, in some embodiments, provided peptides may be further modified, e.g., conjugated with a second entity. In some embodiments, a modification, e.g., conjugate, is at or through a N-terminus. An exemplary procedure for preparing N-terminal for further modification (e.g., conjugation) is described below.

Prior to final Fmoc deprotection and capping with acetic anhydride, the Fmoc protected peptides were stapled via standard protocol, e.g., a protocol described above. Following metathesis, the resin was washed with NMP several times. The resin was swelled in NMP for 20 minutes, and treated four times with 20% piperidine and 0.1 M HOBT in NMP for five minutes each at room temperature. The resin was then washed five times with NMP.

In some embodiments, a peptide is conjugated with biotin. An exemplary procedure for preparing biotinylated peptides, e.g., those in Table 1, is described below.

To prepare biotinylated peptides, a free N-terminus was coupled to biotin with 3 equivalents of biotin (0.5 M in NMP), 3 equivalents of COMU (0.5 M in NMP), and 6 equivalents of DIEA (2 M in NMP) for 1 hour at room temperature (standard coupling conditions on the synthesizer produced similar results). Cleavage and purification was then performed using the standard procedures.

In some embodiments, a peptide is conjugated to a label, e.g., a fluorescent label. An exemplary procedure for preparing such peptides, e.g., those in Table 1, is described below.

To prepare fluorescein-conjugated peptides, a free N-terminus was coupled to FITC using five equivalents of FITC (75 mM final concentration) and 10 equivalents of DIEA (neat) dissolved in NMP for 10 hours, vortexing continuously. Cleavage and purification was then performed using the standard procedures.

In some embodiments, a peptide is conjugated to an entity comprising PEG. An exemplary procedure for preparing such peptides, e.g., those in Table 1, is described below.

To prepare peptides comprising a PEG moiety, e.g., PEG containing a free amine handle, N-terminal Fmoc protected PEG was coupled to the stapled peptide on resin using standard coupling conditions and then the N-terminal Fmoc was removed using standard conditions. Cleavage and purification was then performed using standard procedures.

In some embodiments, provided compounds are purified so that a higher purity is achieved. Various purification technologies can be utilized in accordance with the present disclosure. In some embodiments, purification comprises one or more steps using HPLC or UPLC. In some embodiments, provided compounds, e.g., stapled peptides, where dissolved in a small volume of a solvent, e.g., DMSO, and were purified by reverse phase HPLC using a suitable column (e.g., a Rx-C8 column (Agilent)) with suitable mobile phase conditions. Provided compounds and compositions can be characterized using a number of technologies in accordance with the present disclosure. In some embodiments, provided compounds were characterized by mass spectrometry under suitable conditions (e.g., electrospray in positive ion mode). For example, in some embodiments, provided stapled peptides were dissolved in small volume of DMSO and were purified by reverse phase HPLC using a Rx-C8 column (Agilent) and a gradient of Acetonitrile with 0.1% TFA and Water with 0.1% TFA. HPLC fractions were characterized by LC-MS using electrospray (e.g., in positive ion mode), pooled, and lyophilized to provide products having the correct characterization data (e.g., MS). Exemplary provided stapled peptides were presented below, e.g., Table 3.

Example 2. Provided Agents Bind to Beta-Catenin

Among other things, provided agents, e.g., stapled peptides, interact with beta-catenin and modulate its functions as demonstrated in the present disclosure. Various technologies are known in the art and can be utilized to assess interactions in accordance with the present disclosure.

In some embodiments, a direct fluorescence polarization assay is used to assess binding of provided compounds to beta-catenin. In an exemplary procedure, beta-catenin solutions are prepared in a buffer using serial dilution, for example, in some cases, beta-catenin solutions were prepared in a buffer (50 mM Tris pH 8.0, 250 mM NaCl, 2% glycerol, 0.5 mM EDTA, 0.02% w/v sodium azide) using a 3-fold serial dilution from 5 µM. Probe solution (20 nM 5FAM or FITC labeled peptide in buffer) was prepared and 40 µL per well plated in a black polystyrene 384-well plate (Corning). Equal volume of the serial diluted beta-catenin was added to the plate and incubated protected from light for 15 minutes prior to read. Reads were performed on a Spectramax M5 (Molecular Devices) in duplicate.

In some embodiments, a competition fluorescence polarization assay is used to assess binding of provided compounds to beta-catenin. In an exemplary procedure, solutions of provided compounds, e.g., provided stapled peptides, were prepared in a buffer (e.g., 50 mM Tris pH 8.0, 250 mM NaCl, 2% glycerol, 0.5 mM EDTA, 0.02% w/v sodium azide) using a 3-fold serial dilution from 5 µM. Probe solution (15 nM full-length ß-Catenin, 20 nM FITC labeled peptide in buffer) was prepared and incubated for a period of time, e.g., 5 minutes, and the a volume, e.g., 40 µL per well plated in suitable plate, e.g., a black polystyrene 384-well plate (Corning). Equal volume of the serial diluted peptide was added to the plate and incubated protected from light for 15 minutes prior to read. Reads were performed on a Spectramax M5 (Molecular Devices) in duplicate. Suitable probe was FITC-PEG1-PQ-S5-ILD-S5-HVRRVWR (SEQ ID NO: 1) (hydrocarbon staple formed by two S5 via olefin metathesis) and/or FITC-bA-PQ-S5-ILD-S5-HVRRVWR (SEQ ID NO: 3) (hydrocarbon staple formed by two S5 via olefin metathesis). In a competition fluorescence polarization assay, FP0025c displaced a labeled probe from the axin site of 0-catenin with an EC50<100 nM. Another peptide, FP0217c (Ac-AR$_8$ILDAHIM$_5$RVW (SEQ ID NO: 280), with N-terminal proline removed and valine replaced with isoleucine compared to FP0025c) was prepared. FP0217c Isomer 2 displayed>10-fold better potency than FP0217c Isomer 1 in the competition FP assay; the reduced peptide (FP0217rc) was equivalent to Isomer 2.

Additionally or alternatively, binding to beta-catenin may be measured by Surface Plasmon Resonance. In an exemplary assay, approximately 6 nmol dried peptide diluted in buffer (50 mM Tris pH 8.0, 300 mM NaCl, 2% glycerol, 0.5 mM TCEP, 0.5 mM EDTA, 0.005% Tween-20, 1 mg/mL CM Dextran, 0.02% w/v sodium azide) was assayed on a Biacore X100 using the Biacore Biotin CAPture Kit (GE Healthcare) and biotinylated beta-catenin. Results were analyzed using the Biacore X100 Evaluation Software. As measured, FP0025c displayed a Kd of 15 nM. FP0217c (Isomer 2) bound to the armadillo domain of β-catenin with a Kd of 2 nM. FP0597c showed a Kd of 7 nm. Additional exemplary data were presented in FIG. 1 and Table 2.

Example 3. Provided Agents are Active in Cells

As appreciated by a person having ordinary skill in the art, various technologies can be utilized to assess activities of provided agents, e.g., stapled peptides, in accordance with the present disclosure, e.g., those described in the present disclosure, in WO 2017/062518, etc.

Figure 2:
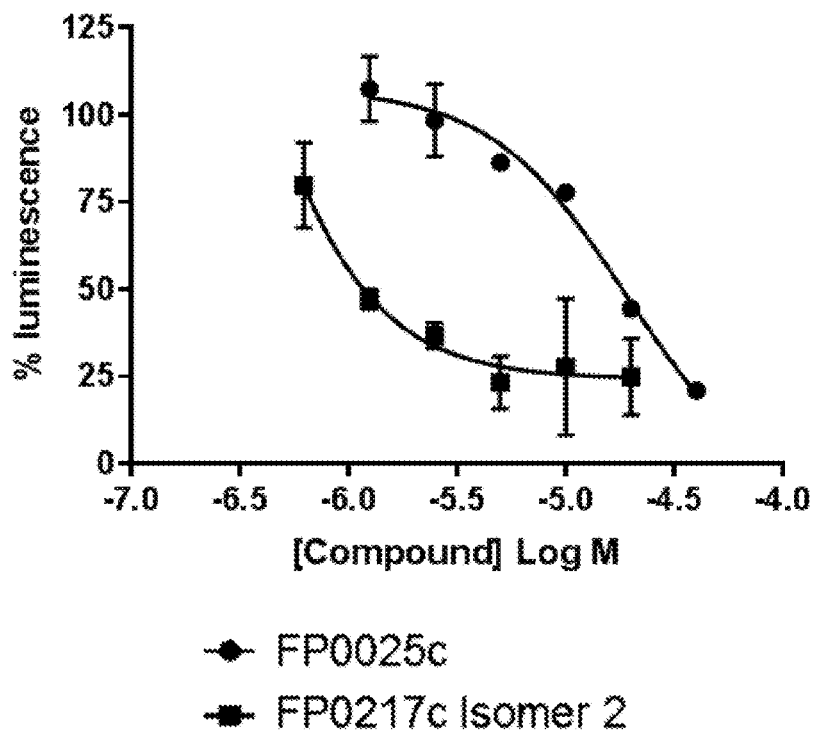
FIG. 2. Provided agents are active in cells.

In some embodiments, a provided assay is a TCF/LEF reporter assay. In some embodiments, in an exemplary such assay, TCF/LEF Luciferase reporter HEK293 cell lines (BPS Bioscience) were treated with dilution series of provided peptides for 18 hours. 300 ng/mL of Wnt3a (Peprotech) was added to the cells for the final 6 hours of incubation. Luciferase activity was measured using Bright-Glo Luciferase Assay (Promega) according to manufacturer's protocol. Exemplary data were presented in FIG. 2 and Table 2. FP0217c exhibited an IC$_{50}$ of 0.743 uM. As demonstrated, provided stapled peptides comprising various e.g., sequences, lengths, modifications, amino acid residues, staples, etc., were active. Applicant notes that for the TCF/LEF reporter assay, subsequent efforts to reproduce results observed for certain peptides described herein did not yield the same results, and in some tests, did not show activities under the specific conditions of those tests (e.g., amounts and/or batches of reagents). Additional assays are being performed to assess the reproducibility of observed properties and/or activities of such peptides. Applicant also notes that teachings of the present disclosure are not restricted to a particular mechanism of action of described agents. For example, in some embodiments, one or more agents may have relevant biological effects that are not specific to any interaction with (or lack of interaction with) beta-catenin or any particular site thereon.

Example 4. Provided Agents Modulate Gene Expression

As appreciated by those skilled in the art, beta-catenin regulates expression of many genes. Many conditions, disorders, and/or diseases are associated with aberrant gene expression, including those connected to one or more beta-catenin functions (e.g., regulated by beta-catenin). In some embodiments, as demonstrated by exemplary data herein, provided technologies can modulate expression of a variety of genes, including inhibition of beta-catenin target genes in various cell lines including a number of types of cancer cells.

Figure 3:
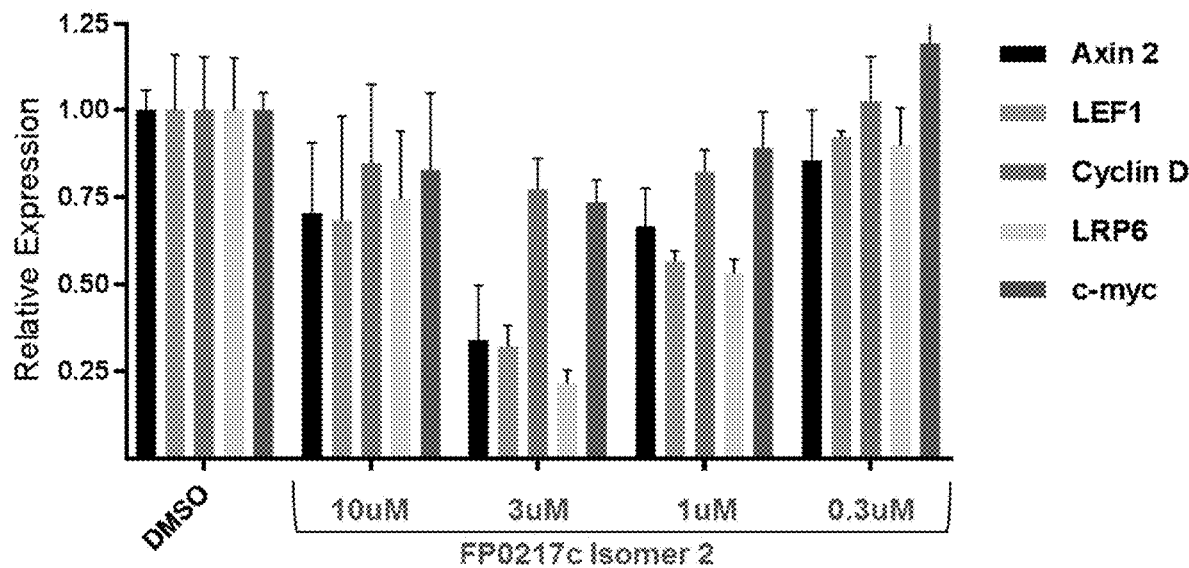
FIG. 3. Provided agents modulate gene expression in cells.
Figure 4:
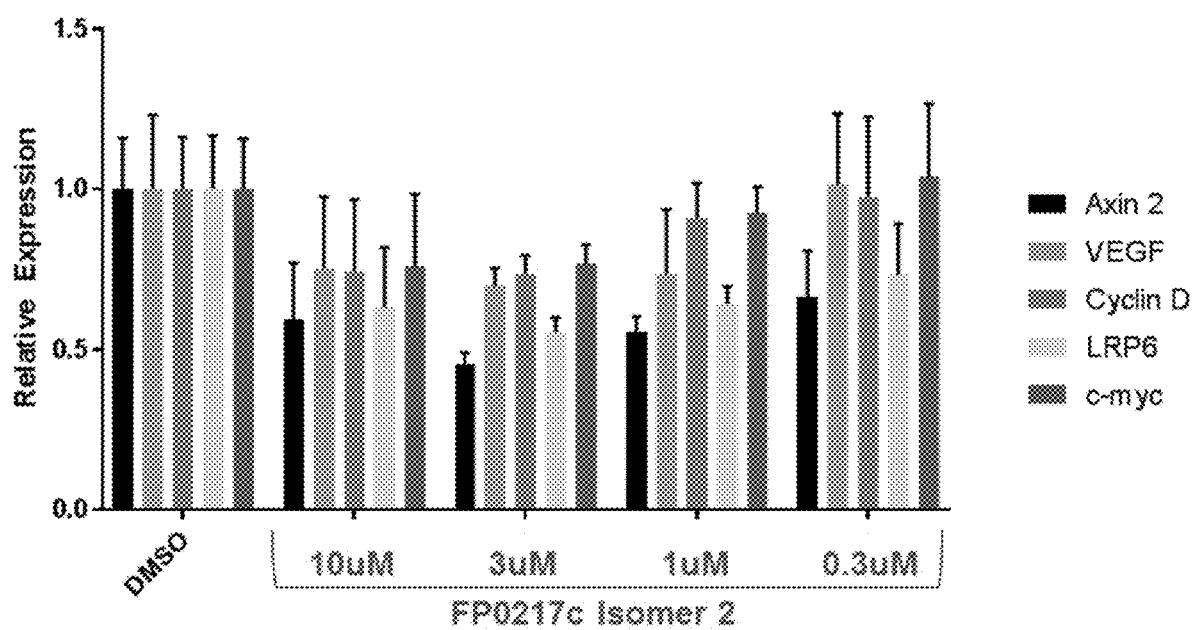
FIG. 4. Provided agents modulate gene expression in cells.
Figure 5:
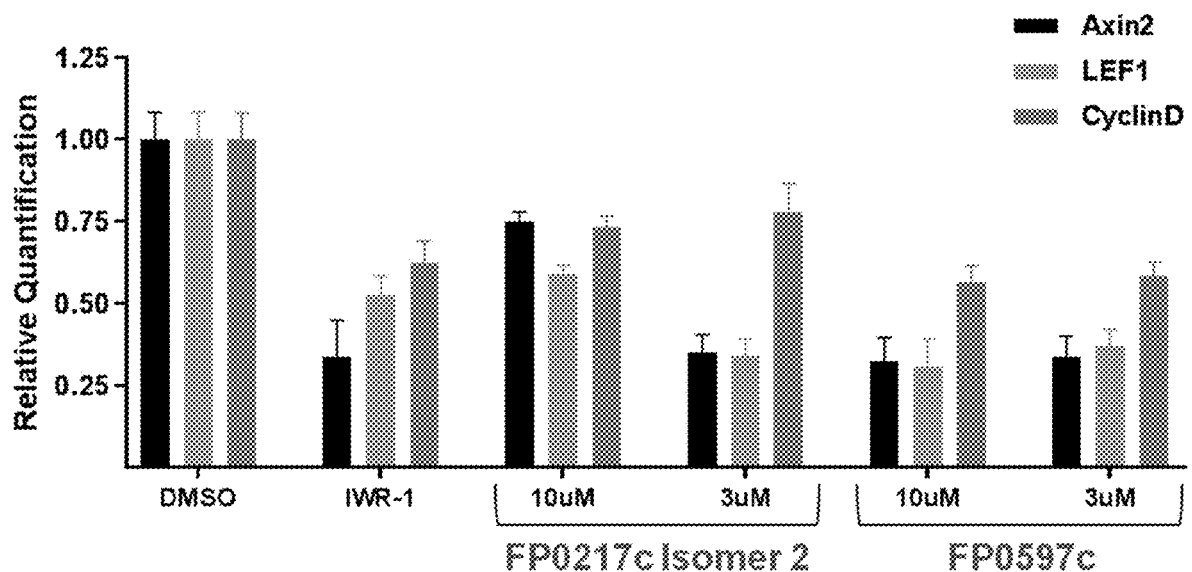
FIG. 5. Provided agents can selectively modulate gene expression. DLD-1 cells were treated with either 3 uM or 10 uM of each compound for 18 hours. Total RNA was extracted using the RNeasy Plus kit (Qiagen) according to manufacturer's protocols, and reverse transcribed to cDNA using SuperScript Vilo IV master mix (ThermoFisher Scientific). Gene expression levels were determined by qPCR using Taqman probes (Applied Biosciences) and Taqman Advanced Fast Master Mix (Applied Biosciences) on a QuantStudio 3 (Applied Biosciences). Relative expression was quantified using delta Ct method. For each group, from left to right: Axin2, LEF1 and Cyclin D.

Many technologies are known in the art, for example, qPCR, can be used to assess levels and/or variations of gene expression and can be utilized in accordance with the present disclosure. In an exemplary qPCR assay, cells, e.g., HCT-116, DLD-1, were treated with a dilution series of provided peptides for a period of time, e.g., 18 hours. Total RNA was extracted using, e.g., commercially available kit such as RNeasy Plus kit (Qiagen) according to manufacturer's protocols, and reverse transcribed to cDNA using, e.g., SuperScript Vilo IV master mix (ThermoFisher Scientific). Gene expression levels were determined by qPCR using, e.g., Taqman probes (Applied Biosciences) and Taqman Advanced Fast Master Mix (Applied Biosciences) on a QuantStudio 3 (Applied Biosciences). Relative expression was quantified using delta Ct method. Exemplary data were presented in FIGS. 3, 4 and 5. In some embodiments, the following reagents were used for qPCR in the examples. In some embodiments, a control for normalization is beta-actin. Methods for qPCR, including design of primers and probes, are widely known and can be utilized in accordance with the present disclosure.

| Gene | Assay ID | Dye Label | Scale | Cat #* |
|---|---|---|---|---|
| ACTB | Hs01060665_g1 | FAM-MGB | 250rxn | 4331182 |
| CTNNB1 | Hs00355045_m1 | FAM-MGB | 250rxn | 4331182 |
| BIRC5 | Hs04194392_s1 | FAM-MGB | 250rxn | 4331182 |
| CCND1 | Hs00765553_m1 | FAM-MGB | 250rxn | 4331182 |
| CD44 | Hs00153304_m1 | FAM-MGB | 250rxn | 4331182 |
| AXIN2 | Hs00610344_m1 | FAM-MGB | 250rxn | 4331182 |
| MYC | Hs00153408_m1 | FAM-MGB | 250rxn | 4331182 |
| LEF1 | Hs01547250_m1 | FAM-MGB | 250rxn | 4331182 |
| LRP6 | Hs00233945_m1 | FAM-MGB | 250rxn | 4331182 |
| VEGFA | Hs00900055_m1 | FAM-MGB | 250rxn | 4331182 |
| GAPDH | Hs02786624_g1 | TAM-MGB | 250rxn | 4331182 |
| Human GUSB Endogenous Control | | VIC/TAMRA | 2500rxn | 4310888E |
| Human B2M Endogenous Control | | VIC/TAMRA | 2500rxn | 4310886E |

*ThermoFisher Scientific.

Example 5. Provided Agents have Improved Properties

Among other things, provided agents, e.g., stapled peptides, have improved properties, including solubility, pharmacokinetic properties, etc.

Among other things, the present disclosure recognizes that one of the challenges associated with stapled peptides for use as therapeutics is solubility. In some embodiments, certain stapled peptides, e.g., those comprising hydrocarbon staples, have relatively low solubility. As appreciated by those skilled in the art, low solubility can negatively impact, e.g., formulation, delivery, efficacy, etc. In some embodiments, the present disclosure provides technologies to improve solubility of improved stapled peptides. In some embodiments, the present disclosure provides stapled peptides with solubility of at least 50, 60, 70, 80, 90, 100, 150, 160, 170, 180, 190, 200, 210, 220, 230, 240, 250, 260, 270, 280, 290, 300, 350, 400, 450, 500 uM in DPBS buffer (per liter, 8 g Sodium Chloride, 0.2 g Potassium Phosphate, monobasic, 1.15 g Sodium Phosphate, dibasic, and 0.2 g Potassium Chloride).

Suitable assays for assessing solubility are widely known in the art and can be utilized in accordance with the present disclosure. In some embodiments, in an exemplary protocol, dried peptide was reconstituted in DPBS (DPBS, 1×, cell culture grade, Sigma D8537) in triplicate, vortexed, sonicated and then centrifuged. Absorbance of the supernatant was measured at A280 (Nanodrop 2000) and the concentration was determined using the extinction coefficient for tryptophan. Exemplary solubility data are presented in, e.g., Table 2.

Example 6. Provided Agents have Improved Pharmacological Properties

Among other things, provided agents, e.g., stapled peptides, have improved properties, including solubility, pharmacokinetic properties, etc. In some embodiments, provided compounds demonstrate, among other things, improved half-life in animals.

Figure 6:
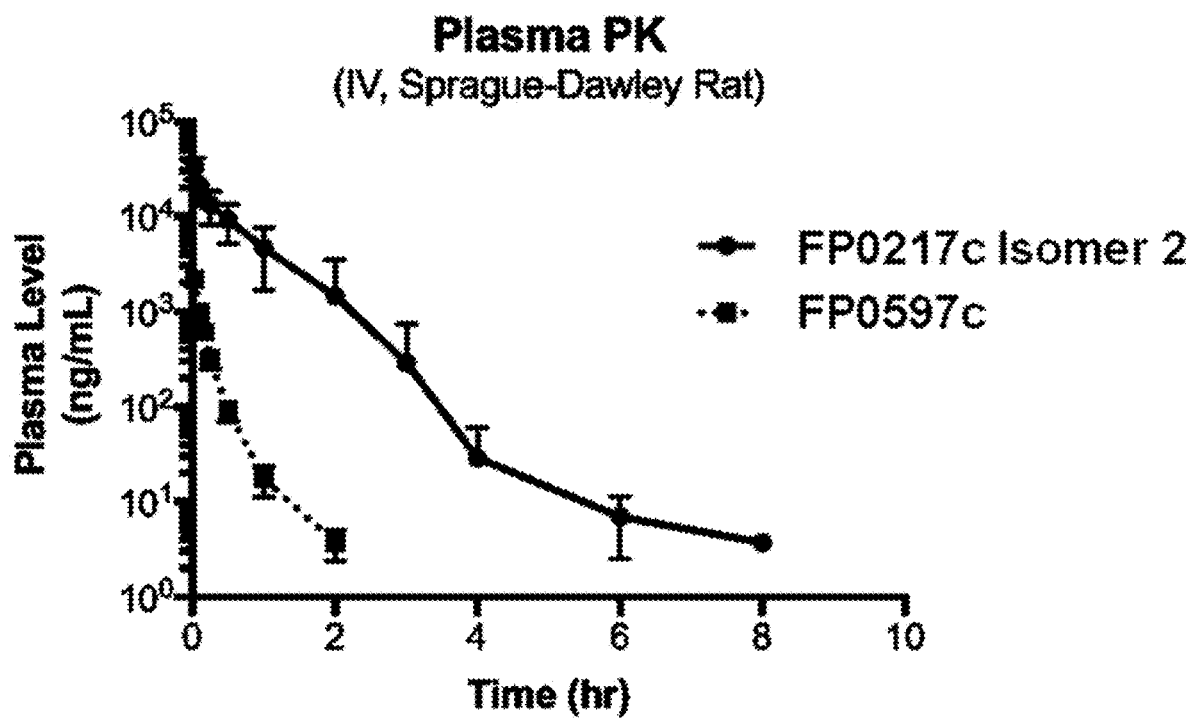
FIG. 6. Exemplary pharmacokinetic properties. Peptides were formulated in 10% DMSO:90% saline and dosed by IV at 0.5 mg/kg per compound in three male Sprague-Dawley rats. Serial bleed time-points were taken at 2 min, 6 min, 10 min, 15 min, 30 min, 1, 2, 4, 6, 8, 12 and 24 h and analyzed by quantitative LC/MS using a Thermo Q-Exactive Focus LC/MS/MS. Samples were prepared by protein precipitation with MeOH. Data were fit to a two-compartment model.

Various technologies can be utilized to assess properties of provided agents, e.g., stapled peptides, in accordance with the present disclosure. In some embodiments, plasma PK methods are used to assess pharmacokinetic properties. In an exemplary assay, peptides were formulated in 10% DMSO: 90% saline and dosed by IV at 0.5 mg/kg per compound in three male Sprague-Dawley rats. Serial bleed time-points were taken at 2 min, 6 min, 10 min, 15 min, 30 min, 1, 2, 4, 6, 8, 12 and 24 h and analyzed by quantitative LC/MS using a Thermo Q-Exactive Focus LC/MS/MS. Samples were prepared by protein precipitation with MeOH. Data were fit to a two-compartment model. In one assay, FP0217c (Isomer 2) showed a plasma half-life of >1 hour, and FP0597c displayed a shorter plasma half-life. Exemplary data are presented, e.g., in FIG. 6.

Example 7. Provided Agents can Selectively Modulate Beta-Catenin Interactions with Axin Over Other Entities In some embodiments, the present disclosure provides agents, e.g. stapled peptides, that selectively bind to one or more beta-catenin sites that interact with Axin. In some embodiments, provided agents, e.g., stapled peptides, selectively compete with interactions with one or more beta-catenin sites that interact with Axin. Particularly, in some embodiments, provided agents selectively modulate interactions with Axin at one or more beta-catenin sites that interact with Axin compared to those at one or more beta-catenin sites that interact with BCL9. In some embodiments, provided agents selectively disrupt beta-catenin interactions with proteins whose beta-catenin interacting sites are identical or overlap with one or more sites that interact with Axin over those whose beta-catenin interacting sites are identical or overlap with one or more sites that interact with BCL9. In some embodiments, provided agents selectively modulate beta-catenin interaction with Axin over beta-catenin interaction with BCL9. In some embodiments, provided agents selectively disrupts beta-catenin interaction with Axin over beta-catenin interaction with BCL9. In some embodiments, a provided agent, e.g., a stapled peptide, has EC50 for disrupting interactions between beta-catenin and BCL9 (or a probe, e.g., Ac-Leu-Ser-Gln-Glu-Gln-Leu-Glu-His-Arg-Glu-Arg-Ser-Leu-Gln-Thr-Leu-Arg-Asp-Ile-Gln-Arg-nLeu-Leu-2NapA-bala-bala-Lys5FAM-NH$_2$ (SEQ ID NO: 2) (from *Biochemistry*, 2009, 48 (40), pp 9534-9541)) that is at least 2, 3, 4, 5, 6, 7, 8, 9, 10, 11, 12, 13, 14, 15, 20, 25, 30, 40, 50, 60, 70, 80, 90, 100, 200, 300, 400, 500, 1000 or more fold of its EC50 for disrupting interactions between beta-catenin and Axin (or a probe, e.g., FITC-PEG1-PQ-S5-ILD-S5-HVRRVWR (SEQ ID NO: 1) (hydrocarbon staple formed by two S5 via olefin metathesis) and/or FITC-bA-PQ-S5-ILD-S5-HVRRVWR (SEQ ID NO: 3) (hydrocarbon staple formed by two S5 via olefin metathesis)) as measured by, e.g., a competition fluorescence polarization assay. In some embodiments, provided agents, e.g., stapled peptides, do not observably disrupt interactions between beta-catenin and BCL9. In such cases, EC50 may not be determinable, but as appreciated by those skilled in the art, can be treated as at least 2, 3, 4, 5, 6, 7, 8, 9, 10, 11, 12, 13, 14, 15, 20, 25, 30, 40, 50, 60, 70, 80, 90, 100, 200, 300, 400, 500, 1000 or more fold of a determinable EC50 from a detectable disruption.

Figure 7:
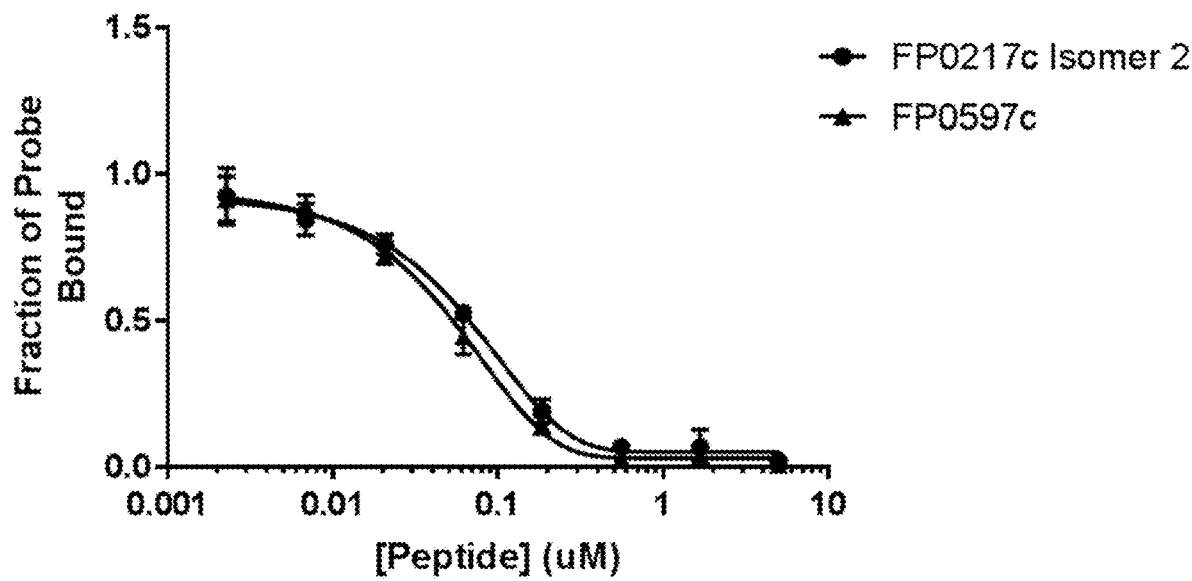
FIG. 7. Provided agents selectively disrupts interactions with Axin. In some embodiments, provided agents, e.g., stapled peptides, selectively disrupts interactions at one or more beta-catenin sites that interact with Axin over interactions at one or more beta-catenin sites that interact with BCL9. As illustrated in Panel A, FP0217c isomer 2 and FP0597c displaced a labeled Axin site probe. They, as shown in Panel B, did not displace the labeled BCL9 site probe but FP0650c (stapled peptides designed to interact with one or more beta-catenin sites that interact with BCL9) did. BCL9 Competition FP assay: Peptide solutions were prepared in buffer (50 mM Tris pH 8.0, 250 mM NaCl, 2% glycerol, 0.5 mM EDTA, 0.02% w/v sodium azide) using a 3-fold serial dilution from 10 µM. Probe solution (250 nM full-length beta-catenin, 20 nM 5FAM labeled peptide in buffer) was prepared and 40 µL per well plated in a black polystyrene 384-well plate (Corning). Equal volume of the titrated peptide was added to the plate and incubated protected from light for 15 minutes prior to read. Reads were performed on a Spectramax M5 (Molecular Devices) in duplicate. Probe: Ac-Leu-Ser-Gln-Glu-Gln-Leu-Glu-His-Arg-Glu-Arg-Ser-Leu-Gln-Thr-Leu-Arg-Asp-Ile-Gln-Arg-nLeu-Leu-2NapA-bala-bala-Lys5FAM-NH2 (SEQ ID NO: 2) (from *Biochemistry*, 2009, 48 (40), pp 9534-9541). Axin Competition FP assay: Peptide solutions were prepared in buffer (50 mM Tris pH 8.0, 250 mM NaCl, 2% glycerol, 0.5 mM EDTA, 0.02% w/v sodium azide) using a 3-fold serial dilution from 5 µM. Probe solution (15 nM full-length beta-catenin, 20 nM FITC labeled peptide in buffer) was prepared and incubated for 5 minutes, then 40 µL per well plated in a black polystyrene 384-well plate (Corning). Equal volume of the titrated peptide was added to the plate and incubated protected from light for 15 minutes prior to read. Reads were performed on a Spectramax M5 (Molecular Devices) in duplicate. Probe: FITC-StAx-33 from Grossmann et al. PNAS 109 17942-17947.
Figure 7:
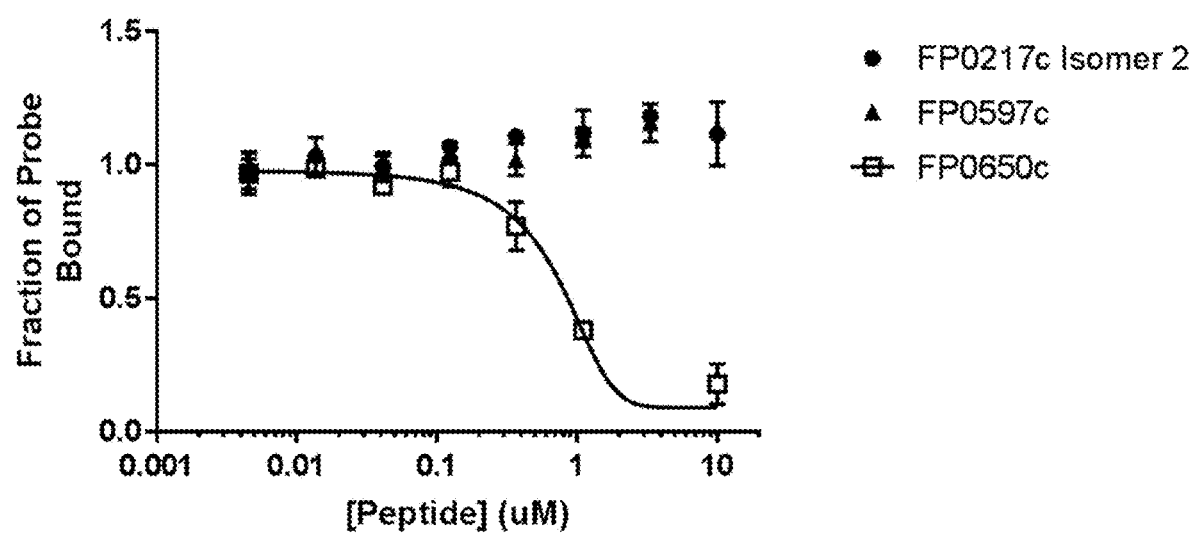

Various technologies can be utilized to assess interactions with beta-catenin at sites, e.g., that interact with BCL9 or Axin. In some embodiments, competition fluorescence polarization is utilized to assess interaction/modulation selectivity. In some embodiments, a competition fluorescence polarization assay for Axin sites (e.g., beta-catenin sites that interacts with Axin) was as described above. In some embodiments, e.g., for assess selectivity between BCL9 sites and Axin sites, a competition fluorescence polarization assay for Axin and/or BCL9 sites may be employed. In some embodiments, in an exemplary BCL9 competition FP assay, peptide solutions were prepared in a buffer (e.g., 50 mM Tris pH 8.0, 250 mM NaCl, 2% glycerol, 0.5 mM EDTA, 0.02% w/v sodium azide) using a, e.g., 3-fold, serial dilution from, e.g., 10 µM. Probe solution (e.g., 250 nM full-length ß-Catenin, 20 nM 5FAM labeled peptide in buffer) was prepared and a volume of, e.g., 40 µL, per well plated in a suitable multi-well plate, e.g., a black polystyrene 384-well plate (Corning). A suitable volume, e.g., an equal volume of the serial diluted peptide was added to the plate and incubated protected from light for a period of time, e.g., 15 minutes prior to read. Reads were performed, e.g., on a Spectramax M5 (Molecular Devices) in duplicate. In some embodiments, a probe is Ac-Leu-Ser-Gln-Glu-Gln-Leu-Glu-His-Arg-Glu-Arg-Ser-Leu-Gln-Thr-Leu-Arg-Asp-Ile-Gln-Arg-nLeu-Leu-2NapA-bala-bala-Lys5FAM-NH$_2$ (SEQ ID NO: 2) (from *Biochemistry*, 2009, 48 (40), pp 9534-9541). As demonstrated, e.g., by exemplary data in FIG. 7, in some embodiments, provided stapled peptides selectively disrupts interactions at one or more Axin sites over those at one or more BCL9 sites.

Example 8. Preparation of Stapled Peptides with Diverse Structural Elements and Assessment of their Properties Among other things, the present disclosure provides various structural elements, including of those of the staples, such as chemistry (hydrocarbon linker v. non-hydrocarbon linker), positioning (positions of staple connection, (i, i+4), (i, i+7), etc.), lengths, stereochemistry, etc., and combinations thereof, that can be utilized to design and prepare stapled peptides with significantly improved properties and/or activities. Various structural elements can also impact preparation of stapled peptides in terms of yield, purity, selectivity, etc. The present example illustrates preparation of stapled peptides with diverse structures using different reaction conditions. Among other things, certain structural features, e.g., those of staples (types, lengths, etc.), that can provide various advantages (preparation yield, purity, selectivity, binding affinity, etc.) are identified. In some embodiments, exemplary stapled peptides has better properties, e.g., solubility, binding affinity, cell permeability, etc. than StAx stapled peptides reported in reported in Grossmann et al. PNAS 109 17942-17947. In some embodiments, exemplified stapled peptides contain amino acid sequences that are highly homologous to StAx33 of Grossman.

A number of stapled peptides were prepared, with staple length of about 10-14 for carbamate staples and 8-12 for amino staples (which in this case comprising —N(R)— not bonded to —C(O)—). In some embodiments, some stapled peptides are double stapled (in some cases, stitched peptide). Table 4A illustrates certain results using 2×30 mol % Grubbs I, at 40° C., 2 hrs. Table 4B illustrates certain results using 2×5 mol % Hoveyda-Grubbs II, at 60° C., 2 hrs. Az is monomer A. PyrS is Monomer B. PyrR is Monomer C. SgN is Monomer D. RgN is Monomer E. SdN is Monomer F. RdN is Monomer G. SeN is Monomer H. ReN is Monomer I.

In some embodiments, staple length of 11 or more may deliver higher yields compared to a shorter staple length (e.g., for azetidine-containing stapled peptides as illustrated). In some embodiments, a preferred staple length is 11 or more. In some embodiments, staple length of 10-14 or more may deliver higher yields compared to a staple of another length (e.g., for pyrrolidine-containing stapled peptides as illustrated). In some embodiments, a preferred staple length is 11 or more. In some embodiments, a preferred staple length is 10-14. In some embodiments, pyrrolidine-containing staples generally are slower to form compared to azetidine-containing staples under comparable conditions. In some embodiments, for acyclic amines, amino acid residues comprising olefin in a hydrocarbon side chain at the N-terminus position typically resulted in lower olefin metathesis product formation.

FP EC50 data of certain stapled peptides were presented in Table 5.

For amino staple formation reaction, most reactions yielded clean amino stapled peptides under the condition used, with a few exceptions where multiple products and/or double isomers were observed. Exemplary results were presented in Table 6. In some embodiments, acyclic amino staples were more difficult to form compared to cyclic amino staples under certain conditions.

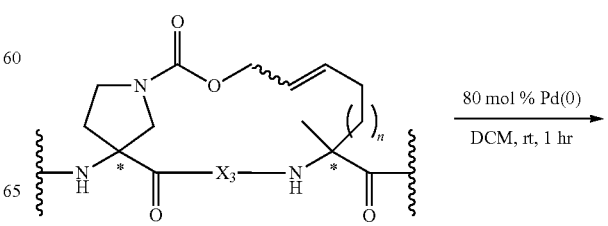

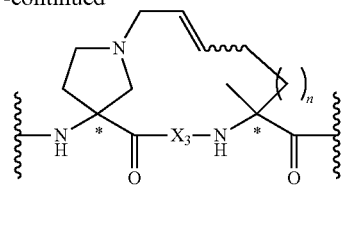

Exemplary FP EC$_{50}$ data were presented in Table 5. In some embodiments, stapled peptides with amino staples have lower binding affinity than stapled peptides with other types of staples, e.g., carbamate staples (in one case, FP-0738c (1800 nM) vs. FP-0738a (200 nM)).

In some embodiments, the following staples provided better results and may be preferred (exemplary stapled peptides in parentheses):

Carbamate Staples:
- Az/R$^6$ (FP-0725c)
- PR/R$^6$ (FP-0745c)
- S7/PS (FP-0763c)
- R4/PR (FP-0765c)
- R5/PR (FP-0766c)
- R6/PR (FP-0767c)
- R7/PR (FP-0768c)
- Staple Length=11 to 14 atoms Amino Staples:
- S7/Az (FP-0738a)
- PR/R$^6$ (FP-0745a)
- Staple Length=11 to 12 atoms By a Surface Plasmon Resonance—Biacore assay, R4/PR (FP-0765c) displayed a Kd about 13 nM, S5/S5 (FP-0787c) Kd about 14 nM, R5/PR (FP-0766c) Kd about 7 nM, Az/R6 (FP-0725c) Kd about 22 nM, S7/Az (FP-0738a) Kd about 43 nM, and PR/R6 (FP-0745a) Kd about 34 nM.

Example 9. Additional Methods for Olefin Metathesis

In some embodiments, the present disclosure provides methods for preparing stapled peptides. In some embodiments, the present disclosure provides methods for preparing stapled peptides, comprising forming a staple through olefin metathesis. In some embodiments, the present disclosure provides methods for ring closing metathesis to form a staple.

Various metathesis catalysts may be utilized in accordance with the present disclosure. In some embodiments, a catalyst is a Ru-catalyst. In some embodiments, a Ru-catalyst is Grubbs I, Grubbs II, Hoveyda-Grubbs I and Hoveyda-Grubbs II. In some embodiments, catalyst loading is 5 mol %. In some embodiments, catalyst loading is 20 mol %. In some embodiments, Hoveyda-Grubbs II provides better results than one or more other catalysts.

Figure 8:
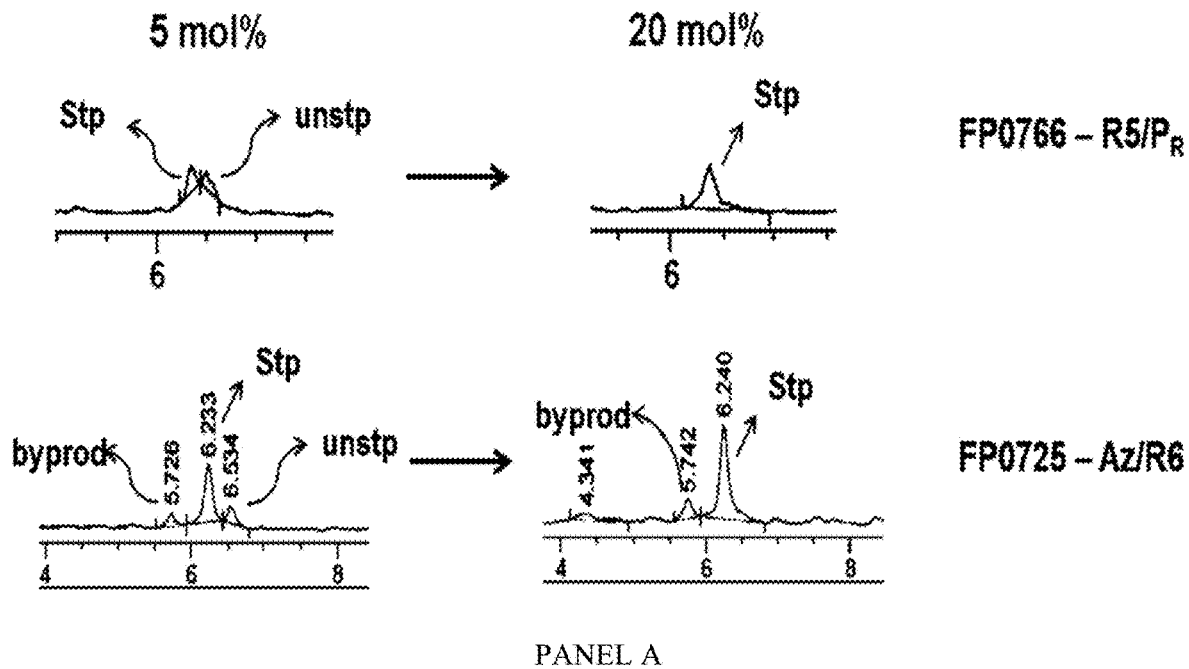
FIG. 8. Exemplary results of various olefin metathesis methods. (A) Grubbs I, one treatment in DCE, at 40° C., 2 hrs. (B) Grubbs II, one treatment in DCE, at 40° C., 2 hrs. (C) Hoveyda-Grubbs I, one treatment in DCE, at 40° C., 2 hrs. (D) Hoveyda-Grubbs II, one treatment in DCE, at 60° C., 2 hrs.
Figure 8:
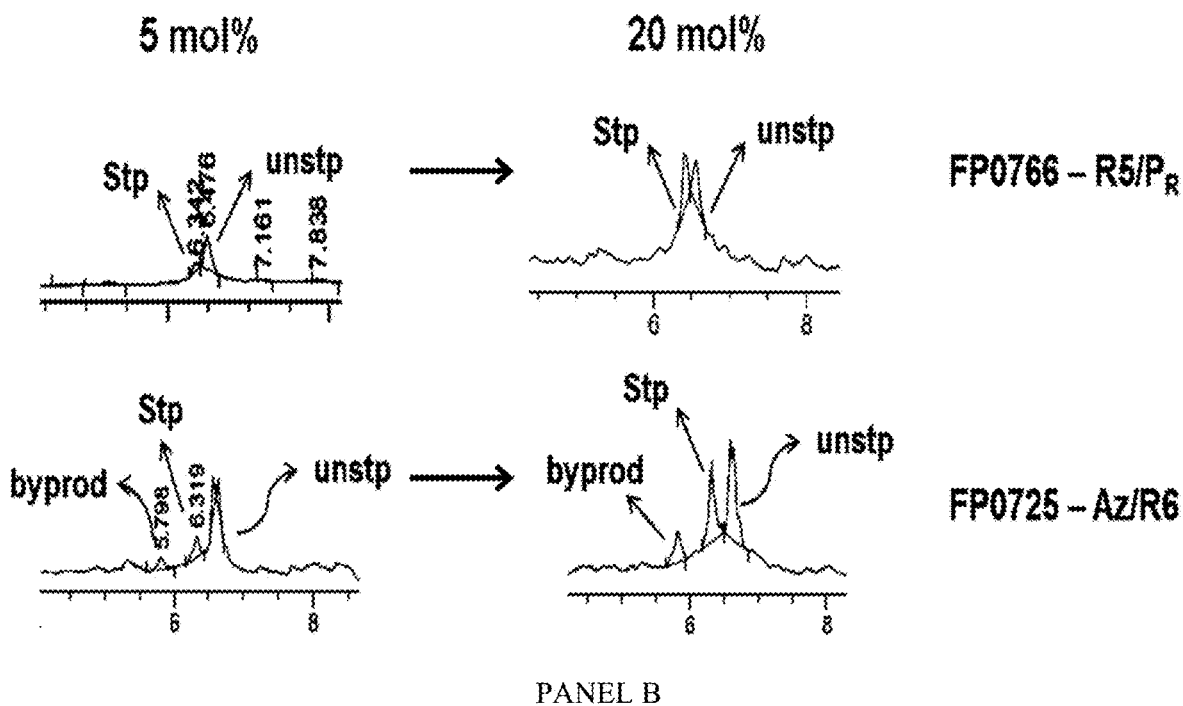
Figure 8:
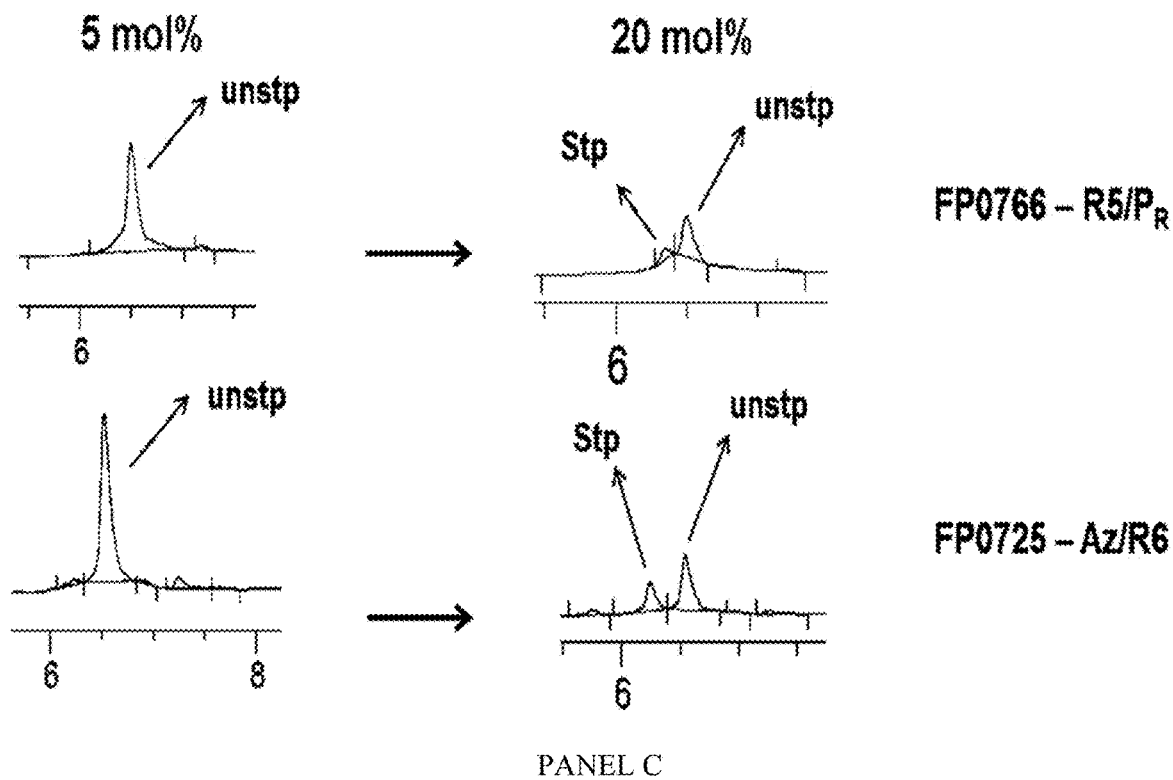
Figure 8:
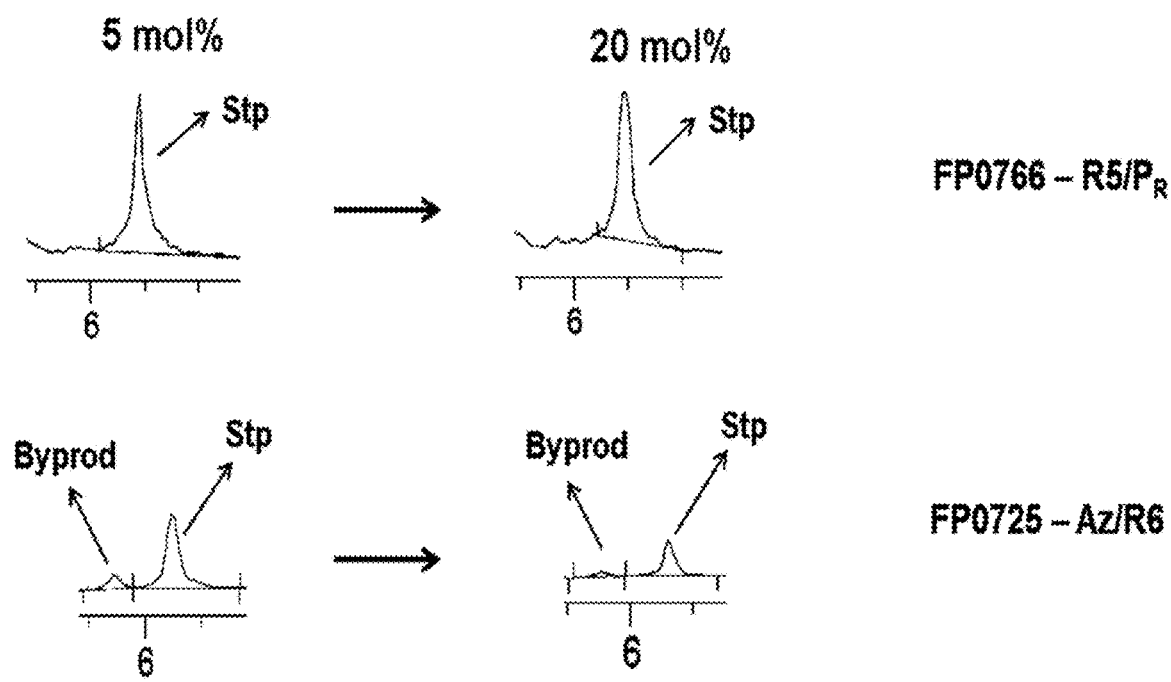

In some embodiments, 11 substrate peptides for olefin metathesis were used to evaluate various conditions, each of which can be fully stapled with a single 30 mol % Grubbs I treatment. Exemplary results were presented in FIG. 8.

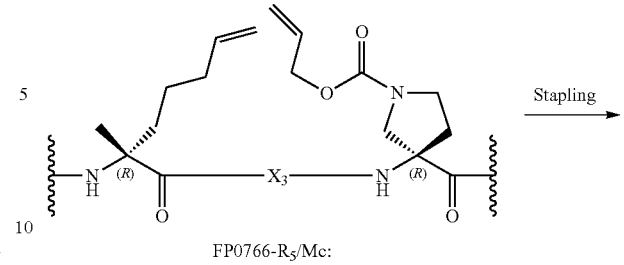

FP0766-R$_5$/Mc:

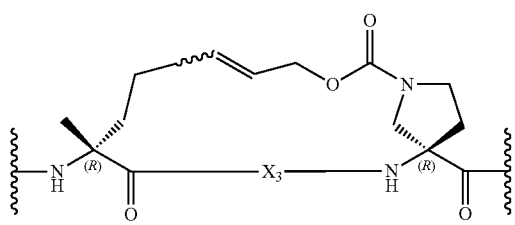

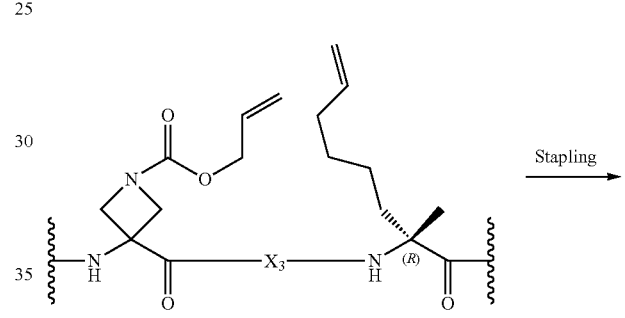

FP0725-M$_A$/R$_6$:

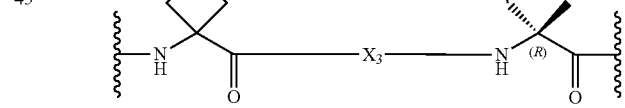

For Grubbs I, one treatment in DCE, at 40° C., 2 hrs, all reactions using 20 mol % were complete with 7 yielding no or traces of byproduct while 4 produced 17% to 50% byproduct. Single treatment with 5 mol % was not sufficient to completely staple peptides, with 3 peptides also showing byproduct formation. For Grubbs II, one treatment in DCE, at 40° C., 2 hrs, lower efficiency was observed compared to Grubbs I, no complete reaction was observed, by-product formation was observed, and starting material was the major species throughout. For Hoveyda-Grubbs I, one treatment in DCE, at 40° C., 2 hrs, no complete reactions were observed, and either trace or no stapled product observed with 5 mol %. For Hoveyda-Grubbs II, one treatment in DCE, at 60° C., 2 hrs, all peptides were fully stapled with 5 mol % of Hoveyda-Grubbs II, and lower byproduct to product ratio than with other catalysts.

169

In some embodiments, an optimized process is

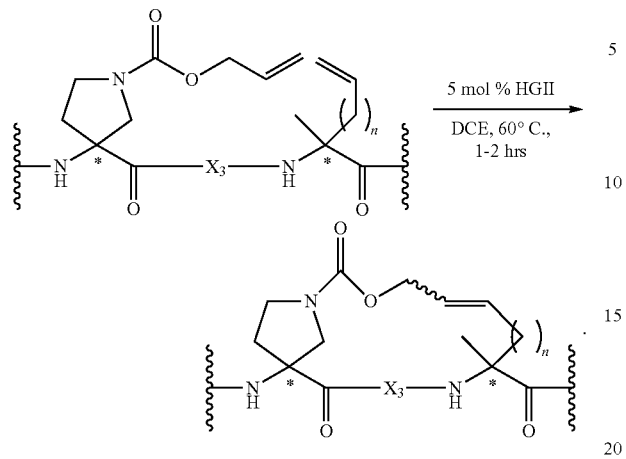

170

In some embodiments, a pre-optimized process is

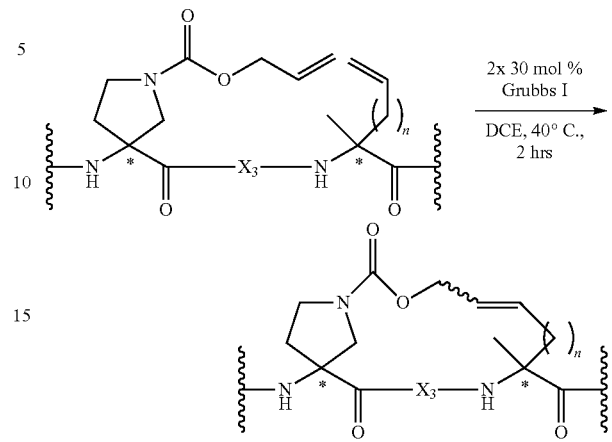

Exemplary results were presented below.

| ID | SEQ ID NO: | Peptide Sequence | 1st Treatment (5 mol % HGII at 60 C.) | Isomers |
|---|---|---|---|---|
| FP-0996 | 281 | Ac-HRERSLQTLR-Az-IQR-R6-LF-NH2 | Rxn complete; trace of unstapled | Single |
| FP-0997 | 282 | Ac-HRERSLQTLR-S5-IQR-Az-LF-NH2 | 50% stapled | Single |
| FP-0998 | 283 | Ac-HRERSLQTLR-PR-IQR-R5-LF-NH2 | 15% unstapled remaining | Single |
| FP-0999 | 284 | Ac-HRERSLQTLR-R6-IQR-PR-LF-NH2 | 30% unstapled remaining | Single |
| FP-1000 | 285 | Ac-HRE-Az-SLQ-R6-LRDIQR-Nle-LF-NH2 | Rxn complete; 13% byproduct | Single |
| FP-1001 | 286 | Ac-HRE-S5-SLQ-Az-LRDIQR-Nle-LF-NH2 | 40% stapled | Single |
| FP-1002 | 287 | Ac-HRE-PR-SLQ-R5-LRDIQR-Nle-LF-NH2 | 10% unstapled remaining | Single |
| FP-1003 | 288 | Ac-HRE-R6-SLQ-PR-LRDIQR-Nle-LF-NH2 | 13% unstapled remaining | Single |
| FP-1004 | 289 | Ac-Az-HRE-R6-SLQ-R8-LRDIQR-P$_S$-LF-NH2 | Rxn complete; trace of unstapled | Double (2:1) |
| FP-1005 | 290 | Ac-S5-HRE-Az-SLQ-R8-LRDIQR-P$_S$-LF-NH2 | 50% stapled | Double (2:1) |
| FP-1006 | 291 | Ac-PR-HRE-R5-SLQ-R8-LRDIQR-P$_S$-LF-NH2 | 10% unstapled remaining | Double (2:1) |
| FP-1007 | 292 | Ac-R6-HRE-PR-SLQ-R8-LRDIQR-P$_S$-LF-NH2 | 15% unstapled remaining | Double (2:1) |

| ID | SEQ ID NO: | Peptide Sequence | 1st Treatment (5 mol % HGII at 60 C.) | 2nd Treatment (5 mol % HGII at 60 C.) |
|---|---|---|---|---|
| FP-0719 | 293 | Ac-Pro-Gln-$M_A$-Ile-Leu-Asp-R3-His-Val-Arg-Arg-Val-Trp-Arg-NH2 | traces of stapled | NA |
| FP-0720 | 294 | Ac-Pro-Gln-$M_A$-Ile-Leu-Asp-S3-His-Val-Arg-Arg-Val-Trp-Arg-NH2 | no reaction | NA |
| FP-0726 | 295 | Ac-Pro-Gln-$M_A$-Ile-Leu-Asp-S6-His-Val-Arg-Arg-Val-Trp-Arg-NH2 | 10% stapled product; double isomers | NA |
| FP-0741 | 296 | Ac-Pro-Gln-$M_C$-Ile-Leu-Asp-R4-His-Val-Arg-Arg-Val-Trp-Arg-NH2 | traces of stapled | NA |
| FP-0748 | 297 | Ac-Pro-Gln-$M_C$-Ile-Leu-Asp-S7-His-Val-Arg-Arg-Val-Trp-Arg-NH2 | traces of stapled | NA |
| FP-0761 | 298 | Ac-Pro-Gln-S6-Ile-Leu-Asp-$M_B$-His-Val-Arg-Arg-Val-Trp-Arg-NH2 | 60% stapled | rxn complete; traces of unstapled |
| FP-0763 | 299 | Ac-Pro-Gln-S7-Ile-Leu-Asp-$M_B$-His-Val-Arg-Arg-Val-Trp-Arg-NH2 | 42% stapled | rxn complete; traces of unstapled |
| FP-0769 | 300 | Ac-Pro-Gln-S5-Ile-Leu-Asp-$M_D$-His-Val-Arg-Arg-Val-Trp-Arg-NH2 | 20% stapled | 46% stapled; double isomers |
| FP-0770 | 301 | Ac-Pro-Gln-S5-Ile-Leu-Asp-$M_F$-His-Val-Arg-Arg-Val-Trp-Arg-NH2 | 50% stapled; double isomers | NA |
| FP-0771 | 302 | Ac-Pro-Gln-S5-Ile-Leu-Asp-$M_H$-His-Val-Arg-Arg-Val-Trp-Arg-NH2 | 25% stapled; double isomers | NA |
| FP-0772 | 303 | Ac-Pro-Gln-R5-Ile-Leu-Asp-$M_D$-His-Val-Arg-Arg-Val-Trp-Arg-NH2 | 20% stapled | 50% stapled |
| FP-0773 | 304 | Ac-Pro-Gln-R5-Ile-Leu-Asp-$M_F$-His-Val-Arg-Arg-Val-Trp-Arg-NH2 | no reaction | NA |
| FP-0774 | 305 | Ac-Pro-Gln-R5-Ile-Leu-Asp-$M_H$-His-Val-Arg-Arg-Val-Trp-Arg-NH2 | no reaction | NA |
| FP-0775 | 306 | Ac-Pro-Gln-R5-Ile-Leu-Asp-$M_E$-His-Val-Arg-Arg-Val-Trp-Arg-NH2 | | |
| FP-0776 | 307 | Ac-Pro-Gln-R5-Ile-Leu-Asp-$M_G$-His-Val-Arg-Arg-Val-Trp-Arg-NH2 | 60% stapled | rxn complete; traces of unstapled |
| FP-0777 | 308 | Ac-Pro-Gln-R5-Ile-Leu-Asp-$M_I$-His-Val-Arg-Arg-Val-Trp-Arg-NH2 | 60% stapled | rxn complete; traces of unstapled |
| FP-0778 | 309 | Ac-Pro-Gln-$M_D$-Ile-Leu-Asp-S5-His-Val-Arg-Arg-Val-Trp-Arg-NH2 | 58% stapled | rxn complete; traces of unstapled |
| FP-0779 | 310 | Ac-Pro-Gln-$M_F$-Ile-Leu-Asp-S5-His-Val-Arg-Arg-Val-Trp-Arg-NH2 | 42% stapled | rxn complete; traces of unstapled |
| FP-0780 | 311 | Ac-Pro-Gln-$M_H$-Ile-Leu-Asp-S5-His-Val-Arg-Arg-Val-Trp-Arg-NH2 | ~33% stapled, coelutes with -$M_H$ truncation | rxn complete; traces of unstapled |

-continued

| ID | SEQ ID NO: | Peptide Sequence | 1st Treatment (5 mol % HGII at 60 C.) | 2nd Treatment (5 mol % HGII at 60 C.) |
|---|---|---|---|---|
| FP-0781 | 312 | Ac-Pro-Gln-$M_E$-Ile-Leu-Asp-R5-His-Val-Arg-Arg-Val-Trp-Arg-NH2 | | |
| FP-0782 | 313 | Ac-Pro-Gln-$M_G$-Ile-Leu-Asp-R5-His-Val-Arg-Arg-Val-Trp-Arg-NH2 | 33% stapled | rxn complete; traces of unstapled |
| FP-0783 | 314 | Ac-Pro-Gln-$M_I$-Ile-Leu-Asp-R5-His-Val-Arg-Arg-Val-Trp-Arg-NH2 | 56% stapled | rxn complete; traces of unstapled |
| FP-0784 | 315 | Ac-Pro-Gln-$M_E$-Ile-Leu-Asp-S5-His-Val-Arg-Arg-Val-Trp-Arg-NH2 | | |
| FP-0785 | 316 | Ac-Pro-Gln-$M_G$-Ile-Leu-Asp-S5-His-Val-Arg-Arg-Val-Trp-Arg-NH2 | traces of stapled | NA |
| FP-0786 | 317 | Ac-Pro-Gln-$M_I$-Ile-Leu-Asp-S5-His-Val-Arg-Arg-Val-Trp-Arg-NH2 | traces of stapled | NA |

NA: data not available/not performed.

In some embodiments, a "stitched" stapled peptides is selected from below:

(SEQ ID NO: 318)
Ac-PyrS-HRE-B5-SLQ-PyrR-LRDIQR-Nle-LF-NH2

(SEQ ID NO: 319)
Ac-SgN-HRE-B5-SLQ-RdN-LRDIQR-Nle-LF-NH2

(SEQ ID NO: 320)
Ac-SdN-HRE-B5-SLQ-RdN-LRDIQR-Nle-LF-NH2

(SEQ ID NO: 321)
Ac-SeN-HRE-B5-SLQ-RdN-LRDIQR-Nle-LF-NH2

(SEQ ID NO: 322)
Ac-SgN-HRE-B5-SLQ-ReN-LRDIQR-Nle-LF-NH2

(SEQ ID NO: 323)
Ac-SdN-HRE-B5-SLQ-ReN-LRDIQR-Nle-LF-NH2

(SEQ ID NO: 324)
Ac-SeN-HRE-B5-SLQ-ReN-LRDIQR-Nle-LF-NH2

(SEQ ID NO: 325)
Ac-HRERSL-PyrS-TLR-B5-IQR-PyrR-LF-NH2

(SEQ ID NO: 326)
Ac-HRERSL-SgN-TLR-B5-IQR-RdN-LF-NH2

(SEQ ID NO: 327)
Ac-HRERSL-SdN-TLR-B5-IQR-RdN-LF-NH2

(SEQ ID NO: 328)
Ac-HRERSL-SeN-TLR-B5-IQR-RdN-LF-NH2

(SEQ ID NO: 329)
Ac-HRERSL-SgN-TLR-B5-IQR-ReN-LF-NH2

(SEQ ID NO: 330)
Ac-HRERSL-SdN-TLR-B5-IQR-ReN-LF-NH2

(SEQ ID NO: 331)
Ac-HRERSL-SeN-TLR-B5-IQR-ReN-LF-NH2

As described in the present disclosure, provided agents, e.g., stapled peptides, have a number of significantly improved properties and activities, in some embodiments particularly when compared to one or more appropriate reference agents. Among other things, improved stability, increased solubility, increased cell permeability, increase activities, increased selectivity, and/or lowered toxicities, were observed when compared to a number of reference agents, e.g., unstapled peptides, small molecule Wnt pathway inhibitors, stapled peptides comprising hydrocarbon staples, stapled peptides not interacting with one or more beta-catenin sites that interact with Axin (e.g., stapled peptides interacting with one or more beta-catenin sites that interact with BCL9 but not Axin). A number of assays, including those described in the present disclosure and variations thereof, can be utilized to assess one or more properties and activities of provided agents, e.g., stapled peptides.

TABLE 2

Exemplary data.

| Peptide | in vitro FP EC$_{50}$ (nM)* | Solubility (mM) | K$_d$ by SPR (nM) | TCF/LEF Reporter IC$_{50}$ (mM) | Inhibition at 10 uM |
|---|---|---|---|---|---|
| FP0001c | | | | | |
| FP0003c | | | | | |
| FP0005c | +++ | | | | 45% |
| FP0006a | +++ | | | | 10% |
| FP0007c | | | | | 54% |
| FP0009c | | | | | 54% |
| FP0011c | | | | | 34% |
| FP0025c | +++ | | 15 | | 65% |
| FP0098 | | | | | 18% |
| FP0099 | | | | | 38% |
| FP0110 | | | | | 19% |
| FP0212s Isomer 2 | ++ | | | | 35% |
| FP0216c | | | | | 37% |
| FP0217a | NB | | 111 | | 0% |
| FP0217c Isomer 1 | + | | | | |
| FP0217c Isomer 2 | +++ | | 7 | 2 | 0.743 | 72% |
| c14-FP0217a | | | | | |
| c14-FP0217c | | | | | 54% |
| c16-FP0217a | | | | | |
| FP0217c_bAfree | +++ | | 155 | 9 | |
| FP0217c_btn | +++ | | | | |
| FP0217c_c18a | | | | | |
| FP0217rc | +++ | | 26 | | |
| FP0217s Isomer 1 | +++ | | 5 | | |
| FP0217s Isomer 2 | +++ | | 2 | | |
| FP0217u | +++ | | | | |
| FP0218c | ++ | | | | 41% |
| FP0219c | ++ | | | | 20% |
| FP0220c | +++ | | 14 | | 39% |
| FP0221c | | | | | 38% |
| FP0222c | | | | | 22% |
| FP0223 a | | | | | 18% |
| FP0224a | | | | | 15% |
| FP0243c | | | | | 35% |
| FP0244c | | | | | 68% |
| FP0247c | | | | | 0% |
| FP0249c | | | | | 0% |
| FP0250c | | | | | 0% |
| FP0253c | | | | | 63% |
| FP0264c | | | | | 59% |
| FP0265c | | | | | 64% |
| FP0268c | | | | | 0% |
| FP0269c | | | | | 0% |
| FP0270c | | | | | 0% |
| FP0271c | | | | | 0% |
| FP0272c | | | | | |
| FP0273c | | | | | 4% |
| FP0274c | | | | | 42% |
| FP0278c | | | | | 0% |
| FP0279c | | | | | 34% |
| FP0280c | | | | | 78% |
| FP0281c | | | | | 38% |
| FP0282c | | | | | 42% |
| FP0284c | | | | | 0% |
| FP0285c | | | | | 19% |
| FP0286c | | | | | 0% |
| FP0290c | | | | | 60% |
| FP0292c | | | | | 23% |
| FP0293c | | | | | 32% |
| FP0295c | | | | | 36% |
| FP0296c | | | | | 64% |
| FP0298c | | | | | 38% |
| FP0299c | | | | | 2% |
| FP0300c | | | | | 39% |
| FP0302c | | | | | 51% |
| FP0306c | | | | | 48% |
| FP0317a | | | | | 34% |
| FP0318a | | | | | |
| FP0318c | | | | | 48% |
| FP0321c | | | | | 59% |
| FP0324c | | | | | 51% |
| FP0325a | | | | | |
| FP0325c | | | | | 73% |
| FP0327c | | | | | 0% |
| FP0335a | ++ | | | | 0% |
| FP0335c Isomer 1 | ++ | | | | 22% |
| FP0335c Isomer 2 | +++ | | | | 37% |
| FP0336c | | | | | 43% |
| FP0338c | ++ | | 3 | | 36% |
| FP0344c | | | | | 0% |
| FP0345c | | | | | 43% |
| FP0346c | | | | | 36% |
| FP0349c | | | | | 50% |
| FP0350c | | | | | 1% |
| FP0352c | | | | | 38% |
| FP0353c | | | | | 0% |
| FP0354c | | | | | 28% |
| FP0355c | | | | | 0% |
| FP0357c | | | | | 37% |
| FP0365c | ++ | | | | |
| FP0365c Isomer 1 | + | | | | |
| FP0365c Isomer 2 | + | | | | |
| FP0368c | | | | | 0% |
| FP0369c | | | | | 38% |
| FP0371c | | | | | 46% |
| FP0380c | | | | | 25% |
| FP0383c | | | | | 22% |
| FP0391c | | | | | |
| FP0395c | | | | | 32% |
| FP0405c | + | | | | |
| FP0406c | ++ | | | | |
| FP0407c | + | | | | |
| FP0408c | NB | | | | |
| FP0409a | NB | | | | |
| FP0409c | | | | | |
| FP0409c_free | | | | | |
| c16-FP0409a | | | | | |
| c16-FP0409c | | | | | |
| FP0410c | ++ | | | | |
| FP0411c | | | | | |
| FP0412c | | | | | |
| FP0495a | + | | | | 18% |
| FP0495c | ++ | | | | 20% |
| FP0501c | ++ | | | | 33% |
| FP0502a | + | | | | 49% |
| FP0502c Isomer 1 | +++ | | | | 20% |
| FP0502c Isomer 2 | ++ | | | | 27% |
| FP0503a | ++ | | 236 | | 32% |
| FP0503c | ++ | | 35 | | 10% |
| FP0506a | + | | | | |
| FP0506c Isomer 1 | ++ | | | | |
| FP0506c Isomer 2 | +++ | | | | |
| FP0507a | +++ | | | | |
| FP0507c | + | | | | |
| FP0509a | + | | 192 | | |
| FP0509c | +++ | | 32 | 3 | |
| FP0510a | + | | 165 | | |
| FP0510c Isomer 1 | +++ | | 65 | | |
| FP0510c Isomer 2 | +++ | | 31 | | |
| FP0511a | +++ | | 170 | | |
| FP0511c Isomer 1 | +++ | | 49 | | |
| FP0511c Isomer 2 | +++ | | 24 | | |
| FP0516a Isomer 1 | ++ | | | | |
| FP0516a Isomer 2 | + | | | | |
| FP0516c | ++ | | | | |
| FP0536c | NB | | | | |
| FP0537c | NB | | | | |
| FP0538c | + | | | | |
| FP0539c | | | | | |
| FP0539c Isomer 1 | | | | | 52% |
| FP0539c Isomer 2 | | | | | 36% |
| FP0540c | NB | | | | |
| FP0541c | NB | | | | |
| FP0542c | + | | | | 18% |

TABLE 2-continued

Exemplary data.

| Peptide | in vitro FP EC$_{50}$ (nM)* | Solubility (mM) | K$_d$ by SPR (nM) | TCF/LEF Reporter IC$_{50}$ (mM) | Inhibition at 10 uM |
|---|---|---|---|---|---|
| FP0554c Isomer 1 | NB | | | | 29% |
| FP0554c Isomer 2 | NB | | | | 35% |
| FP0555c Isomer 1 | NB | | | | 43% |
| FP0555c Isomer 2 | NB | | | | 32% |
| FP0556c Isomer 1 | NB | | | | 33% |
| FP0556c Isomer 2 | NB | | | | 38% |
| FP0557c Isomer 1 | NB | | | | 43% |
| FP0557c Isomer 2 | NB | | | | 30% |
| FP0558c Isomer 1 | NB | | | | 38% |
| FP0558c Isomer 2 | NB | | | | 40% |
| FP0559c Isomer 1 | NB | | | | 44% |
| FP0559c Isomer 2 | NB | | | | 31% |
| FP0560c Isomer 1 | NB | | | | 40% |
| FP0560c Isomer 2 | NB | | | | 22% |
| FP0561c Isomer 1 | NB | | | | 38% |
| FP0561c Isomer 2 | NB | | | | 35% |
| FP0562c Isomer 1 | NB | | | | 22% |
| FP0562c Isomer 2 | NB | | | | 32% |
| FP0563c Isomer 1 | NB | | | | 34% |
| FP0563c Isomer 2 | NB | | | | 30% |
| FP0564c Isomer 1 | NB | | | | 46% |
| FP0564c Isomer 2 | NB | | | | |
| FP0565c Isomer 1 | NB | | | | |
| FP0565c Isomer 2 | NB | | | | |
| FP0566c Isomer 1 | NB | | | | |
| FP0567c Isomer 1 | NB | | | | |
| FP0567c Isomer 2 | NB | | | | |
| FP0568c Isomer 1 | NB | | | | |
| FP0568c Isomer 2 | NB | | | | |
| FP0569c Isomer 1 | NB | | | | |
| FP0569c Isomer 2 | NB | | | | |
| FP0570c Isomer 1 | NB | | | | |
| FP0570c Isomer 2 | NB | | | | |
| FP0571c Isomer 1 | NB | | | | |
| FP0571c Isomer 2 | NB | | | | |
| FP0572c Isomer 1 | NB | | | | |
| FP0573c Isomer 1 | NB | | | | |
| FP0573c Isomer 2 | NB | | | | |
| FP0574c Isomer 1 | NB | | | | |
| FP0574c Isomer 2 | NB | | | | |
| FP0575c Isomer 1 | NB | | | | |
| FP0575c Isomer 2 | NB | | | | |
| FP0576c Isomer 1 | NB | | | | |
| FP0576c Isomer 2 | NB | | | | |
| FP0577c Isomer 1 | NB | | | | |
| FP0578c Isomer 1 | NB | | | | |
| FP0578c Isomer 2 | NB | | | | |
| FP0587c | +++ | | | | 33% |
| FP0588c | +++ | 133 | | | 61% |
| FP0594c | ++ | 166 | | | 23% |
| FP0596c | + | | | | 21% |
| FP0597c | +++ | 98 | 4 | 1.021 | 81% |
| FP0597c_c12 | | 4 | | | |
| FP0597c_c8 | | 2 | | | |
| FP0598c | +++ | | | | 23% |
| FP0601c | +++ | | | | 30% |
| FP0604c | +++ | | | | 32% |
| FP0605c | +++ | | | | 30% |
| FP0611c | +++ | | | | 56% |
| FP0616c | +++ | 56 | | | 51% |
| FP0617c | +++ | 63 | | | 62% |
| FP0625c | ++ | | | | 20% |
| FP0626c | +++ | 40 | | | 53% |
| FP0628_aib | ++ | 88 | | | |
| FP0629c | + | | | | 49% |
| FP0630c | ++ | | | | 53% |
| FP0631c | + | | | | 0% |
| FP0632c | ++ | 13 | | | 57% |
| FP0633c | + | | | | 16% |
| FP0634c | +++ | | | | 45% |
| FP0635c | ++ | | | | 19% |
| FP0636c | ++ | | | | 41% |
| FP0639c | +++ | | | | 40% |
| FP0640c | +++ | | | | 25% |
| FP0644c | ++ | | | | 34% |
| FP0645c | +++ | | | | 26% |
| FP0721a | | | | | |
| FP0721c | + | | | | |
| FP0723a | | | | | |
| FP0723c | + | | | | |
| FP0724c | + | | | | |
| FP0725a | + | | | | |
| FP0725c | +++ | | 22 | | |
| FP0727c | + | | | | |
| FP0728c | + | | | | |
| FP0731c | + | | | | |
| FP0733c | + | | | | |
| FP0734a | NB | | | | |
| FP0734c | NB | | | | |
| FP0735a | + | | | | |
| FP0735c | + | | | | |
| FP0736a | ++ | | | | |
| FP0736c | + | | | | |
| FP0738a | ++ | | 43 | | |
| FP0738c | + | | | | |
| FP0743a | NB | | | | |
| FP0743c | + | | | | |
| FP0745a | ++ | | 34 | | |
| FP0745c | ++ | | | | |
| FP0751a | NB | | | | |
| FP0751c | + | | | | |
| FP0752c | + | | | | |
| FP0753a | NB | | | | |
| FP0758a | NB | | | | |
| FP0758c | + | | | | |
| FP0761c | ++ | | | | |
| FP0763a | + | | | | |
| FP0763c | ++ | | | | |
| FP0765c | +++ | | 13 | N/A | N/A |
| FP0766c | ++ | | 7 | N/A | N/A |
| FP0767a | + | | | | |
| FP0767c | ++ | | | | |
| FP0768a | NB | | | | |
| FP0768c | ++ | | | | |
| FP0776c | + | | | | |
| FP0776a | + | | | | |
| FP0777c | + | | | | |
| FP0777a | + | | | | |
| FP0778c | + | | | | |
| FP0779c | + | | | | |
| FP0780c | + | | | | |
| FP0782c | ++ | | | | |
| FP0783c | + | | | | |
| FP0783a | + | | | | |
| FP0787s | ++ | | 14 | | |

*+++: <= 100 nM EC50; ++: 100-500 nM EC50; +: 500-5000 nM EC50;

N/A, N.D.: relevant values not determined from currently available data collected from utilized assay conditions, e.g., dose ranges, concentrations, etc.;

NB: no binding detected under utilized assay conditions.

TABLE 3

Exemplary results.

Part A

| ID | Metathesis Efficiency | Target Binding | Binding Kd (nM) | Solubility in DPBS (uM) | Beta-Catenin Luciferase Reporter % Inhibition at 10 uM |
|---|---|---|---|---|---|
| FP0512c | fair | N.D. | N.D. | N.D. | N.D. |
| FP0513c | good | N.D. | N.D. | N.D. | N.D. |
| FP0514c | poor | N.D. | N.D. | N.D. | N.D. |
| FP0515c | fair | N.D. | N.D. | N.D. | N.D. |
| FP0516c | fair | 151 | N.D. | N.D. | 27% |
| FP0517c | poor | N.D. | N.D. | N.D. | N.D. |
| FP0335c | fair | Yes (Isomer 2 more tightly than Isomer 1) | N.D. | N.D. | 22% (Isomer 1) 37% (Isomer 2) |
| FP0492c | fair | N.D. | N.D. | N.D. | N.D. |
| FP0491c | poor | N.D. | N.D. | N.D. | N.D. |
| FP0490c | poor | N.D. | N.D. | N.D. | N.D. |
| FP0338c | good | Yes | 10 | N.D. | 30% |
| FP0495c | good | Yes | N.D. | N.D. | 20% |
| FP0494c | poor | N.D. | N.D. | N.D. | N.D. |
| FP0493c | poor | N.D. | N.D. | N.D. | N.D. |
| FP0499c | fair | N.D. | N.D. | N.D. | N.D. |
| FP0498c | poor | N.D. | N.D. | N.D. | N.D. |
| FP0497c | poor | N.D. | N.D. | N.D. | N.D. |
| FP0496c | fair | N.D. | N.D. | N.D. | N.D. |
| FP0503c | fair | Yes | N.D. | 35 | 10% |
| FP0502c | fair | Yes | N.D. | N.D. | 20% (Peak 1) 27% (Peak 2) |
| FP0501c | fair | Yes | N.D. | N.D. | 33% |
| FP0500c | poor | N.D. | N.D. | N.D. | N.D. |
| FP0507c | good but two isomers | Yes | N.D. | N.D. | 32% (Only one isomer isolated) |
| FP0506c | fair | Yes | N.D. | N.D. | 36% |
| FP0505c | poor | N.D. | N.D. | N.D. | N.D. |
| FP0504c | poor | N.D. | N.D. | N.D. | N.D. |
| FP0486c | poor | N.D. | N.D. | N.D. | N.D. |
| FP0485c | poor | N.D. | N.D. | N.D. | N.D. |
| FP0484c | poor | N.D. | N.D. | N.D. | N.D. |
| FP0483c | poor | N.D. | N.D. | N.D. | N.D. |
| FP0217c | fair | Yes (Isomer 2 more tightly than Isomer 1) | 4 (Isomer 2) | 12 (Isomer 2) | 62% (Isomer 2) |
| FP0489c | fair | N.D. | N.D. | N.D. | N.D. |
| FP0488c | No data | N.D. | N.D. | N.D. | N.D. |
| FP0487c | poor | N.D. | N.D. | N.D. | N.D. |
| FP0508c | poor | N.D. | N.D. | N.D. | N.D. |
| FP0509c | fair | Yes | 3 | 42 | 39% |
| FP0510c | good but two isomers | Yes (Isomer 2 more tightly than Isomer 1) | N.D. | 65 (Isomer 1) 31 (Isomer 2) | 22% (Isomer 1) 33% (Isomer 2) |
| FP0511c | good but two isomers | Yes (Isomer 2 more tightly than Isomer 1) | N.D. | 49 (Isomer 1) 24 (Isomer 2) | 17% (Isomer 1) 18% (Isomer 2) |
| FP0520c | good | N.D. | N.D. | N.D. | N.D. |
| FP0521c | fair | N.D. | N.D. | N.D. | N.D. |
| FP0522c | good but two isomers | N.D. | N.D. | N.D. | N.D. |
| FP0523c | good | N.D. | N.D. | N.D. | N.D. |
| FP0617c | good | Yes | N.D. | 63 | 62% |
| FP0616c | good | Yes | N.D. | 56 | 51% |
| FP0615c | poor | N.D. | N.D. | N.D. | N.D. |
| FP0611c | good | Yes | N.D. | N.D. | 58% |
| FP0623c | poor | N.D. | N.D. | N.D. | N.D. |
| FP0624c | poor | N.D. | N.D. | N.D. | N.D. |
| FP0625c | fair | Yes | N.D. | N.D. | 0% |
| FP0592c | good but 2 isomers | N.D. | N.D. | N.D. | N.D. |
| FP0599c | good | N.D. | N.D. | N.D. | N.D. |
| FP0606c | poor | N.D. | N.D. | N.D. | N.D. |
| FP0627c | fair | N.D. | N.D. | N.D. | N.D. |
| FP0618c | poor | N.D. | N.D. | N.D. | N.D. |
| FP0619c | poor | N.D. | N.D. | N.D. | N.D. |
| FP0613c | poor | N.D. | N.D. | N.D. | N.D. |
| FP0609c | poor | N.D. | N.D. | N.D. | N.D. |
| FP0610c | poor | N.D. | N.D. | N.D. | N.D. |
| FP0612c | poor | N.D. | N.D. | N.D. | N.D. |
| FP0614c | poor | N.D. | N.D. | N.D. | N.D. |
| FP0620c | poor | N.D. | N.D. | N.D. | N.D. |

TABLE 3-continued

| | Exemplary results. |

| | | | | | |
|---|---|---|---|---|---|
| FP0621c | poor | N.D. | N.D. | N.D. | N.D. |
| FP0622c | fair | N.D. | N.D. | N.D. | N.D. |
| FP0587c | good | Yes | N.D. | N.D. | 43% |
| FP0588c | good but 2 isomers | Yes | N.D. | 133 | 61% |
| FP0589c | good but 2 isomers | N.D. | N.D. | N.D. | N.D. |
| FP0590c | good but 2 isomers | N.D. | N.D. | N.D. | N.D. |
| FP0591c | good but 2 isomers | N.D. | N.D. | N.D. | N.D. |
| FP0593c | good but 2 isomers | N.D. | N.D. | N.D. | N.D. |
| FP0594c | good | Yes | N.D. | 166 | 23% |
| FP0595c | fair | N.D. | N.D. | N.D. | N.D. |
| FP0596c | good | Yes | N.D. | N.D. | 11% |
| FP0597c | good | Yes | 4 | 98 | 81% |
| FP0598c | good | Yes | N.D. | 91 | 23% |
| FP0600c | good but 2 isomers | N.D. | N.D. | N.D. | N.D. |
| FP0601c | good | Yes | N.D. | N.D. | 40% |
| FP0602c | fair | N.D. | N.D. | N.D. | N.D. |
| FP0603c | poor | N.D. | N.D. | N.D. | N.D. |
| FP0604c | good | Yes | N.D. | N.D. | 46% |
| FFP0607c | poor | N.D. | N.D. | N.D. | N.D. |
| FP0608c | fair | N.D. | N.D. | N.D. | N.D. |
| FP0626c | good | Yes | N.D. | 40 | 60% |

Poor: <1:2 stapled:unstapled or <1:1 stapled:unstapled with two isomers
Fair: between approx. 1:2 stapled:unstapled and 2:1 stapled:unstapled, potentially with two isomers (also in this category is combinations that gave up to 3:1 or so stapled:unstapled but gave either two major isomers or significant amount of neither stapled nor unstapled byproduct)
Good: better than 2:1 stapled:unstapled with one major isomer
Good but two isomers: Better than approx. 4:1 stapled but with two major isomers
N.D.-Not determined or not presented in this Table.

Part B

| Carbamate-Stapled Starting Material | Amino-Stapled Product | $CO_2$ Extrusion | Target Binding | Solubility in DPBS (uM) | Beta-Catenin Luciferase Reporter % Inhibition at 10 uM |
|---|---|---|---|---|---|
| FP0516c | FP0516a | Yes (Two isomers isolated) | Yes (Isomer 1 binds more tightly than Isomer 2) | N.D. | N.D. |
| FP0335c | FP0335a | Yes | Yes | N.D. | 0% |
| FP0338c | FP0338a | Yes | N.D. | N.D. | N.D. |
| FP0495c | FP0495a | Yes | Yes | N.D. | 18% |
| FP0503c | FP0503a | Yes | Yes | 236 | 32% |
| FP0502c | FP0502a | Yes | No | N.D. | 49% |
| FP0507c | FP0507a | Yes | Yes | N.D. | 32% |
| FP0506c | FP0506a | Yes | No | N.D. | 0% |
| FP0217c | FP0217a | Yes | No | 111 | 0% |
| FP0509c | FP0509a | Yes | Yes | 192 | 0% |
| FP0510c | FP0510a | Yes | Yes | 165 | 49% |
| FP0511c | FP0511a | Yes | Yes | 170 | 0% |

N.D.-Not determined or not presented in this Table.

TABLE 4

Exemplary results (TABLE 4 discloses SEQ ID NOS 293, 294, 229, 231, 232, 234, 295, 235, 236, 332, 333, 237, 238, 240, 242, 244, 334, 246, 335, 296, 248, 336, 250, 337, 297, 338, 252, 253, 339, 340, 256, 341, 342, 257, 259, 343, 260, 261, 263, 265, 300-305, 266, 268, 270-274, 316 and 317, respectively, in order of appearance).

| Peptide ID | Sequence | Complete with single treatment | Complete after 2 treatments | Incomplete or No Reaction | Byproduct formation | Double Isomer |
|---|---|---|---|---|---|---|
| A - 2x 30 mol % Grubbs I, at 40° C., 2 hrs | | | | | | |
| Azetidine Carbamate Staples | | | | | | |
| FP-0719 | Ac-P-Q-Az-I-L-D-R3-H-V-R-R-V-W-R-NH2 | | | x | | |
| FP-0720 | Ac-P-Q-Az-I-L-D-S3-H-V-R-R-V-W-R-NH2 | | | x | | |
| FP-0721 | Ac-P-Q-Az-I-L-D-R4-H-V-R-R-V-W-R-NH2 | | x | | | |
| FP-0723 | Ac-P-Q-Az-I-L-D-R5-H-V-R-R-V-W-R-NH2 | x | | | 25% | |
| FP-0724 | Ac-P-Q-Az-I-L-D-S5-H-V-R-R-V-W-R-NH2 | | x | | | |
| FP-0725 | Ac-P-Q-Az-I-L-D-R6-H-V-R-R-V-W-R-NH2 | x | | | | |
| FP-0726 | Ac-P-Q-Az-I-L-D-S6-H-V-R-R-V-W-R-NH2 | | | x | 50% | x |
| FP-0727 | Ac-P-Q-Az-I-L-D-R7-H-V-R-R-V-W-R-NH2 | x | | | | |
| FP-0728 | Ac-P-Q-Az-I-L-D-S7-H-V-R-R-V-W-R-NH2 | | x | | 28% | |
| FP-0729 | Ac-P-Q-R3-I-L-D-Az-H-V-R-R-V-W-R-NH2 | | | x | | |
| FP-0730 | Ac-P-Q-S3-I-L-D-Az-H-V-R-R-V-W-R-NH2 | | | x | | |
| FP-0731 | Ac-P-Q-R4-I-L-D-Az-H-V-R-R-V-W-R-NH2 | | | x (80%) | | |
| FP-0733 | Ac-P-Q-R5-I-L-D-Az-H-V-R-R-V-W-R-NH2 | | x | | | |
| FP-0734 | Ac-P-Q-S5-I-L-D-Az-H-V-R-R-V-W-R-NH2 | x | | | | |
| FP-0735 | Ac-P-Q-R6-I-L-D-Az-H-V-R-R-V-W-R-NH2 | x | | | | |
| FP-0736 | Ac-P-Q-S6-I-L-D-Az-H-V-R-R-V-W-R-NH2 | x | | | | |
| FP-0737 | Ac-P-Q-R7-I-L-D-Az-H-V-R-R-V-W-R-NH2 | | x | | | |
| FP-0738 | Ac-P-Q-S7-I-L-D-Az-H-V-R-R-V-W-R-NH2 | x | | | 22% | |
| Pyrrolidine Carbamate Staples | | | | | | |
| FP-0739 | Ac-P-Q-P$_R$-I-L-D-R3-H-V-R-R-V-W-R-NH2 | | | x | | |
| FP-0741 | Ac-P-Q-P$_R$-I-L-D-R4-H-V-R-R-V-W-R-NH2 | | | x | | |
| FP-0743 | Ac-P-Q-P$_R$-I-L-D-R5-H-V-R-R-V-W-R-NH2 | | x | | | |
| FP-0744 | Ac-P-Q-P$_R$-I-L-D-S5-H-V-R-R-V-W-R-NH2 | | x | | | |
| FP-0745 | Ac-P-Q-P$_R$-I-L-D-R6-H-V-R-R-V-W-R-NH2 | | | x | | |
| FP-0746 | Ac-P-Q-P$_R$-I-L-D-S6-H-V-R-R-V-W-R-NH2 | | | x | | |
| FP-0748 | Ac-P-Q-P$_R$-I-L-D-S7-H-V-R-R-V-W-R-NH2 | | | x | | |
| FP-0749 | Ac-P-Q-P$_S$-I-L-D-S3-H-V-R-R-V-W-R-NH3 | | x | | | |
| FP-0751 | Ac-P-Q-P$_S$-I-L-D-S5-H-V-R-R-V-W-R-NH2 | | x | | | |
| FP-0752 | Ac-P-Q-P$_S$-I-L-D-S6-H-V-R-R-V-W-R-NH2 | | x | | | |
| FP-0753 | Ac-P-Q-P$_S$-I-L-D-S7-H-V-R-R-V-W-R-NH2 | | | | 28% | |

TABLE 4-continued

Exemplary results (TABLE 4 discloses SEQ ID NOS 293, 294, 229, 231, 232, 234, 295, 235, 236, 332, 333, 237, 238, 240, 242, 244, 246, 334, 335, 296, 248, 336, 250, 337, 297, 338, 252, 253, 339, 340, 256, 341, 342, 257, 259, 343, 260, 261, 263, 265, 300-305, 266, 268, 270-274, 316 and 317, respectively, in order of appearance).

| Peptide ID | Sequence | Complete with single treatment | Complete after 2 treatments | Incomplete or No Reaction | Byproduct formation | Double Isomer |
|---|---|---|---|---|---|---|
| FP-0756 | Ac-P-Q-R4-I-L-D-$P_S$-H-V-R-R-V-W-R-NH2 | | | x | | |
| FP-0758 | Ac-P-Q-R5-I-L-D-$P_S$-H-V-R-R-V-W-R-NH2 | | | x (80%) | | x |
| FP-0759 | Ac-P-Q-S5-I-L-D-$P_S$-H-V-R-R-V-W-R-NH3 | x | | | | |
| FP-0760 | Ac-P-Q-R6-I-L-D-$P_S$-H-V-R-R-V-W-R-NH2 | | | x | | |
| FP-0761 | Ac-P-Q-S6-I-L-D-$P_S$-H-V-R-R-V-W-R-NH2 | | x | | | |
| FP-0763 | Ac-P-Q-S7-I-L-D-$P_S$-H-V-R-R-V-W-R-NH2 | | x | | | |
| FP-0764 | Ac-P-Q-R3-I-L-D-$P_R$-H-V-R-R-V-W-R-NH2 | | | x | | |
| FP-0765 | Ac-P-Q-R4-I-L-D-$P_R$-H-V-R-R-V-W-R-NH2 | | x | | | |
| FP-0766 | Ac-P-Q-R5-I-L-D-$P_R$-H-V-R-R-V-W-R-NH2 | x | | | | |
| FP-0767 | Ac-P-Q-R6-I-L-D-$P_R$-H-V-R-R-V-W-R-NH2 | x | | | | |
| FP-0768 | Ac-P-Q-R7-I-L-D-$P_R$-H-V-R-R-V-W-R-NH3 | x | | | | |

B - 2x 5 mol % Hoveyda-Grubbs II, at 60° C., 2 hrs

Alkyl Carbamate Staples

| FP-0769 | Ac-P-Q-S5-I-L-D-SgN-H-V-R-R-V-W-R-NH2 | | | x | | x |
| FP-0770 | Ac-P-Q-S5-I-L-D-SdN-H-V-R-R-V-W-R-NH2 | | | x | | x |
| FP-0771 | Ac-P-Q-S5-I-L-D-SeN-H-V-R-R-V-W-R-NH2 | | | x | | |
| FP-0772 | Ac-P-Q-R5-I-L-D-SgN-H-V-R-R-V-W-R-NH2 | | | x | | |
| FP-0773 | Ac-P-Q-R5-I-L-D-SdN-H-V-R-R-V-W-R-NH2 | | | x | | |
| FP-0774 | Ac-P-Q-R5-I-L-D-SeN-H-V-R-R-V-W-R-NH2 | | x | | | |
| FP-0776 | Ac-P-Q-R5-I-L-D-RdN-H-V-R-R-V-W-R-NH2 | | x | | | |
| FP-0777 | Ac-P-Q-R5-I-L-D-ReN-H-V-R-R-V-W-R-NH2 | | x | | | |
| FP-0778 | Ac-P-Q-Q-SgN-I-L-D-S5-H-V-R-R-V-W-R-NH2 | | x | | | |
| FP-0779 | Ac-P-Q-SdN-I-L-D-S5-H-V-R-R-V-W-R-NH2 | | x | | | |
| FP-0780 | Ac-P-Q-SeN-I-L-D-S5-H-V-R-R-V-W-R-NH2 | | x | | | |
| FP-0782 | Ac-P-Q-RdN-I-L-D-R5-H-V-R-R-V-W-R-NH2 | | x | | | |
| FP-0783 | Ac-P-Q-ReN-I-L-D-R5-H-V-R-R-V-W-R-NH2 | | x | | | |
| FP-0785 | Ac-P-Q-RdN-I-L-D-S5-H-V-R-R-V-W-R-NH2 | | | x | | |
| FP-0786 | Ac-P-Q-ReN-I-L-D-S5-H-V-R-R-V-W-R-NH2 | | | x | | |

TABLE 5

Exemplary FP EC50 data (nM) (Table 5 discloses
SEQ ID NOS 229, 231, 232, 234-238, 240, 242, 244,
334, 246, 248, 250, 252, 253, 339, 256, 257, 259,
260, 261, 263, 265, 266, 268, 270-274, 228, 230,
233, 239, 241, 243, 245, 247, 249, 251, 254, 255,
258, 262, 264, 267, 269 and 275).

| Azefidine Carbamate Staples | | |
|---|---|---|
| Peptide ID | Sequence | FP EC$_{50}$ (nM) |
| FP-0721c | Ac-P-Q-Az-I-L-D-R4-H-V-R-R-V-W-R-NH2 | 1300 |
| FP-0723c | Ac-P-Q-Az-I-L-D-R5-H-V-R-R-V-W-R-NH2 | 1400 |
| FP-0724c | Ac-P-Q-Az-I-L-D-S5-H-V-R-R-V-W-R-NH2 | 540 |
| FP-0725c | Ac-P-Q-Az-I-L-D-R6-H-V-R-R-V-W-R-NH2 | 80 |
| FP-0727c | Ac-P-Q-Az-I-L-D-R7-H-V-R-R-V-W-R-NH2 | 520 |
| FP-0728c | Ac-P-Q-Az-I-L-D-S7-H-V-R-R-V-W-R-NH2 | 2100 |
| FP-0731c | Ac-P-Q-R4-I-L-D-Az-H-V-R-R-V-W-R-NH2 | 4700 |
| FP-0733c | Ac-P-Q-R5-I-L-D-Az-H-V-R-R-V-W-R-NH2 | 920 |
| FP-0734c | Ac-P-Q-S5-I-L-D-Az-H-V-R-R-V-W-R-NH2 | >5000 |
| FP-0735c | Ac-P-Q-R6-I-L-D-Az-H-V-R-R-V-W-R-NH2 | 1600 |
| FP-0736c | Ac-P-Q-S6-I-L-D-Az-H-V-R-R-V-W-R-NH2 | 890 |
| FP-0737c | Ac-P-Q-R7-I-L-D-Az-H-V-R-R-V-W-R-NH2 | TBD |
| FP-0738c | Ac-P-Q-S7-I-L-D-Az-H-V-R-R-V-W-R-NH2 | 1800 |

| Pyrrolidine Carbamate Staples | | |
|---|---|---|
| Peptide ID | Sequence | FP EC$_{50}$ (nM) |
| FP-0743c | Ac-P-Q-P$_R$-I-L-D-R5-H-V-R-R-V-W-R-NH2 | 740 |
| FP-0745c | Ac-P-Q-P$_R$-I-L-D-R6-H-V-R-R-V-W-R-NH2 | 110 |
| FP-0751c | Ac-P-Q-P$_S$-I-L-D-S5-H-V-R-R-V-W-R-NH2 | 2000 |
| FP-0752c | Ac-P-Q-P$_S$-I-L-D-S6-H-V-R-R-V-W-R-NH2 | 2600 |
| FP-0753c | Ac-P-Q-P$_S$-I-L-D-S7-H-V-R-R-V-W-R-NH2 | low yield |
| FP-0758c | Ac-P-Q-R5-I-L-D-P$_S$-H-V-R-R-V-W-R-NH2 | 2700 |
| FP-0761c | Ac-P-Q-S6-I-L-D-P$_S$-H-V-R-R-V-W-R-NH2 | 460 |
| FP-0763c | Ac-P-Q-S7-I-L-D-P$_S$-H-V-R-R-V-W-R-NH2 | 115 |
| FP-0765c | Ac-P-Q-R4-I-L-D-P$_R$-H-V-R-R-V-W-R-NH2 | 30 |
| FP-0766c | Ac-P-Q-R5-I-L-D-P$_R$-H-V-R-R-V-W-R-NH2 | 20 |
| FP-0767c | Ac-P-Q-R6-I-L-D-P$_R$-H-V-R-R-V-W-R-NH2 | 110 |
| FP-0768c | Ac-P-Q-R7-I-L-D-P$_R$-H-V-R-R-V-W-R-NH2 | 150 |

| Alkyl Carbamate Staples | | |
|---|---|---|
| Peptide ID | Sequence | FP EC$_{50}$ (nM) |
| FP-0776c | Ac-P-Q-R5-I-L-D-RdN-H-V-R-R-V-W-R-NH2 | 570 |
| FP-0777c | Ac-P-Q-R5-I-L-D-ReN-H-V-R-R-V-W-R-NH2 | 560 |
| FP-0778c | Ac-P-Q-SgN-I-L-D-S5-H-V-R-R-V-W-R-NH2 | 1000 |
| FP-0779c | Ac-P-Q-SdN-I-L-D-S5-H-V-R-R-V-W-R-NH2 | 1300 |
| FP-0780c | Ac-P-Q-SeN-I-L-D-S5-H-V-R-R-V-W-R-NH2 | 1700 |

TABLE 5-continued

Exemplary FP EC50 data (nM) (Table 5 discloses
SEQ ID NOS 229, 231, 232, 234-238, 240, 242, 244,
334, 246, 248, 250, 252, 253, 339, 256, 257, 259,
260, 261, 263, 265, 266, 268, 270-274, 228, 230,
233, 239, 241, 243, 245, 247, 249, 251, 254, 255,
258, 262, 264, 267, 269 and 275).

| Peptide ID | Sequence | FP EC$_{50}$ (nM) |
|---|---|---|
| FP-0782c | Ac-P-Q-RdN-I-L-D-R5-H-V-R-R-V-W-R-NH2 | 380 |
| FP-0783c | Ac-P-Q-ReN-I-L-D-R5-H-V-R-R-V-W-R-NH2 | 990 |

Amino Staples (Cyclic)

| Peptide ID | Sequence | FP EC$_{50}$ (nM) |
|---|---|---|
| FP-0721 | Ac-P-Q-Az-I-L-D-R4-H-V-R-R-V-W-R-NH2 | TBD |
| FP-0723 | Ac-P-Q-Az-I-L-D-R5-H-V-R-R-V-W-R-NH2 | TBD |
| FP-0725 | Ac-P-Q-Az-I-L-D-R6-H-V-R-R-V-W-R-NH2 | 580 |
| FP-0734 | Ac-P-Q-S5-I-L-D-Az-H-V-R-R-V-W-R-NH2 | >5000 |
| FP-0735 | Ac-P-Q-R6-I-L-D-Az-H-V-R-R-V-W-R-NH2 | 2360 |
| FP-0736 | Ac-P-Q-S6-I-L-D-Az-H-V-R-R-V-W-R-NH2 | 470 |
| FP-0738 | Ac-P-Q-S7-I-L-D-Az-H-V-R-R-V-W-R-NH2 | 200 |
| FP-0743 | Ac-P-Q-P$_R$-I-L-D-R5-H-V-R-R-V-W-R-NH2 | >5000 |
| FP-0745 | Ac-P-Q-P$_R$-I-L-D-R6-H-V-R-R-V-W-R-NH2 | 210 |
| FP-0751 | Ac-P-Q-P$_S$-I-L-D-S5-H-V-R-R-V-W-R-NH2 | >5000 |
| FP-0753 | Ac-P-Q-P$_S$-I-L-D-S7-H-V-R-R-V-W-R-NH2 | >5000 |
| FP-0758 | Ac-P-Q-R5-I-L-D-P$_S$-H-V-R-R-V-W-R-NH2 | >5000 |
| FP-0763 | Ac-P-Q-S7-I-L-D-P$_S$-H-V-R-R-V-W-R-NH2 | 1110 |
| FP-0767 | Ac-P-Q-R6-I-L-D-P$_R$-H-V-R-R-V-W-R-NH2 | 700 |
| FP-0768 | Ac-P-Q-R7-I-L-D-P$_R$-H-V-R-R-V-W-R-NH2 | >5000 |

Amino Staples (Acyclic)

| Peptide ID | Sequence | FP EC$_{50}$ (nM) |
|---|---|---|
| FP-0776 | Ac-P-Q-R5-I-L-D-RdN-H-V-R-R-V-W-R-NH2 | 580 |
| FP-0777 | Ac-P-Q-R5-I-L-D-ReN-H-V-R-R-V-W-R-NH2 | 4750 |
| FP-0783 | Ac-P-Q-ReN-I-L-D-R5-H-V-R-R-V-W-R NH2 | 1400 |

Control: FP-0787 (EC$_{50}$)~100 nM.

TABLE 6

Exemplary amino staple formation results (Table 6 discloses
SEQ ID NOS 228, 230, 344, 233, 345, 346, 239, 241, 243, 347,
245, 247, 249, 251, 348, 255, 349, 298, 258, 350, 351, 262,
264, 267, 269, 309-311, 313 and 275).

Amino Staples Cyclic)

| Peptide ID | Sequence | Reaction Complete | Incomplete | Mulitple byproducts | Double Isomer |
|---|---|---|---|---|---|
| FP-0721 | Ac-P-Q-Az-I-L-D-R4-H-V-R-R-V-W-R-NH2 | no info | | no info | no info |
| FP-0723 | Ac-P-Q-Az-I-L-D-R5-H-V-R-R-V-W-R-NH2 | x | | | |
| FP-0724 | Ac-P-Q-Az-I-L-D-S5-H-V-R-R-V-W-R-NH2 | x | | x | |
| FP-0725 | Ac-P-Q-Az-I-L-D-R6-H-V-R-R-V-W-R-NH2 | x | | | |
| FP-0731 | Ac-P-Q-R4-I-L-D-Az-H-V-R-R-V-W-R-NH2 | x | | x | x |

TABLE 6-continued

Exemplary amino staple formation results (Table 6 discloses SEQ ID NOS 228, 230, 344, 233, 345, 346, 239, 241, 243, 347, 245, 247, 249, 251, 348, 255, 349, 298, 258, 350, 351, 262, 264, 267, 269, 309-311, 313 and 275).

| Peptide ID | Sequence | Reaction Complete | Incomplete | Multiple byproducts | Double Isomer |
|---|---|---|---|---|---|
| FP-0733 | Ac-P-Q-R5-I-L-D-Az-H-V-R-R-V-W-R-NH2 | x | | x | |
| FP-0734 | Ac-P-Q-S5-I-L-D-Az-H-V-R-R-V-W-R-NH2 | x | | | |
| FP-0735 | Ac-P-Q-R6-I-L-D-Az-H-V-R-R-V-W-R-NH2 | x | | | |
| FP-0736 | Ac-P-Q-S6-I-L-D-Az-H-V R-R-V-W-R-NH2 | x | | | |
| FP 0737 | Ac-P-Q-R7-I-L-D-Az-H-V R-R-V-W-R-NH2 | x | | | |
| FP-0738 | Ac-P-Q-S7-I-L-D-Az-H-V-R-R-V-W-R-NH2 | x | | | |
| FP-0743 | Ac-P-Q-P$_R$-I-L-D-R5-H-V-R-R-V-W-R-NH2 | x | | | |
| FP-0745 | Ac-P-Q-P$_R$-I-L-D-R6-H-V-R-R-V-W-R-NH2 | x | | | |
| FP-0751 | Ac-P-Q-P$_S$-I-L-D-S5-H-V-R-R-V-W-R-NH2 | x | | | |
| FP-0752 | Ac-P-Q-P$_S$-I-L-D-S6-H-V-R-R-V-W-R-NH2 | x | | | x |
| FP-0758 | Ac-P-Q-R5-I-L-D-P$_S$-H-V-R-R-V-W-R-NH2 | x | | | |
| FP-0759 | Ac-P-Q-S5-I-L-D-P$_S$-H-V-R-R-V-W-R-NH2 | x | | | x |
| FP-0761 | Ac-P-Q-S6-I-L-D-P$_S$-H-V-R-R-V-W-R-NH2 | | x | | |
| Fp-0763 | Ac-P-Q-S7-I-L-D-P$_S$-H-V-R-R-V-W-R-NH2 | x | | | |
| FP-0765 | Ac-P-Q-R4-I-L-D-P$_R$-H-V-R-R-V-W-R-NH2 | x | | | x |
| FP-0766 | Ac-P-Q-R5-I-L-D-P$_R$-H-V-R-R-V-W-R-NH2 | x | | | x |
| FP-0767 | Ac-P-Q-R6-I-L-D-P$_R$-H-V-R-R-V-W-R-NH2 | x | | | |
| FP-0768 | Ac-P-Q-R7-I-L-D-P$_R$-H-V-R-R-V-W-R-NH2 | x | | | |

Amino Staples (Acyclic)

| Peptide ID | Sequence | Reaction Complete | Incomplete | Multiple byproducts | Double Isomer |
|---|---|---|---|---|---|
| FP-0776 | Ac-P-Q-R5-I-L-D-RdN-H-V-R-R-V-W-R-NH2 | x | | | |
| FP-0777 | Ac-P-Q-R5-I-L-D-ReN-H-V-R-R-V-W-R-NH2 | x | | | |
| FP-0778 | Ac-P-Q-SgN-I-L-D-S5-H-V-R-R-V-W-R-NH2 | | x | | x |
| FP-0779 | Ac-P-Q-SdN-I-L-D-S5-H-V-R-R-V-W-R-NH2 | | x | | |
| FP-0780 | Ac-P-Q-SeN-I-L-D-S5-H-V-R-R-V-W-R-NH2 | | x | | |
| FP-0782 | Ac-P-Q-RdN-I-L-D-R5-H-V-R-R-V-W-R-NH2 | | x | | |
| FP-0783 | Ac-P-Q-ReN-I-L-D-R5-H-V-R-R-V-W-R-NH2 | x | | | |

While various embodiments have been described and illustrated herein, those of ordinary skill in the art will readily envision a variety of other means and/or structures for performing the functions and/or obtaining the results and/or one or more of the advantages described in the present disclosure, and each of such variations and/or modifications is deemed to be included. More generally, those skilled in the art will readily appreciate that all parameters, dimensions, materials, and configurations described herein are meant to be example and that the actual parameters, dimensions, materials, and/or configurations will depend upon the specific application or applications for which the teachings of the present disclosure is/are used. Those skilled in the art will recognize, or be able to ascertain using no more than routine experimentation, many equivalents to the specific embodiments of the disclosure described in the present disclosure. It is, therefore, to be understood that the foregoing embodiments are presented by way of example only and that, provided technologies, including those to be claimed, may be practiced otherwise than as specifically described and claimed. In addition, any combination of two or more features, systems, articles, materials, kits, and/or methods, if such features, systems, articles, materials, kits, and/or methods are not mutually inconsistent, is included within the scope of the present disclosure.

The invention claimed is:

1. A peptide comprising:

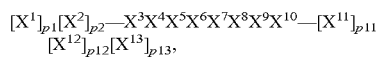

wherein:
  each of p1, p2, p11, p12 and p13 is independently 0 or 1;
  each of $X^1$, $X^2$, $X^3$, $X^4$, $X^5$, $X^6$, $X^7$, $X^8$, $X^9$, $X^{10}$, $X^{11}$, $X^{12}$, and $X^{13}$ is independently an amino acid residue;
  at least two of $X^1$, $X^2$, $X^3$, $X^4$, $X^5$, $X^6$, $X^7$, $X^8$, $X^9$, $X^{10}$, $X^{11}$, $X^{12}$, and $X^{13}$ comprise side chains that are linked together to form a staple, wherein the peptide comprises a structure selected from:

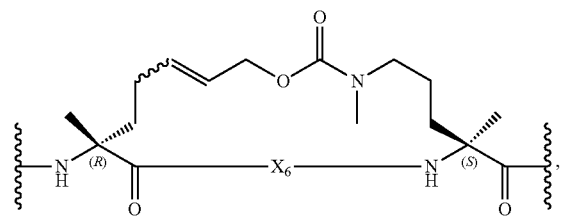

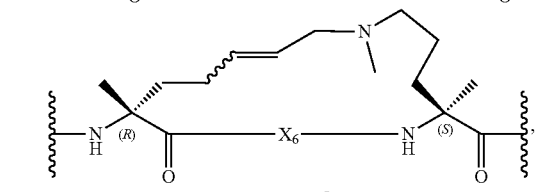

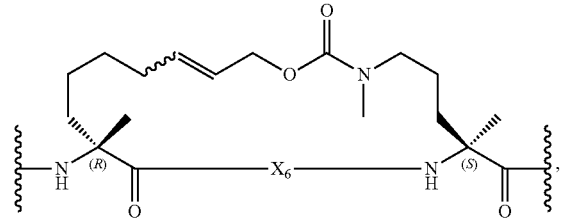

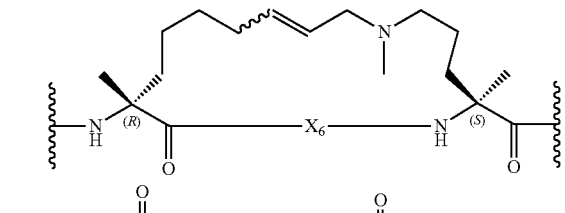

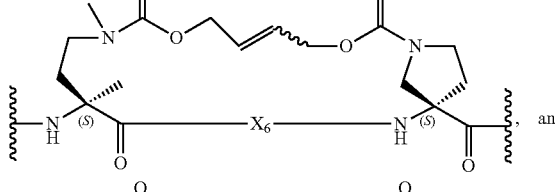

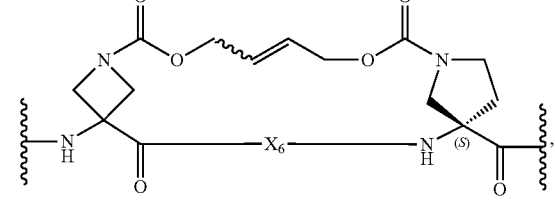

wherein each X is independently an amino acid residue.

2. The peptide of claim 1, wherein the peptide comprises

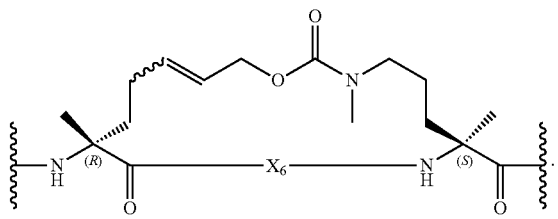

3. The peptide of claim 1, wherein the peptide comprises

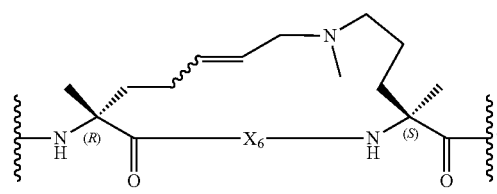

4. The peptide of claim 1, wherein the peptide comprises

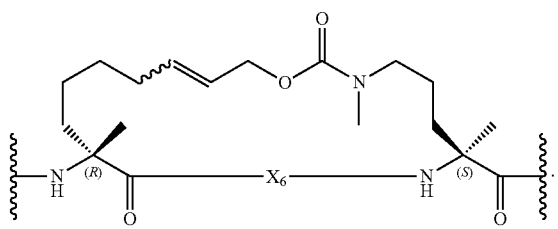

5. The peptide of claim 1, wherein the peptide comprises

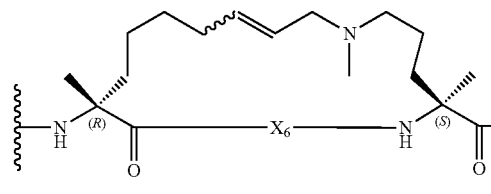

6. The peptide of claim 1, wherein the peptide comprises

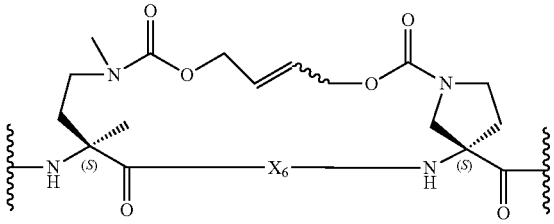

7. The peptide of claim 1, wherein the peptide comprises

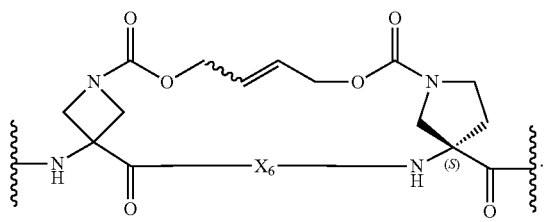

8. The peptide of claim 1, wherein the peptide comprises one and no more than one staple.

9. The peptide of claim 1, wherein the peptide comprises a structure selected from:

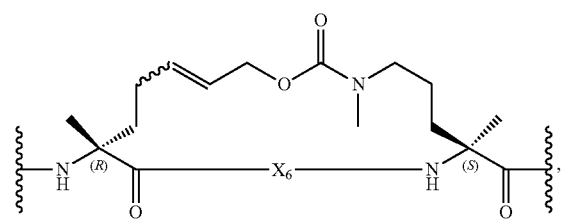

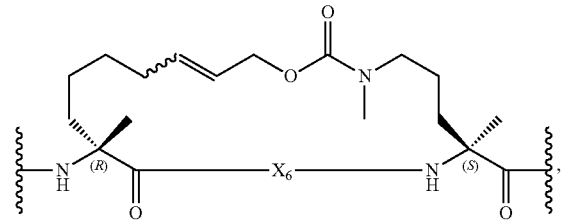

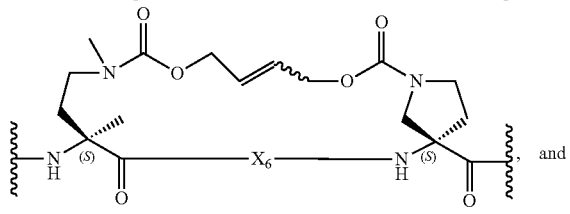

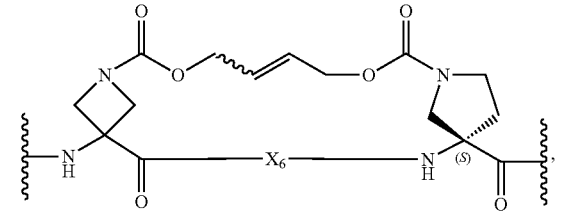

and wherein the peptide comprises two or more staples.

10. The peptide of claim 9, wherein at least two staples are bonded to the same peptide backbone atom.

11. The peptide of claim 9, wherein no two staples are bonded to the same peptide backbone atom.

12. A peptide comprising:

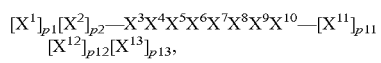

wherein:
each of p1, p2, p11, p12 and p13 is independently 0 or 1;
each of $X^1$, $X^2$, $X^3$, $X^4$, $X^5$, $X^6$, $X^7$, $X^8$, $X^9$, $X^{10}$, $X^{11}$, $X^{12}$, and $X^{13}$ is independently an amino acid residue;
at least two of $X^1$, $X^2$, $X^3$, $X^4$, $X^5$, $X^6$, $X^7$, $X^8$, $X^9$, $X^{10}$, $X^{11}$, $X^{12}$, and $X^{13}$ comprise side chains that are linked together to form a staple; and
the peptide comprises two or more staples, wherein the peptide comprises a structure selected from:

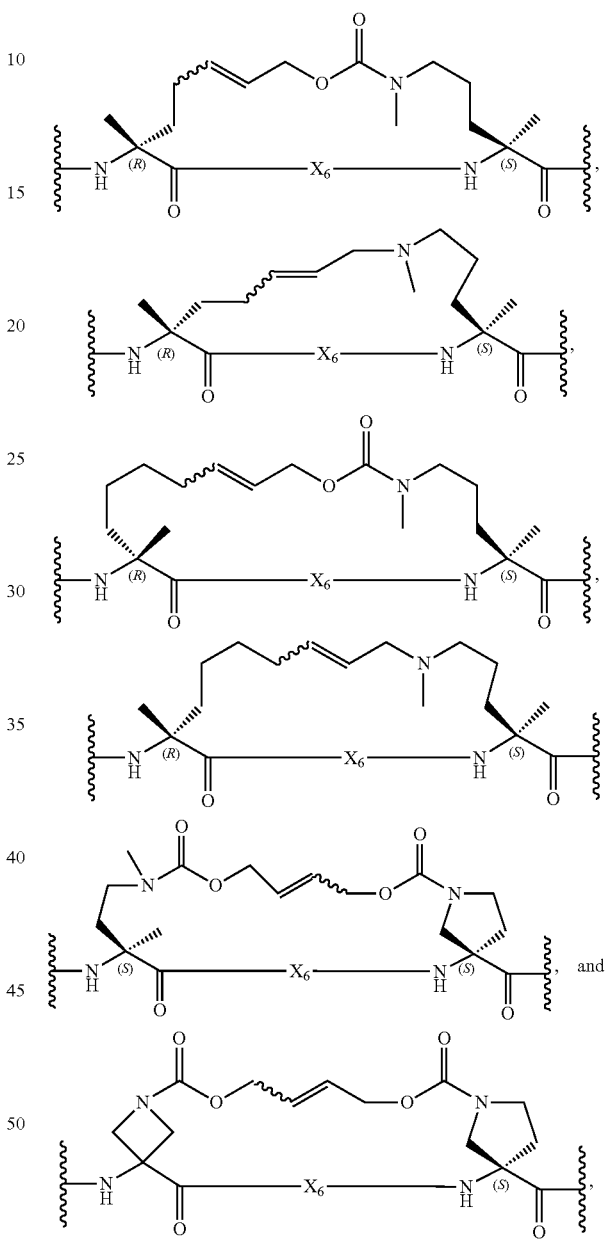

wherein each X is independently an amino acid residue.

13. The peptide of claim 12, wherein at least two staples are bonded to the same peptide backbone atom.

14. The peptide of claim 12, wherein no two staples are bonded to the same peptide backbone atom.

15. A peptide having the structure of:

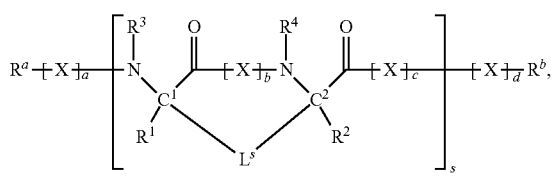

or a salt thereof, wherein
each of $R^a$, $R^1$, $R^2$, $R^3$, and $R^4$ is independently R';
$R^b$ is R', —OR' or —N(R')$_2$;
each X is independently an amino acid residue;
a is 0-20;
each of b, c, s, and d is independently 1-20;
each of $C^1$ and $C^2$ is independently a carbon atom;
each $L^s$ is independently -$L^{s1}$-$L^{s2}$-$L^{s3}$-, wherein $L^{s1}$ is bonded to $C^1$ and $L^{s3}$ is bonded to $C^2$;
each of $L^{s1}$, $L^{s2}$, and $L^{s3}$ is independently L;
each L is independently a covalent bond, or an optionally substituted, bivalent $C_1$-$C_{20}$ aliphatic group wherein one or more methylene units of the aliphatic group are optionally and independently replaced with —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, or —C(O)O—;
each -Cy- is independently an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus and silicon;
each R' is independently —R, —C(O)R, —CO$_2$R, or —SO$_2$R;
each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or
two R groups are optionally and independently taken together to form a covalent bond, or:
two or more R groups on the same atom are optionally and independently taken together with the atom to form an optionally substituted, 3-30 membered, monocyclic, bicyclic or polycyclic ring having, in addition to the atom, 0-10 heteroatoms independently selected from oxygen, nitrogen, sulfur, phosphorus and silicon; or
two or more R groups on two or more atoms are optionally and independently taken together with their intervening atoms to form an optionally substituted, 3-30 membered, monocyclic, bicyclic or polycyclic ring having, in addition to the intervening atoms, 0-10 heteroatoms independently selected from oxygen, nitrogen, sulfur, phosphorus and silicon;
wherein the peptide comprises a structure selected from:

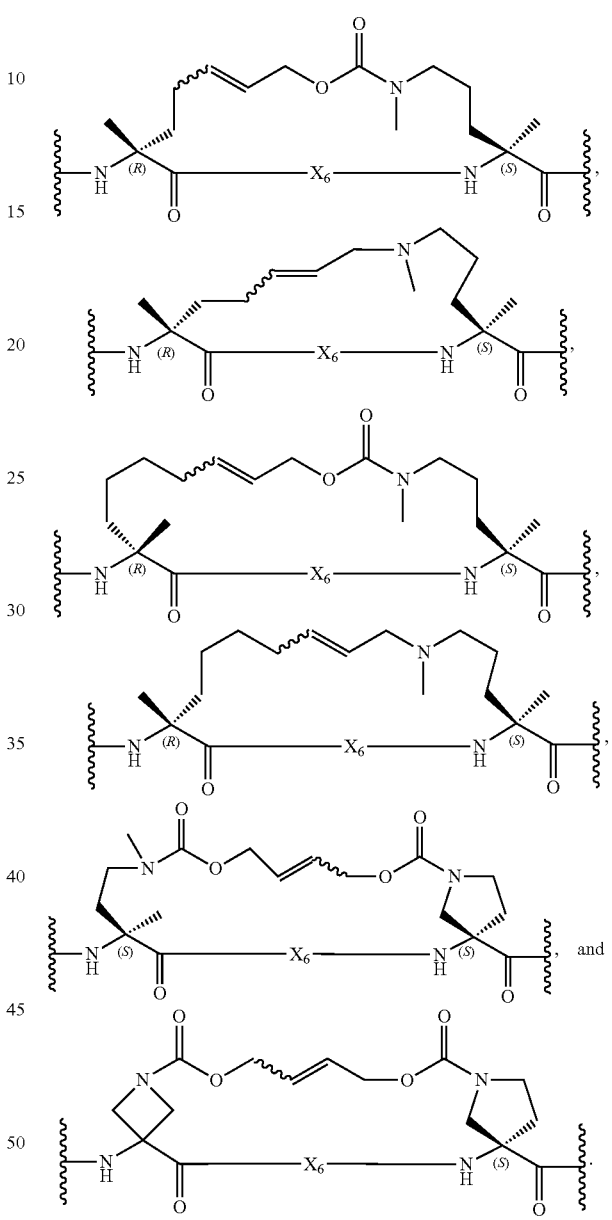

16. The peptide of claim 15, wherein the peptide comprises a structure selected from:

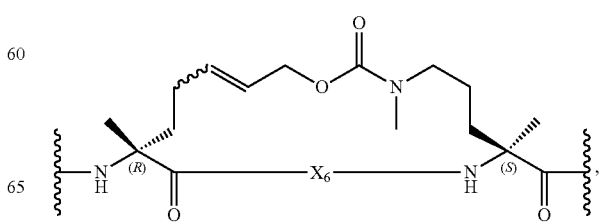

413

-continued

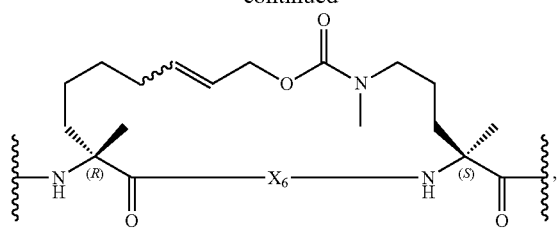

414

-continued

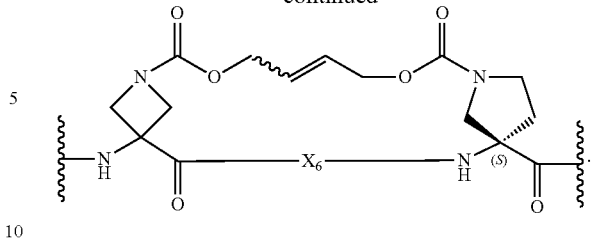

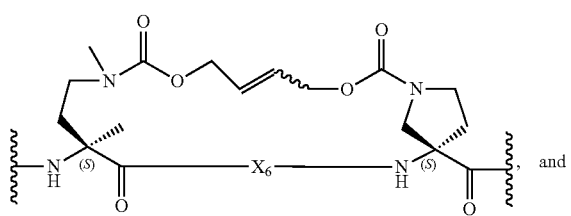, and

17. The peptide of claim 15, wherein the peptide comprises two staples.

18. The peptide of claim 16, wherein the peptide comprises two staples.

19. A pharmaceutical composition comprising a peptide of claim 1 or a pharmaceutically acceptable salt thereof, and a pharmaceutically acceptable carrier.

20. A pharmaceutical composition comprising a peptide of claim 12 or a pharmaceutically acceptable salt thereof, and a pharmaceutically acceptable carrier.

21. A pharmaceutical composition comprising a peptide of claim 15 or a pharmaceutically acceptable salt thereof, and a pharmaceutically acceptable carrier.

* * * * *